US009315587B2

(12) United States Patent
Schwoerer et al.

(10) Patent No.: US 9,315,587 B2
(45) Date of Patent: Apr. 19, 2016

(54) OLIGOSACCHARIDE COMPOUNDS

(75) Inventors: Ralf Schwoerer, Lower Hutt (NZ);
Jeremy E. Turnbull, Mortimer (GB);
Peter Charles Tyler, Wellington (NZ);
Olga Vladimirovna Zubkova, Kapiti (NZ)

(73) Assignees: Victoria Link Limited, Wellington (NZ); The University of Liverpool, Liverpool (GB)

( * ) Notice: Subject to any disclaimer, the term of this patent is extended or adjusted under 35 U.S.C. 154(b) by 113 days.

(21) Appl. No.: 14/001,399

(22) PCT Filed: Mar. 9, 2012

(86) PCT No.: PCT/NZ2012/000035
§ 371 (c)(1),
(2), (4) Date: Nov. 1, 2013

(87) PCT Pub. No.: WO2012/121617
PCT Pub. Date: Sep. 13, 2012

(65) Prior Publication Data
US 2014/0051659 A1    Feb. 20, 2014

Related U.S. Application Data

(60) Provisional application No. 61/451,572, filed on Mar. 10, 2011.

(51) Int. Cl.
| | | |
|---|---|---|
| *A61K 31/726* | (2006.01) | |
| *A61K 31/727* | (2006.01) | |
| *A61K 31/736* | (2006.01) | |
| *C08B 37/10* | (2006.01) | |
| *C08B 37/00* | (2006.01) | |
| *A61K 31/737* | (2006.01) | |

(52) U.S. Cl.
CPC ........... *C08B 37/0063* (2013.01); *A61K 31/726* (2013.01); *A61K 31/727* (2013.01); *A61K 31/737* (2013.01); *C08B 37/006* (2013.01); *C08B 37/0075* (2013.01); *C08B 37/0078* (2013.01)

(58) Field of Classification Search
None
See application file for complete search history.

(56) References Cited

U.S. PATENT DOCUMENTS

| 5,039,529 A | 8/1991 | Bergendal et al. |
| 2006/0183712 A1 | 8/2006 | McKeehan |
| 2006/0240473 A1 | 10/2006 | Powell |

FOREIGN PATENT DOCUMENTS

| WO | WO 03/022860 | * 3/2003 |
| WO | 2007115372 | 10/2007 |
| WO | 2007138263 | 12/2007 |
| WO | 2009007224 | 1/2009 |
| WO | WO 2009/137793 | 11/2009 |
| WO | 2010029185 | 3/2010 |
| WO | WO 2010/117803 | 10/2010 |

OTHER PUBLICATIONS

Vassar, R. et al "Function, therapeutic potential and cell biology of BACE proteases . . . " J. Neurochem. (2014) vol. 130, pp. 4-28.*
Yan, R. et al "Targeting the beta secretase BACE1 . . . " Lancet Neurol. (2014) vol. 13, pp. 319-329.*
Bettens, K. et al "Current status on Alzheimer's disease . . . " Hum. Mol. Genet. (2010) vol. 19, rev. issue 1, pp. R-4-R11.*
Wong, C. H. et al. (1998) "Assembly of Oligosaccharide Libraries with a Designed Building Block and an Efficient Orthogonal Protection-Deprotection Strategy", J. Am. Chem. Soc., 120:7137-7138.
Orgueira, H.A. et al. (2003) "Modular Synthesis of Heparin Oligosaccharides", Chem. Eur. J., 9(1):140-169.
Codee, J.D.C. et al. (2005) "A Modular Strategy Toward the Synthesis of Heparin-like Oligosaccharides Using Monomeric Building Blocks in a Sequential Glycosylation Strategy", J. Am. Chem. Soc. 127:3767-3773.
Codee, J.D.C. et al. (2004) "The synthesis of well-defined heparin and heparan sulfate fragments", Drug Discovery Today: Technologies, 1(3):317-326.
Lu, L.D. et al. (2006) "Synthesis of 48 Disaccharide Building Blocks for the Assembly of a Heparin and Heparan Sulfate Oligosaccharide Library". Org. Let., 8(26):5995-5998.
Haller and Boons (2002) "Selectively Protected Disaccharide Building Blocks for Modular Synthesis of Heparin Fragments", Eur. J. Org. Chem., 2033-2038.
Ojeda, R. et al. (2002) "The activation of fibroblast growth factors by heparin: Synthesis and structural study of rationally modified heparin-like oligosaccharides", Can. J. Chem., 80:917-936.
Arungundram, S. et al. (2009) "Modular Synthesis of Heparan Sulfate Oligosaccharides for Structure-Activity Relationship Studies", J. Am. Chem. Soc., 131:17394-17405.
Patey, S. J. et al. (2008) "Engineered Heparins: Novel b-secretase inhibitors as potential Alzheimer's Disease Therapeutics", Neurodegenerative Dis., 5:197-199.
Polat, T. et al. (2007) "Anomeric Reactivity-Based One-Pot Synthesis of Heparin-Like Oligosaccharide", J. Am. Chem. Soc., 129:12795-12800.
Scholefield, Z. et al. (2003) "Heparan sulfate regulates amyloid precursor protein processing by BACE1, the Alzheimer β-secretase", J. Cell Biol., 163:97-107.
Wang, Z. et al. (2010) "Preactivation-Based, One-Pot Combinatorial Synthesis of Heparin-like Hexasaccharides for the Analysis of Heparin-Protein Interactions", Chem. Eur. J. 16:8365-8375.

(Continued)

*Primary Examiner* — Leigh C Maier
(74) *Attorney, Agent, or Firm* — Glenn J. Foulds; Bozicevic, Field & Francis LLP

(57) ABSTRACT

The invention relates generally to oligosaccharide compounds and the use of these compounds as pharmaceuticals for treating diseases or conditions in which it is desirable to inhibit β-secretase.

22 Claims, 5 Drawing Sheets

(56) References Cited

OTHER PUBLICATIONS

Schwoerer, R. et al. (2009) "Towards the Synthesis of Heparan Sulfate Oligosaccharides", ANZGG meeting, Gold Coast, Australia, Seminar Presentation, 1-16.

Schwoerer R. et al. (2008) "Building Blocks for the Synthesis of Heparan Sulfate Oligosaccharides", ICS-2008, Oslo, Norway, Poster Presentation, 1 page.

Zubkova O. V. et al. (2010) "Synthesis of Defined Gluco- and Ido-configured Octasaccharide Fragments of Heparan Sulfates", ICS-2010, Chiba, Japan, Abstract No. A-P2-029, 1 page.

Zubkova O. V. et al. (2010) "A Modular Strategy for the Synthesis of Heparan Sulfate Oligosaccharides", ICS-2010, Chiba, Japan, Abstract No. A-P5-044, 1 page.

Zubkova O. V. et al. (2008) "Synthesis of Tri- and Tetrasaccharide Building Blocks of Hepara Sulfates", RACI-2008, Hobart, Australia, poster presentation, 1 page.

Zubkova O. V. et al. (2011) "Fully synthetic defined octa- and decasaccharide fragments of heparan sulfate as potential therapeutic agents for Alzheimer's disease", ComBio. Cairns Poster. 1 page.

De Paz et al. (2001) "The activation of fibroblast growth factors by heparin: synthesis, structure, and biological activity of heparin-like oligosaccharides" Chembiochem 2(9):673-685.

Patey et al. (2006) "Heparin derivatives as inhibitors of BACE-1, the Alzheimer's beta-secretase, with reduced activity against factor Xa and other proteases" J Med Chem 49(20):6129-6132.

\* cited by examiner

OLIGOSACCHARIDE COMPOUNDS

TECHNICAL FIELD

This invention relates generally to oligosaccharide compounds, the use of these compounds as pharmaceuticals, pharmaceutical compositions containing the compounds, processes for preparing the compounds, and methods of treating diseases or conditions in which it is desirable to inhibit β-secretase.

BACKGROUND

As populations age neurodegenerative disorders such as Alzheimer's disease become more prevalent. Alzheimer's disease is a common form of dementia, and is progressive and irreversible. The pathogenesis of the disease is thought to involve cerebral deposits of aggregated amyloid β-peptide. The first (and rate-limiting) step in the generation of amyloid β-peptide is cleavage of amyloid precursor protein by β-secretase (β-site amyloid precursor protein cleaving enzyme-1, β-secretase-1, hereinafter "BACE-1"). This makes BACE-1 an attractive target for new Alzheimer's therapies.

Heparan sulfate (HS) and its highly sulfated analogue heparin have been shown to inhibit BACE-1 activity. HS and heparin are both glycosaminoglycans comprising 1,4-linked disaccharide units of β-D-iduronic acid or α-L-iduronic acid with N-acetyl-α-D-glucosamine (dominant in the case of HS) or N-sulfo-α-D-glucosamine (dominant in the case of heparin) and additional O-sulfate ester substituents. Heparin is a well-known pharmaceutical with anti-coagulant activity. However, the anti-coagulant properties of heparin need to be attenuated if it is to be used for other pharmaceutical applications otherwise possible side effects, such as internal bleeding and impaired blood clotting, can be problematic.

Turnbull et al. have examined the activities of modified heparins against BACE-1 (S. J. Patey, E. A. Edwards, E. A. Yates, J. E. Turnbull, *J. Med. Chem.* 2006, 49, 6129-6132). They found that, after porcine mucosal heparin (PIMH), the next most effective inhibitor was a modified PIMH which had undergone N-desulfation and N-re-acetylation. Turnbull et al. also reported the preparation of oligosaccharides by enzymatic digestion of PIMH, and the activities of these oligosaccharides against BACE-1 were also determined. They found that the decasaccharide fraction was about 40-fold less active than PIMH, and the octasaccharide fraction was 10-fold less active than the decasaccharide fraction. Oligosaccharides containing 18 saccharide units were about as active as PIMH itself. As these oligosaccharide fractions are derived from a very complex polymer, the derived fractions are not single chemical species.

WO 2007/138263 describes a study by Scholefield et al., that showed that an N-acetylated heparin which is highly sulfated at the 2-O and 6-O positions is active against BACE-1 and that removal of the 2-O or 6-O sulfates decreased the activity against BACE-1. WO 2007/138263 suggests that removal of one or more sulfates would therefore be expected to have a deleterious effect on the activity. WO 2007/138263 describes and claims such de-sulfated oligosaccharides. WO 2007/138263 further states that neither N- nor 2-O-sulfation is an absolute requirement for high level activity when accompanied by 6-O sulfation. As these oligosaccharide fractions are derived from a very complex polymer, the derived fractions are not single chemical species.

WO 2010/029185 describes oligosaccharides, including decasaccharides and octasaccharides, which are said to be heparan sulfate mimetics and useful in the treatment of cancer, pathological angiogenesis and/or for inducing hematopoietic stem cell mobilisation. These oligosaccharides have an L-iduronic acid moiety at the non-reducing terminus.

There is a need for further oligosaccharides which are inhibitors of BACE-1. Furthermore, if such oligosaccharides were synthetic, in other words, if they could be synthesised de novo, they would, advantageously, be well-characterised single chemical entities. This would make them attractive for use as pharmaceuticals.

It is therefore an object of the present invention to provide oligosaccharide compounds that are inhibitors of BACE-1, or to at least provide a useful choice.

SUMMARY OF INVENTION

In a first aspect, the present invention provides an octasaccharide, decasaccharide or dodecasaccharide compound of the formula (I):

$$H\text{-}Q\text{-}V\text{-}W\text{-}X\text{-}Y\text{-}Z\text{-}A \qquad (I)$$

where:
A is an optionally substituted alkoxy, aralkoxy, aryloxy group;
W, X, Y and Z are each independently a disaccharide of formula (i);
V is a disaccharide of formula (i) or V is absent; and
Q is a disaccharide of formula (i) or Q is absent

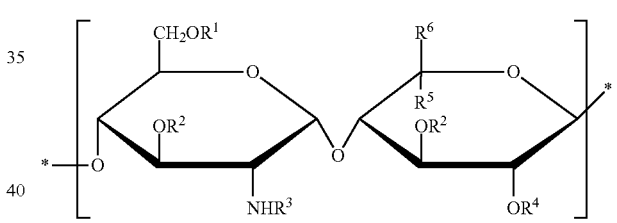

where:
$R^1$ is $SO_3H$;
$R^2$ is H;
$R^3$ is acyl;
$R^4$ is H or $SO_3H$; and
each $R^5$ and $R^6$ is independently selected from COOH and H; provided that one of $R^5$ and $R^6$ in each disaccharide is H and the other is COOH;
and provided that all $R^3$ groups in the octasaccharide, decasaccharide or dodecasaccharide are the same as each other and provided that all $R^4$ groups in the octasaccharide, decasaccharide or dodecasaccharide are the same as each other; or a pharmaceutically acceptable salt thereof.

Preferably $R^5$ is H and $R^6$ is COOH. Alternatively it is preferred that $R^5$ is COOH and $R^6$ is H. Alternatively, the octasaccharide, decasaccharide or dodecasaccharide contains at least one disaccharide of formula (i) where $R^5$ is H and $R^6$ is COOH and at least one disaccharide of formula (i) where $R^5$ is COOH and $R^6$ is H.

In a second aspect, the present invention provides an octasaccharide, decasaccharide or dodecasaccharide compound of the formula (Ia):

$$H\text{-}Q\text{-}V\text{-}W\text{-}X\text{-}Y\text{-}Z\text{-}A \qquad (Ia)$$

where:
A is an optionally substituted alkoxy, aralkoxy, aryloxy group;
W, X, Y and Z are each independently a disaccharide of formula (i);
V is a disaccharide of formula (i) or V is absent; and
Q is a disaccharide of formula (i) or Q is absent

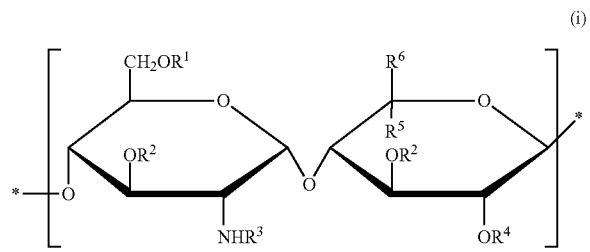

(i)

where:
$R^1$ is $SO_3H$;
$R^2$ is H;
$R^3$ is acyl;
$R^4$ is H or $SO_3H$;
$R^5$ is H; and
$R^6$ is COOH;
provided that all $R^3$ groups in the octasaccharide, decasaccharide or dodecasaccharide are the same as each other and provided that all $R^4$ groups in the octasaccharide, decasaccharide or dodecasaccharide are the same as each other; or a pharmaceutically acceptable salt thereof.

In a third aspect, the present invention provides an octasaccharide, decasaccharide or dodecasaccharide compound of the formula (Ib):

H-Q-V-W-X-Y-Z-A        (Ib)

where:
A is an optionally substituted alkoxy, aralkoxy, aryloxy group;
W, X, Y and Z are each independently a disaccharide of formula (i);
V is a disaccharide of formula (i) or V is absent; and
Q is a disaccharide of formula (i) or Q is absent

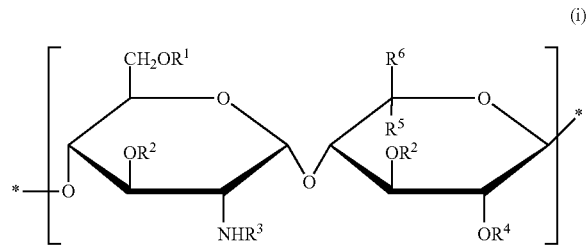

(i)

where:
$R^1$ is $SO_3H$;
$R^2$ is H;
$R^3$ is acyl;
$R^4$ is H or $SO_3H$;
$R^5$ is COOH; and
$R^6$ is H;
provided that all $R^3$ groups in the octasaccharide, decasaccharide or dodecasaccharide are the same as each other and provided that all $R^4$ groups in the octasaccharide, decasaccharide or dodecasaccharide are the same as each other; or a pharmaceutically acceptable salt thereof.

Preferably the pharmaceutically acceptable salt is an ammonium salt, a metal salt, e.g. a sodium salt, or a salt of an organic cation, or a mixture thereof.

In some examples, Q and V are absent and the compound of formula (I), (Ia) or (Ib) is an octasaccharide.

In other examples, one of Q or V is absent and the other is a disaccharide of formula (i) and the compound of formula (I), (Ia) or (Ib) is a decasaccharide.

In still other examples, Q and V are each independently a disaccharide of formula (i) and the compound of formula (I), (Ia) or (Ib) is a dodecasaccharide.

Preferably $R^3$ is a lower acyl group, e.g. an acetyl group.
Preferably $R^4$ is $SO_3H$ or a salt form thereof, e.g. $R^4$ may be $SO_3Na$ or $SO_3NH_4$. Alternatively it is preferred that $R^4$ is H.

In some examples $R^1$ is a salt form of $SO_3H$, e.g. $R^1$ may be $SO_3NH_4$ or $SO_3Na$.

In some examples $R^5$ or $R^6$ is a salt form of COOH, e.g. $R^5$ or $R^6$ may be COONa or $COONH_4$.

Preferably A is an optionally substituted aryloxy group, such as an aryloxy group, e.g. a phenoxy group, substituted with an alkoxy group, e.g. a lower alkoxy group, e.g. a 4-methoxyphenoxy group.

Alternatively A is an optionally substituted alkoxy group, preferably hexyloxy or octyloxy group, or an ω-(N-benzyloxycarbonylamino)-alkyloxy group, preferably an 8-(N-benzyloxycarbonylamino)-octyl, or 6-(N-benzyloxycarbonylamino)hexyl group, or an ω-aminoalkyloxy group, preferably an 8-aminooctyl or 6-aminohexyl group, or a methoxy-per(ethyleneoxy) group, preferably a methoxy-tris(ethylenoxy)-group.

In another aspect the invention provides a compound selected from the group consisting of:

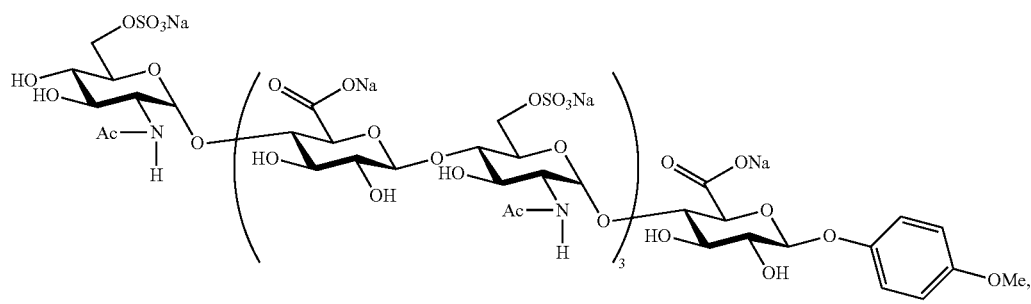

(a)

-continued
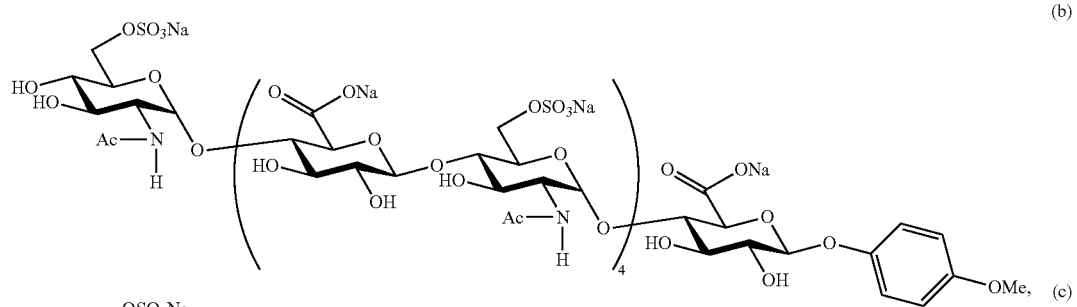
(b)
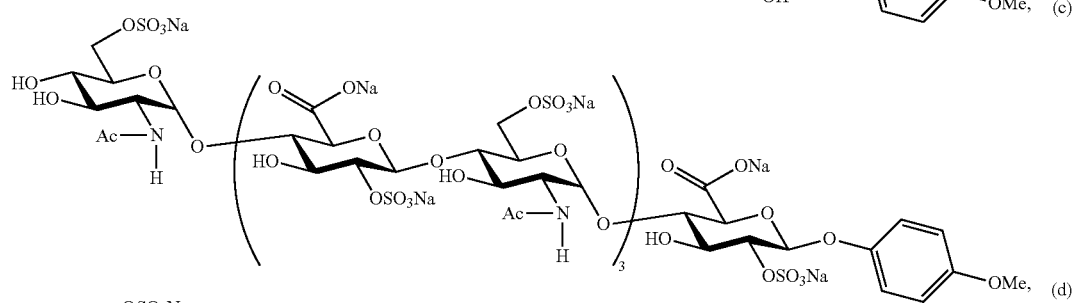
(c)
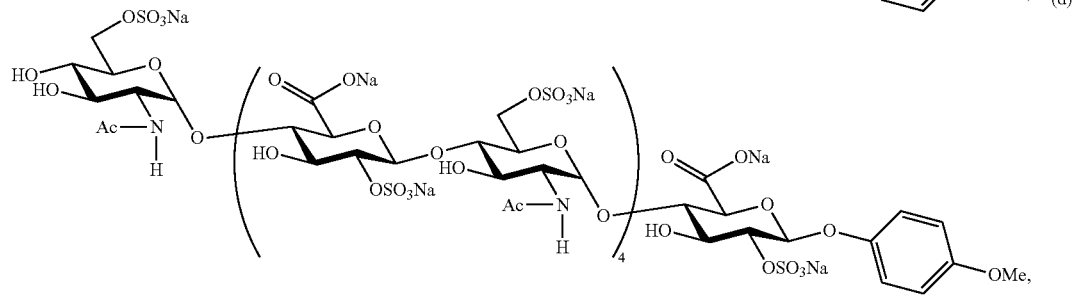
(d)
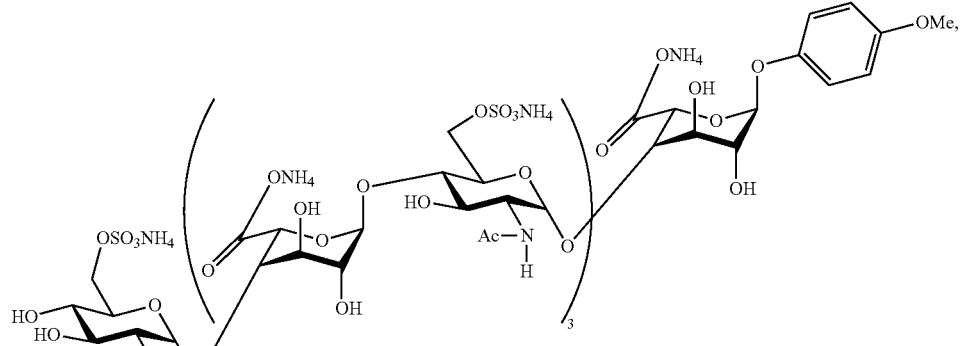
(e)
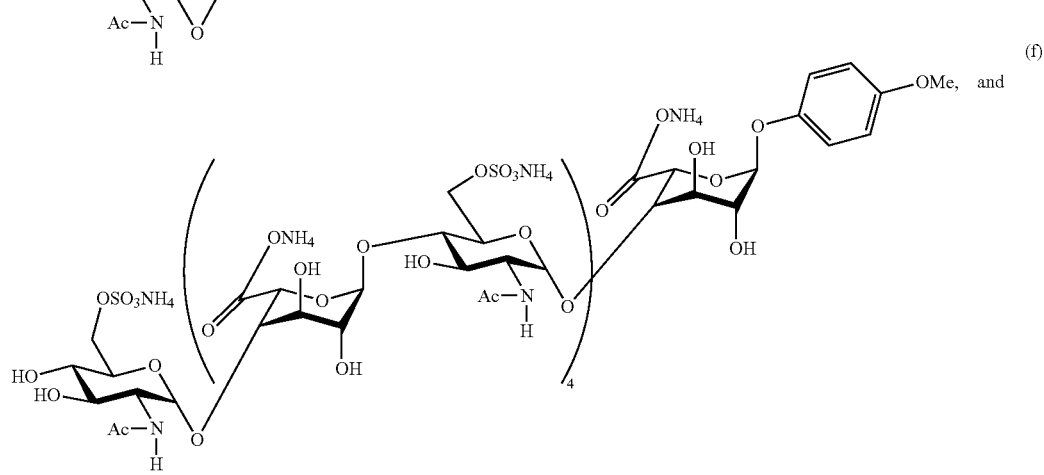
(f)
and

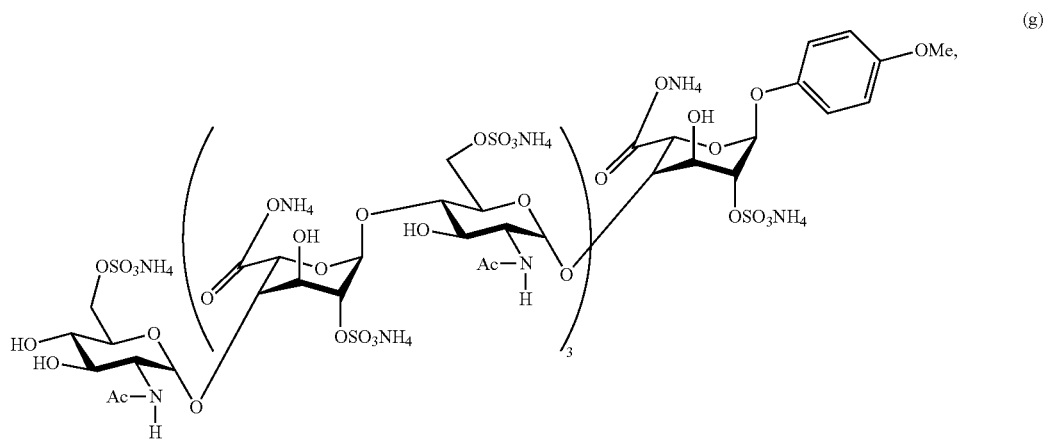
(g)
or a pharmaceutically acceptable salt thereof.
In another aspect the invention provides a compound selected from the group consisting of:
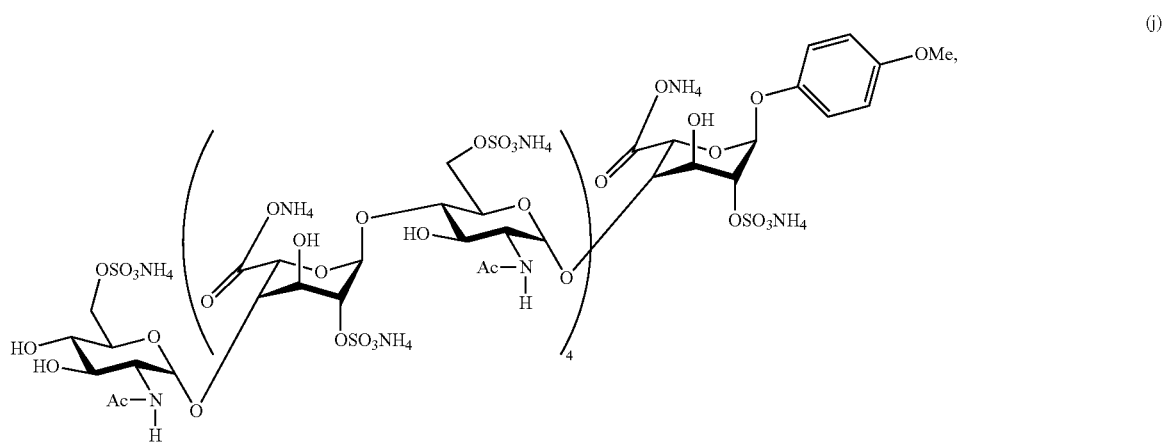
(j)
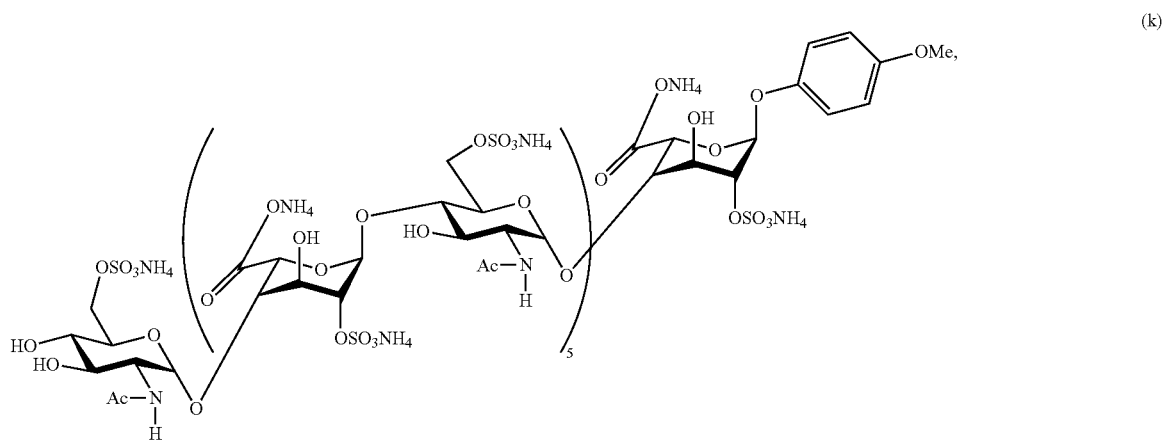
(k)

(l)
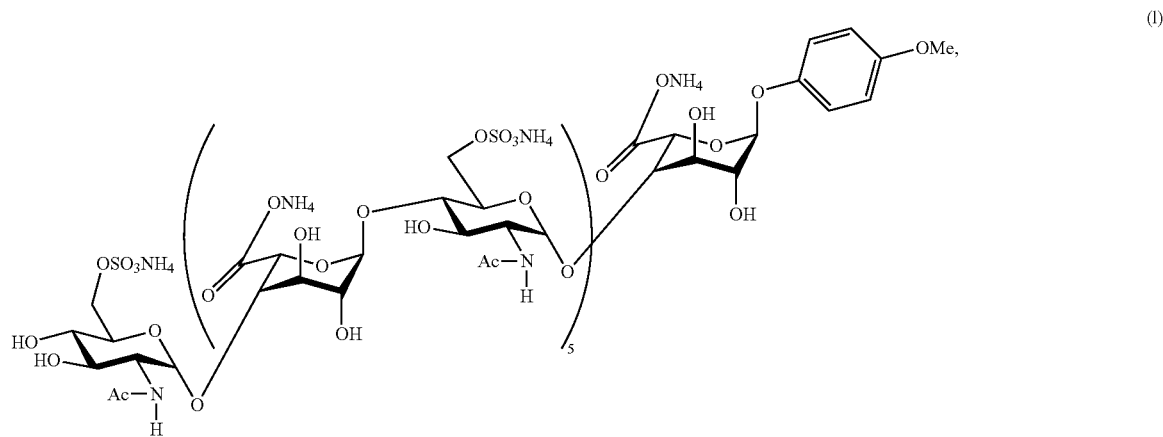
(m)
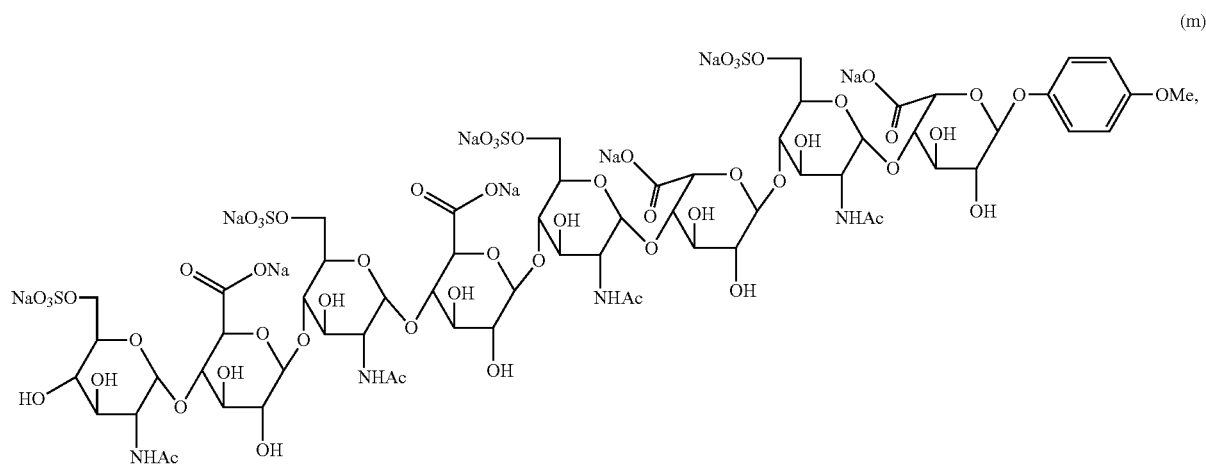
(n)
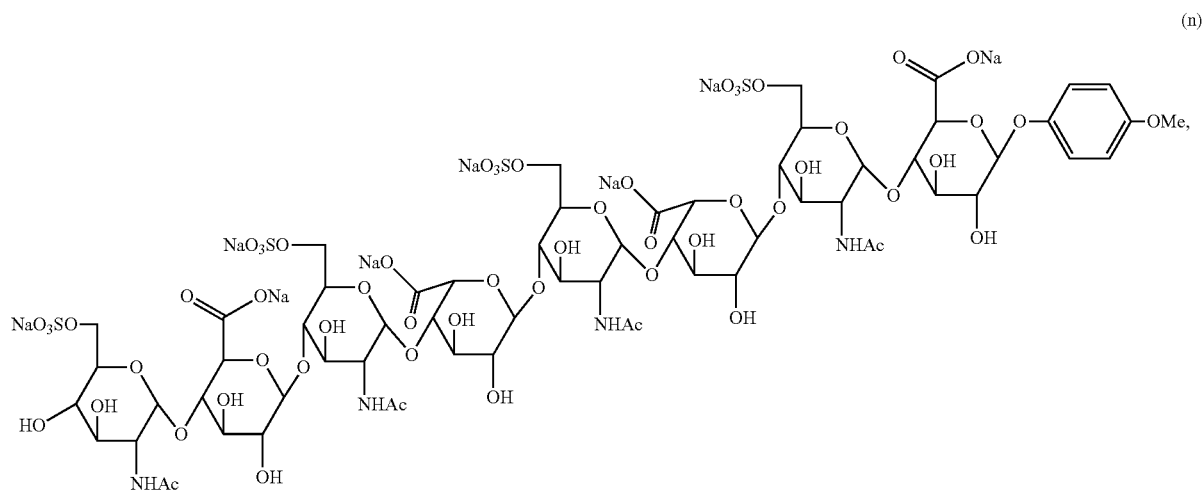

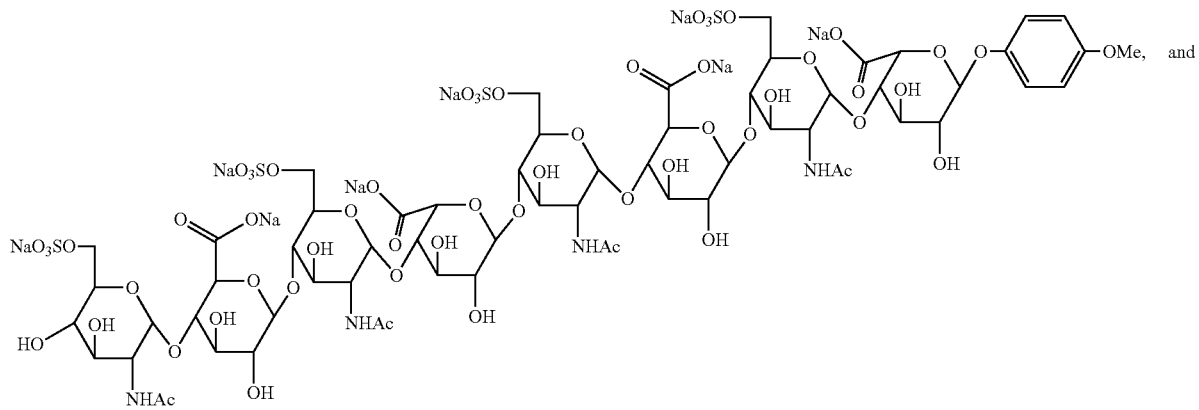
(o)
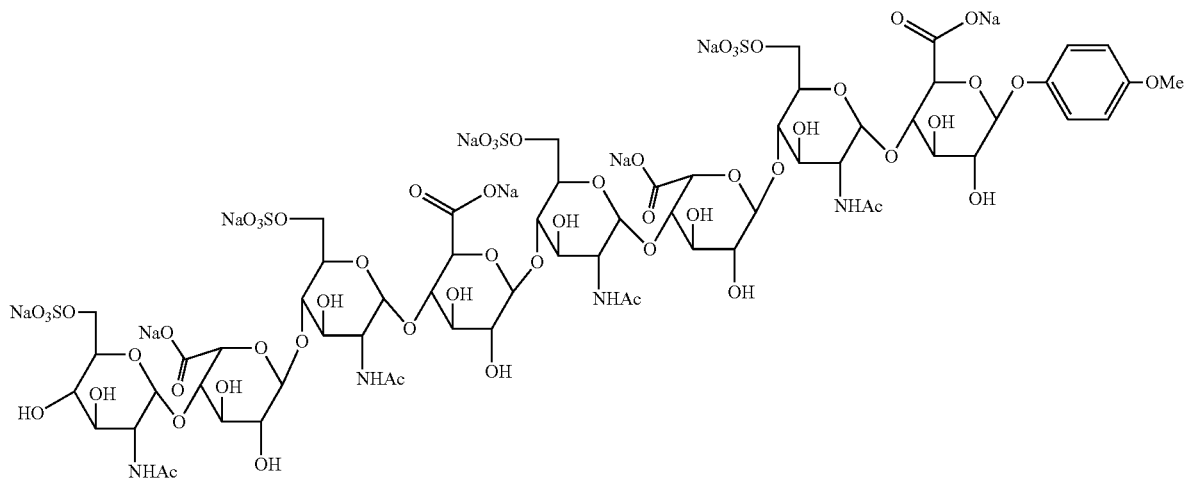
(p)
or a pharmaceutically acceptable salt thereof.
The invention also provides an acid form of any one of the compounds (a) to (g) or (j) to (p) above.
In another aspect, the invention provides a prodrug, e.g. an ester prodrug, of a compound of formula (I), (Ia) or (Ib).
In another aspect the invention provides a compound of formula 13, 14, 15, 16 or 27:
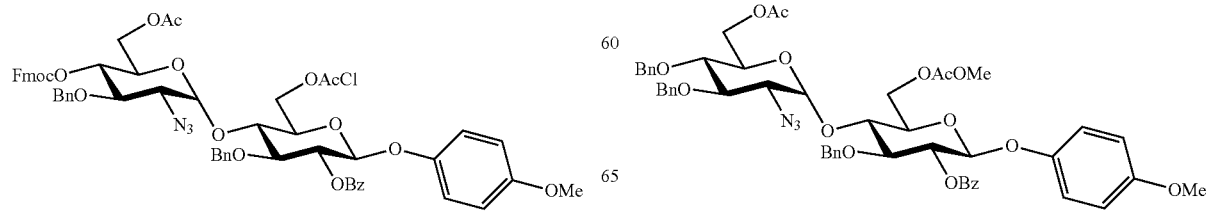

-continued

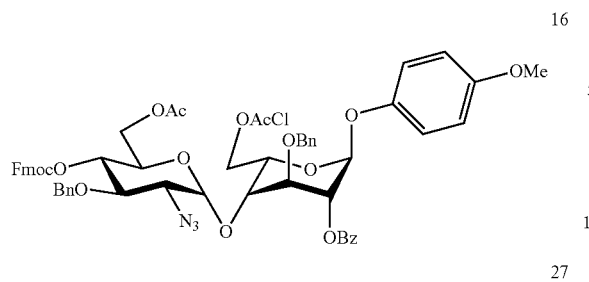

16

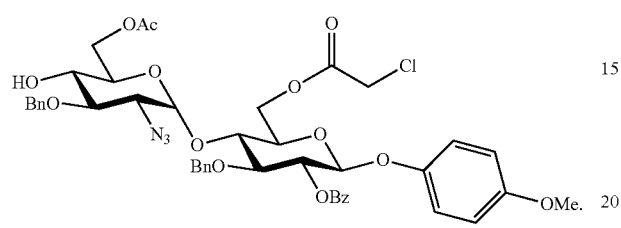

27

In another aspect the invention provides a crystalline compound of formula 13, 14, 15, 16 or 27:

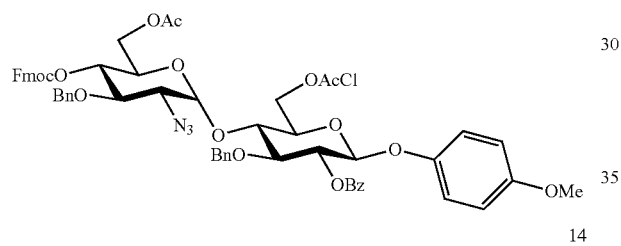

13

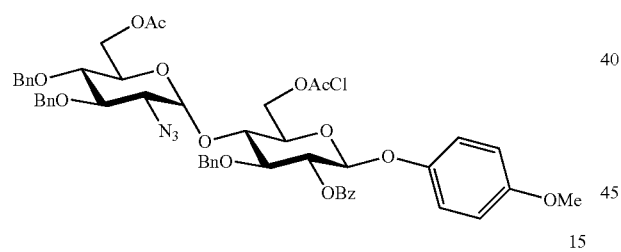

14

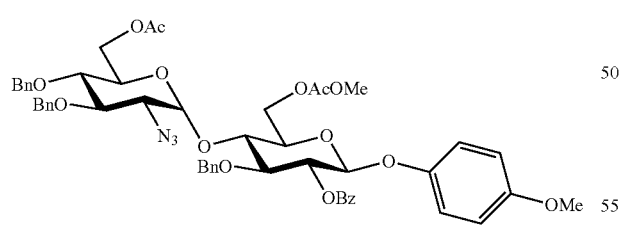

15

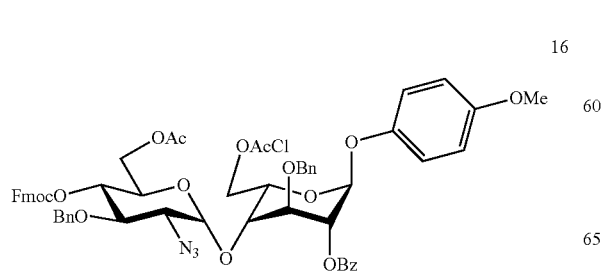

16

-continued

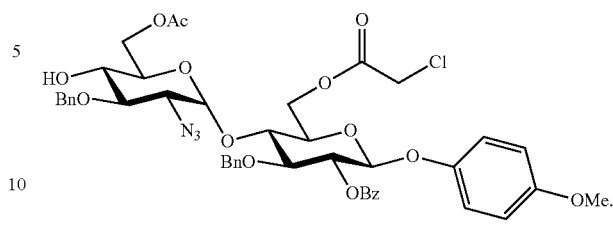

27

In another aspect, the invention provides a crystalline compound of formula 13, having a melting point of about 131° C.

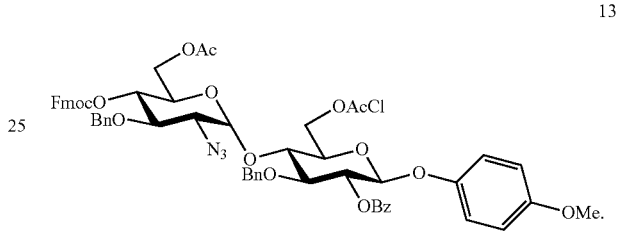

13

In another aspect, the invention provides a crystalline compound of formula 14, having a melting point of about 140-141° C.

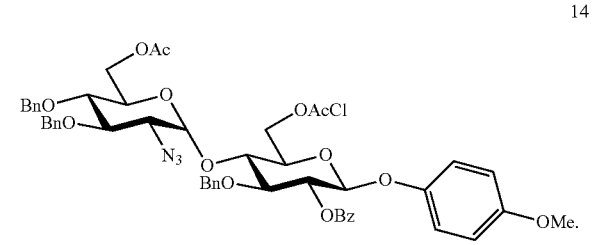

14

In another aspect, the invention provides a crystalline compound of formula 16, having a melting point of about 144° C.

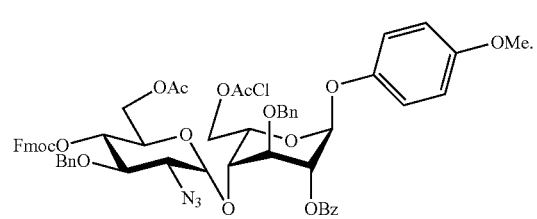

16

In another aspect, the invention provides a crystalline compound of formula 27, having a melting point of about 144° C.

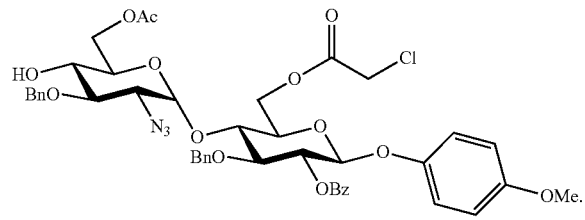

27

In another aspect, the invention provides a crystalline compound of formula 13, having:
i. a crystal structure as shown in FIG. 1; and/or
ii. crystal lattice parameters at 123(2) K of: a=10.454(2) Å, b=35.610(7) Å, c=14.408(3) Å, α=90°, β=95.61(3)°, γ=90°; and/or
iii. a crystal structure belonging to a monoclinic space group, e.g. P2$_1$
determined by X-ray crystal structure analysis

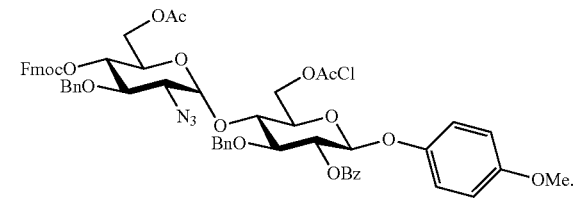

13

In another aspect, the invention provides a crystalline compound of formula 14, having:
i. a crystal structure as shown in FIG. 2; and/or
ii. crystal lattice parameters at 164(2) K of: a=9.2713(7) Å, b=17.4067(11) Å, c=15.0036(11) Å, α=90°, β=97.449(7)°, γ=90°; and/or
iii. a crystal structure belonging to a monoclinic space group, e.g. P2$_1$
determined by X-ray crystal structure analysis

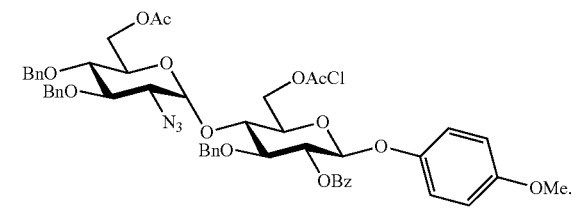

14

In another aspect, the invention provides a crystalline compound of formula 15, having:
i. a crystal structure as shown in FIG. 3; and/or
ii. crystal lattice parameters at 118(2) K of: a=38.3346(13) Å, b=8.0744(3) Å, c=16.1659(6) Å, α=90°, β=91.222(2)°, γ=90°; and/or
iii. a crystal structure belonging to a monoclinic space group, e.g. C2
determined by X-ray crystal structure analysis

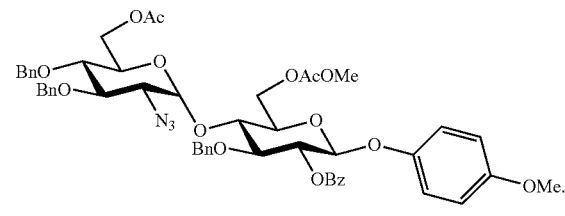

15

In another aspect, the invention provides a crystalline compound of formula 16, having:
i. a crystal structure as shown in FIG. 4; and/or
ii. crystal lattice parameters at 123(2) K of: a=14.8343(11) Å, b=8.4771(6) Å, c=21.8112(17) Å, α=90°, β=91.780(7)°, γ=90°; and/or
iii. a crystal structure belonging to a monoclinic space group, e.g. P2$_1$
determined by X-ray crystal structure analysis

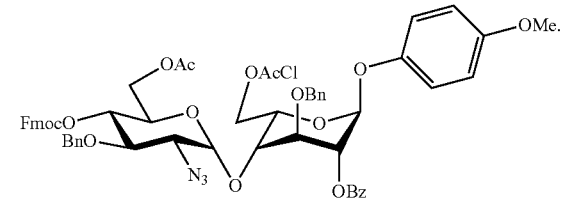

16

In another aspect, the invention provides a crystalline compound of formula 27, having:
i. a crystal structure as shown in FIG. 5; and/or
ii. crystal lattice parameters at 164(2) K of: a=8.1104(2) Å, b=19.5548(6) Å, c=27.2321(19) Å, α=90°, β=90°, γ=90°; and/or
iii. a crystal structure belonging to a orthorhombic space group, e.g. P2$_1$2$_1$2$_1$
determined by X-ray crystal structure analysis

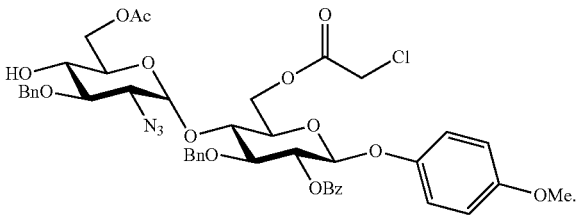

27

In another aspect the invention provides the use of a compound of formula 13, 14, 15, 16 or 27 for preparing a compound of formula (I), (Ia) or (Ib).

In another aspect the invention provides a composition comprising a pharmaceutically effective amount of a compound of formula (I), (Ia) or (Ib) and optionally a carrier.

In another aspect the invention provides a pharmaceutical composition comprising a pharmaceutically effective amount of a compound of formula (I), (Ia) or (Ib) and optionally a pharmaceutically acceptable carrier, diluent or excipient.

In another aspect the invention provides a compound of formula (I), (Ia) or (Ib) in combination with at least one other compound, e.g. a second drug compound. The other compound may be, for example, an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation or memantine.

In another aspect the invention provides the use of a compound of formula (I), (Ia) or (Ib) for inhibiting BACE-1.

In another aspect the invention provides the use of a compound of formula (I), (Ia) or (Ib) as a medicament.

In another aspect the invention provides the use of a compound of formula (I), (Ia) or (Ib) for treating or preventing a disease or disorder in which it is desirable to inhibit BACE-1.

In another aspect the invention provides the use of a compound of formula (I), (Ia) or (Ib) for treating or preventing a neurodegenerative disorder such as senile dementia, pre-senile dementia, multi-infarct dementia or Alzheimer's disease, preferably Alzheimer's disease.

In another aspect the invention provides the use of a pharmaceutical composition comprising a pharmaceutically effective amount of a compound of formula (I), (Ia) or (Ib) for treating or preventing a disease or disorder in which it is desirable to inhibit BACE-1.

In another aspect the invention provides the use of a pharmaceutical composition comprising a pharmaceutically effective amount of a compound of formula (I), (Ia) or (Ib) for treating or preventing a neurodegenerative disorder such as senile dementia, pre-senile dementia, multi-infarct dementia or Alzheimer's disease, preferably Alzheimer's disease.

In another aspect the invention provides the use of a compound of formula (I), (Ia) or (Ib) for use in the manufacture of a medicament.

In another aspect the invention provides a pharmaceutical composition for treating or preventing a disease or disorder in which it is desirable to inhibit BACE-1 comprising a compound of formula (I), (Ia) or (Ib).

In another aspect the invention provides a pharmaceutical composition for treating or preventing a neurodegenerative disorder such as senile dementia, pre-senile dementia, multi-infarct dementia or Alzheimer's disease, preferably Alzheimer's disease, comprising a compound of formula (I), (Ia) or (Ib).

In another aspect the invention provides the use of a compound of formula (I), (Ia) or (Ib) in the manufacture of a medicament for the treatment or prevention of a disease or disorder in which it is desirable to inhibit BACE-1.

In another aspect the invention provides a method of treating or preventing a disease or disorder in which it is desirable to inhibit BACE-1 comprising administering a pharmaceutically effective amount of a compound of formula (I), (Ia) or (Ib) to a patient requiring treatment.

In another aspect the invention provides a method of treating or preventing a neurodegenerative disorder such as senile dementia, pre-senile dementia, multi-infarct dementia or Alzheimer's disease, preferably Alzheimer's disease, comprising administering a pharmaceutically effective amount of a compound of formula (I), (Ia) or (Ib) to a patient requiring treatment.

In another aspect the invention provides the use of a compound of formula (I), (Ia) or (Ib) in combination with at least one other compound, e.g. a second drug compound, e.g. an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation or memantine, for treating or preventing a disease or disorder in which it is desirable to inhibit BACE-1 (e.g. a neurodegenerative disorder such as senile dementia, pre-senile dementia, multi-infarct dementia or Alzheimer's disease, preferably Alzheimer's disease).

In another aspect the invention provides a method of treating or preventing a disease or disorder in which it is desirable to inhibit BACE-1 (e.g. a neurodegenerative disorder such as senile dementia, pre-senile dementia, multi-infarct dementia or Alzheimer's disease, preferably Alzheimer's disease) comprising administering a pharmaceutically effective amount of a compound of formula (I), (Ia) or (Ib) in combination with at least one other compound, e.g. a second drug compound, e.g. an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation or memantine. The compound of formula (I), (Ia) or (Ib) and the other compound may be administered separately, simultaneously or sequentially.

The diseases or disorders include neurodegenerative disorders such as senile dementia, pre-senile dementia, multi-infarct dementia or Alzheimer's disease, preferably Alzheimer's disease.

The compound of formula (I), (Ia) or (Ib) may be selected from the group consisting of compounds (a) to (g) and (j) to (p) as defined above.

Compounds of formulae (I), (Ia) or (Ib) are hereinafter described as "compounds of the invention". A compound of the invention includes a compound in any form, e.g. in free form or in the form of a salt or a solvate. For example, the compounds of the invention, e.g. the compounds of formula (I), (Ia), (Ib) and the compounds (a) to (g) and (j) to (p) can exist as the free acid form and the invention is intended to cover such acid forms.

It will be appreciated that any of the sub-scopes disclosed herein, e.g. with respect to $R^1$, $R^2$, $R^3$, $R^4$, $R^5$, $R^6$, A, Q, V, W, X, Y and Z may be combined with any of the other sub-scopes disclosed herein to produce further sub-scopes.

DETAILED DESCRIPTION

Definitions

Figure 1:
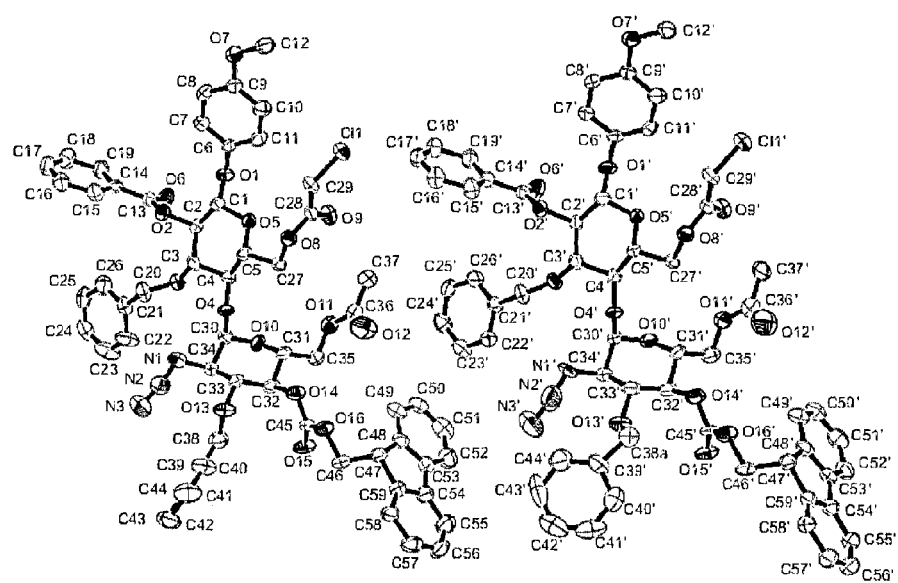
FIG. 1 shows an ORTEP diagram of compound 13.
Figure 2:
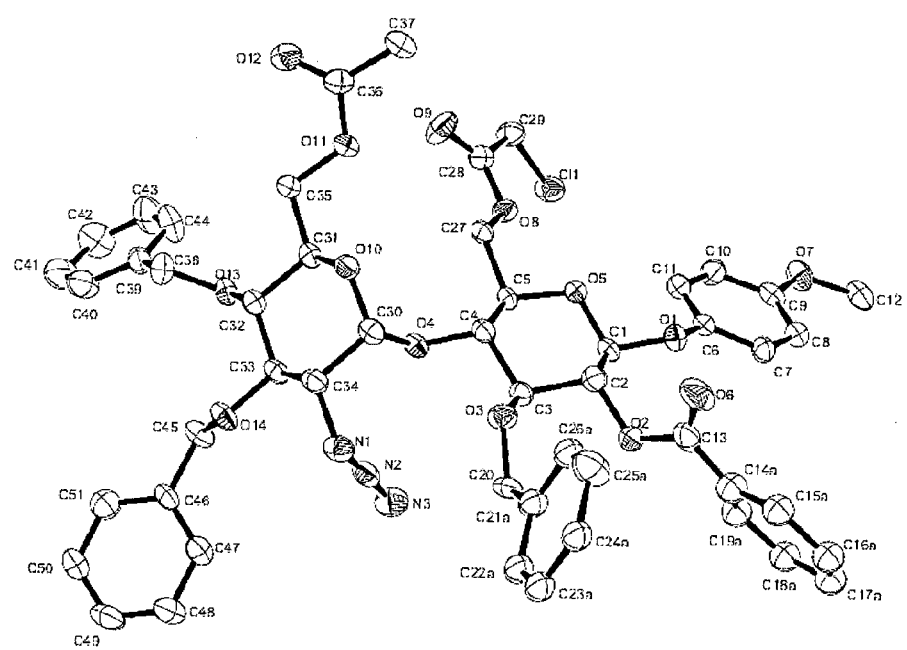
FIG. 2 shows an ORTEP diagram of compound 14.
Figure 3:
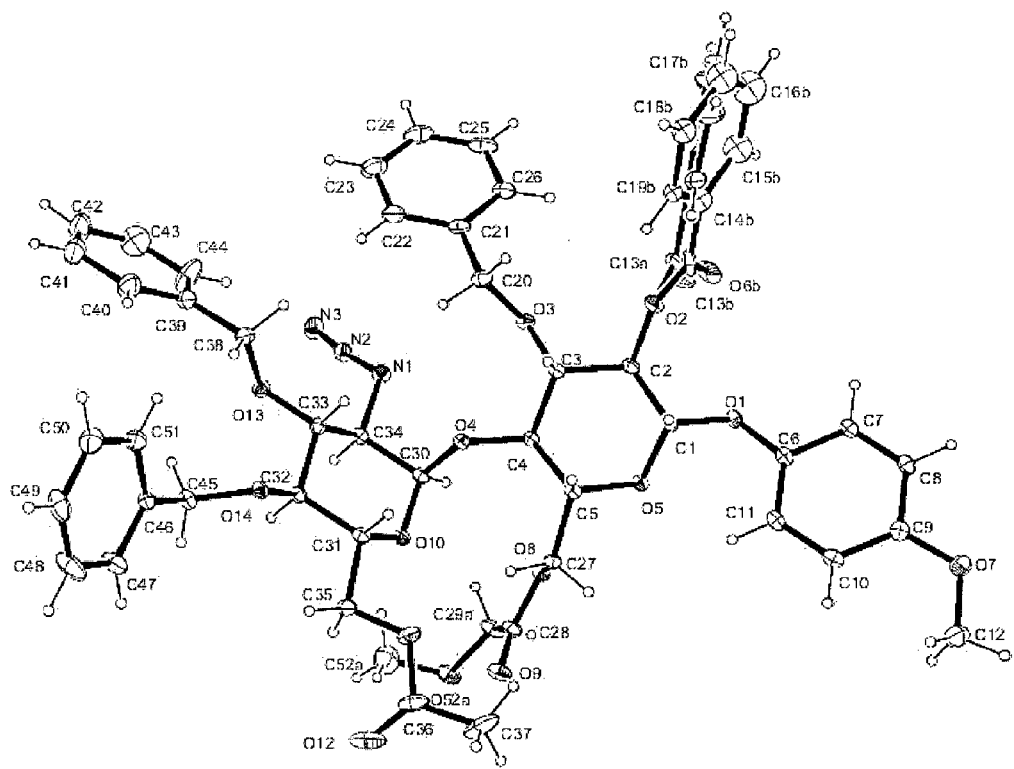
FIG. 3 shows an ORTEP diagram of compound 15.
Figure 4:
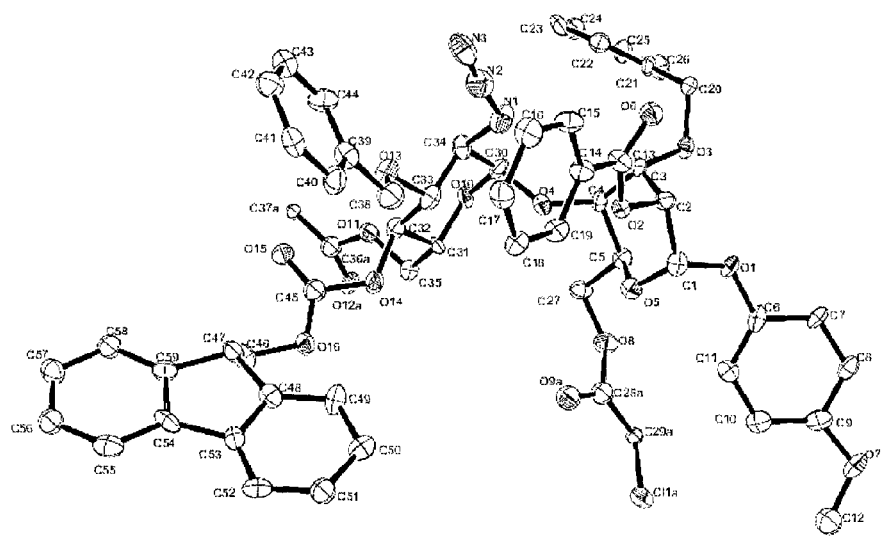
FIG. 4 shows an ORTEP diagram of compound 16.
Figure 5:
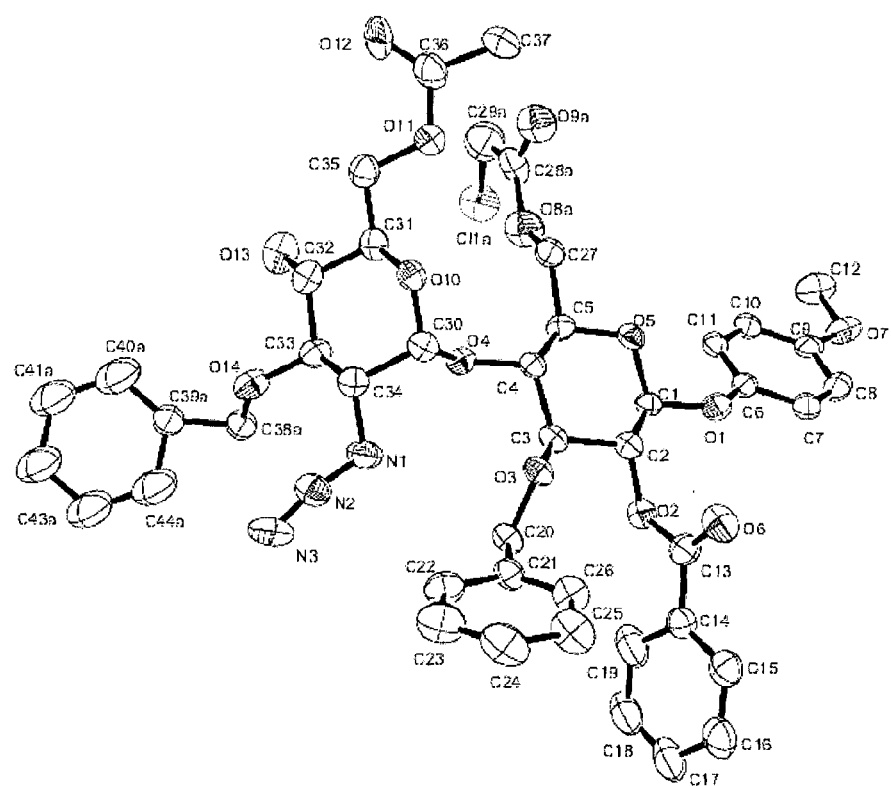
FIG. 5 shows an ORTEP diagram of compound 27.

The term "alkyl" means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include cyclic, straight- and branched-chain alkyl groups. Cyclic alkyl groups include those groups having one or more ring oxygen atoms. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1,2-dimethylbutyl group, cyclopropyl group, cyclobutyl group, cyclopentyl group, cyclohexyl group, cycloheptyl group, cyclooctyl group, tetrahydrofuranyl group and tetrahydropyranyl group.

The term "lower alkyl" means any saturated hydrocarbon radical having from 1 to 6 carbon atoms and is intended to include cyclic, straight- and branched-chain alkyl groups.

The term "alkoxy" means —OR where R is alkyl as defined above. The term "lower alkoxy" means —OR where R is lower alkyl as defined above.

Any alkoxy group may optionally be substituted with one or more substituents selected from the group consisting of fluorine, chlorine, methoxy, ethoxy, $O(CH_2CH_2)_nOMe$ where n is 1-10, $NH_2$, $NHCO_2Bn$, and $CO_2H$ or pharmaceutically acceptable salt form thereof.

The term "aryl" means an aromatic radical having 4 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

Any aryl group may optionally be substituted with one or more substituents selected from the group consisting of fluorine, chlorine, alkoxy (including methoxy and ethyoxy), alkyl (including methyl and ethyl), cyano, acylamino, azido or $NHCO_2Bn$.

The term "aryloxy" means —OR' where R' is aryl as defined above.

The term "aralkyl" means an aryl group covalently linked to an alkylene group.

The term "aralkoxy" means —OR" where R" is aralkyl as defined above.

Any aralkoxy group may optionally be substituted with one or more substituents selected from the group consisting of fluorine, chlorine, alkoxy (including methoxy and ethyoxy), alkyl (including methyl and ethyl), cyano, acylamino, azido or $NHCO_2Bn$.

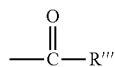

The term "acyl" means where R''' is alkyl, aralkyl or aryl as defined above. The term "lower acyl" means a $C_2$-$C_6$ acyl group, having a corresponding meaning to "lower alkyl" as defined above.

The term "halogen" includes fluorine, chlorine, bromine and iodine.

The term "prodrug" as used herein means a pharmacologically acceptable derivative of the compounds of formulae (I), (Ia) and (Ib), such that an in vivo biotransformation of the derivative gives the compound as defined in formulae (I), (Ia) and (Ib). Prodrugs of compounds of formulae (I), (Ia) and (Ib) may be prepared by modifying functional groups present in the compounds in such a way that the modifications are cleaved in vivo to give the parent compound. Typically, prodrugs of the compounds of formulae (I), (Ia) and (Ib) will be ester prodrug forms.

The term "pharmaceutically acceptable salts" is intended to apply to non-toxic salts such as ammonium salts, metal salts, e.g. sodium salts, or salts of organic cations, or a mixture thereof.

The term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in *Protective Groups in Organic Synthesis* (3$^{rd}$ Ed.), T. W. Greene and P. G. M. Wuts, John Wiley & Sons Inc (1999). Examples of protecting groups include, but are not limited to: O-benzyl, O-benzhydryl, O-trityl, O-tert-butyldimethylsilyl, O-tert-butyldiphenylsilyl, O-4-methylbenzyl, O-acetyl, O-chloroacetyl, O-methoxyacetyl, O-benzoyl, O-4-bromobenzoyl, O-4-methylbenzoyl, O-fluorenylmethoxycarbonyl and O-levulinoyl.

The term "patient" includes human and non-human animals.

The terms "treatment", "treating" and the like include the alleviation of one or more symptoms, or improvement of a state associated with the disease or disorder, for example, improvement in cognition, improvement in memory function.

The terms "preventing", "prevention" and the like include the prevention of one or more symptoms associated with the disease or disorder.

The Compounds of the Invention

The compounds of the invention, particularly those exemplified, are inhibitors of BACE-1 and are useful as pharmaceuticals, particularly for the treatment or prevention of diseases or conditions in which it is desirable to inhibit BACE-1, e.g. neurodegenerative disorders such as senile dementia, pre-senile dementia, multi-infarct dementia or Alzheimer's disease, particularly Alzheimer's disease. The compounds of the invention are useful in both free base form and in the form of salts and/or solvates.

Those skilled in the art will appreciate that the compounds of the invention can exist as stereoisomers. For example, depending on the stereochemistry at the carbon marked (#) in the disaccharide of formula (i), the disaccharide can be either gluco or ido form. Thus, each $R^5$ and each $R^6$ in each disaccharide of formula (i) is independently selected from COOH and H; provided that one of $R^5$ and $R^6$ in each disaccharide is H and the other is COOH.

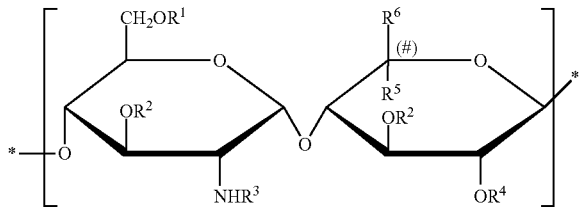

The octasaccharides, decasaccharides and dodecasaccharides of the invention are made up of the disaccharides of formula (i). The skilled person will therefore further appreciate that the octasaccharides, decasaccharides and dodecasaccharides of the invention may be all gluco form (where all disaccharides of formula (i) in the compound are gluco), all ido form (where all disaccharides of formula (i) in the compound are ido) or a mixture of gluco and ido forms (where the disaccharides of formula (i) in the compound are a mixture of gluco and ido).

As described in Example 4, heparin has an $IC_{50}$ of 0.002 µg/mL against human recombinant BACE-1 and N-acetylated low molecular weight heparin (NAcLMWH) has an $IC_{50}$ of 0.007 µg/mL. Surprisingly, the oligosaccharides of the invention are potent inhibitors of BACE-1. For example, compounds 90, 91 and 92 all have an $IC_{50}$ of about 0.01 µg/mL against human recombinant BACE-1. Indeed, some compounds of the invention are only approximately 5-fold less potent than heparin by mass. This is surprising when compared to the activities of the octasaccharide and decasaccharide fractions reported in J. Med. Chem. 2006, 49, 6129-6132, and indicates a role for synthetic oligosaccharides in treating diseases or disorders where it is desirable to inhibit BACE-1. The synthetic oligosaccharides of the invention also have the advantage that they are discrete chemical entities of known structure.

Interestingly, not only are the 6-sulfated compounds of the invention surprisingly potent synthetic oligosaccharides, but, even more surprisingly, the synthetic oligosaccharides of the invention which are sulfated at the 2- and 6-positions tend to be significantly more active than the corresponding 6-sulfated oligosaccharides. This would not have been predicted based on previous studies on modified full length heparins.

Advantageously, the compounds of the invention have attenuated anti-coagulent activity. Referring to Example 5, none of the compounds of the invention display any measurable ability to accelerate antithrombin-III mediated inactivation of Factor Xa, as measured by cleavage of a peptide substrate.

The compounds of the invention may be administered to a patient by a variety of routes, including orally, parenterally, by inhalation spray, topically, rectally, nasally, buccally or via an implanted reservoir. The compounds may also be administered by intracerebral, intracerebroventricular or intrathecal delivery. For parenteral administration, injections may be given intravenously, intra-arterially, intramuscularly or subcutaneously.

The amount of a compound of the invention to be administered to a patient will vary widely according to the nature of the patient and the nature and extent of the disorder to be treated. Typically the dosage for an adult human will be in the range of about 0.01 µg/kg to about 1 g/kg, preferably about 0.01 mg/kg to about 100 mg/kg. The specific dosage required for any particular patient will depend upon a variety of factors, such as the patient's age, body weight, general health, gender and diet. Optimal doses will depend on other factors such as mode of administration and level of progression of the disease or disorder. Doses may be given once daily, or two or more doses may be required per day. For example, a dosage regime for an Alzheimer's patient might require one dose in the morning and one in the evening. Alternatively, a dosage regime for such a patient might require four hourly doses.

For oral administration the compounds can be formulated into solid or liquid preparations, for example tablets, capsules, granules, powders, solutions, suspensions, syrups, elixirs and dispersions. Such preparations are well known in the art as are other oral dosage regimes not listed here.

For parenteral administration, compounds of the invention can be formulated into sterile solutions, emulsions and suspension.

Compounds of the invention may be mixed with suitable vehicle and then compressed into the desired shape and size. The compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added. Tablets, capsules or powders for oral administration may contain up to about 99% of a compound of the invention.

When liquid preparations are required for oral use, a compound of the invention may be combined with a pharmaceutically acceptable carriers such as water, an organic solvent such as ethanol, or a mixture of both, and optionally other additives such as emulsifying agents, suspending agents, buffers, preservatives, and/or surfactants may be used. Colourings, sweeteners or flavourings may also be added.

The compounds may also be administered by injection in a pharmaceutically acceptable diluent such as water or saline. The diluent may comprise one or more other ingredients such as ethanol, propylene glycol, an oil or a pharmaceutically acceptable surfactant.

The compounds of the invention may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds of the invention may further be administered by means of sustained release systems. For example, they may be incorporated into a slowly dissolving tablet or capsule.

Synthesis of the Compounds of the Invention

The compounds of the invention may be prepared by a variety of different methods. The following are representative non-limiting general methods for synthesising compounds of the invention.

The synthetic strategy involves disaccharide building blocks as intermediates for the preparation of the compounds of the invention. The present invention therefore also relates to intermediates and methods for the synthesis of compounds of the invention.

The Disaccharide Building Blocks

The octa-deca- and dodecasaccharide compounds of the invention are prepared from three, four or five neutral disaccharide building blocks of general formula (A) and/or (B), respectively, selected independently for the reducing terminal and internal disaccharide units, and one of (C) or (D) selected independently for the non-reducing terminal disaccharide unit.

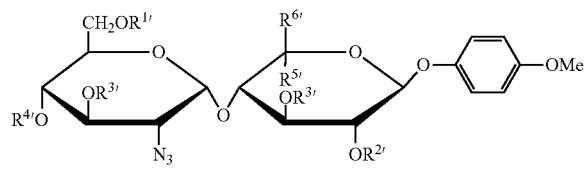

(A) $R^{5\prime}$ = H, $R^{6\prime}$ = $CH_2OR^{7\prime}$; (D-gluco-configuration)
(B) $R^{5\prime}$ = $CH_2OR^{7\prime}$, $R^{6\prime}$ = H; (L-ido-configuration)

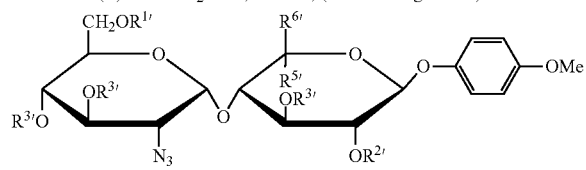

(C) $R^{5\prime}$ = H, $R^{6\prime}$ = $CH_2OR^{7\prime}$; (D-gluco-configuration)
(D) $R^{5\prime}$ = $CH_2OR^{7\prime}$, $R^{6\prime}$ = H; (L-ido-configuration)

wherein $R^{1\prime}$, $R^{2\prime}$, $R^{3\prime}$, $R^{4\prime}$ and $R^{7\prime}$ are protecting groups chosen with differing reactivity so that they can be selectively removed as required in the process detailed below, namely $R^{4\prime}$ before $R^{7\prime}$ before $R^{1\prime}$ before $R^{2\prime}$ before $R^{3\prime}$.

Ester groups are suitable $R^{1\prime}$, $R^{2\prime}$ and $R^{7\prime}$ protecting groups. The ester protecting group $R^{2\prime}$ facilitates the control of the anomeric stereochemistry of the glycosylation reactions to give products with the required 1,2-trans-stereochemistry with high selectivity.

The acetyl group is a suitable $R^{1\prime}$ protecting group.

The benzoyl group is a suitable $R^{2\prime}$ protecting group.

The benzyl group is a suitable $R^{3\prime}$ protecting group.

The chloroacetyl group is a suitable $R^{7\prime}$ protecting group. The methoxyacetyl and levulinoyl groups are alternative $R^{7\prime}$ protecting groups. Levulinoyl groups are described by Wang et al., Chem. J. Eur., 16 (2010) 8365.

The fluorenylmethoxycarbonyl group is a suitable $R^{4\prime}$ protecting group.

Advantageously and surprisingly, some disaccharide building blocks are crystalline compounds. This makes them particularly suitable intermediates for the synthesis of compounds of the invention, as they can be easily stored and transported. The present invention also relates to such crystalline disaccharide intermediates.

Synthesis of a 4-Methoxyphenyl Glycoside Octasaccharide Compound of the Invention An octasaccharide compound of the invention is synthesised from three neutral disaccharide building blocks of general formula (A) and/or (B), respectively, selected independently for the reducing terminal and internal disaccharide units, and one of (C) or (D) selected independently for the non-reducing terminal disaccharide unit.

Stage 1, the First Glycosylation Reaction

The tetrasaccharide (G) is prepared by:
a) synthesis of an acceptor (E) from a building block (A) or (B) by selective removal of the protecting group $R^{4\prime}$;
b) synthesis of a glycosyl donor (F) from a building block (A) or (B) by selective removal of the 4-methoxyphenyl group and introducing a suitable leaving group at C-1 of the reducing sugar; and
c) coupling of the donor (F) and acceptor (E).

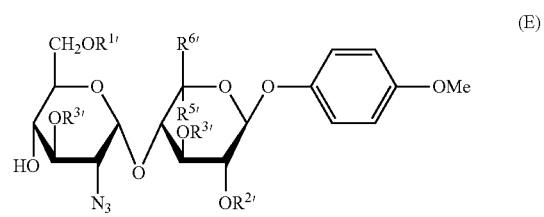

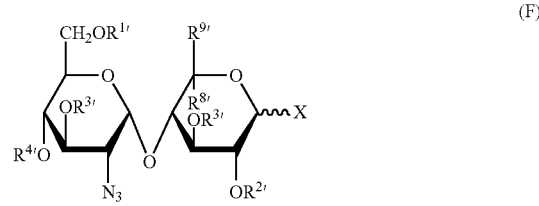

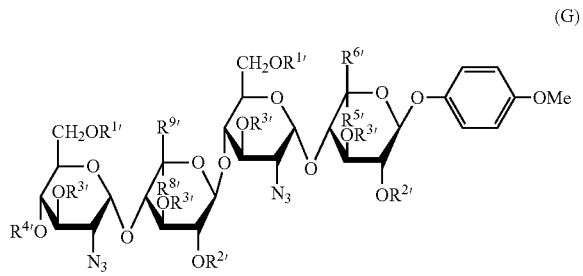

where $R^{8\prime}$ and $R^{9\prime}$ are independently chosen from hydrogen and $CH_2OR^{7\prime}$ with the proviso that when one is hydrogen, the other is $CH_2OR^{7\prime}$.

Selective removal of a fluorenylmethoxycarbonyl protecting group is conveniently achieved by dissolution in mixture of dichloromethane and triethylamine, typically about 4:1 v/v, 20 mL per mmol, at ambient temperature, typically in the range of about 10° C. to about 30° C.

Selective removal of the 4-methoxyphenyl group is conveniently achieved by use of CAN.

The trichloroacetimidate group is a suitable leaving group X. The methylthio, phenylthio and 4-methylphenylthio groups are alternative leaving groups X.

Glycosyl trichloroacetimidates are conveniently synthesised from the free-sugar precursors by reaction with excess trichloroacetonitrile and a base. NaH is a suitable base. DBU is alternative base (see WO 03/022860). DCM is a suitable solvent and the reaction can be conducted in the range of about −10° C. to about 40° C., preferably about 0° C. to about 10° C., typically in an ice bath.

Suitable glycosidation conditions are described below.

Syntheses of suitable 1-thioglycoside donors and conditions suitable for glycosylation using them are reported in Wang et al., Chem. J. Eur., 16 (2010) 8365 and in WO 03/0228860.

Stage 2, the Second Glycosylation Reaction

The hexasaccharide (H) is prepared by:
a) synthesis of a tetrasaccharide acceptor by selective removal of the protecting group $R^{4\prime}$ from (G) to generate a free secondary hydroxy group; and
b) coupling of the donor (F) from Stage 1 to this tetrasaccharide acceptor.

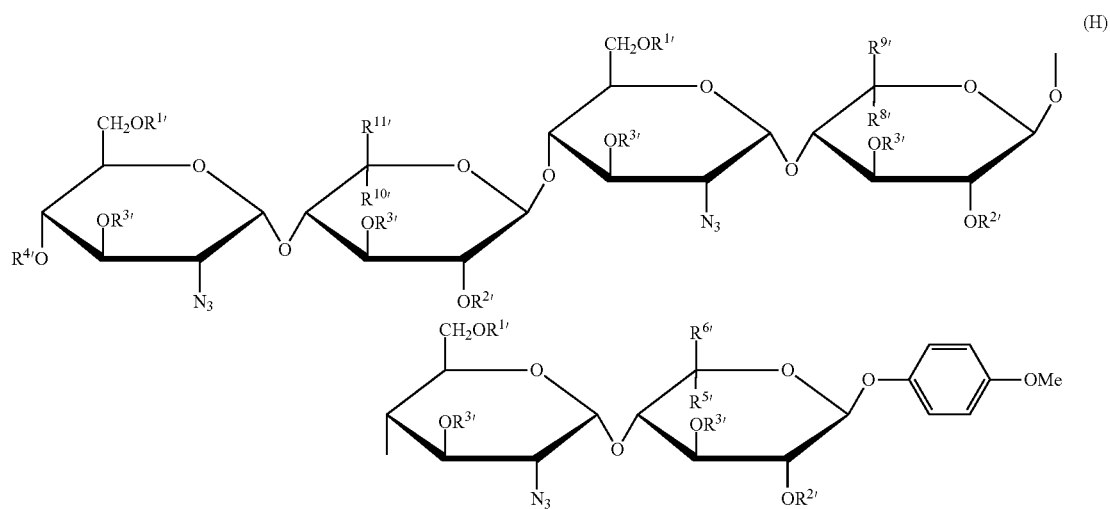

(H)

where $R^{10'}$ and $R^{11'}$ are independently chosen from hydrogen and $CH_2OR^{7'}$ with the proviso that when one is hydrogen, the other is $CH_2OR^{7'}$.

Stage 3, the Third Glycosylation Reaction

The octasaccharide (J) is prepared by:

a) synthesis of a hexasaccharide acceptor by selective removal of the protecting group $R^{4'}$ from (H) to generate a free secondary hydroxy group;

b) synthesis of a glycosyl donor (I) from a building block (C) or (D) by selective removal of the 4-methoxyphenyl group and introducing a suitable leaving group at C-1 of the reducing sugar; and c) coupling of the donor (I) with this hexasaccharide acceptor.

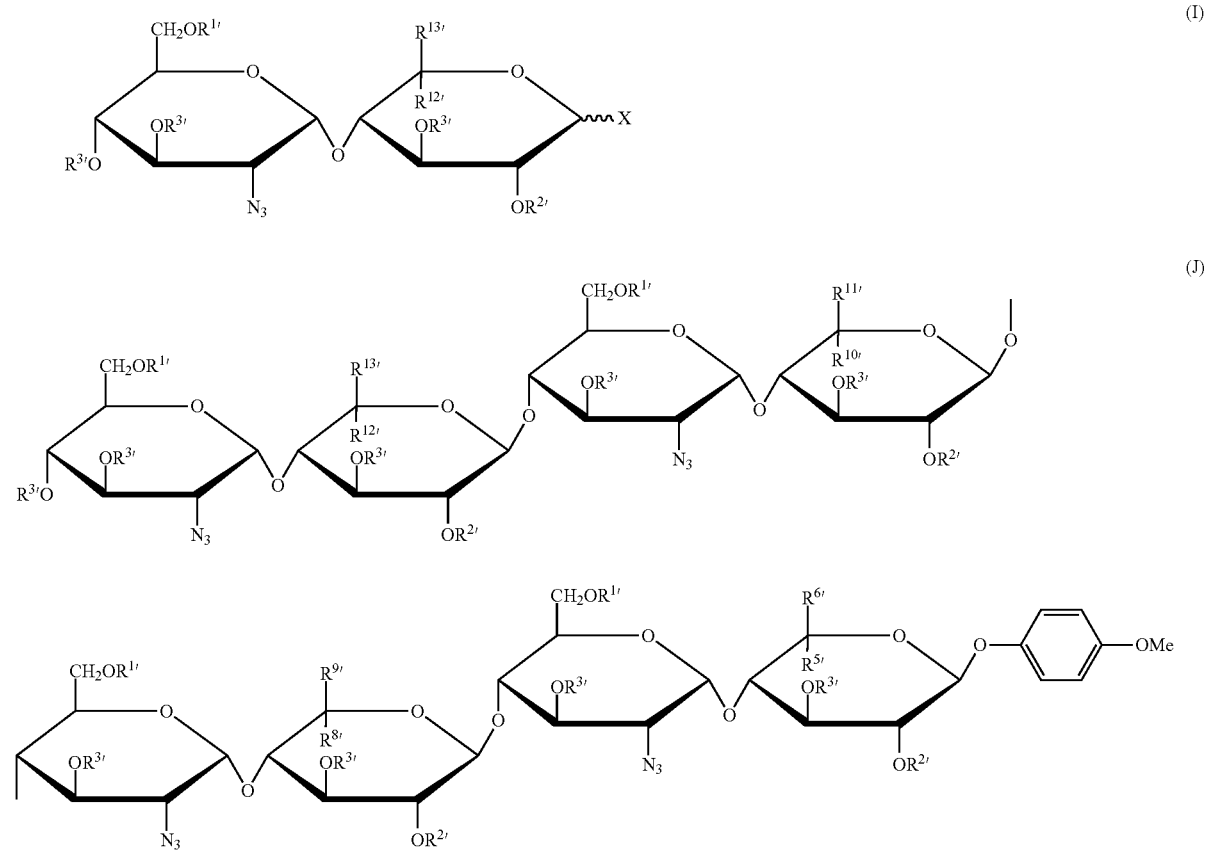

(I)

(J)

where $R^{12'}$ and $R^{13'}$ are independently chosen from hydrogen and $CH_2OR^{7'}$ with the proviso that when one is hydrogen, the other is $CH_2OR^{7'}$.

Stage 4, Conversion to Final Product

The octasaccharide of the invention is prepared by:
a) selective removal of all protecting groups $R^{7'}$ from the neutral octasaccharide derivative (J);
b) oxidation of all the resulting free primary hydroxy groups to the corresponding carboxylic acid groups (or salt forms thereof);
c) conversion of all the carboxylic acid moieties into their corresponding methyl esters;
d) converting all the azide-groups into the corresponding acylamino-groups;
e) selective removal of all $R^{1'}$ protecting groups;
f) sulfation of the resulting primary hydroxy groups;
g) selective removal of all $R^{2'}$ protecting groups and hydrolysis of the methyl esters;
h) sulfation of the resulting secondary hydroxy groups, or proceeding directly to step i);
i) removal of the $R^{3'}$ protecting groups; and
j) conversion to the desired cationic salt form of the final product.

Selective removal of the chloroacetyl $R^{7'}$ protecting group is conveniently achieved using DABCO (6 equiv. per chloroacetyl group) in dry ethanol heated at about 60° C. to about 70° C. under argon.

Oxidation of the resulting free primary hydroxy group is conveniently achieved using the TEMPO-BAIB system in aqueous acetonitrile at room temperature. Conversion of the resulting carboxylic acid into corresponding methyl ester is conveniently achieved by reaction with diazomethane, TMS-diazomethane, or a combination of iodomethane and a base, conveniently potassium bicarbonate, in DMF. An alternative TEMPO oxidation system is described in WO 03/022860.

Conversion of the azido-group into the corresponding acetamido-group is conveniently achieved by reaction with thiolacetic acid in dry pyridine at room temperature. Conversion of the azido-group into an alternative acylamino-group is achieved by reduction of the azido-group, conveniently with trialkylphosphine (e.g. $nBu_3P$), triarylphosphine (e.g. $Ph_3P$), or a metal catalyst (e.g. Pd/C) and reaction, either in the same reaction mixture or separately, with an acylating agent (e.g. an acyl anhydride or an acyl chloride).

Selective removal of the acetyl $R^{1'}$ protecting group is conveniently achieved using HCl in a DCM-MeOH solution in the temperature range of about 0° C. to about 30° C. The HCl can be generated in situ by use of acetyl chloride.

Cleavage of ester $R^{2'}$ protecting groups is conveniently conducted by saponification with sodium hydroxide in aqueous methanol.

Sulfation reactions are conveniently conducted using sulfur trioxide trimethylamine complex (5 equiv per hydroxyl group) in dry DMF at about 50° C. to about 60° C. under argon.

Removal of the benzyl $R^{3'}$ protecting group is conveniently conducted using hydrogen and a palladium catalyst, typically palladium hydroxide on carbon, in aqueous tetrahydrofuran in the range of about 10° C. to about 30° C.

Final products are converted into the desired salt form by elution with water through a Strong acid ion exchange resin column, e.g. Dowex 50WX8-200 (Dow Chemical Company, USA) in the desired salt form, e.g. $Na^+$.

Synthesis of a 4-Methoxyphenyl Glycoside Decasaccharide of the Invention

A decasaccharide compound of the invention is synthesised from four neutral disaccharide building blocks of general formula (A) and/or (B), respectively, selected independently for the reducing terminal and internal disaccharide units, and one of (C) or (D) selected independently for the non-reducing terminal disaccharide unit.

Thus, the octasaccharide (K) is prepared by:
a) synthesis of a hexasaccharide acceptor by selective removal of the protecting group $R^{4'}$ from hexasaccharide derivative (H) to generate a free secondary hydroxy group;
b) coupling of the donor (F) with this hexasaccharide acceptor.

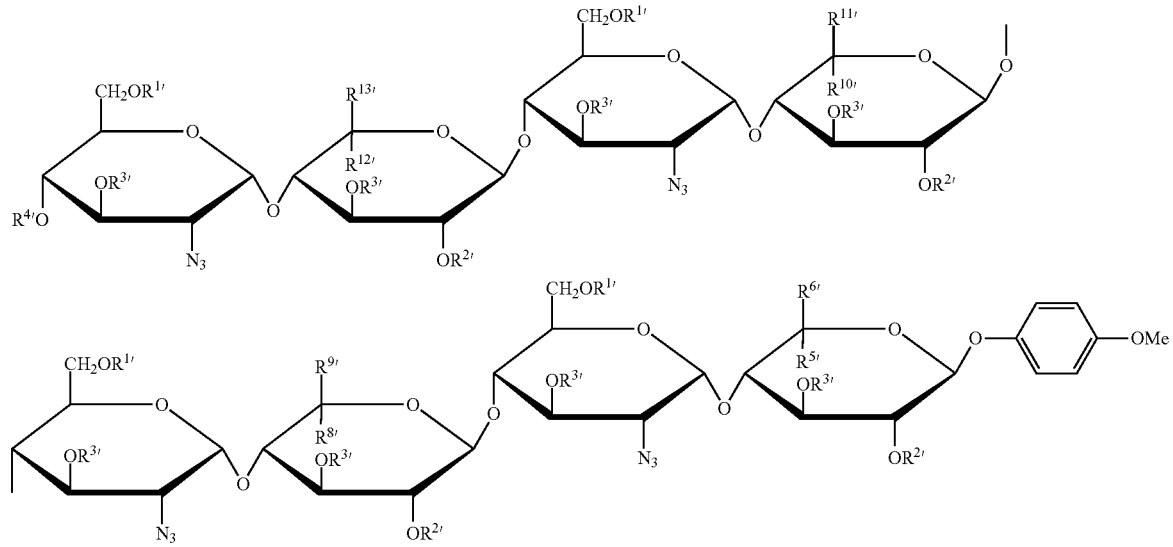

(K)

Then decasaccharide (L) is prepared by:
a) synthesis of an octasaccharide acceptor by selective removal of the protecting group $R^{4'}$ from octasaccharide derivative (K) to generate a free secondary hydroxy group;

b) coupling of the donor (I) with this octasaccharide acceptor.

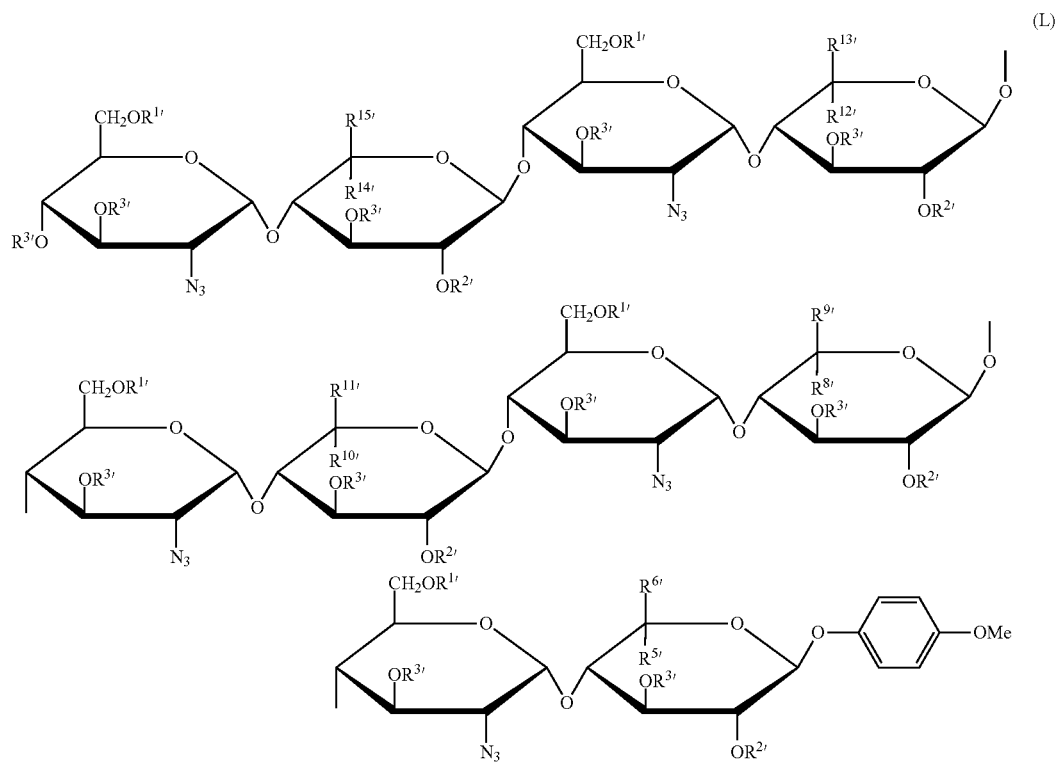

where $R^{14'}$ and $R^{15'}$ are independently chosen from hydrogen and $CH_2OR^{7'}$ with the proviso that when one is hydrogen, the other is $CH_2OR^{7'}$.

Finally, the decasaccharide of the invention is prepared by:
a) selective removal of all protecting groups $R^{7'}$ from the neutral decasaccharide derivative (L);
b) oxidation of all the resulting free primary hydroxy groups to the corresponding carboxylic acid groups (or salt forms thereof);
c) conversion of all the carboxylic acid moieties into their corresponding methyl esters;
d) converting all the azido-groups into the corresponding acylamino-groups;
e) selective removal of all $R^{1'}$ protecting groups;
f) sulfation of the resulting primary hydroxy groups;
g) selective removal of all $R^{2'}$ protecting groups and hydrolysis of the methyl esters;
h) sulfation of the resulting secondary hydroxy groups or proceeding directly to step (i).

i) removal of the $R^{3'}$ protecting groups; and
j) conversion to the desired cationic salt form of the final product.

Synthesis of a 4-Methoxyphenyl Glycoside Dodecasaccharide of the Invention

A dodecasaccharide compound of the invention is synthesised from five neutral disaccharide building blocks of general formula (A) and/or (B), respectively, selected independently for the reducing terminal and internal disaccharide units, and one of (C) or (D) selected independently for the non-reducing terminal disaccharide unit.

Thus, the decasaccharide (M) is prepared by:
a) synthesis of an octasaccharide acceptor by selective removal of the protecting group $R^{4'}$ from octasaccharide derivative (K) to generate a free secondary hydroxy group;
b) coupling of the donor (F) with this octasaccharide acceptor.

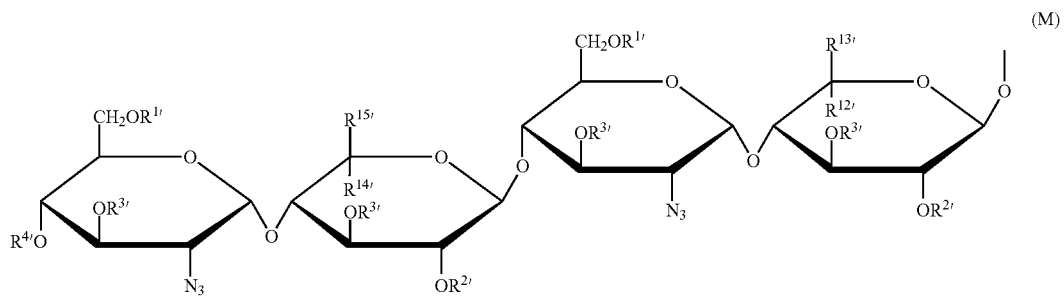

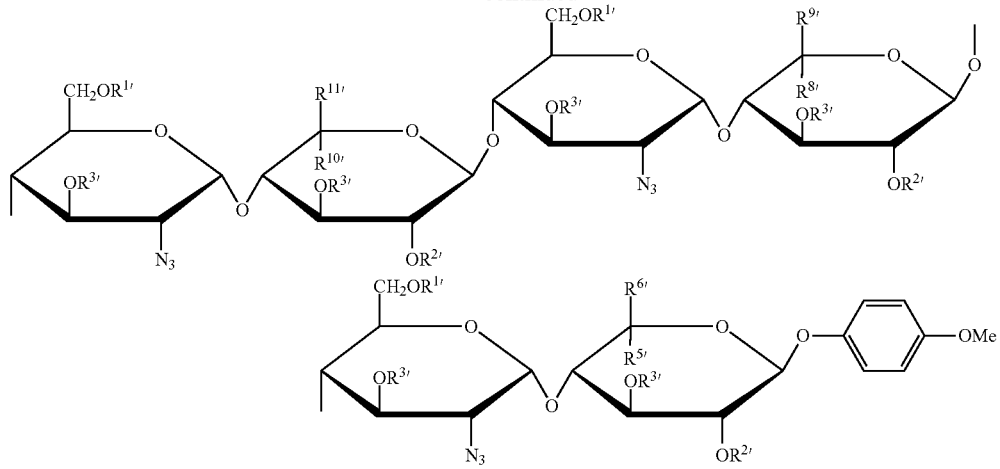

Then dodecasaccharide (N) is prepared by:
a) synthesis of an decasaccharide acceptor by selective removal of the protecting group $R^{4'}$ from octasaccharide derivative (M) to generate a free secondary hydroxy group;
b) coupling of the donor (I) with this octasaccharide acceptor.

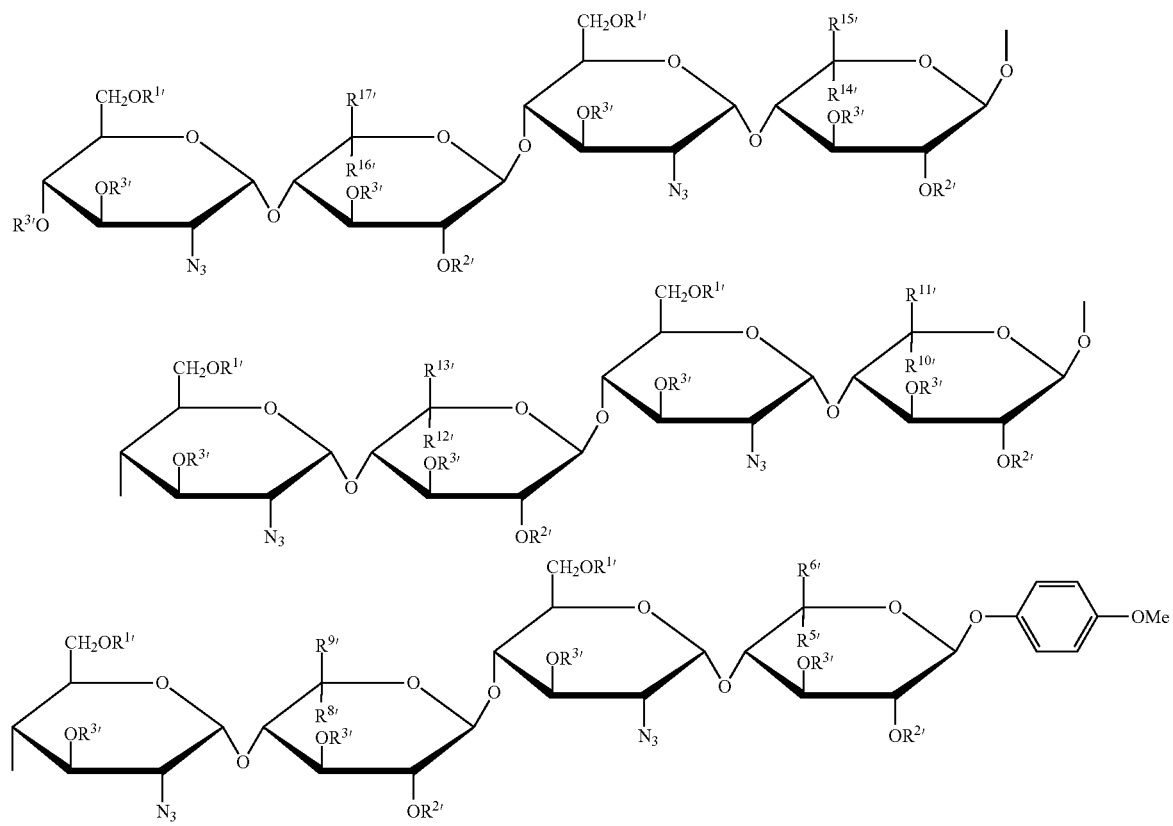

where $R^{16'}$ and $R^{17'}$ are independently chosen from hydrogen and $CH_2OR^{7'}$ with the proviso that when one is hydrogen, the other is $CH_2OR^{7'}$.

Finally, the dodecasaccharide of the invention is prepared by:
a) selective removal of all protecting groups $R^{7\prime}$ from the neutral decasaccharide derivative (N);
b) oxidation of all the resulting free primary hydroxy groups to the corresponding carboxylic acid groups (or salt forms thereof);
c) conversion of all the carboxylic acid moieties into their corresponding methyl esters;
d) converting all the azido-groups into the corresponding acylamino-groups;
e) selective removal of all $R^{1\prime}$ protecting groups;
f) sulfation of the resulting primary hydroxy groups;
g) selective removal of all $R^{2\prime}$ protecting groups and hydrolysis of the methyl esters;
h) sulfation of the resulting secondary hydroxy groups or proceeding directly to step i).
i) removal of the $R^{3\prime}$ protecting groups; and
j) conversion to the desired cationic salt form of the final product.

Synthesis of Alternative Compounds of the Invention

An octa-deca- or dodecasaccharide compound of the invention having an optionally substituted alkyl, aralkyl or aryl aglycone is synthesised by selective cleavage of the 4-methoxyphenyl residue from C-1 of the reducing sugar moiety on a hexasaccharide derivative (K) or the decasaccharide moiety (L) or the dodecasaccharide moiety (N), respectively, and introducing a suitable leaving group at C-1 of the reducing sugar and then coupling the resulting oligoglycosyl donor with an optionally substituted alkyl, aralkyl or aryl alcohol. The stereochemistry of the newly formed anomeric centre is typically beta due to neighbouring group participation by the adjacent $R^{2\prime}$ ester protecting group in the glycosidation reaction.

In an alternative approach, an octa- or deca- or dodecasaccharide compound of the invention having an optionally substituted alkyl, aralkyl or aryl aglycone is synthesised by substituting the disaccharide building block (P) for the disaccharide building block (E) that provides the reducing sugar disaccharide moiety in a octa-deca- or dodecasaccharide of the invention in the processes outlined above (under "synthesis of a 4-methoxyphenyl glycoside octasaccharide of the invention", "synthesis of a 4-methoxyphenyl glycoside decasaccharide of the invention" and "synthesis of a 4-methoxyphenyl glycoside dodecasaccharide of the invention").

(P)

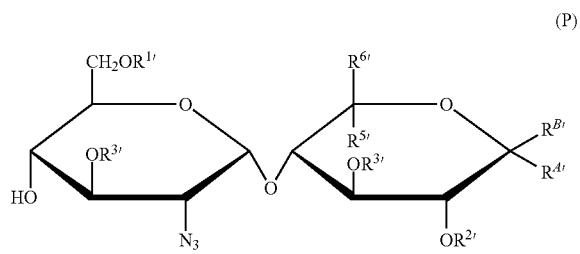

where $R^{A\prime}$ and $R^{B\prime}$ are chosen from an optionally substituted alkyloxy, aralkyloxy or aryloxy group and hydrogen, with the proviso that when one is hydrogen, the other is an optionally substituted alkyloxy, aralkyloxy or aryloxy group.

A disaccharide building block (P) is conveniently synthesised by reaction of the glycosyl donor (F) with the desired optionally substituted alkyl, aralkyl or aryl alcohol. As the $R^{2\prime}$ is a ester protecting group, the product is usually the beta-anomer (in which $R^{A\prime}$ is hydrogen).

Synthesis of the Disaccharide Building Blocks

The neutral disaccharide building blocks of general formula (A) and (B) are synthesised by coupling a glycosyl donor of formula (Q) with a monosaccharide acceptor of formula (S) or (T), respectively.

The neutral disaccharide building blocks of general formula (C) and (D) are synthesised by coupling a glycosyl donor of formula (R) with a monosaccharide acceptor of formula (S) or (T), respectively.

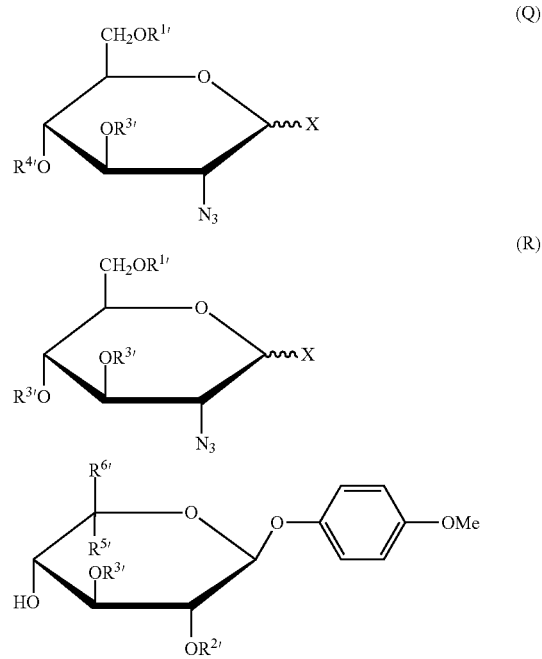

(S) ($R^{5\prime}$ = H, $R^{6\prime}$ = $CH_2R^{7\prime}$; (β-D-gluco-configuration)
(T) $R^{5\prime}$ = $CH_2R^{7\prime}$, $R^{6\prime}$ = H; (α-L-ido-configuration)

The required 1,2-cis-configuration at C-1 and C-2 of the non-reducing sugar residue in the disaccharide building blocks (A), (B), (C) and (D) is attained by suitable choice of leaving group X and glycosidation reagent. Suitable choices of X and glycosidation reagent are X=beta-(methylthio)-, beta-(phenylthio)- or beta-(4-methylthio)-, with the combination of N-iodosuccinimide and silver triflate as glycosidation reagents.

Typical Glycosidation Reaction Conditions

For the glycosidation reactions in which a disaccharide (A), (B), (C) or (D), a tetrasaccharide (G), a hexasaccharide (H), an octasaccharide (J) or (K), or a decasaccharide (L) or (M), or a dodecasaccharide (N), is synthesised, the donor is conveniently used in a molar ratio to the acceptor in the range 1.0 to 1.5 equivalents, preferably in a range between 1.05 and 1.5 equivalents, preferably 1.2 to 1.3 equivalents, preferably 1.3 equivalents.

Conveniently the glycosyl donor is a glycosyl trichloroacetimidate. Reactions with acceptor alcohols are conveniently carried out in anhydrous toluene (40 mL per mmol acceptor) at between −10 and 40° C., in the presence of powdered molecular sieves (4 Å) and trimethylsilyl trifluoromethanesulfonate (0.3 eq).

ABBREVIATIONS

NMR Nuclear magnetic resonance
TLC Thin layer chromatography

RT Room temperature
DCM Dichloromethane
Ac Acetyl
AcOH Acetic acid
BAIB Bis(acetoxy)iodobenzen
Bn Benzyl
Bz Benzoyl
CAN Ceric ammonium (IV) nitrate
ClAc Chloroacetyl
DABCO 1,4-Diazabicyclo[2.2.2]octane
DMAP 4-N,N-Dimethylaminopyridine
DMF N,N-Dimethylformamide
ESI Electrospray ionization
EtOAc Ethyl acetate
Fmoc Fluorenylmethoxycarbonyl
Fmoc-Cl Fluorenylmethoxycarbonyl chloride
HSQC Heteronuclear single quantum correlation
HRMS High resolution mass spectrum
gl.AcOH Glacial acetic acid
MeOAc Methoxyacetyl
MeOH Methanol
MS Mass spectrum
NBS N-Bromosuccinimide
NI N-Iodosuccinimide
TEMPO 2,2,6,6-Tetramethyl-1-piperidinyloxyl
TFA Trifluoroacetic acid
THF Tetrahydrofuran
TMS-diazomethane Trimethylsilylmethyl diazomethane

EXAMPLES

The following examples further illustrate the invention. It is to be appreciated that the invention is not limited to the examples.

Example 1

Synthesis of Compounds is dissolved in 200 mL dry pyridine. Trityl chloride (30 g, 108 mmol) is added and the mixture stirred overnight. More trityl chloride (2 g) is added and stirring continued for 3 h until TLC (petroleum ether/ethyl acetate 1:1) confirms completion. The mixture is concentrated in vacuo, coevaporated with toluene (2×150 mL), washed with CuSO4, water, brine, concentrated to dryness and coevaporated with DCM to an off-white foam. This is dissolved in dry DMF (100 mL), cooled in an ice-bath and benzyl bromide (30.3 ml, 255 mmol) is added, followed by sodium hydride 60% (11.22 g, 281 mmol) in portions, the ice-bath is removed after addition of the first 2 g of NaH. After stirring at room temperature for 1 h, the reaction is again cooled in an ice-bath and quenched by addition of ethanol, then diluted with 500 mL toluene, washed with water (3×1000 mL), brine (300 mL) and dried over magnesium sulfate. Solvents are evaporated and the resulting syrup is coevaporated with dichloromethane, the residue is taken up in toluene and crytallised by addition of methanol. The solids are collected, washed with methanol and dried under vacuum to give the benzyl/trityl-derivative 1 in 94% yield (52.3 g, 80 mmol) as a white powder. $^{13}$C-NMR (125 MHz, CDCl$_3$) δ 143.9, 137.8, 137.6, 129.1, 128.8, 128.6, 128.3, 128.2, 128.1, 127.9, 127.8, 127.1, 86.5, 85.0, 84.0, 79.1, 77.8, 76.0, 75.0, 65.8, 62.4, 11.9

Preparation of 2

Tritylated compound 1 (55.3 g, 84 mmol) is combined with acetic acid (300 mL), water (80 mL) is added and the mixture heated to 80° C. for 8 h. The reaction mixture is concentrated and the product crystallises from ethyl acetate (100 mL) by addition of petroleum ether in 80% yield (27.8 g, colourless crystals). The obtained alcohol is dissolved in pyridine/acetic anhydride 2:1 (300 mL) and stirred for 6 h at ambient temperature, subsequently the solvents are evaporated to a syrup, which crystallises on standing and is triturated with petrol (450 mL) for 3d. Solids are collected and dried under vacuum to give 2 (27.1 g, 65.2 mmol) as a white powder. $^{13}$C-NMR (125 MHz, CDCl$_3$) δ 170.6, 137.6, 137.4, 128.6, 128.5, 128.4, 128.1, 128.0, 127.8, 85.1, 84.5, 76.8, 65.7, 63.00, 20.8, 12.5

Scheme 1

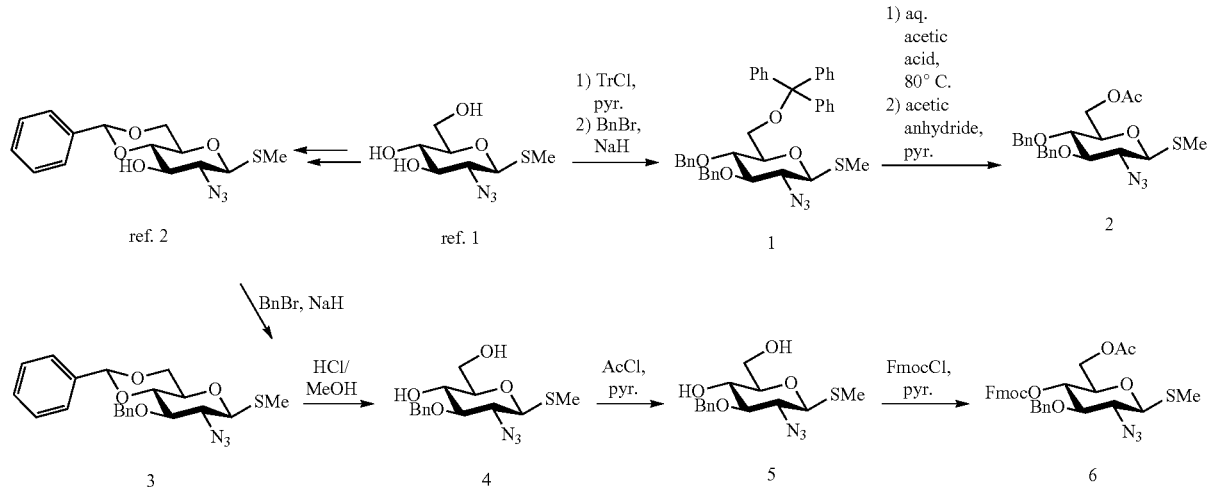

Preparation of 1

Methyl 2-azido-2-deoxy-1-thio-β-D-glucopyranoside (Pozsgay, V.; Glaudemans, C. P. J.; Robbins, J. B.; Schneerson, R. Tetrahedron 1992, 48, 10249-10264) (20 g, 85 mmol)

Preparation of 3

Methyl 2-azido-4,6-di-O-benzylidene-2-deoxy-1-thio-β-D-glucopyranoside (Rajaratnam, P.; Gupta, P.; Katavic, P.; Kuipers, K; Huyh, N.; Ryan, S.; Falzun, T.; Tometzki, G. B.;

Bornaghi, L.; Le Thanh, G.; Abbenante, G.; Liu, L.; Meutermans, W.; Wimmer, N.; West, M. L. *Aust. J. Chem.* 2010, 63, 693-699. Dekany, G.; Alchemia Pty. Ltd., US Patent Publication, U.S. Pat. No. 6,953,850 B1, 2005) (62.1 g, 192 mmol) is dissolved in dry DMF (150 mL), benzyl bromide (27.4 ml, 230 mmol) is added and cooled in an ice bath. Then sodium hydride 60% (9.99 g, 250 mmol) is added portion-wise and the reaction stirred at room temperature until TLC shows full conversion to a less polar product. The reaction is quenched with MeOH, then evaporated under high vacuum. Chloroform is added to the residue and washed three times with water and dried over magnesium sulfate to give a solid residue. Then diethyl ether is added to dissolve a part of the solids and precipitated with petroleum ether. Solids are collected and washed with petroleum ether to yield an off-white solid (56.7 g) Evaporation of the mother liquor, followed by trituration with ether/petroleum ether gives more yellow solid, (12.67 g). Total of benzyl ether 3 68.37 g, 86%. $^{13}$C-NMR (125 MHz, CDCl$_3$) δ 137.7, 137.2, 129.1, 128.5, 128.4, 128.3, 128.0, 126.0, 101.3, 85.2, 81.6, 80.9, 75.1, 70.5, 68.5, 65.3, 12.7

Preparation of 4

Dioxane (125 mL) and methanol (400 mL) are added to benzyl ether 3 (68.3 g, 165 mmol) and the mixture is stirred at room temperature. Acetyl chloride (8 mL, 113 mmol) is added and the reaction mixture is stirred at room temperature for 1.5 h, until TLC shows full conversion. The reaction is neutralized with Amberlyst A26 (OH—) resin, filtered and the filtrate evaporated to dryness. Silica chromatography (EtOAc/Hex 1:2-3:2) gives a pale yellow syrup that crystallizes: methyl 2-azido-3-O-benzyl-2-deoxy-1-thio-β-D-glucopyranoside 4 49.14 g, 91%. $^{13}$C-NMR (125 MHz, CDCl$_3$) δ 137.9, 128.7, 128.5, 128.3, 128.1, 127.8, 84.9, 84.5, 79.5, 75.4, 70.1, 65.2, 62.0, 12.7

Preparation of 5

Compound 4 (47.9 g, 147 mmol) is dissolved in dry dichloromethane (590 mL), Pyridine (71.4 ml, 883 mmol) is added and cooled to –75° C. Acetyl chloride (10.47 ml, 147 mmol) is added slowly and the reaction is allowed to warm up to room temperature over night. TLC confirms complete conversion and the reaction mixture is washed with 10% HCl, aq. sodium bicarbonate and brine (400 mL resp.), dried over magnesium sulfate, concentrated and dissolved in hot toluene (100 ml). The product crystallises in the fridge (4° C.), is collected by filtration, washed with petroleum ether and dried under oil-pump vacuum: methyl 6-O-acetyl-2-azido-3-O-benzyl-2-deoxy-1-thio-β-D-glucopyranoside 5 (50 g, 92% yield). $^{13}$C-NMR (125 MHz, CDCl$_3$) δ 171.7, 137.8, 128.7, 128.6, 128.2, 127.9, 127.7, 84.7, 84.2, 77.9, 75.5, 70.1, 65.2, 63.2, 20.8, 12.5

Preparation of 6

DMAP (700 mg, 5.73 mmol) is added to a solution of 5 (50 g, 136 mmol) in anhydrous pyridine (100 ml) and cooled in an ice-bath. Fmoc-Cl (141 g, 544 mmol) is added and the ice-bath is removed after 15 min. The resulting suspension is stirred at room temperature for 1.5 h. The solvents are evaporated and the residue is purified by repeated silica chromatography (toluene/ethyl acetate 4%); clean fractions are combined and co-evaporated with dichloromethane to form a foam: methyl 6-O-acetyl-2-azido-3-O-benzyl-2-deoxy-4-O-(9-fluorenylmethyloxycarbonyl)-1-thio-β-D-glucopyranoside 6 (69 g, 117 mmol, 86% yield). R$_f$=0.15 (toluene/ethyl acetate 19:1), $^{13}$C-NMR (125 MHz, CDCl$_3$) δ 170.6, 154.2, 143.2, 143.0, 141.3, 137.1, 128.4, 128.0, 127.2, 125.1, 124.9, 120.1, 84.6, 82.1, 75.7, 75.5, 74.3, 70.3, 65.1, 62.3, 46.8, 20.7, 12.4

Ido-Configured Monosaccharide Building Block Synthesis 01

Reaction of a known tetra-benzoate (Barroca, N.; Jacquinet, J.-C. 2000, *Carbohydr. Res.*, 329, 667-679) with 4-methoxyphenol and subsequent Zemplen deacetylation affords a triol 7. Isopropylidenation gives the compound 8. Benzylation afforded a benzoate 9. Acidic hydrolysis gives a diol 10. Selective chloroacetylation furnishes a mono-chloroacetate acceptor 11.

Scheme 2

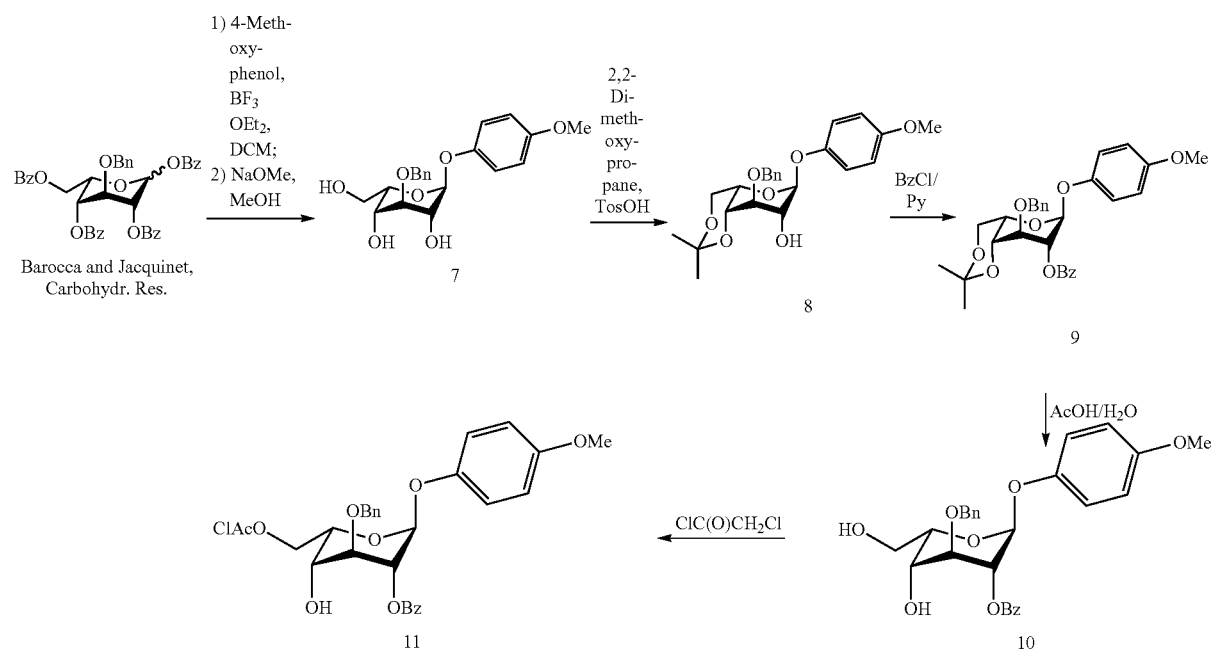

Synthesis of 7

A solution of tetra-benzoate (Barroca, N.; Jacquinet, J.-C. 2000, *Carbohydr. Res.*, 329, 667-679) (56.2 g, 82 mmol) in dry dichloromethane (400 mL) is treated with 4-methoxyphenol (2 equiv., 20.3 g, 164 mmol) and boron trifluoride diethyl etherate (0.5 equiv., 5 ml, 40.9 mmol) and stirred at room temperature for 2 hours. Then the reaction mixture is washed with saturated aq. sodium bicarbonate twice, dried and concentrated. The residue is dissolved in dry methanol (500 mL) and treated with 25% solution of sodium methoxide (15 mL) and stirred at room temperature for 18 hours. The reaction mixture is neutralized with ion-exchange resin (Amberlyst-W) and the resin is filtered off. The residue is purified by silica gel chromatography (EtOAc: petroleum ether, 1:2) to furnish the triol 7 as a syrup: 25.0 g (81%), $R_f$=0.15 (EtOAc:petroleum ether, 1:1). HRMS (ESI) calcd for $C_{20}H_{24}O_7Na(M+Na)^+$ m/z 399.142. found 399.1421. $^1$H-NMR (500 MHz, CDCl$_3$) δ 7.39-7.23 (m, 5H), 6.99 (d, J=9.1 Hz, 2H), 6.82 (d, J=9.2 Hz, 2H), 5.53 (d, J=4.5 Hz, 1H), 4.79 (d, J=12.4 Hz, 1H), 4.58 (d, J=11.9 Hz, 1H), 4.23 (d, J=8.8 Hz, 1H), 4.07 (dd, J=4.0, J=12.1, 1H), 3.89-3.83 (m, 3H), 3.81 (d, J=9.5, 1H), 3.74 (s, 3H); $^{13}$C-NMR (CDCl$_3$) δ 154.9, 1501, 138.0, 133.3, 130.1, 129.9, 128.5, 127.8, 127.6, 123.2, 117.9, 114.7, 100.4, 75.1, 71.7, 70.8, 66.1, 65.1, 60.5, 55.7.

Synthesis of 8

A solution of 7 (17 g, 45.2 mmol) in dry DMF (150 mL) is treated with 2,2-dimethoxypropane (100 mL) and p-toluenesulfonic acid monohydrate (100 mg) and stirred at room temperature for 5 hours. Then the reaction mixture is diluted with ethyl acetate, washed with saturated aq. sodium bicarbonate and water, dried and concentrated. The residue is purified by silica gel chromatography (EtOAc: petroleum ether, 1:2) to afford the isopropylidene derivative 8 as a syrup: 17.9 g, 43 mmol (95%), $R_f$=0.75 (EtOAc:petroleum ether, 1:1). HRMS (ESI) calcd for $C_{23}H_{28}O_7Na(M+Na)^+$ m/z 439.1733. found 439.1725. $^1$H-NMR (500 MHz, CDCl$_3$) δ 7.43-7.29 (m, 5H), 7.04 (d, J=9.2 Hz, 2H), 6.82 (d, J=9.1 Hz, 2H), 5.59 (d, J=5.3 Hz, 1H), 4.8 (d, J=11.8 Hz, 1H), 4.62 (d, J=11.1 Hz, 1H), 4.08 (d, J=8.5 Hz, 1H), 4.03-3.97 (m, 3H), 3.81 (dd, J=4.2, J=12.3, 1H), 3.75 (s, 3H), 3.61 (d, J=11.2 Hz, 1H), 1.47 (s, 3H), 1.44 (s, 3H); $^{13}$C-NMR (125 MHz, CDCl$_3$) δ 154.7, 150.9, 137.9, 128.5, 127.9, 127.7, 117.4, 114.6, 99.6, 99.3, 74.9, 71.7, 68.2, 65.2, 63.1, 60.5, 60.4, 55.7, 29.3, 18.5.

Synthesis of 9

A solution of 8 (17 g, 40.8 mmol) in dry dichloromethane (100 mL) and dry pyridine (50 mL) is treated with benzoyl chloride (2 equiv., 9.48 mL, 82 mmol) at 0° C. The reaction mixture is stirred at 0° C. for 30 min followed by stirring at room temperature for 5 hours. Then the mixture is diluted with ethyl acetate and washed with saturated aq. sodium bicarbonate and water, dried and concentrated. The residue is purified by silica gel chromatography (EtOAc: petroleum ether, 1:3) to afford the benzoate 9 as a syrup: 20.0 g, 38.4 mmol (95%), $R_f$=0.4 (EtOAc:petroleum ether, 1:2). HRMS (ESI) calcd for $C_{30}H_{32}O_8Na(M+Na)^+$ m/z 543.1995. found 543.1985. $^1$H-NMR (500 MHz, CDCl$_3$) δ 8.14 (d, J=7.6 Hz, 2H), 7.56-7.52 (m, 1H), 7.43-7.38 (m, 4H), 7.34-7.28 (m, 3H), 7.05 (d, J=9.2 Hz, 2H), 6.81 (d, J=9.1 Hz, 2H), 5.68 (d, J=6.1 Hz, 1H), 5.49 (dd, J=2.5, J=6.2 Hz, 1H), 4.94 (d, J=11.4 Hz, 1H), 4.72 (d, J=11.5 Hz, 1H), 4.12-4.04 (m, 3H), 3.91 (dd, J=4.3, J=13.1, 1H), 3.82 (t, J=7.2, 1H), 3.74 (s, 3H), 3.61 (d, J=11.2 Hz, 1H), 1.49 (s, 3H), 1.45 (s, 3H); $^{13}$C-NMR (125 MHz, CDCl$_3$) δ 165.5, 154.9, 150.7, 137.9, 133.5, 133.3, 130.1, 130.0, 129.8, 129.5, 128.4, 128.3, 127.8, 117.6, 114.6, 98.75, 97.55, 75.1, 72.1, 67.7, 67.1, 62.7, 61.1, 60.4, 55.7, 28.9, 18.9.

Synthesis of 10

A solution of 9 (20 g, 38.4 mmol) in gl.AcOH (160 mL) and water (80 mL) is stirred at 80° C. for 1 hour. Then the solvents are removed in vacuo and the residue is purified by silica gel chromatography (EtOAc: petroleum ether, 1:1) to give the diol 10 as a foam, 16.0 g, 33.3 mmol (87%), $R_f$=0.15 (EtOAc: petroleum ether, 1:2). HRMS (ESI) calcd for $C_{27}H_{28}O_8Na$ $(M+Na)^+$ m/z 503.1682. found 503.1689. $^1$H-NMR (500 MHz, CDCl$_3$) δ 8.04 (d, J=7.6 Hz, 2H), 7.61-7.56 (m, 1H), 7.47-7.39 (m, 4H), 7.36-7.27 (m, 3H), 7.05 (d, J=9.2 Hz, 2H), 6.83 (d, J=9.1 Hz, 2H), 5.57 (bs, 1H), 5.47-5.45 (m, 1H), 4.93 (d, J=12.0 Hz, 1H), 4.70 (d, J=11.5 Hz, 1H), 4.47-4.44 (m, 1H), 3.94-3.88 (m, 2H), 3.85-3.80 (m, 1H), 3.75 (s, 3H); $^{13}$C-NMR (125 MHz, CDCl$_3$) δ 171.2, 165.1, 155.2, 150.4, 137.8, 133.7, 129.8, 129.2, 128.7, 128.5, 127.9, 127.7, 118.3, 114.7, 97.9, 75.2, 72.0, 68.4, 68.1, 67.9, 63.2, 60.4, 55.6.

Synthesis of 11

A solution of 10 (15 g, 31.2 mmol) in dry dichloromethane (100 mL) and dry pyridine (20 mL) is treated with a solution of chloroacetyl chloride (0.85 equiv., 2.11 mL, 26.5 mmol) in dry dichloromethane (5 mL) dropwise at −78° C. The reaction mixture is stirred at −78° C. for 45 min, allowed to warm up to 0° C. and quenched with water (5 mL). Then the mixture is diluted with dichloromethane, washed with saturated aq. sodium bicarbonate and water, dried and concentrated. The residue is purified by silica gel chromatography (EtOAc: petroleum ether, 1:3) to afford the chloroacetate 11 as a foam, 15.0 g, 26.9 mmol (86%), $R_f$=0.35 (EtOAc:petroleum ether, 1:2). HRMS (ESI) calcd for $C_{29}H_{29}O_9ClNa(M+Na)^+$ m/z 579.1398. found 579.1395. $^1$H-NMR (500 MHz, CDCl$_3$) δ 8.03 (d, J=7.5 Hz, 2H), 7.62-7.59 (m, 1H), 7.49-7.41 (m, 3H), 7.39-7.35 (m, 2H), 7.33-7.29 (m, 1H), 7.05 (d, J=10.0 Hz, 2H), 6.85 (d, J=8.9 Hz, 2H), 5.56 (bs, 1H), 5.47-5.45 (m, 1H), 4.95 (d, J=11.8 Hz, 1H), 4.70 (d, J=11.8 Hz, 1H), 4.66-4.63 (m, 2H), 4.55-4.51 (m, 1H), 4.35-4.31 (m, 1H), 3.93-3.91 (m, 1H), 3.85 (s, 2H); 3.78 (s, 3H); $^{13}$C-NMR (125 MHz, CDCl$_3$) δ 166.9, 164.9, 155.3, 150.1, 137.6, 133.8, 129.8, 128.9, 128.8, 128.5, 127.9, 127.8, 118.3, 114.6, 97.3, 74.7, 72.1, 67.5, 67.1, 66.3, 65.2, 60.4, 55.7, 40.6.

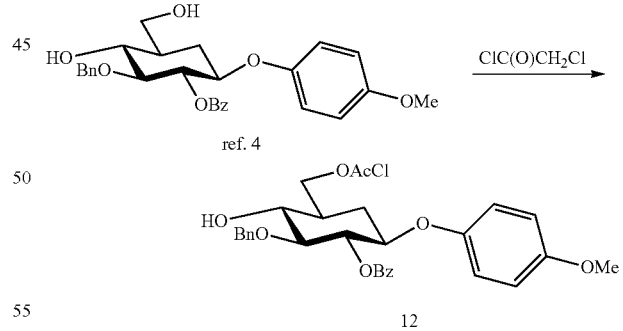

Scheme 3

Preparation of 12

Pyridine (0.447 ml, 5.53 mmol) is added to p-methoxyphenyl 2-O-benzoyl-3-O-benzyl-β-D-glucopyranoside (Karst, N.; Jacquinet, J.-C. 2002, *Eur. J. Org. Chem.*, 815-825) (0.443 g, 0.922 mmol) in dry dichloromethane (5 mL) and cooled to −75° C. Chloroacetyl chloride (0.074 ml, 0.922 mmol) (1.0 mL of a solution of 0.74 mL in 9.3 mL of DCM) is added slowly and the reaction is kept in cold bath for 1 h, then water (1 mL) is added and warmed to RT. The reaction mixture is washed with water, dil. HCl, aq. sodium bicarbonate and dried over magnesium sulfate. Evaporation of solvents gives a white solid which recrystallises from EtOAc/hexanes: alcohol 12, 0.41 g, 80%. $^{13}$C-NMR (75 MHz, CDCl$_3$) δ 167.8, 165.6, 156.1, 151.6, 138.0, 133.7, 130.2, 130.0, 129.0, 128.9, 128.5, 119.2, 114.9, 101.3, 82.6, 75.1, 73.9, 73.8, 70.3, 65.1, 56.0, 41.1

Scheme 4

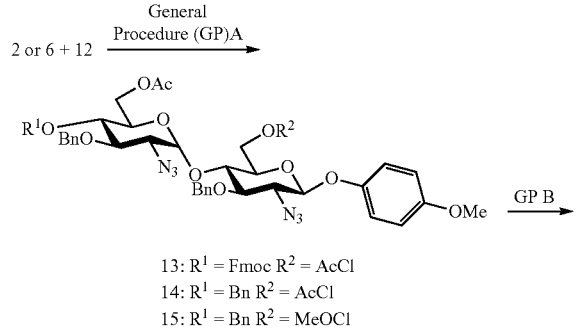

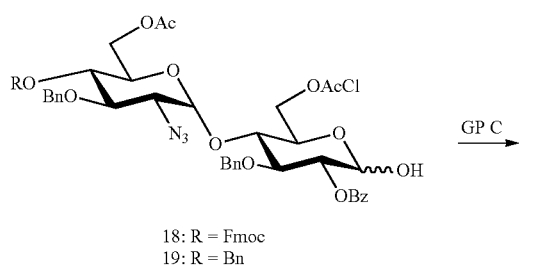

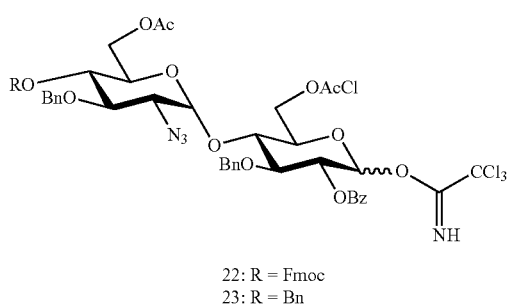

Scheme 5

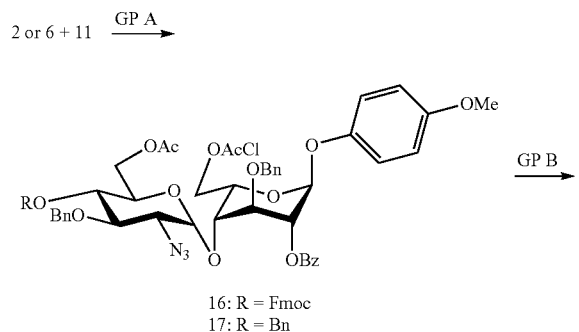

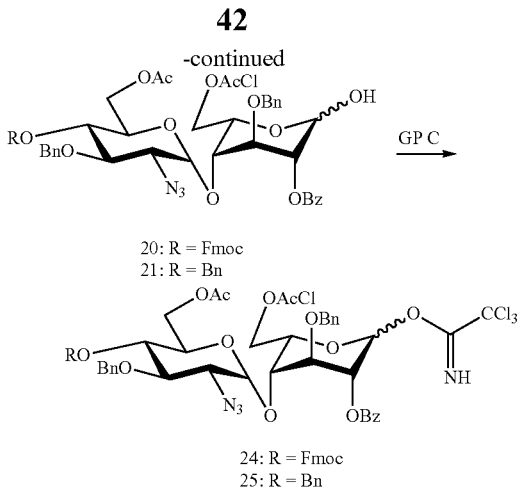

General Procedure A (GPA): Disaccharide Building Block Synthesis.

Thioglycoside donor (1.5 eq) and alcohol (1.0 eq) are dissolved in a mixture of anhydrous toluene and anhydrous dichloromethane (25 mL per mmol acceptor) and cooled to −15° C. and powdered molecular sieves (4 Å) are added. After 10 min N-iodosuccinimide (1.7 eq) and silver trifluoromethanesulfonate (0.4 eq) are added. The reaction mixture is allowed to warm up to room temperature over 1 h. The mixture is diluted with ethyl acetate and filtered through celite. The filtrate is washed with a 1:1 mixture of saturated aq. sodium bicarbonate and aq. thiosulfate (30%), washed with saturated aq. sodium chloride, dried over magnesium sulfate and concentrated. The residue is purified by flash chromatography or crystallisation.

Synthesis of 13

Compound 13 is prepared from compound 12 and compound 6 according to general procedure A1: 11.2 g (71% crystalline α-anomer), crystallised from hot toluene (60 mL) after addition of petroleum ether. $^{13}$C-NMR (125 MHz, CDCl$_3$) δ 170.5, 169.9, 165.1, 155.7, 154.2, 151.0, 143.2, 143.0, 141.3, 137.3, 137.1, 135.5, 129.8, 129.5, 129.0, 128.9, 128.6, 128.5, 128.4, 128.2, 128.0, 127.9, 127.7, 127.2, 125.3, 125.1, 124.9, 120.1, 118.7, 114.6, 100.0, 97.9, 82.5, 75.1, 74.8, 74.7, 74.1, 73.5, 72.4, 70.4, 68.8, 64.9, 62.6, 62.0, 55.7, 46.7, 40.6, 20.7

Synthesis of 14

Compound 14 is prepared from compound 12 and compound 2 according to general procedure A1: 1.11 g (79% α-anomer), crystallised from toluene after addition of petroleum ether. $^{13}$C-NMR (125 MHz, CDCl$_3$) δ 170.5, 166.9, 165.1, 155.7, 151.0, 137.5, 137.4, 137.2, 133.5, 129.8, 129.5, 129.1, 129.0, 128.8, 128.6, 128.5, 128.4, 128.1, 128.0, 127.8, 125.3, 118.7, 114.5, 100.1, 98.1, 82.7, 80.1, 79.5, 77.9, 75.5, 75.3, 74.9, 74.7, 74.2, 73.6, 72.4, 70.4, 64.9, 63.2, 62.6, 55.6, 40.4, 20.7

Synthesis of 15

Compound 15 is prepared from compound 2 and p-methoxyphenyl 2-O-benzoyl-3-O-benzyl-6-O-methoxyacetyl-β-D-glucopyranoside according to general procedure A1: 850 mg (79% α-anomer), crystallised from toluene after addition of petroleum ether. $^{13}$C-NMR (125 MHz, CDCl$_3$) δ 170.5, 169.9, 165.1, 155.7, 151.1, 137.6, 137.4, 137.2, 133.4, 129.8, 129.5, 129.0, 128.6, 128.5, 128.2, 128.1, 128.0, 127.8, 127.7, 125.3, 118.8, 114.5, 100.2, 98.0, 82.8, 80.1, 77.9, 75.5, 75.2, 74.5, 74.2, 73.7, 72.6, 70.3, 69.5, 63.5, 63.2, 62.6, 59.4, 55.6, 20.8

Synthesis of 16

Compound 16 is prepared from compound 11 and compound 6 according to general procedure A: 7.7 g (89%) crystalline α-anomer, $R_f$=0.45 (EtOAc:petroleum ether, 1:2). Crystallised from hot ethyl acetate (80 mL) after addition of petroleum ether (20%). HRMS (ESI) calcd for $C_{33}H_{56}ClN_3O_{16}Na(M+Na)^+$ m/z 1120.3247. found 1120.3246. $^1$H-NMR (500 MHz, CDCl$_3$) δ 8.18 (dd, J=3.7 Hz, J=9.9 Hz, 2H), 7.79 (d, J=8.6 Hz, 2H), 7.61 (d, J=8.6 Hz, 1H), 7.56 (d, J=7.5 Hz, 1H), 7.47-7.42 (m, 4H), 7.41-7.35 (m, 3H), 7.33-7.26 (m, 4H), 7.18-7.15 (m, 3H), 7.06 (d, J=9.1 Hz 2H), 7.03-6.99 (m, 3H), 6.86 (d, J=10.1 Hz 2H), 5.63 (d, J=4.1 Hz, 1H), 5.38 (d, J=3.9 Hz, 1H), 5.03 (d, J=12.1 Hz, 1H), 4.18 (d, J=12.1 Hz, 2H), 4.77 (t, J=9.9 Hz, 1H), 4.66 (d, J=4.3 Hz, 1H), 4.61-4.58 (m, 3H), 4.56-4.52 (m, 1H), 4.51-4.47 (m, 1H), 4.33-4.27 (m, 1H), 4.25-4.20 (m, 1H), 4.19-4.15 (m, 1H), 4.10 (d, J=3.3 Hz, 1H), 4.09-4.05 (m, 1H), 4.01 (d, J=11.0 Hz, 3H), 3.85 (d, J=2.5, 2H), 3.77 (s, 3H), 3.72 (d, J=7.3 Hz, 1H), 3.65 (t, J=10.2 Hz, 1H), 3.36-3.33 (m, 1H), 2.01 (s, 3H); $^{13}$C-NMR (125 MHz, CDCl$_3$) δ 170.5, 166.9, 165.6, 155.3, 154.2, 150.1, 143.2, 143.1, 141.3, 137.6, 137.1, 133.5, 129.9, 129.8, 128.7, 128.5, 128.2, 128.1, 128.0, 127.9, 127.8, 127.7, 127.2, 125.1, 124.9, 120.1, 118.3, 114.6, 98.9, 97.6, 78.3, 75.7, 75.0, 74.5, 72.4, 72.3, 70.3, 68.9, 68.1, 65.6, 65.0, 63.3, 62.1, 55.7, 46.7, 40.5, 20.6.

Synthesis of 17

Compound 17 is prepared from compound 11 and compound 2 according to general procedure A: The residue is purified by silica gel chromatography (EtOAc: petroleum ether, 1:3) to furnish the disaccharide as a foam, 3.7 g (93%), α-anomer, $R_f$=0.45 (EtOAc:petroleum ether, 1:2). HRMS (ESI) calcd for $C_{51}H_{52}ClN_3O_{14}Na(M+Na)^+$ m/z 988.3036. found 988.3043. $^1$H-NMR (500 MHz, CDCl$_3$) δ 8.16 (d, J=8.1 Hz, 2H), 7.46 (d, J=7.9 Hz, 2H), 7.42 (d, J=7.1 Hz, 2H), 7.39-7.34 (m, 3H), 7.33-7.28 (m, 5H), 7.26-7.22 (m, 4H), 7.16 (dd, J=7.5 Hz, J=12.3 Hz, 2H), 7.05 (d, J=10.1 Hz, 2H), 6.85 (d, J=9.3 Hz, 2H), 5.61 (d, J=4.0 Hz, 1H), 5.35 (d, J=3.7 Hz, 1H), 5.02 (d, J=12.1 Hz, 1H), 4.81 (d, J=12.2 Hz, 2H), 4.75 (d, J=10.8 Hz, 2H), 4.64 (d, J=4.3 Hz, 2H), 4.59-4.55 (m, 3H), 4.53-4.51 (m, 1H), 4.50-4.48 (m, 1H), 4.35-4.30 (m, 1H), 4.29 (d, J=3.0 Hz, 1H), 4.29 (d, J=3.0 Hz, 1H), 4.27 (d, J=3.0 Hz, 1H), 4.21-4.17 (m, 1H), 4.13 (d, J=8.0 Hz, 2H), 4.10 (d, J=10.0 Hz, 2H), 3.94-3.91 (m, 1H), 3.84 (d, J=4.8, 2H), 3.77 (s, 3H), 3.72-3.69 (m, 1H), 3.65 (t, J=10.2 Hz, 1H), 3.39 (t, J=9.2 Hz, 1H), 3.31 (dd, J=6.5 Hz, J=12.9 Hz, 1H), 2.0 (s, 3H); $^{13}$C-NMR (125 MHz, CDCl$_3$) δ 170.5, 166.8, 165.6, 155.2, 150.2, 137.6, 137.4, 137.3, 133.3, 129.9, 129.8, 128.7, 128.5, 128.4, 128.12, 128.1, 127.9, 127.96, 127.9, 127.7, 118.3, 114.5, 98.8, 97.5, 80.7, 77.8, 75.2, 75.1, 72.3, 70.4, 68.2, 65.8, 65.1, 63.8, 62.8, 55.7, 40.5, 20.7.

General Procedure B (GPB):

Anomeric Deprotection. Ammonium cerium(IV) nitrate (2 eq) is added to a solution of the starting p-methoxyphenyl glycoside (1 eq) in acetonitrile/water 7:1 (12.5 mL per mmol). The mixture is stirred at room temperature until TLC (hexanes/ethyl acetate 1:1) indicates complete consumption of the starting material, 0.5 to 3 d. The reaction mixture is diluted with ethyl acetate, washed with water (twice), saturated aq. sodium chloride, dried over magnesium sulfate and concentrated. The residue is purified by flash chromatography to give the product as a foam.

Synthesis of 18

Compound 18 is prepared from compound 13 following general procedure B: 4.37 g, 90% (2 anomers), $R_f$=0.2/0.25 (Toluene/EtOAc 5:1); $^{13}$C-NMR (125 MHz, CDCl$_3$) δ 170.5, 166.7, 165.7, 164.8, 161.0, 160.5, 154.1, 143.2, 143.0, 141.3, 137.8, 137.3, 137.2, 137.1, 133.8, 133.5, 129.9, 129.8, 129.4, 129.0, 128.6, 128.4, 128.3, 128.0, 127.9, 127.7, 127.3, 127.2, 125.1, 124.9, 120.1, 98.1, 97.9, 95.6, 90.2, 82.4, 79.4, 77.5, 76.4, 75.2, 74.8, 74.7, 74.3, 72.5, 70.4, 68.8, 68.7, 68.1, 64.9, 64.7, 62.7, 62.6, 61.9, 46.7, 40.7, 20.7

Synthesis of 19

Compound 19 is prepared from compound 14 following general procedure B: 2.9 g, 72% (2 anomers), $R_f$=0.4/0.5 (Toluene/EtOAc 7:3); $^{13}$C-NMR (125 MHz, CDCl$_3$) δ 170.5, 167.1, 166.7, 165.7, 137.9, 137.6, 137.3, 133.5, 129.9, 129.8, 129.4, 129.0, 128.6, 128.4, 128.3, 128.1, 128.0, 127.8, 127.6, 127.3, 98.3, 98.1, 90.2, 80.1, 79.5, 77.9, 76.5, 75.6, 75.2, 75.0, 74.8, 74.4, 70.4, 70.3, 68.3, 65.0, 64.8, 63.3, 62.5, 62.4, 40.7, 20.8

Synthesis of 20

Compound 20 is prepared from compound 16 following general procedure B: to obtain a mixture of disaccharides as a foam, 6.0 g, 78% yield (2 anomers), TLC $R_f$=0.25/0.3 (EtOAc:petroleum ether, 1:2). HRMS (ESI) calcd for $C_{52}H_{50}ClN_3O_{15}Na(M+Na)^+$ m/z 1014.2828. found 1014.283. $^1$H-NMR (500 MHz, CDCl$_3$) δ 8.18-8.12 (m, 4H), 7.77 (d, J=7.5 Hz, 4H), 7.59 (d, J=7.6 Hz, 2H), 7.55 (d, J=7.8 Hz, 2H), 7.44-7.35 (m, 8H), 7.35-7.30 (m, 8H), 7.29-7.26 (m, 6H), 7.24 (d, J=3.0 Hz, 4H), 7.17-7.14 (m, 4H), 6.99-6.55 (m, 4H), 5.30 (d, J=8.6 Hz, 2H), 5.26 (d, J=5.5 Hz, 2H), 4.91 (d, J=11.3 Hz, 1H), 4.88 (d, J=12.1 Hz, 1H), 4.78 (d, J=11.4 Hz, 2H), 4.75 (d, J=9.0 Hz, 2H), 4.74-4.72 (m, 1H), 4.71 (dd, J=3.0 Hz, J=6.1 Hz, 1H), 4.69 (d, J=9.0 Hz, 2H), 4.56-4.53 (m, 2H), 4.52-4.51 (m, 2H), 4.50-4.47 (m, 2H), 4.39-4.35 (m, 2H), 4.34-4.32 (m, 2H), 4.30-4.28 (m, 2H), 4.25-4.21 (m, 2H), 4.29-4.20 (m, 2H), 4.19-4.14 (m, 2H), 4.13 (bs, 2H), 4.10 (s, 2H), 4.09 (s, 2H), 4.09-4.0 (m, 1H), 3.93 (t, J=4.6 Hz, 1H), 3.89 (d, J=3.2 Hz, 2H), 3.84-3.82 (m, 1H), 3.81-3.80 (m, 1H), 3.64-3.60 (m, 1H), 3.54-3.52 (m, 1H), 3.49-3.44 (m, 1H), 3.31 (dd, J=3.9 Hz, J=13.8 Hz, 1H), 2.04 (s, 3H), 2.03 (s, 3H); $^{13}$C-NMR (125 MHz, CDCl$_3$) δ 170.6, 170.5, 167.1, 167.0, 165.8, 165.7, 154.2, 143.2, 143.1, 141.4, 141.3, 137.0, 136.3, 133.6, 133.5, 129.9, 129.8, 129.7, 129.6, 128.9, 128.8, 128.7, 128.6, 128.4, 128.3, 128.2, 127.9, 127.8, 127.7, 127.3, 125.0, 124.8, 120.1, 114.7, 99.8, 99.6, 93.2, 92.1, 79.7, 78.3, 78.2, 76.8, 76.1, 75.8, 74.9, 74.8, 74.4, 73.6, 73.2, 73.1, 72.5, 72.2, 70.2, 69.3, 69.1, 69.0, 67.6, 65.2, 65.1, 64.3, 63.3, 63.2, 61.9, 60.4, 46.8, 40.7, 20.7.

Synthesis of 21

Compound 21 is prepared from compound 17 following general procedure B: to obtain a mixture of anomers as a syrup 4.1 g, 80% yield (2 anomers), $R_f$=0.2/0.25 (EtOAc: petroleum ether, 1:2). HRMS (ESI) calcd for $C_{44}H_{46}ClN_3O_{13}Na(M+Na)^+$ m/z 882.2617. found 882.2619. $^1$H-NMR (500 MHz, CDCl$_3$) δ 8.16-8.11 (m, 4H), 7.39-7.36 (m, 8H), 7.35-7.31 (m, 8H), 7.29-7.26 (m, 6H), 7.25 (d, J=3.8 Hz, 10H), 7.23-7.20 (m, 2H), 7.12-7.09 (m, 2H), 5.28 (d, J=9.6 Hz, 2H), 5.24 (dd, J=7.8 Hz, J=12.3 Hz, 2H), 5.08-5.05 (m, 4H), 4.90 (bs, 2H), 4.88 (d, J=3.4 Hz, 1H), 4.85 (bs, 1H), 4.78 (d, J=11.8 Hz, 2H), 4.75 (d, J=11.5 Hz, 2H), 4.71 (d, J=10.8 Hz, 2H), 4.54-4.51 (m, 2H), 4.50-4.46 (m, 4H), 4.40-4.36 (m, 2H), 4.32-4.27 (m, 2H), 4.24-4.21 (m, 2H), 4.20-4.16 (m, 2H), 4.12 (bs, 1H), 4.105 (s, 2H), 4.101 (s, 2H), 3.93-3.87 (m, 2H), 3.62-3.61 (m, 1H), 3.54 (t, J=5.3 Hz, 1H), 3.50 (d, J=9.6 Hz, 1H), 3.47 (d, J=7.3 Hz, 1H), 3.41 (d, J=10.8 Hz, 1H), 3.36 (t, J=9.5 Hz, 1H), 3.28-3.24 (m, 1H), 2.04 (s, 3H), 2.02 (s, 3H); $^{13}$C-NMR (125 MHz, CDCl$_3$) δ 170.6, 167.1, 167.0, 165.9, 165.8, 137.4, 137.3, 137.1, 136.3, 133.4, 133.3, 129.84, 129.8, 128.8, 128.7, 128.6, 128.5, 128.4, 128.3, 128.1, 127.9, 99.6, 99.5, 93.1, 92.0, 80.7, 80.6, 76.8, 75.6, 75.3, 75.2, 74.9, 73.6, 73.1, 72.3, 72.2, 70.5, 69.4, 67.8, 65.4, 65.2, 64.5, 63.8, 62.7, 60.4, 40.7, 20.7.

General Procedure C (GPC): Trichloroacetimidate Formation.

Hemi-acetal starting material (1 eq) is dissolved in trichloroacetonitrile (20 eq) and the same volume of dichloromethane. The mixture is cooled in an ice-bath and sodium hydride (60% in mineral oil) (0.05 eq) is added. After 5 min the ice-bath is removed and the reaction allowed to warm up to room temperature and left until completion. The reaction mixture is subjected to flash chromatography to yield the trichloroacetimidate donor as an off-white foam.

Synthesis of 22

Compound 22 is prepared from compound 18 following general procedure C: 3.8 g, 81% (2 anomers), $R_f$=0.6/0.7 (Toluene/EtOAc 5:1). $^{13}$C-NMR (125 MHz, CDCl$_3$) δ 170.5, 170.4, 167.0, 165.3, 164.8, 161.0, 160.5, 154.2, 154.1, 143.2, 143.0, 141.3, 137.4, 137.1, 133.6, 129.8, 129.7, 129.2, 129.1, 129.0, 128.7, 128.5, 128.4, 128.3, 128.2, 127.9, 127.8, 127.7, 127.3, 127.2, 125.3, 125.1, 124.9, 120.1, 98.4, 98.2, 95.6, 93.2, 80.8, 80.1, 79.9, 77.4, 75.1, 75.0, 74.8, 74.6, 73.7, 72.9, 72.8, 68.9, 68.8, 64.8, 64.4, 62.7, 62.5, 61.9, 61.8, 46.7, 40.7, 40.6, 20.7

Synthesis of 23

Compound 23 is prepared from compound 19 following general procedure C, 2.84 g, 85% (2 anomers), $R_f$=0.45/0.5 (Toluene/EtOAc 9:1); $^{13}$C-NMR (125 MHz, CDCl$_3$) δ 170.5, 170.4, 167.0, 165.3, 164.8, 137.6, 137.2, 133.6, 133.5, 129.8, 129.7, 129.3, 129.1, 129.0, 128.6, 128.5, 128.4, 128.25, 128.2, 128.15, 128.1, 128.0, 127.8, 127.7, 127.4, 125.3, 98.7, 98.3, 95.7, 93.2, 81.4, 80.1, 79.9, 77.9, 77.8, 75.6, 75.5, 75.2, 75.0, 74.6, 74.5, 73.8, 73.0, 72.9, 68.8, 64.4, 63.3, 63.1, 62.6, 62.4, 40.7, 40.6, 20.8

Synthesis of 24

Compound 24 is prepared from compound 20 following general procedure C: to obtain a mixture of anomers as a, foam 6.1 g, 82% yield (2 anomers), $R_f$=0.35/0.4 (EtOAc: petroleum ether, 1:2). HRMS (ESI) calcd for C$_{54}$H$_{50}$Cl$_4$N$_4$O$_{15}$Na(M+Na)$^+$ m/z 1157.1924. found 1157.1929. $^1$H-NMR (500 MHz, CDCl$_3$) δ 8.70 (s, 1H), 8.59 (s, 1H), 8.18-8.15 (m, 2H), 8.07 (dd, J=7.4 Hz, J=9.6 Hz, 2H), 7.78-7.75 (m, 2H), 7.61-7.58 (m, 2H), 7.61-7.58 (m, 4H), 7.57-7.54 (m, 4H), 7.49-7.46 (m, 2H), 7.44-7.38 (m, 4H), 7.37-7.34 (m, 4H), 7.32-7.31 (m, 2H), 7.31-7.27 (m, 2H), 7.27-7.26 (m, 2H), 7.25 (s, 4H), 7.20-7.15 (m, 4H), 7.12 (dd, J=4.4 Hz, J=10.0 Hz, 2H), 7.0 (dd, J=6.4 Hz, J=9.2 Hz, 2H), 6.50 (d, J=2.7 Hz, 1H), 6.45 (s, 1H), 5.41-5.39 (m, 1H), 5.36 (t, J=2.1 Hz, 1H), 5.02 (d, J=2.9 Hz, 1H), 4.97 (d, J=11.4 Hz, 1H), 4.89 (s, 2H), 4.87 (d, J=8.3 Hz, 1H), 4.83 (d, J=9.8 Hz, 1H), 4.80 (d, J=9.8 Hz, 2H), 4.78-4.72 (m, 1H), 4.69 (d, J=3.4 Hz, 1H), 4.68-4.64 (m, 1H), 4.63 (d, J=5.3 Hz, 2H), 4.60 (d, J=7.6 Hz, 2H), 4.58 (d, J=6.0 Hz, 2H), 4.55 (d, J=4.3 Hz, 2H), 4.53 (d, J=3.2 Hz, 2H), 4.52 (d, J=3.7 Hz, 2H), 4.50 (d, J=2.5 Hz, 2H), 4.48 (d, J=3.9 Hz, 2H), 4.46-4.42 (m, 1H), 4.39-4.35 (m, 1H), 4.32 (d, J=3.4 Hz, 1H), 4.31-4.28 (m, 1H), 4.25-4.22 (m, 1H), 4.22-4.20 (m, 1H), 4.19-4.16 (m, 1H), 4.14-4.07 (m, 1H), 4.058 (s, 2H), 4.054 (s, 2H), 3.99 (d, J=10.8 Hz, 1H), 3.92 (d, J=10.8 Hz, 1H), 3.76-3.71 (m, 1H), 3.60 (t, J=9.8 Hz, 1H), 3.40 (t, J=5.3 Hz, 1H), 3.37 (dd, J=6.8 Hz, J=13.9 Hz, 1H), 2.05 (s, 3H), 2.04 (s, 3H); $^{13}$C-NMR (CDCl$_3$) δ 171.1, 170.5, 167.0, 166.9, 165.7, 165.4, 160.6, 160.5, 154.2, 143.2, 143.1, 141.3, 137.3, 137.2, 137.0, 133.6, 133.5, 129.9, 129.8, 129.5, 129.4, 128.8, 128.6, 128.5, 128.4, 128.3, 128.2, 128.1, 128.0, 127.9, 127.8, 127.7, 127.3, 125.0, 124.9, 124.8, 120.1, 99.5, 99.3, 95.5, 94.9, 78.3, 77.9, 76.8, 75.6, 75.4, 75.1, 74.9, 74.6, 74.5, 73.5, 72.4, 71.6, 70.4, 70.2, 69.9, 69.0, 68.8, 67.0, 66.4, 65.4, 64.9, 63.3, 63.1, 62.1, 62.0, 60.4, 46.8, 40.6, 40.5, 20.7.

Synthesis of 25

Compound 25 is prepared from compound 21 following general procedure C: to obtain a mixture of anomers as a foam, 4.4 g, 94% yield (2 anomers), TLC, $R_f$=0.45/0.5, (EtOAc:petroleum ether, 1:2). HRMS (ESI) calcd for C$_{46}$H$_{46}$Cl$_4$N$_4$O$_{13}$Na(M+Na)$^+$ m/z 1025.1713. found 1025.1718. $^1$H-NMR (500 MHz, CDCl$_3$) δ 8.68 (s, 1H), 8.57 (s, 1H), 8.16 (dd, J=7.3 Hz, J=9.5 Hz, 2H), 8.05 (dd, J=7.1 Hz, J=9.4 Hz, 2H), 7.49-7.44 (m, 2H), 7.42-7.38 (m, 4H), 7.37-7.30 (m, 10H), 7.29-7.23 (m, 12H), 7.14-7.12 (m, 6H), 6.50 (d, J=2.8 Hz, 1H), 6.43 (s, 1H), 5.38 (dd, J=4.5 Hz, J=10.2 Hz, 1H), 5.35-5.33 (m, 1H), 5.28 (s, 1H), 5.04 (d, J=3.4 Hz, 1H), 4.96 (d, J=11.5 Hz, 1H), 4.87 (s, 1H), 4.80 (d, J=10.2 Hz, 1H), 4.76 (t, J=10.2 Hz, 1H), 4.68 (d, J=3.4 Hz, 1H), 4.66-4.63 (m, 1H), 4.62 (d, J=6.2 Hz, 1H), 4.60-4.56 (m, 1H), 4.54-53 (m, 1H), 4.52-4.49 (m, 2H), 4.50-4.44 (m, 1H), 4.43 (d, J=5.9 Hz, 2H), 4.40 (d, J=4.2 Hz, 2H), 4.38 (t, J=2.5 Hz, 1H), 4.36 (d, J=7.0 Hz, 2H), 4.32 (t, J=2.5 Hz, 1H), 4.30-4.28 (m, 1H), 4.27 (d, J=10.8 Hz, 1H), 4.23-4.17 (m, 1H), 4.15-4.13 (m, 1H), 4.12 (s, 2H), 4.11 (s, 2H), 4.06 (s, 1H), 4.04 (d, J=2.4 Hz, 1H), 4.04-4.02 (m, 1H), 4.0-3.97 (m, 1H), 3.96-3.93 (m, 1H), 3.73 (t, J=9.8 Hz, 1H), 3.61 (d, J=9.8 Hz, 1H), 3.59 (d, J=9.8 Hz, 1H), 3.46-3.41 (m, 1H), 3.40-3.36 (m, 1H), 3.35 (d, J=3.8 Hz, 1H), 3.33 (dd, J=3.3 Hz, J=6.1 Hz, 1H), 2.03 (s, 6H); $^{13}$C-NMR (125 MHz, CDCl$_3$) δ 171.1, 170.6, 167.0, 166.9, 165.7, 165.5, 163.4, 160.6, 160.5, 137.5, 137.4, 137.3, 137.2, 133.4, 129.9, 129.8, 129.6, 129.3, 128.7, 128.6, 128.5, 128.4, 128.1, 128.0, 127.9, 99.4, 99.2, 95.5, 94.9, 80.7, 80.4, 77.8, 77.0, 76.8, 75.4, 75.3, 75.2, 75.0, 74.6, 74.5, 73.6, 72.3, 71.5, 70.6, 70.3, 67.2, 66.5, 65.7, 65.0, 63.9, 63.6, 62.7, 60.4, 40.7, 40.6, 21.0, 20.8.

General Procedure D (GPD): Fmoc Deprotection.

The appropriate Fmoc derivative is dissolved in a mixture of dichloromethane and triethylamine 4:1 (v/v, 20 mL per mmol) and left at ambient temperature until completion, usually 3 to 5 h. Subsequently the mixture is diluted with dichloromethane, washed with diluted aq. HCl, water and saturated aq. sodium chloride, dried over magnesium sulfate and concentrated. The residue is purified by flash chromatography to afford the desired alcohols as foams.

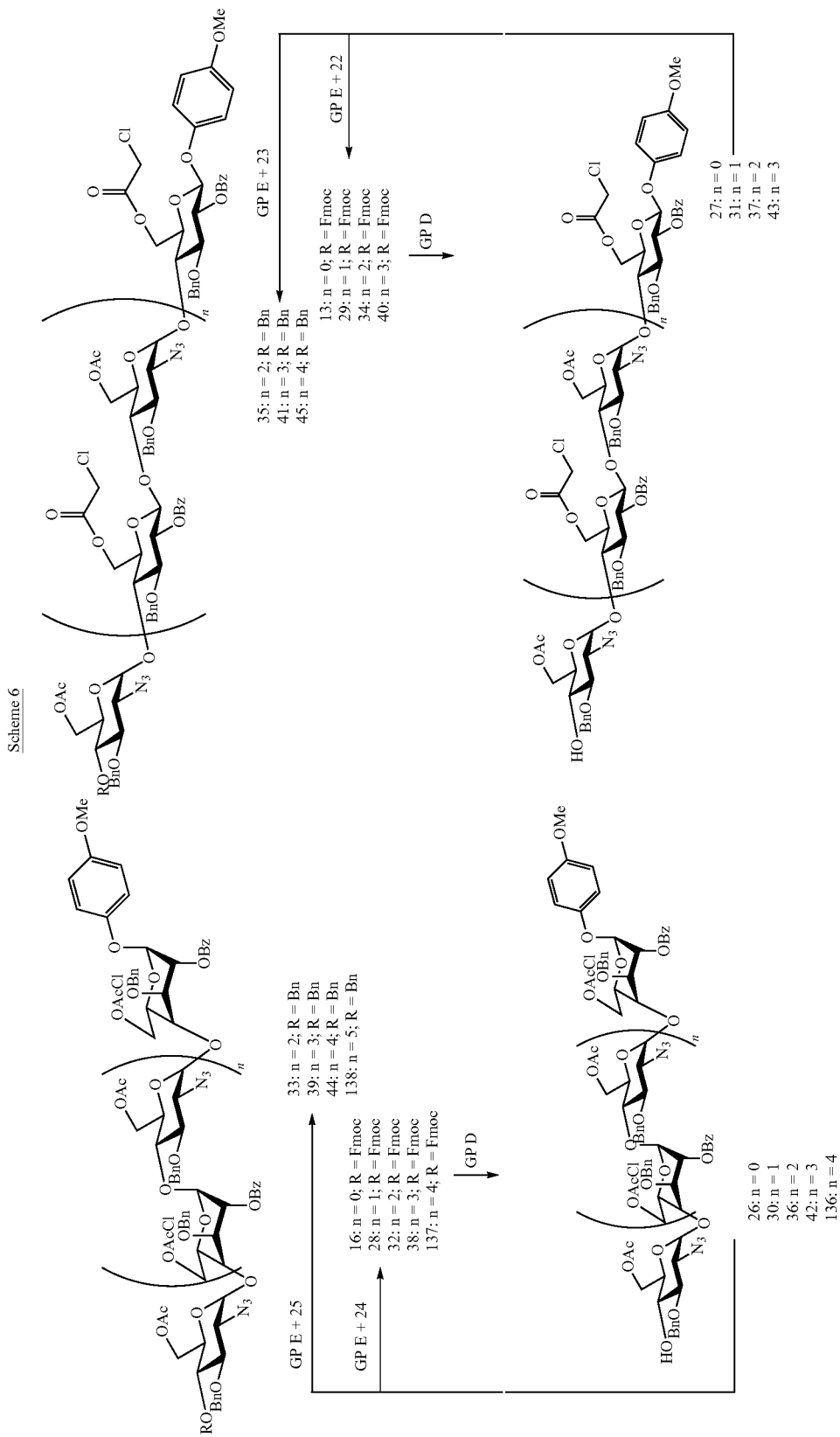

General Procedure E (GPE): Chain Extension Glycosylation.

A solution of the trichloroacetimidate donor (1.3 eq) and the glycosyl acceptor alcohol (1 eq) in anhydrous toluene (40 mL per mmol acceptor) is cooled to reaction temperature (between −10 and −20° C.), powdered molecular sieves (4 Å) are added and the suspension stirred at the temperature. After 15 min, trimethylsilyl trifluoromethanesulfonate (0.3 eq) is added and the reaction mixture stirred at reaction temperature until TLC (toluene/ethyl acetate 4:1) indicated completion. The mixture is diluted with ethyl acetate and filtered through celite into aq. sodium bicarbonate, the organic layer is washed with water and saturated aq. sodium chloride, dried over magnesium sulfate and concentrated. The residue is purified by flash chromatography to yield the fully protected oligosaccharides.

Synthesis of 26

Compound 26 is prepared from compound 16 following general procedure D: 2.55 g, 88% yield, TLC, $R_f$=0.2 (EtOAc:petroleum ether, 1:2). HRMS (ESI) calcd for $C_{44}H_{46}ClN_3O_{14}Na(M+Na)^+$ m/z 898.2566. found 898.2555. $^1$H-NMR (500 MHz, CDCl$_3$) δ 8.18 (dd, J=7.1 Hz, J=9.4 Hz, 2H), 7.52-7.48 (m, 3H), 7.47-7.43 (m, 3H), 7.38-7.35 (m, 2H), 7.34-7.27 (m, 3H), 7.24-7.13 (m, 2H), 7.06 (d, J=9.5 Hz, 2H), 6.85 (d, J=9.5 Hz, 2H), 5.62 (s, 1H), 5.36 (s, 1H), 5.02 (d, J=10.3 Hz, 1H), 4.81 (d, J=10.8 Hz, 1H), 4.67 (d, J=3.6 Hz, 1H), 4.61-4.58 (m, 1H), 4.53 (d, J=9.1 Hz, 1H), 4.51 (dd, J=6.7 Hz, J=10.3 Hz, 1H), 4.49 (d, J=4.3 Hz, 1H), 4.39 (d, J=10.6 Hz, 1H), 4.33 (d, J=3.5 Hz, 1H), 4.33 (d, J=4.4 Hz, 1H), 4.22-4.20 (m, 1H), 4.17 (d, J=2.2 Hz, 1H), 3.87 (d, J=2.0 Hz, 2H), 3.78 (s, 3H), 3.73 (t, J=2.8 Hz, 1H), 3.50 (d, J=8.2 Hz, 1H), 3.37 (d, J=8.9 Hz, 1H), 3.36-3.31 (m, 1H), 3.26 (dd, J=6.1 Hz, J=13.6 Hz, 1H), 2.05 (s, 3H); $^{13}$C-NMR (CDCl$_3$) δ 171.8, 166.9, 165.7, 155.3, 150.2, 137.7, 137.6, 133.4, 129.9, 129.8, 129.0, 128.7, 128.6, 128.4, 128.2, 128.13, 128.1, 128.0, 125.3, 118.3, 114.6, 98.9, 97.6, 80.1, 75.2, 75.0, 72.4, 72.36, 72.35, 70.5, 68.3, 65.8, 65.1, 63.3, 62.9, 55.7, 40.5, 20.7.

Synthesis of 27

Compound 27 is prepared from compound 13 following general procedure D: 4.36 g, 91%, $R_f$=0.3 (Toluene/EtOAc 4:1). $^{13}$C-NMR (125 MHz, CDCl$_3$) δ 171.9, 167.0, 165.1, 155.7, 151.0, 137.8, 137.3, 133.5, 129.8, 129.5, 128.7, 128.6, 128.4, 128.2, 127.8, 127.7, 118.7, 114.5, 100.1, 98.2, 82.8, 79.2, 75.4, 74.5, 74.2, 73.6, 72.5, 71.4, 70.7, 64.9, 62.9, 62.7, 55.6, 40.6, 20.8

Synthesis of 28

Compound 28 is prepared from compound 26 and compound 24 following general procedure E: 450 mg, 95% yield (beta), TLC, $R_f$=0.35 (EtOAc:petroleum ether, 1:2). HRMS (ESI) calcd for $C_{96}H_{94}Cl_2N_6O_{28}Na(M+Na)^+$ m/z 1871.5391. found 1871.5383. $^1$H-NMR (500 MHz, CDCl$_3$) δ 8.17 (dd, J=6.8 Hz, J=9.4 Hz, 2H), 8.11 (dd, J=6.8 Hz, J=9.8 Hz, 2H), 7.77 (d, J=7.4 Hz, 2H), 7.60 (d, J=7.4 Hz, 2H), 7.55 (d, J=7.5 Hz, 1H), 7.47-7.43 (m, 4H), 7.43-7.39 (m, 3H), 7.39-7.36 (m, 3H), 7.35-7.32 (m, 4H), 7.32-7.31 (m, 4H), 7.30-7.23 (m, 4H), 7.20-7.15 (m, 4H), 7.08-7.05 (m, 4H), 7.06 (d, J=9.5 Hz, 2H), 6.85 (d, J=8.9 Hz, 2H), 5.64 (bd, 1H), 5.35 (t, J=2.4 Hz, 1H), 5.15 (t, J=3.9 Hz, 1H), 5.12 (d, J=3.5 Hz, 1H), 5.02 (d, J=11.8 Hz, 1H), 4.87 (d, J=11.5 Hz, 1H), 4.81 (d, J=11.3 Hz, 1H), 4.76 (d, J=2.5 Hz, 1H), 4.73 (t, J=4.6 Hz, 1H), 4.65 (d, J=3.7 Hz, 1H), 4.59-4.55 (m, 1H), 4.51-4.48 (m, 2H), 4.48-4.44 (m, 2H), 4.38-4.34 (m, 3H), 4.33-4.29 (m, 4H), 4.28-4.25 (m, 2H), 4.24-4.23 (m, 1H), 4.22-4.20 (m, 2H), 4.19-4.15 (m, 2H), 4.09-4.07 (m, 1H), 4.05-4.03 (m, 1H), 4.03-4.01 (m, 1H), 4.0 (d, J=10.2 Hz, 1H), 3.96-3.94 (m, 1H), 3.92 (d, J=3.0 Hz, 2H), 3.83 (d, J=3.6 Hz, 2H), 3.77 (s, 3H), 3.72-3.68 (m, 1H), 3.68-3.65 (m, 1H), 3.60 (t, J=9.8 Hz, 1H), 3.38-3.28 (m, 1H), 2.03 (s, 3H), 2.02 (s, 3H); $^{13}$C NMR (CDCl$_3$) δ 171.1, 170.5, 170.4, 166.8, 166.7, 165.7, 165.4, 155.2, 154.2, 150.1, 143.2, 143.0, 141.35, 141.3, 137.7, 137.6, 137.2, 137.1, 133.5, 133.4, 129.9, 129.7, 129.5, 128.7, 128.6, 128.5, 128.4, 128.3, 128.2, 128.1, 128.0, 127.9, 127.8, 127.7, 127.3, 125.0, 124.8, 120.1, 118.3, 114.6, 98.8, 98.1, 97.8, 97.6, 79.1, 77.9, 75.2, 75.1, 74.99, 74.9, 74.5, 74.4, 73.9, 73.4, 73.2, 72.4, 72.1, 70.3, 69.9, 68.8, 68.3, 67.2, 65.8, 64.9, 63.9, 63.7, 64.9, 63.9, 63.7, 63.1, 62.3, 61.9, 60.4, 55.7, 46.7, 40.6, 40.5, 20.7.

Synthesis of 29

Compound 29 is prepared from compound 27 and compound 22 following general procedure E: 8.0 g, 87% (beta), $R_f$=0.45 (toluene/EtOAc 4:1). $^{13}$C-NMR (125 MHz, CDCl$_3$) δ 170.5, 170.4, 169.9, 166.4, 165.1, 164.9, 155.7, 154.1, 150.9, 143.2, 153.0, 141.0, 138.3, 137.3, 137.2, 137.1, 133.8, 135.5, 129.8, 129.5, 129.0, 128.9, 128.8, 128.6, 128.4, 128.35, 128.3, 128.2, 128.0, 127.9, 127.7, 127.7, 127.5, 127.4, 127.2, 125.3, 125.1, 124.9, 120.1, 118.8, 114.5, 101.0, 100.1, 97.9, 97.7, 82.7, 77.9, 77.7, 77.4, 75.4, 75.2, 75.1, 74.7, 74.6, 74.5, 74.3, 74.1, 73.6, 72.4, 70.4, 69.8, 68.8, 64.9, 64.7, 64.2, 62.7, 62.6, 62.0, 61.8, 55.6, 46.7, 40.7, 40.4, 20.75, 20.7

Synthesis of 30

Compound 30 is prepared from compound 28 following general procedure D: 388 mg, 84% yield, TLC $R_f$=0.45 (EtOAc:petroleum ether, 1:1). HRMS (ESI) calcd for $C_{81}H_{84}Cl_2N_6O_{26}Na(M+Na)^+$ m/z 1649.471. found 1649.4702. $^1$H-NMR (500 MHz, CDCl$_3$) δ 8.16 (dd, J=6.5 Hz, J=9.0 Hz, 2H), 8.11 (dd, J=7.1 Hz, J=9.2 Hz, 2H), 7.52-7.48 (m, 4H), 7.46-7.39 (m, 4H), 7.38-7.34 (m, 8H), 7.33-7.29 (m, 4H), 7.28-7.23 (m, 4H), 7.18-7.16 (m, 2H), 7.05 (d, J=9.2 Hz, 2H), 6.85 (d, J=9.2 Hz, 2H), 5.62 (s, 1H), 5.34 (s, 1H), 5.15 (t, J=4.3 Hz, 1H), 5.0 (d, J=11.9 Hz, 1H), 4.86 (d, J=11.5 Hz, 1H), 4.80 (d, J=11.8 Hz, 1H), 4.77-4.76 (m, 2H), 4.53 (d, J=8.0 Hz, 1H), 4.50 (d, J=7.6 Hz, 1H), 4.47 (d, J=5.7 Hz, 1H), 4.59 (bs, 1H), 4.58-4.54 (m, 1H), 4.53 (d, J=7.6 Hz, 1H), 4.50 (d, J=8.3 Hz, 1H), 4.47 (d, J=6.0 Hz, 1H), 4.45-4.42 (m, 1H), 4.40-4.39 (m, 1H), 4.35-4.30 (m, 1H), 4.29 (d, J=4.5 Hz, 1H), 4.27-4.24 (m, 1H), 4.23-4.22 (m, 1H), 4.19-4.16 (m, 1H), 4.15 (d, J=2.6 Hz, 1H), 4.12 (d, J=9.8 Hz, 1H), 4.08 (s, 1H), 4.05 (d, J=4.3 Hz, 1H), 4.03 (d, J=4.5 Hz, 1H), 3.97 (d, J=10.3 Hz, 2H), 3.90 (d, J=2.1 Hz, 2H), 3.81 (d, J=3.5 Hz, 2H), 3.76 (s, 3H), 3.74-3.70 (m, 1H), 3.70-3.67 (m, 1H), 3.60 (d, J=10.5 Hz, 1H), 3.56 (d, J=9.7 Hz, 1H), 3.41-3.36 (m, 1H), 3.31 (d, J=5.7 Hz, J=13.5 Hz, 1H), 3.23 (dd, J=6.8 Hz, J=13.7 Hz, 1H), 3.06 (d, J=4.5 Hz, 1H), 2.02 (s, 3H), 2.01 (s, 3H); $^{13}$C-NMR (125 MHz, CDCl$_3$) δ 171.6, 171.1, 170.7, 167.0, 166.8, 165.7, 165.5, 155.2, 150.1, 137.7, 137.6, 137.3, 133.5, 133.4, 129.9, 129.8, 129.5, 128.7, 128.6, 128.5, 128.4, 128.3, 128.1, 127.7, 118.3, 114.6, 98.9, 98.3, 97.8, 97.5, 79.7, 78.9, 76.9, 75.5, 75.2, 74.9, 74.6, 74.4, 73.4, 72.4, 72.1, 71.3, 70.6, 70.3, 68.3, 67.9, 65.7, 64.9, 63.8, 63.6, 63.1, 62.8, 62.4, 60.4, 55.6, 40.5, 20.7.

Synthesis of 31

Compound 31 is prepared from compound 29 following general procedure D: 600 mg, 85%, $R_f$=0.2 (Toluene/EtOAc 7:3). $^{13}$C-NMR (125 MHz, CDCl$_3$) δ 171.9, 170.5, 166.9, 166.4, 165.1, 164.9, 155.7, 150.9, 138.3, 137.8, 137.3, 137.2, 133.8, 133.5, 129.8, 129.5, 128.9, 128.8, 128.7, 128.6, 128.4, 128.3, 128.2, 128.1, 127.7, 127.5, 127.3, 127.0, 125.3, 118.8, 114.5, 101.0, 100.0, 98.3, 97.7, 82.8, 82.7, 79.2, 77.9, 77.7, 75.4, 75.0, 74.7, 74.6, 74.3, 73.6, 72.5, 71.4, 70.6, 69.8, 64.9, 64.2, 62.7, 62.0, 55.6, 40.4, 20.7

Synthesis of 32

Compound 32 is prepared from compound 30 and compound 24 following general procedure E: 1.51 g, 86% yield (beta), $R_f$=0.21 (EtOAc:petroleum ether, 1:2). HRMS (ESI) calcd for $C_{133}H_{132}Cl_3N_9O_{40}Na(M+Na)^+$ m/z 2622.7535.

found 2622.7549. $^1$H-NMR (500 MHz, CDCl$_3$) δ 8.17 (dd, J=6.5 Hz, J=8.9 Hz, 2H), 8.12-8.08 (m, 4H), 7.76-7.73 (m, 2H), 7.59 (d, J=7.3 Hz, 2H), 7.54 (d, J=7.7 Hz, 8H), 7.50-7.43 (m, 6H), 7.42-7.35 (m, 12H), 7.34-7.29 (m, 8H), 7.28-7.19 (m, 6H), 7.18-7.13 (m, 4H), 7.08-7.04 (m, 2H), 7.05 (d, J=9.1 Hz, 2H), 6.85 (d, J=8.7 Hz, 2H), 5.63 (d, J=4.6 Hz, 1H), 5.35 (t, J=3.6 Hz, 1H), 5.17-5.12 (m, 1H), 5.10 (d, J=4.6 Hz, 1H), 5.01 (d, J=11.9 Hz, 1H), 4.87 (d, J=7.7 Hz, 1H), 4.84 (d, J=7.7 Hz, 1H), 4.81-4.79 (m, 2H), 4.78-4.75 (m, 3H), 4.74 (d, J=5.9 Hz, 1H), 4.71 (bs, 1H), 4.70 (d, J=3.8 Hz, 1H), 4.63 (d, J=4.0 Hz, 1H), 4.59-4.54 (m, 4H), 4.54-4.49 (m, 4H), 4.48-4.42 (m, 3H), 4.41-4.37 (m, 4H), 4.35-4.29 (m, 4H), 4.28-4.25 (m, 3H), 4.24-4.22 (m, 2H), 4.21-4.17 (m, 2H), 4.16-4.14 (m, 2H), 4.08-4.04 (m, 2H), 4.03-4.01 (m, 1H), 3.97 (d, J=10.2 Hz, 1H), 3.90 (s, 2H), 3.89 (s, 2H), 3.81 (d, J=4.0 Hz, 2H), 3.75 (s, 3H), 3.74-3.71 (m, 1H), 3.71-3.67 (m, 1H), 3.67-3.64 (m, 1H), 3.64-3.60 (m, 1H), 3.58 (t, J=9.5, 1H), 3.32 (d, J=4.3, 1H), 3.30-3.28 (m, 1H), 3.28 (d, J=3.9, 1H), 2.03 (s, 3H), 2.0 (s, 3H), 2.0 (s, 3H); $^{13}$C NMR (125 MHz, CDCl$_3$) δ 171.6, 171.1, 170.5, 170.4, 166.9, 166.8, 166.7, 165.7, 165.5, 165.4, 163.2, 155.2, 154.2, 150.2, 143.2, 143.1, 141.4, 137.7, 137.6, 137.3, 137.2, 137.1, 136.5, 134.1, 133.6, 133.4, 129.9, 129.8, 129.5, 129.4, 128.8, 128.7, 128.6, 128.5, 128.4, 128.35, 128.3, 128.25, 128.2, 128.1, 128.0, 127.9, 127.8, 127.3, 125.0, 124.8, 120.2, 118.3, 114.6, 98.8, 98.3, 98.1, 97.9, 97.8, 97.5, 80.1, 79.0, 78.9, 78.3, 77.9, 76.9, 76.2, 75.8, 75.4, 75.1, 74.9, 74.7, 74.6, 74.5, 74.1, 74.0, 73.8, 73.5, 73.3, 73.2, 72.4, 72.1, 71.4, 70.7, 70.4, 70.3, 70.2, 69.8, 69.5, 68.9, 68.8, 68.3, 67.9, 67.6, 67.1, 65.9, 65.7, 65.2, 64.9, 64.4, 63.9, 63.8, 63.7, 63.6, 63.3, 63.1, 62.3, 62.2, 61.9, 60.4, 55.7, 46.8, 40.7, 40.5, 22.7

Synthesis of 33

Compound 33 is prepared from compound 30 and compound 25 following general procedure E: The residue is purified by silica gel chromatography (EtOAc: petroleum ether, 1:2) to furnish the disaccharide as a foam, 375 mg, 74% yield, TLC, R$_f$=0.15 (EtOAc:petroleum ether, 1:2) HRMS (ESI) calcd for C$_{125}$H$_{123}$Cl$_3$N$_8$O$_{38}$Na(M+Na)$^+$ m/z 2490.7324. found 2490.7297. $^1$H-NMR (500 MHz, CDCl$_3$) δ 8.15 (dd, J=6.7 Hz, J=9.6 Hz, 2H), 8.09 (d, J=8.1 Hz, 4H), 7.50-7.40 (m, 4H), 7.39-7.34 (m, 6H), 7.33-7.28 (m, 6H), 7.27-7.20 (m, 10H), 7.20-7.16 (m, 10H), 7.14-7.11 (m, 8H), 7.05 (d, J=8.9 Hz, 2H), 6.85 (d, J=9.5 Hz, 2H), 5.62 (d, J=4.0 Hz, 1H), 5.35 (d, J=3.7 Hz, 1H), 5.14 (dd, J=5.2 Hz, J=13.1 Hz, 1H), 5.10 (d, J=3.6 Hz, 1H), 5.07 (d, J=3.7 Hz, 1H), 5.01 (d, J=11.5 Hz, 1H), 4.84 (d, J=4.4 Hz, 1H), 4.82 (t, J=4.3 Hz, 2H), 4.77-4.73 (m, 2H), 4.72 (d, J=3.6 Hz, 2H), 4.71 (d, J=3.7 Hz, 2H), 4.63 (d, J=3.8 Hz, 2H), 4.57-4.53 (m, 2H), 4.53-4.48 (m, 3H), 4.47-4.45 (m, 2H), 4.45-4.43 (m, 2H), 4.42-4.39 (m, 2H), 4.35-4.30 (m, 2H), 4.29 (d, J=3.7 Hz, 2H), 4.26 (d, J=4.3 Hz, 1H), 4.24-4.18 (m, 1H), 4.18-4.15 (m, 1H), 4.10 (d, J=2.2 Hz, 2H), 4.08-4.05 (m, 2H), 4.04-4.01 (m, 2H), 4.0 (d, J=4.6 Hz, 2H), 3.90 (d, J=10.3 Hz, 2H), 3.92-3.89 (m, 1H), 3.88-3.87 (m, 4H), 3.81 (d, J=4.8 Hz, 2H), 3.77 (s, 3H), 3.73 (d, J=8.8 Hz, 1H), 3.70-3.64 (m, 1H), 3.62 (d, J=10.6 Hz, 1H), 3.58 (d, J=10.6 Hz, 1H), 3.54 (d, J=8.8 Hz, 1H), 3.43 (t, J=9.3 Hz, 1H), 3.30 (d, J=3.9 Hz, 1H), 3.28-3.25 (m, 1H), 3.25-3.23 (m, 1H), 2.013 (s, 3H), 1.99 (s, 3H), 1.97 (s, 3H); $^{13}$C NMR (CDCl$_3$) δ 171.1, 170.5, 170.4, 166.8, 166.7, 165.7, 165.5, 165.4, 164.9, 155.2, 143.2, 143.1, 143.0, 141.3, 137.7, 137.6, 137.3, 137.0, 133.6, 133.4, 129.8, 129.7, 129.5, 129.4, 128.9, 128.8, 128.6, 128.5, 128.4, 128.3, 128.2, 128.1, 128.0, 127.9, 127.8, 127.7, 127.6, 127.5, 127.2, 125.0, 124.8, 120.1, 118.2, 114.5, 99.6, 98.8, 98.3, 98.0, 97.9, 97.8, 78.9, 78.8, 77.9, 77.3, 77.0, 76.8, 75.8, 75.3, 75.1, 75.0, 74.9, 74.6, 74.5, 74.4, 74.2, 74.0, 73.8, 73.6, 73.5, 73.4, 73.3, 72.3, 72.2, 72.1, 70.4, 70.3, 70.2, 69.8, 69.1, 68.8, 68.2, 65.7, 65.2, 65.0, 64.9, 64.3, 63.8, 63.7, 63.6, 63.3, 63.1, 62.3, 62.2, 61.9, 60.4, 55.7, 46.8, 40.7, 40.5, 40.3, 20.7.

Synthesis of 34

Compound 34 is prepared from compound 31 and compound 22 following general procedure E: 5.25 g, 94% (beta), R$_f$=0.45 (Toluene/EtOAc 4:1). $^{13}$C-NMR (125 MHz, CDCl$_3$) δ 170.4, 169.9, 166.4, 165.9, 165.1, 165.0, 164.9, 155.7, 154.1, 151.0, 143.2, 143.0, 141.3, 138.3, 137.3, 137.2, 137.1, 133.8, 133.5, 129.8, 129.7, 129.5, 129.0, 128.9, 128.6, 128.4, 128.35, 128.3, 128.2, 128.0, 127.9, 127.8, 127.7, 127.6, 127.5, 127.45, 127.4, 127.3, 125.1, 124.9, 120.1, 118.8, 114.5, 100.9, 100.8, 100.1, 97.8, 97.7, 82.8, 82.7, 77.7, 77.6, 77.5, 74.5, 75.3, 75.2, 75.1, 74.9, 74.7, 74.6, 74.3, 74.2, 74.1, 73.6, 72.4, 72.3, 70.4, 69.8, 68.8, 64.9, 64.2, 62.7, 62.6, 61.9, 61.8, 55.6, 46.7, 40.4, 40.3, 20.75, 20.7

Synthesis of 35

Compound 35 is prepared from compound 31 and compound 23 following general procedure E: 591 mg, 78% (beta), R$_f$=0.5 (Toluene/EtOAc 4:1). $^{13}$C-NMR (125 MHz, CDCl$_3$) δ 170.5, 166.9, 166.4, 165.1, 165.0, 164.9, 155.7, 150.9, 138.3, 138.2, 137.5, 137.3, 137.3, 137.2, 133.8, 133.7, 133.4, 129.8, 129.7, 129.5, 129.1, 129.0, 128.9, 128.8, 128.6, 128.5, 128.4, 128.3, 128.1, 128.0, 127.7, 127.6, 127.5, 127.4, 125.3, 118.8, 114.5, 100.9, 100.8, 100.0, 98.0, 97.8, 97.7, 82.8, 82.7, 80.1, 77.8, 77.7, 77.5, 75.6, 75.5, 75.2, 75.0, 74.9, 74.7, 74.6, 74.3, 74.2, 74.1, 73.5, 72.4, 72.3, 70.3, 69.8, 65.0, 64.4, 64.2, 63.2, 62.7, 62.6, 62.4, 61.9, 61.8, 55.6, 40.5, 40.4, 40.3, 20.7

Synthesis of 36

Compound 36 is prepared from compound 32 following general procedure D: The residue is purified by silica gel chromatography (EtOAc: petroleum ether, 1:1) to furnish the disaccharide as a foam, 550 mg, 88% yield; TLC, R$_f$=0.45 (EtOAc:petroleum ether, 1:1). HRMS (ESI) calcd for C$_{118}$H$_{122}$Cl$_3$N$_9$O$_{38}$Na(M+Na)$^+$ m/z 2400.6854. found 2400.6853. $^1$H-NMR (500 MHz, CDCl$_3$) δ 8.16-8.07 (m, 6H), 7.51-7.46 (m, 5H), 7.46-7.38 (m, 10H), 7.37-7.22 (m, 8H), 7.21-7.18 (m, 10H), 7.16-7.12 (m, 6H), 7.05 (d, J=10.1 Hz, 2H), 6.84 (d, J=9.3 Hz, 2H), 5.62 (bd, 1H), 5.35 (t, J=2.1 Hz, 1H), 5.15 (dd, J=3.3 Hz, J=10.0 Hz, 1H), 5.11 (d, J=3.6 Hz, 1H), 5.09 (d, J=3.8 Hz, 1H), 5.0 (d, J=11.5 Hz, 1H), 4.86 (d, J=7.0 Hz, 1H), 4.83 (d, J=7.5 Hz, 2H), 4.80 (d, J=11.6 Hz, 1H), 4.76-4.73 (m, 2H), 4.72 (d, J=10.4 Hz, 1H), 4.63 (d, J=4.1 Hz, 2H), 4.59-4.54 (m, 3H), 4.53-4.51 (m, 1H), 4.51 (d, J=3.5 Hz, 2H), 4.49 (d, J=10.3 Hz, 2H), 4.45-4.43 (m, 1H), 4.43-4.40 (m, 1H), 4.39-4.38 (m, 2H), 4.37-4.33 (m, 2H), 4.33-4.30 (m, 2H), 4.30-4.27 (m, 2H), 4.27-4.20 (m, 2H), 4.19-4.16 (m, 1H), 4.15 (d, J=2.8 Hz, 1H), 4.12-4.07 (m, 1H), 4.07-4.04 (m, 1H), 4.04 (d, J=4.0 Hz, 1H), 4.02 (d, J=4.5 Hz, 1H), 3.97 (d, J=10.2 Hz, 1H), 3.89-3.87 (m, 4H), 3.81 (d, J=4.2 Hz, 2H), 3.75 (s, 3H), 3.64 (d, J=9.8 Hz, 2H), 3.60 (d, J=9.1 Hz, 2H), 3.57 (dd, J=4.9 Hz, J=13.3 Hz, 1H), 3.41-3.35 (m, 1H), 3.31 (d, J=3.9 Hz, 1H), 3.29 (t, J=3.25 Hz, 1H), 3.27 (d, J=3.9 Hz, 1H), 3.23 (d, J=3.9 Hz, 2H), 3.21 (d, J=3.8 Hz, 1H), 3.07 (d, J=4.0 Hz, 1H), 2.02 (s, 3H), 2.016 (s, 3H), 2.01 (s, 3H); $^{13}$C-NMR (125 MHz, CDCl$_3$) δ 171.6, 171.1, 170.7, 170.6, 167.0, 165.8, 165.7, 165.52, 165.5, 155.2, 150.1, 137.8, 137.6, 137.3, 137.2, 133.5, 133.4, 130.9, 129.9, 129.8, 129.7, 129.5, 129.4, 128.7, 128.66, 128.6, 128.5, 128.4, 128.3, 128.2, 128.1, 128.0, 127.9, 127.7, 127.6, 125.7, 118.3, 114.6, 99.6, 98.9, 98.3, 98.2, 97.8, 97.5, 80.1, 79.8, 78.9, 78.7, 76.9, 75.4, 75.2, 74.9, 74.6, 74.5, 74.3, 74.2, 73.44, 73.4, 72.3, 72.1, 71.7, 71.3, 70.6, 70.5, 70.4, 70.3, 70.2, 68.3, 67.8, 67.6, 65.7, 64.9, 63.9, 63.6, 63.5, 63.3, 63.1, 62.9, 62.3, 62.2, 60.4, 55.7, 40.7, 40.51, 20.7.

Synthesis of 37

Compound 37 is prepared from compound 34 following general procedure D: 2.62 g, 80%, $R_f$=0.18 (Toluene/EtOAc 7:3). $^{13}$C-NMR (125 MHz, CDCl$_3$) δ 171.9, 170.5, 166.9, 166.4, 165.1, 165.0, 164.9, 155.7, 150.9, 138.3, 138.0, 137.8, 137.3, 137.2, 133.7, 133.5, 129.8, 129.5, 129.0, 128.95, 128.9, 128.8, 128.7, 128.6, 128.4, 128.3, 128.2, 128.1, 127.7, 127.5, 127.45, 127.3, 127.0, 125.3, 118.8, 114.5, 100.9, 100.8, 100.0, 98.3, 97.8, 97.7, 82.8, 82.7, 79.2, 77.7, 77.65, 77.6, 76.55, 75.4, 75.0, 74.9, 74.7, 74.6, 74.3, 73.6, 72.5, 72.3, 71.4, 70.6, 69.8, 64.9, 64.4, 64.2, 62.7, 61.9, 61.8, 55.6, 40.4, 40.3, 20.7

Synthesis of 38

Compound 38 is prepared from compound 36 and compound 24 following general procedure E: 272 mg, 80% yield (beta), $R_f$=0.15 (EtOAc:petroleum ether, 1:2). HRMS (ESI) calcd for $C_{170}H_{170}Cl_4N_{12}O_{52}Na(M+Na)^+$ m/z 3373.9672. found 3373.9951. $^1$H-NMR (500 MHz, CDCl$_3$) δ 8.16 (dd, J=7.0 Hz, J=9.7 Hz, 2H), 8.12-8.07 (m, 4H), 7.76 (d, J=7.8 Hz, 1H), 7.60 (d, J=7.6 Hz, 1H), 7.55 (d, J=7.6 Hz, 1H), 7.51 (bd, 1H), 7.49-7.46 (m, 6H), 7.46-7.43 (m, 8H), 7.43-7.40 (m, 8H), 7.40-7.37 (m, 5H), 7.37-7.35 (m, 4H), 7.35-7.30 (m, 8H), 7.29-7.24 (m, 6H), 7.23-7.19 (m, 2H), 7.19-7.16 (m, 4H), 7.15-7.12 (m, 4H), 7.08-7.05 (m, 2H), 7.05 (d, J=9.1 Hz, 2H), 6.85 (d, J=9.1 Hz, 2H), 5.63 (d, J=3.7 Hz, 1H), 5.35 (t, J=3.6 Hz, 1H), 5.16-5.11 (m, 3H), 5.10 (d, J=4.4 Hz, 1H), 5.08 (d, J=4.0 Hz, 1H), 5.01 (d, J=11.8 Hz, 1H), 4.86-4.79 (m, 8H), 4.78-4.71 (m, 6H), 4.71 (dd, J=4.7 Hz, J=10.2 Hz, 2H), 4.63 (d, J=3.9 Hz, 1H), 4.58-4.53 (m, 6H), 4.53 (d, J=5.5 Hz, 1H), 4.50 (d, J=4.3 Hz, 1H), 4.48-4.46 (m, 4H), 4.45-4.40 (m, 6H), 4.39-4.35 (m, 6H), 4.35-4.31 (m, 4H), 4.30-4.27 (m, 3H), 4.27-4.23 (m, 2H), 4.23-4.19 (m, 2H), 4.19-4.15 (m, 2H), 4.10-4.07 (m, 2H), 4.06-4.0 (m, 1H), 3.97 (d, J=11.4 Hz, 1H), 3.90-3.87 (m, 4H), 3.81 (d, J=4.7 Hz, 2H), 3.76 (s, 3H), 3.75-3.74 (m, 1H), 3.73-3.65 (m, 1H), 3.64 (q, J=8.1 Hz, 2H), 3.57 (t, J=8.8, 1H), 3.32 (d, J=3.5, 1H), 3.31-3.27 (m, 1H), 3.27 (t, J=3.0, 1H), 2.03 (s, 3H), 2.01 (s, 3H), 2.0 (s, 3H), 1.99 (3H); $^{13}$C NMR (125 MHz, CDCl$_3$) δ 170.6, 170.5, 170.4, 166.9, 166.8, 166.77, 166.7, 165.6, 165.5, 165.4, 155.3, 154.2, 150.2, 143.2, 143.1, 141.4, 137.7, 137.6, 137.3, 137.2, 137.16, 137.1, 133.6, 133.5, 129.9, 129.8, 129.5, 129.4, 128.8, 128.7, 128.5, 128.4, 128.35, 128.3, 128.27, 128.2, 128.1, 128.0, 127.9, 127.8, 127.7, 127.3, 125.1, 124.9, 120.2, 118.3, 114.6, 98.8, 98.3, 98.2, 98.1, 98.06, 98.0, 97.9, 97.8, 97.6, 79.0, 78.9, 78.7, 77.9, 76.9, 75.4, 75.3, 75.1, 75.0, 74.9, 74.7, 74.6, 74.3, 74.2, 74.0, 73.9, 73.5, 73.4, 72.4, 72.1, 70.4, 70.3, 70.2, 69.8, 68.3, 67.7, 67.5, 67.2, 65.7, 64.9, 64.7, 63.9, 63.8, 63.77, 63.7, 63.6, 63.58, 63.5, 63.1, 62.3, 62.2, 61.9, 55.7, 46.8, 40.7, 40.5, 20.8.

Synthesis of 39

Compound 39 is prepared from compound 36 and compound 25 following general procedure E: The residue is purified by silica gel chromatography (EtOAc: petroleum ether, 1:2) to furnish the disaccharide as a foam, 260 mg, 82% yield, $R_f$=0.22

(EtOAc:petroleum ether, 2:3). HRMS (ESI) calcd for $C_{162}H_{170}Cl_4N_{12}O_{50}Na(M+Na)^+$ m/z 3245.9781. found 3245.9404. $^1$H-NMR (500 MHz, CDCl$_3$) δ 8.15 (dd, J=6.8 Hz, J=9.5 Hz, 2H), 8.10-8.06 (m, 4H), 7.50-7.46 (m, 4H), 7.45-7.40 (m, 8H), 7.40-7.34 (m, 8H), 7.33-7.28 (m, 12H), 7.27-7.22 (m, 10H), 7.21-7.16 (m, 8H), 7.14-7.11 (m, 9H), 7.05 (d, J=9.5 Hz, 2H), 6.85 (d, J=8.9 Hz, 2H), 5.62 (d, J=3.4 Hz, 1H), 5.34 (t, J=3.7 Hz, 2H), 5.14-5.10 (m, 2H), 5.10 (t, J=3.9 Hz, 2H), 5.07 (d, J=4.1 Hz, 1H), 5.01 (d, J=11.6 Hz, 1H), 4.84-4.81 (m, 4H), 4.81-4.78 (m, 2H), 4.76-4.73 (m, 2H), 4.73-4.70 (m, 2H), 4.70 (d, J=5.0 Hz, 1H), 4.67 (bs, 2H), 4.63 (d, J=3.8 Hz, 1H), 4.57-4.53 (m, 2H), 4.53-4.48 (m, 3H), 4.48 (d, J=3.5 Hz, 1H), 4.46 (d, J=2.5 Hz, 1H), 4.44 (d, J=3.0 Hz, 2H), 4.42-4.40 (m, 4H), 4.40-4.38 (m, 4H), 4.35-4.29 (m, 2H), 4.29-4.24 (m, 4H), 4.24-4.18 (m, 4H), 4.18-4.15 (m, 2H), 4.08-4.05 (m, 2H), 4.05-3.99 (m, 4H), 3.97 (d, J=10.4 Hz, 1H), 3.88-3.87 (m, 6H), 3.81 (d, J=4.8 Hz, 2H), 3.77 (s, 3H), 3.75 (d, J=3.7 Hz, 1H), 3.73 (d, J=3.5 Hz, 1H), 3.71 (d, J=3.5 Hz, 1H), 3.69-3.64 (m, 2H), 3.62 (d, J=3.1 Hz, 1H), 3.60-3.58 (m, 2H), 3.58 (d, J=3.5 Hz, 1H), 3.56 (t, J=9.7 Hz, 2H), 3.44 (t, J=9.7 Hz, 2H), 3.30 (d, J=3.7 Hz, 1H), 3.28-3.23 (m, 1H), 2.01 (s, 6H), 1.99 (s, 3H), 1.97 (s, 3H); $^{13}$C NMR (CDCl$_3$) δ 170.5, 166.9, 166.8, 165.7, 165.5, 165.4, 155.2, 150.1, 137.7, 137.6, 137.4, 137.2, 137.1, 133.4, 129.8, 129.7, 129.5, 129.4, 128.9, 128.6, 128.4, 128.3, 128.2, 128.1, 128.0, 127.9, 127.7, 127.6, 127.5, 118.3, 114.5, 98.7, 98.3, 98.1, 98.0, 97.9, 97.8, 97.7, 97.5, 80.4, 78.9, 78.7, 78.6, 77.7, 75.4, 75.3, 75.2, 75.1, 74.9, 74.6, 74.5, 74.3, 74.2, 74.1, 74.0, 73.5, 72.4, 72.1, 70.3, 70.2, 70.1, 68.3, 67.7, 67.5, 65.7, 64.9, 63.8, 63.7, 63.5, 62.6, 62.1, 55.7, 40.6, 40.5, 20.7.

Synthesis of 40

Compound 40 is prepared from compound 37 and compound 22 following general procedure E: 1.4 g, quant (beta), $R_f$=0.4 (Toluene/EtOAc 4:1). $^{13}$C-NMR (125 MHz, CDCl$_3$) δ 170.6, 169.8, 166.6, 166.0, 165.9, 165.4, 165.1, 155.6, 154.1, 151.0, 143.2, 142.9, 141.3, 141.2, 137.9, 137.7, 137.3, 137.2, 137.0, 133.4, 133.2, 129.8, 129.7, 129.6, 129.5, 129.4, 129.0, 128.6, 128.4, 128.3, 128.2, 128.15, 128.1, 128.0, 127.9, 127.8, 127.7, 127.6, 125.3, 124.9, 120.0, 118.9, 114.5, 100.3, 98.3, 97.8, 97.7, 97.6, 97.5, 97.1, 82.8, 78.6, 78.5, 75.3, 75.1, 74.9, 74.1, 74.0, 73.8, 73.6, 73.4, 73.2, 72.7, 71.5, 70.5, 70.3, 70.1, 69.5, 68.6, 68.0, 67.4, 63.5, 63.4, 62.9, 62.8, 62.5, 62.2, 62.0, 61.9, 59.3, 59.2, 55.6, 46.7, 40.7, 20.7

Synthesis of 41

Compound 34 is prepared from compound 37 and compound 23 following general procedure E: 785 mg, 88% (beta), $R_1$=0.48 (toluene/EtOAc 4:1). $^{13}$C-NMR (125 MHz, CDCl$_3$) δ 170.4, 166.9, 166.4, 165.1, 165.0, 164.9, 155.7, 150.9, 138.2, 137.5, 137.2, 133.8, 133.7, 133.4, 129.8, 129.7, 129.5, 129.0, 128.9, 128.8, 128.6, 128.5, 128.3, 128.2, 128.1, 128.0, 127.7, 127.6, 127.5, 118.8, 114.5, 100.9, 100.8, 100.7, 100.0, 98.0, 97.8, 97.8, 97.7, 82.8, 82.7, 80.1, 77.8, 77.7, 77.6, 75.6, 75.5, 75.4, 75.2, 75.0, 74.9, 74.7, 74.6, 74.3, 74.2, 73.5, 72.4, 72.3, 70.3, 69.8, 65.0, 64.4, 64.2, 63.2, 62.7, 62.7, 62.6, 62.4, 61.9, 61.8, 61.7, 55.6, 40.5, 40.4, 40.3, 40.3, 20.7

Synthesis of 42

Compound 42 is prepared from compound 38 following general procedure D: The residue is purified by silica gel chromatography (EtOAc: petroleum ether, 1:1) to furnish the disaccharide as a foam, 170 mg, 86% yield, $R_f$=0.45 (EtOAc: petroleum ether, 1:1). HRMS (ESI) calcd for $C_{155}H_{160}Cl_4N_{12}O_{50}Na(M+Na)^+$ m/z 3151.8998. found 3151.8971. $^1$H-NMR (500 MHz, CDCl$_3$) δ 8.16 (dd, J=6.8 Hz, J=9.4 Hz, 2H), 8.11-8.07 (m, 6H), 7.51-7.38 (m, 6H), 7.37-7.27 (m, 5H), 7.27-7.16 (m, 5H), 7.46-7.38 (m, 8H), 7.37-7.22 (m, 10H), 7.21-7.18 (m, 12H), 7.15 (dd, J=6.1 Hz, J=8.4 Hz, 6H), 7.05 (d, J=8.9 Hz, 2H), 6.85 (d, J=9.1 Hz, 2H), 5.63 (bd, 1H), 5.35 (t, J=3.4 Hz, 1H), 5.15-5.11 (m, 2H), 5.11-5.06 (m, 2H), 5.01 (d, J=11.4 Hz, 1H), 4.85-4.79 (m, 2H), 4.78-4.74 (m, 5H), 4.74-4.66 (m, 10H), 4.63 (d, J=4.1 Hz, 2H), 4.58-4.54 (m, 8H), 4.53 (d, J=6.8 Hz, 2H), 4.51 (d, J=6.6 Hz, 4H), 4.47-4.43 (m, 6H), 4.43-4.39 (m, 4H), 4.36-4.26 (m, 4H), 4.26-4.19 (m, 2H), 4.19-4.16 (m, 2H), 4.09-4.06 (m, 1H), 4.05-3.99 (m, 2H), 3.97 (d, J=10.4 Hz, 1H), 3.89-3.86 (m, 4H), 3.82 (d, J=4.8 Hz, 2H), 3.76 (s, 3H), 3.75-3.71 (m, 2H), 3.71-3.65 (m, 2H), 3.63-3.57 (m, 2H), 3.56 (t, J=10.1 Hz, 1H), 3.44 (t, J=9.7 Hz, 1H), 3.31 (d, J=4.1 Hz, 1H), 3.29-3.24 (m, 2H), 2.01 (s, 3H), 2.01 (s, 3H), 2.0 (s, 3H), 2.0 (s, 3H) $^{13}$C-NMR (125 MHz, CDCl$_3$) δ 169.9, 168.9, 168.74, 168.7, 165.2, 164.9, 163.9, 163.7, 163.6, 153.4, 148.3, 135.9, 135.8, 135.4, 135.37, 135.35, 131.7, 128.0, 127.9, 127.7, 127.6, 126.8, 126.7, 126.6, 126.57, 126.5, 126.3, 126.28, 126.2, 125.9, 125.87, 125.8, 116.4, 112.7, 97.1, 96.4, 96.3, 96.1, 95.9, 95.7, 77.9, 77.2, 76.9, 73.6, 73.5, 73.47, 73.4, 73.3, 73.1, 72.8, 72.5, 72.3, 72.2, 71.6, 70.6, 70.3, 69.5, 68.7, 68.5, 68.4, 66.5, 65.9, 65.8, 65.7, 63.9, 63.1, 62.0, 61.8, 61.7, 61.6, 61.3, 60.9, 60.5, 60.3, 53.9, 38.8, 38.7, 18.9.

Synthesis of 136

Compound 136 is prepared from compound 137 following general procedure D: The residue is purified by silica gel chromatography (EtOAc: petroleum ether, 2:3) to furnish the disaccharide as a foam, 890 mg, 229 µmol, 97% yield; TLC (EtOAc:petroleum ether, 1:1, v/v): $R_f$=0.45; HRMS (ESI) calcd for $C_{192}H_{198}Cl_5N_{15}O_{62}Na_2(M+2Na)^{2+}$ m/z 1965.054. found 1965.0496. $^1$H-NMR (500 MHz, CDCl$_3$) δ 8.16-8.13 (m, 2H), 8.12-8.07 (m, 6H), 7.52-7.47 (m, 6H), 7.45-7.39 (m, 12H), 7.38-7.34 (m, 15H), 7.32-7.27 (m, 10H), 7.27-7.22 (m, 8H), 7.21-7.16 (m, 10H), 7.14-7.11 (m, 6H), 7.05 (d, J=8.9 Hz, 2H), 6.85 (d, J=9.1 Hz, 2H), 5.62 (d, J=3.5 Hz, 1H), 5.35 (d, J=3.4 Hz, 1H), 5.15-5.11 (m, 2H), 5.10-5.06 (m, 2H), 5.01 (d, J=11.4 Hz, 1H), 4.86-4.79 (m, 2H), 4.77-4.71 (m, 6H), 4.70-4.66 (m, 10H), 4.63 (d, J=4.0 Hz, 1H), 4.58-4.53 (m, 6H), 4.53-4.51 (m, 2H), 4.50 (d, J=3.5 Hz, 1H), 4.49-4.47 (m, 6H), 4.46-4.39 (m, 8H), 4.36-4.33 (m, 4H), 4.32-4.27 (m, 6H), 4.26-4.21 (m, 4H), 4.20-4.15 (m, 3H), 4.13-4.12 (m, 2H), 4.11 (d, J=7.1 Hz, 1H), 4.09-4.07 (m, 1H), 4.06-3.99 (m, 2H), 3.97-3.95 (m, 1H), 3.94-3.93 (m, 1H), 3.88-3.87 (m, 4H), 3.87-3.86 (m, 4H), 3.81 (d, J=5.0 Hz, 2H), 3.76 (s, 3H), 3.73-3.65 (m, 4H), 3.62-3.57 (m, 2H), 3.56-3.52 (m, 2H), 3.40-3.35 (m, 2H), 3.31 (d, J=4.1 Hz, 1H), 3.29-3.26 (m, 2H), 3.26 (d, J=4.3 Hz, 1H), 3.23 (d, J=3.7 Hz, 1H), 3.21 (d, J=3.7 Hz, 1H), 2.94 (d, J=4.8 Hz, 1H), 2.03 (s, 3H), 2.02 (s, 3H), 2.01 (s, 3H), 2.0 (s, 3H), 1.99 (s, 3H); $^{13}$C-NMR (125 MHz, CDCl$_3$) δ 171.6, 171.1, 170.7, 170.6, 170.5, 167.0, 166.8, 165.7, 165.5, 155.2, 150.2, 137.7, 137.6, 137.3, 137.2, 133.5, 129.9, 129.7, 129.5, 129.4, 128.7, 128.6, 128.5, 128.4, 128.3, 128.1, 127.7, 127.6, 118.3, 114.6, 98.9, 98.3, 98.1, 97.9, 97.8, 97.7, 97.5, 79.7, 78.9, 78.7, 75.4, 75.3, 75.2, 75.1, 74.9, 74.6, 74.3, 74.1, 73.5, 72.4, 72.1, 71.3, 70.6, 70.5, 70.4, 70.3, 70.2, 68.3, 67.8, 67.6, 67.5, 65.7, 64.9, 63.8, 63.6, 63.5, 63.1, 62.8, 62.3, 62.1, 60.4, 55.7, 40.6, 40.5, 21.0, 20.7

Synthesis of 43

Compound 43 is prepared from compound 40 following general procedure D: 960 mg, 72%, $R_f$=0.15 (toluene/EtOAc 7:3); $^{13}$C-NMR (125 MHz, CDCl$_3$) δ 171.9, 170.5, 170.4, 166.9, 166.4, 165.1, 165.0, 164.9, 155.7, 150.9, 138.3, 138.2, 138.0, 137.8, 137.3, 137.2, 133.7, 133.5, 129.8, 129.5, 129.0, 128.95, 128.9, 128.8, 128.7, 128.6, 128.4, 128.3, 128.2, 128.1, 127.7, 127.5, 127.45, 127.3, 127.0, 125.3, 118.8, 114.5, 100.9, 100.8, 100.7, 100.0, 98.3, 97.8, 97.7, 82.9, 82.8, 82.7, 79.2, 77.7, 77.65, 77.6, 76.55, 75.4, 75.0, 74.9, 74.7, 74.6, 74.3, 73.6, 72.5, 72.3, 71.4, 70.6, 69.8, 64.9, 64.4, 64.2, 62.7, 62.6, 61.9, 61.8, 61.7, 55.6, 40.4, 40.3, 20.7

Synthesis of 44

Compound 44 is prepared from compound 42 and compound 25 following general procedure E: The residue is purified by silica gel chromatography (EtOAc: petroleum ether, 1:2) to furnish the disaccharide as a foam, 173 mg, 89% yield, $R_f$=0.23 (EtOAc:petroleum ether, 1:2). HRMS (ESI) calcd for $C_{199}H_{204}Cl_5N_{15}O_{62}Na(M+Na)^+$ m/z 3993.16. found 3993.1611. $^1$H-NMR (500 MHz, CDCl$_3$) δ 8.16 (dd, J=7.0 Hz, J=9.7 Hz, 2H), 8.11-8.07 (m, 6H), 7.51-7.47 (m, 8H), 7.45-7.38 (m, 10H), 7.37-7.33 (m, 14H), 7.33-7.27 (m, 12H), 7.26-7.19 (m, 10H), 7.18-7.16 (m, 10H), 7.14-7.12 (m, 8H), 7.05 (d, J=9.1 Hz, 2H), 6.85 (d, J=9.1 Hz, 2H), 5.63 (d, J=4.0 Hz, 1H), 5.35 (t, J=3.8 Hz, 2H), 5.15-5.11 (m, 2H), 5.10-5.06 (m, 2H), 5.01 (d, J=11.4 Hz, 1H), 4.85-4.82 (m, 4H), 4.81-4.79 (m, 2H), 4.78-4.74 (m, 2H), 4.73-4.71 (m, 4H), 4.71-4.69 (m, 1H), 4.68-4.66 (m, 10H), 4.63 (d, J=3.9 Hz, 1H), 4.58-4.53 (m, 10H), 4.53-4.51 (m, 6H), 4.51 (d, J=3.9 Hz, 1H), 4.49-4.47 (m, 2H), 4.46-4.43 (m, 6H), 4.43-4.41 (m, 6H), 4.41-4.39 (m, 2H), 4.35-4.26 (m, 2H), 4.25-4.20 (m, 4H), 4.19-4.16 (m, 4H), 4.09-3.99 (m, 2H), 3.97 (d, J=9.9 Hz, 1H), 3.89-3.86 (m, 8H), 3.82 (d, J=5.4 Hz, 2H), 3.76 (s, 3H), 3.75 (bd, 1H), 3.74 (bd, 1H), 3.72 (bd, 1H), 3.70-3.65 (m, 2H), 3.63-3.58 (m, 2H), 3.58 (d, J=3.6 Hz, 1H), 3.56 (t, J=9.2 Hz, 1H), 3.44 (t, J=9.6 Hz, 2H), 3.31 (d, J=4.1 Hz, 1H), 3.29-3.27 (m, 1H), 3.27-3.24 (m, 1H), 2.014 (s, 3H), 2.012 (s, 3H), 2.0 (s, 3H), 1.99 (s, 3H), 1.97 (s, 3H); $^{13}$C NMR (CDCl$_3$) δ 168.8, 168.7, 168.6, 168.5, 165.1, 165.0, 164.9, 163.9, 163.7, 163.6, 163.5, 153.4, 148.4, 135.9, 135.8, 135.7, 135.5, 135.4, 135.3, 131.7, 131.6, 128.3, 128.1, 127.9, 127.7, 126.9, 126.8, 126.7, 126.6, 126.5, 126.4, 126.3, 126.2, 126.1, 125.9, 125.8, 116.5, 112.8, 96.9, 96.5, 96.3, 96.2, 96.1, 95.9, 95.8, 95.7, 78.6, 77.2, 77.0, 76.9, 75.9, 75.6, 75.3, 73.6, 73.5, 73.4, 73.3, 73.1, 72.8, 72.7, 72.5, 72.3, 71.7, 71.6, 70.6, 70.3, 68.6, 68.5, 68.4, 68.3, 66.5, 65.9, 65.8, 65.7, 65.6, 63.9, 63.1, 62.1, 61.9, 61.8, 61.7, 60.8, 60.5, 60.3, 53.9, 38.9, 38.7, 20.9.

Synthesis of 137

Compound 137 is prepared from compound 24 and compound 42 following general procedure E: 1.16 g, 0.282 mmol, 86% yield; TLC, (EtOAc:petroleum ether, 1:2 v/v): $R_f$=0.2. HRMS (ESI) calcd for $C_{207}H_{208}Cl_5N_{15}O_{64}Na(M+Na)^+$ m/z 4129.1865. found 4129.1802. $^1$H-NMR (500 MHz, CDCl$_3$) δ 8.17 (dd, J=6.7 Hz, J=9.6 Hz, 2H), 8.12-8.08 (m, 4H), 7.75 (d, J=2.5 Hz, 2H), 7.73 (d, J=2.5 Hz, 2H), 7.59 (d, J=7.4 Hz, 2H), 7.54 (d, J=7.6 Hz, 2H), 7.50-7.45 (m, 10H), 7.44-7.38 (m, 14H), 7.37-7.29 (m, 12H), 7.28-7.21 (m, 10H), 7.20-7.17 (m, 8H), 7.16-7.13 (m, 4H), 7.08-7.06 (m, 3H), 7.06 (d, J=9.0 Hz, 2H), 6.85 (d, J=9.0 Hz, 2H), 5.63 (d, J=3.7 Hz, 1H), 5.35 (t, J=3.6 Hz, 2H), 5.17-5.07 (m, 5H), 5.01 (d, J=12.0 Hz, 1H), 4.88-4.81 (m, 8H), 4.78-4.68 (m, 10H), 4.59-4.53 (m, 6H), 4.53 (d, J=5.0 Hz, 1H), 4.51 (d, J=5.0 Hz, 1H), 4.49-4.41 (m, 8H), 4.41-4.37 (m, 12H), 4.36-4.28 (m, 8H), 4.28-4.22 (m, 6H), 4.21-4.18 (m, 4H), 4.17-4.13 (m, 4H), 4.11-4.0 (m, 3H), 3.98 (d, J=10.5 Hz, 1H), 3.91-3.87 (m, 6H), 3.81 (d, J=5.0 Hz, 2H), 3.73 (s, 3H), 3.71-3.65 (m, 2H), 3.64-3.58 (m, 2H), 3.58-3.52 (m, 2H), 3.32-3.26 (m, 3H), 2.03 (s, 3H), 2.01 (s, 6H), 2.0 (s, 3H), 1.99 (3H); $^{13}$C-NMR (125 MHz, CDCl$_3$) δ 170.6, 170.5, 166.8, 165.7, 165.6, 165.5, 155.2, 154.2, 150.2, 143.2, 143.1, 141.4, 137.7, 137.6, 137.3, 137.2, 137.1, 133.5, 129.9, 129.8, 129.6, 129.5, 128.8, 128.7, 128.5, 128.4, 128.3, 128.2, 128.0, 127.9, 127.8, 127.3, 125.1, 124.8, 120.2, 118.3, 114.6, 98.8, 98.3, 98.2, 98.1, 97.9, 97.8, 97.5, 79.1, 78.9, 78.8, 75.4, 75.3, 75.1, 75.0, 74.7, 74.6, 74.2, 74.0, 73.9, 73.5, 73.4, 72.4, 72.1, 70.4, 70.3, 69.8, 68.8, 67.6, 67.2, 66.4, 65.7, 64.9, 63.9, 63.7, 63.6, 63.2, 62.4, 62.2, 62.0, 60.4, 55.7, 40.7, 40.6, 20.8, 20.7.

Synthesis of 138

Compound 138 is prepared from compound 25 and compound 136 following general procedure E: The residue is purified by silica gel chromatography (EtOAc: petroleum ether, 1:2) to furnish the disaccharide as a foam, 780 mg, 0.165 mmol, 92% yield; TLC (EtOAc:petroleum ether, 1:2, v/v): $R_f$=0.18; HRMS (ESI) calcd for $C_{236}H_{242}Cl_6N_{18}O_{74}Na_2(M+2Na)^{2+}$ m/z 2386.1851. found 2386.1833. $^1$H-NMR (500 MHz, CDCl$_3$) δ 8.16 (dd, J=7.0 Hz, J=9.6 Hz, 2H), 8.12-8.07 (m, 6H), 7.51-7.46 (m, 8H), 7.45-7.37 (m, 12H), 7.37-7.34 (m, 18H), 7.34-7.29 (m, 22H), 7.29-7.27 (m, 12H), 7.26-7.20 (m, 10H), 7.20-7.16 (m, 10H), 7.15-7.12 (m, 5H), 7.06 (d, J=9.2 Hz, 2H), 6.85 (d, J=9.2 Hz, 2H), 5.63 (d, J=4.0 Hz, 1H), 5.35 (t, J=3.9 Hz, 2H), 5.17-5.06 (m, 6H), 5.0 (d, J=12.0 Hz, 1H), 4.86-4.79 (m, 12H), 4.81-4.79 (m, 10H), 4.78-4.66 (m, 14H), 4.65 (d, J=4.6 Hz, 1H), 4.59-4.54 (m, 6H), 5.54 (t, J=10.2 Hz, 2H), 4.48-4.40 (m, 10H), 4.37-4.27 (m, 8H), 4.27-4.20 (m, 6H), 4.20-4.17 (m, 4H), 4.10-4.0 (m, 4H), 3.97-3.95 (m, 1H), 3.95-3.93 (m, 2H), 3.93-3.91 (m, 3H), 3.90-3.87 (m, 4H), 3.86-3.84 (m, 6H), 3.82 (d, J=4.2 Hz, 6H), 3.74 (s, 3H), 3.73-3.71 (m, 1H), 3.70-3.67 (m, 2H), 3.64-3.58 (m, 3H), 3.57-3.52 (m, 2H), 3.45-3.40 (m, 2H), 3.33-3.25 (m, 3H), 2.01 (s, 6H), 2.0 (s, 6H), 1.99 (s, 3H), 1.97 (s, 3H); $^{13}$C-NMR (125 MHz, CDCl$_3$) δ 170.7, 170.6, 170.5, 167.0, 166.9, 166.8, 165.8, 165.7, 165.6, 155.4, 150.3, 137.8, 137.7, 137.6, 137.4, 137.3, 133.6, 133.5, 129.9, 129.8, 129.6, 128.8, 128.7, 128.6, 128.5, 128.4, 128.36, 128.3, 128.2, 128.1, 128.0, 127.8, 127.7, 118.4, 116.6, 114.7, 98.9, 98.4, 98.3, 98.2, 98.1, 98.0, 97.9, 97.7, 91.9, 80.5, 79.1, 78.9, 78.8, 77.4, 77.1, 76.9, 75.5, 75.4, 75.3, 75.2, 75.1, 75.0, 74.7, 74.6, 74.3, 74.2, 73.6, 73.5, 72.5, 72.3, 70.5, 70.4, 70.2, 68.6, 68.4, 67.7, 67.6, 66.6, 66.5, 66.4, 66.3, 65.0, 63.9, 63.8, 63.7, 63.6, 62.7, 62.4, 62.3, 55.7, 40.8, 40.7, 19.3.

Synthesis of 45

Compound 45 is prepared from compound 43 and compound 23 following general procedure E: 1.05 g, 89% (beta), $R_f$=0.46 (Toluene/EtOAc 4:1). $^{13}$C-NMR (125 MHz, CDCl$_3$) δ 170.45, 170.44, 170.43, 170.38, 166.9, 166.4, 166.4, 165.1, 165.0, 164.9, 155.7, 150.9, 138.3, 138.26, 138.25 137.9, 137.5, 137.35, 137.3, 137.28, 137.26, 133.8, 133.7, 133.5, 129.8, 129.7, 129.5, 129.1, 129.0, 128.9, 128.8, 128.62, 128.59, 128.57, 128.4, 128.3, 128.2, 128.1, 128.0, 127.7, 127.6, 127.5, 127.4, 118.8, 114.5, 100.9, 100.8, 100.7 (2C), 100.0, 98.1, 97.9, 97.8 (2C), 97.7, 82.8, 82.7, 80.1, 77.8, 77.7, 77.6, 77.6, 77.5, 75.6, 75.5, 75.4, 75.2, 75.2, 75.1, 74.9, 74.7, 74.6, 74.3, 74.2, 74.2, 73.6, 72.4, 72.3, 70.4, 69.8, 65.0, 64.4, 64.2, 63.2, 62.7, 62.7, 62.6, 62.4, 61.9, 61.8, 61.7, 55.6, 40.5, 40.4, 40.3, 40.3, 20.8, 20.7

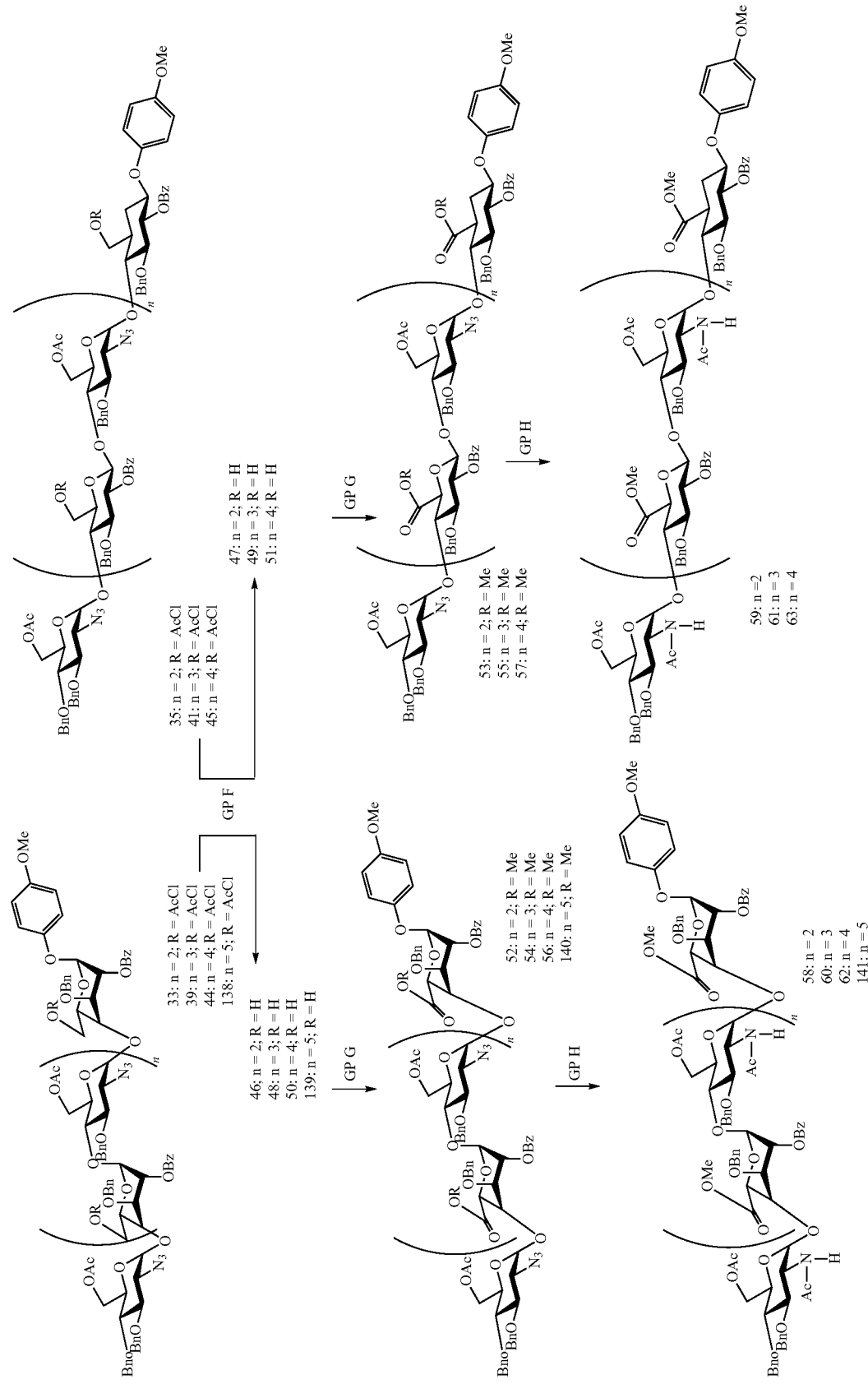

General Procedure F (GPF): Selective De-Chloroacetylation.

DABCO (6 equiv. per chloroacetyl group) is added to the starting material in dry ethanol (5 mL for 40 µmol) at room temperature. The mixture is heated at 60-70° C. under argon for 2 h. After TLC (EtOAc: petroleum ether, 3:2) indicated the completion of the reaction Dowex 50WX8-200 ion-exchange resin is added to neutralize the solution. After 15 min the resin is filtered off and the solution is concentrated to dryness. Chromatography (EtOAc: petroleum ether, 3:2) affords the products with unblocked primary hydroxyl groups.

Synthesis of 46

Compound 46 is prepared from compound 33 following general procedure F: The residue is purified by silica gel chromatography (EtOAc: petroleum ether, 1:1) to furnish the disaccharide as a foam, 330 mg, 98% yield, $R_f$=0.2 (EtOAc: petroleum ether, 1:1). HRMS (ESI) calcd for $C_{119}H_{125}N_9O_{35}Na(M+Na)^+$ m/z 2262.8176. found 2262.8201. $^1$H-NMR (500 MHz, CDCl$_3$) δ 8.15 (dd, J=6.2 Hz, J=9.6 Hz, 2H), 8.10-8.07 (m, 4H), 7.47-7.44 (m, 4H), 7.43-7.41 (m, 6H), 7.40-7.38 (m, 4H), 7.37-7.32 (m, 4H), 7.31-7.25 (m, 6H), 7.24-7.21 (m, 8H), 7.20-7.17 (m, 6H), 7.16-7.14 (m, 6H), 7.06 (d, J=9.5 Hz, 2H), 6.85 (d, J=8.9 Hz, 2H), 5.64 (d, J=4.0 Hz, 1H), 5.37 (t, J=3.1 Hz, 2H), 5.15 (t, J=3.3 Hz, 2H), 5.12 (t, J=2.6 Hz, 2H), 5.06 (d, J=2.6 Hz, 1H), 5.02 (d, J=6.6 Hz, 1H), 4.98 (bs, 1H), 4.88 (d, J=5.7 Hz, 1H), 4.85 (d, J=6.2 Hz, 1H), 4.82 (d, J=11.9 Hz, 1H), 4.76 (d, J=2.7 Hz, 1H), 4.74 (d, J=2.7 Hz, 1H), 4.72 (t, J=3.0 Hz, 2H), 4.68 (d, J=3.7 Hz, 1H), 4.63 (d, J=4.0 Hz, 1H), 4.51 (d, J=5.5 Hz, 1H), 4.49-4.46 (m, 2H), 4.46-4.44 (m, 2H), 4.39 (d, J=10.2 Hz, 1H), 4.33 (d, J=2.7 Hz, 1H), 4.31 (d, J=2.7 Hz, 1H), 4.29-4.25 (m, 2H), 4.25-4.21 (m, 2H), 4.25-4.17 (m, 2H), 4.16 (d, J=4.7 Hz, 1H), 4.14-4.10 (m, 1H), 4.05 (q, J=3.7 Hz, 2H), 3.98 (d, J=10.5 Hz, 1H), 3.96-3.93 (m, 1H), 3.87-3.82 (m, 1H), 3.79-3.76 (m, 3H), 3.75 (s, 3H), 3.73 (d, J=2.4 Hz, 1H), 3.68 (d, J=4.0 Hz, 1H), 3.66 (d, J=9.2 Hz, 1H), 3.62-3.57 (m, 1H), 3.57 (d, J=3.6 Hz, 1H), 3.53 (q, J=7.6 Hz, 2H), 3.42 (t, J=9.3 Hz, 2H), 3.35 (d, J=3.8 Hz, 1H), 3.33 (d, J=3.8 Hz, 1H), 3.32 (d, J=3.8 Hz, 1H), 3.30 (d, J=3.8 Hz, 1H), 3.28 (d, J=3.8 Hz, 1H), 3.27 (d, J=3.6 Hz, 1H), 3.25-3.22 (m, 1H), 2.01 (s, 3H), 2.00 (s, 3H), 1.98 (s, 3H); $^{13}$C-NMR (125 MHz, CDCl$_3$) δ 170.6, 170.5, 165.8, 165.7, 155.2, 150.4, 137.7, 137.6, 137.5, 137.4, 133.4, 133.3, 129.9, 129.8, 129.7, 129.6, 128.7, 128.6, 128.5, 128.4, 128.3, 128.2, 128.1, 128.0, 127.9, 127.8, 127.7, 127.5, 118.3, 114.7, 98.2, 97.9, 97.8, 97.7, 97.3, 97.2, 80.6, 79.3, 79.2, 77.8, 77.6, 76.8, 75.2, 75.1, 75.0, 74.6, 74.2, 74.0, 73.9, 73.4, 73.3, 73.2, 73.0, 72.9, 72.5, 72.3, 72.1, 70.5, 70.1, 70.0, 69.5, 69.2, 68.9, 68.1, 67.9, 67.8, 64.1, 63.9, 63.8, 63.1, 62.8, 62.7, 62.4, 61.6, 61.2, 61.1, 55.7, 20.8, 20.7.

Synthesis of 47

Compound 47 is prepared from compound 35 following general procedure F: 342 mg, 74%, $R_f$=0.17 (Toluene/EtOAc 7:3). $^{13}$C-NMR (125 MHz, CDCl$_3$) δ 170.6, 170.4, 165.0, 155.6, 151.1, 138.2, 138.1, 137.8, 137.6, 137.4, 137.3, 133.6, 133.5, 133.3, 129.8, 129.6, 129.1, 129.0, 128.7, 128.6, 128.5, 128.4, 128.3, 128.2, 128.1, 128.0, 128.0, 127.9, 127.7, 127.6, 127.5, 127.2, 127.1, 118.4, 114.6, 101.1, 101.0, 100.4, 97.6, 97.3, 97.2, 83.5, 83.35, 83.3, 80.3, 78.0, 77.9, 77.8, 77.7, 77.6, 75.5, 75.2, 75.1, 75.0, 74.9, 74.8, 74.5, 74.4, 73.9, 73.4, 73.3, 72.3, 70.0, 69.6, 69.5, 63.2, 62.9, 62.7, 62.6, 62.2, 62.1, 61.8, 61.5, 61.4, 55.6, 20.8

Synthesis of 48

Compound 48 is prepared from compound 39 following general procedure F: The residue is purified by silica gel chromatography (EtOAc: petroleum ether, 3:2) to furnish the disaccharide as a foam, 99 mg, 84% yield, $R_f$=0.25 (EtOAc: petroleum ether, 3:2). HRMS (ESI) calcd for $C_{154}H_{162}N_{12}O_{46}Na(M+Na)^+$ m/z 2938.0604. found 2938.0603. $^1$H-NMR (500 MHz, CDCl$_3$) δ 8.15 (dd, J=6.1 Hz, J=9.7 Hz, 2H), 8.10-8.07 (m, 4H), 7.46-7.44 (m, 4H), 7.43-7.39 (m, 6H), 7.39-7.36 (m, 4H), 7.36-7.33 (m, 4H), 7.33-7.30 (m, 6H), 7.30-7.26 (m, 8H), 7.24-7.21 (m, 2H), 7.20-7.17 (m, 6H), 7.16-7.14 (m, 6H), 7.07 (d, J=9.5 Hz, 2H), 6.84 (d, J=9.1 Hz, 2H), 5.64 (d, J=4.0 Hz, 1H), 5.36 (t, J=3.1 Hz, 2H), 5.15 (t, J=2.6 Hz, 2H), 5.13-5.10 (m, 2H), 5.07 (dd, J=4.2 Hz, J=7.8 Hz, 2H), 5.02 (d, J=12.5 Hz, 1H), 4.88 (d, J=7.2 Hz, 1H), 4.86 (bd, 1H), 4.85 (d, J=2.7 Hz, 1H), 4.82 (d, J=11.7 Hz, 1H), 4.77 (d, J=5.8 Hz, 1H), 4.74 (d, J=3.8 Hz, 1H), 4.72 (d, J=5.3 Hz, 1H), 4.68 (d, J=3.5 Hz, 1H), 4.63 (d, J=4.1 Hz, 1H), 4.51 (bs, 1H), 4.49 (t, J=3.8 Hz, 2H), 4.46 (d, J=3.5 Hz, 1H), 4.39 (d, J=10.6 Hz, 1H), 4.33-4.30 (m, 5H), 4.28-4.25 (m, 3H), 4.24-4.21 (m, 4H), 4.21-4.16 (m, 6H), 4.16-4.11 (m, 5H), 4.05 (q, J=3.7 Hz, 2H), 4.01-4.0 (m, 3H), 3.98-3.93 (m, 3H), 3.87-3.82 (m, 2H), 3.81-3.76 (m, 3H), 3.75 (s, 3H), 3.74 (d, J=6.1 Hz, 1H), 3.68 (d, J=9.1 Hz, 1H), 3.66 (d, J=9.0 Hz, 1H), 3.64 (bs, 1H), 3.63-3.57 (m, 1H), 3.57-3.54 (m, 1H), 3.53-3.45 (m, 2H), 3.42 (t, J=9.8 Hz, 2H), 3.35 (d, J=3.8 Hz, 1H), 3.34 (q, J=2.2 Hz, 2H), 3.32 (d, J=3.7 Hz, 1H), 3.30 (d, J=4.0 Hz, 1H), 3.28 (d, J=3.6 Hz, 1H), 3.26 (d, J=3.7 Hz, 1H), 3.25-3.18 (m, 1H), 2.01 (s, 3H), 2.01 (s, 6H), 2.01 (s, 3H), 1.98 (s, 3H); $^{13}$C-NMR (125 MHz, CDCl$_3$) δ 170.6, 170.5, 165.8, 165.5, 155.2, 150.4, 137.7, 137.4, 137.3, 133.3, 130.8, 129.8, 129.7, 129.6, 128.6, 128.5, 128.4, 128.2, 128.0, 127.9, 127.8, 118.4, 114.7, 98.2, 97.9, 97.4, 97.3, 80.6, 79.3, 79.2, 77.9, 77.4, 76.8, 75.2, 75.1, 75.0, 74.6, 74.2, 74.0, 73.9, 73.8, 73.3, 73.2, 73.15, 73.1, 72.9, 72.3, 72.1, 70.5, 70.1, 70.0, 69.5, 69.2, 69.1, 68.9, 68.0, 67.9, 67.8, 67.7, 64.1, 64.0, 63.8, 62.8, 62.7, 62.4, 61.6, 61.2, 61.1, 55.6, 20.8.

Synthesis of 49

Compound 49 is prepared from compound 41 following general procedure F: 820 mg, 95%, $R_f$=0.1 (Toluene/EtOAc 7:3). $^{13}$C-NMR (125 MHz, CDCl$_3$) δ 170.6, 170.4, 165.0, 155.6, 151.1, 138.24, 138.2, 138.17, 137.9, 137.6, 137.44, 137.4, 133.7, 133.6, 133.4, 129.8, 129.6, 129.1, 129.0, 128.7, 128.6, 128.5, 128.3, 128.2, 128.1, 128.0, 128.0, 127.9, 127.7, 127.6, 127.2, 127.1, 118.4, 114.6, 101.1, 101.0, 100.9, 100.4, 97.6, 97.3, 97.2, 83.5, 83.4, 83.35, 80.3, 78.0, 77.9, 77.8, 77.7, 77.6, 75.6, 75.2, 75.1, 75.0, 74.9, 74.8, 74.5, 74.4, 73.9, 73.5, 73.4, 72.3, 70.0, 69.6, 69.5, 63.2, 62.9, 62.8, 62.7, 62.6, 62.2, 62.0, 61.8, 61.5, 61.4, 61.3, 55.6, 20.8

Synthesis of 50

Compound 50 is prepared from compound 44 following general procedure F: The residue is purified by silica gel chromatography (EtOAc: petroleum ether, 3:2) to furnish the disaccharide as a foam, 115 mg, 83% yield, $R_f$=0.25 (EtOAc: petroleum ether, 3:2). HRMS (ESI) calcd for $C_{189}H_{199}N_{15}O_{57}Na(M+Na)^+$ m/z 3613.3085. found 3613.3083. $^1$H-NMR (500 MHz, CDCl$_3$) δ 8.15 (dd, J=6.4 Hz, J=9.1 Hz, 2H), 8.10-8.07 (m, 6H), 7.47-7.44 (m, 4H), 7.43-7.40 (m, 6H), 7.40-7.36 (m, 10H), 7.37-7.32 (m, 8H), 7.32-7.30 (m, 12H), 7.30-7.25 (m, 12H), 7.24-7.21 (m, 8H), 7.20-7.16 (m, 6H), 7.16-7.14 (m, 6H), 7.07 (d, J=9.1 Hz, 2H), 6.84 (d, J=9.1 Hz, 2H), 5.65 (d, J=4.0 Hz, 1H), 5.37 (t, J=3.1 Hz, 2H), 5.15-5.10 (m, 6H), 5.06-5.02 (m, 4H), 5.02 (d, J=11.1 Hz, 1H), 4.88-4.83 (m, 3H), 4.82 (d, J=12.3 Hz, 1H), 4.77 (d, J=4.6 Hz, 1H), 4.74-4.70 (m, 10H), 4.68-4.65 (m, 12H), 4.63 (d, J=3.8 Hz, 1H), 4.51 (bs, 1H), 4.49-4.43 (m, 6H), 4.39 (d, J=10.3 Hz, 1H), 4.33-4.30 (m, 6H), 4.26-4.21 (m, 3H), 4.21-4.17 (m, 6H), 4.16-4.10 (m, 3H), 4.05-4.0 (m, 3H), 3.99-3.94 (m, 3H), 3.87-3.82 (m, 2H), 3.81-3.77 (m, 3H), 3.76 (s, 3H), 3.75-3.72 (m, 1H), 3.68 (d, J=9.0 Hz, 1H), 3.66 (d, J=9.0 Hz, 1H), 3.62-3.57 (m, 1H), 3.57-3.53 (m, 1H), 3.52-3.45 (m, 2H), 3.41 (t, J=8.1 Hz, 2H), 3.35 (d, J=3.8 Hz, 1H), 3.34 (d, J=3.6 Hz, 1H), 3.32 (d, J=3.7 Hz, 1H), 3.30 (dd, J=4.0 Hz, J=9.0 Hz, 2H), 3.29 (t, J=5.6 Hz, 2H), 3.27 (d, J=3.8 Hz, 1H), 3.24-3.18 (m, 1H), 2.009 (s, 6H), 2.004 (s, 6H), 1.98 (s, 3H); $^{13}$C-NMR (125 MHz, CDCl$_3$) δ 170.6, 170.5, 165.9, 165.8, 165.7, 155.3, 150.4, 137.7, 137.6, 137.5, 137.4, 133.4, 133.3, 130.9, 129.9, 129.84, 129.8, 129.7, 129.66, 129.6, 128.6, 128.58, 128.57, 128.5, 128.47, 128.4, 128.23, 128.22, 128.18, 128.14, 128.1, 128.0, 127.9, 127.93, 127.9, 127.8, 118.4, 114.7, 98.2, 98.1 (3C), 97.9 (3C), 97.8, 97.7, 97.3, 80.6, 79.3, 79.2, 77.8, 77.4, 77.1, 76.9, 75.2, 75.1, 75.0, 74.6, 74.2, 74.0, 73.9, 73.8, 73.5, 73.4, 73.3, 73.2, 73.1, 73.0, 72.9, 72.3, 72.1, 70.5, 70.1, 70.05, 70.0, 69.5, 69.2, 69.1, 68.9, 68.0, 67.9, 67.8, 67.7, 64.1, 64.0, 63.8, 62.8, 62.4, 61.6, 61.2, 61.1, 61.0, 55.7, 20.8.

Synthesis of 139

Compound 139 is prepared from compound 138 following general procedure F: The residue is purified by silica gel chromatography (EtOAc: toluene, 3:2) to furnish the disaccharide as a foam (518 mg, 121 μmol, 80% yield); TLC (EtOAc:petroleum ether, 3:2, v/v): R$_f$=0.22; HRMS (ESI) calcd for C$_{224}$H$_{236}$N$_{18}$O$_{68}$Na$_2$(M+2Na)$^{2+}$ m/z 2156.7711. found 2156.7732. $^1$H-NMR (500 MHz, CDCl$_3$) δ 8.16 (dd, J=6.0 Hz, J=9.7 Hz, 2H), 8.12-8.08 (m, 6H), 7.47 (d, J=7.2 Hz, 2H), 7.43-7.38 (m, 12H), 7.37-7.31 (m, 14H), 7.31-7.24 (m, 18H), 7.24-7.21 (m, 22H), 7.21-7.16 (m, 14H), 7.16-7.10 (m, 5H), 7.07 (d, J=9.0 Hz, 2H), 6.84 (d, J=9.0 Hz, 2H), 5.64 (d, J=4.0 Hz, 1H), 5.37 (t, J=3.3 Hz, 2H), 5.17-5.11 (m, 6H), 5.08-5.05 (m, 4H), 5.04-5.02 (m, 1H), 5.01 (d, J=11.0 Hz, 1H), 4.89-4.83 (m, 5H), 4.82 (d, J=11.7 Hz, 1H), 4.77-4.76 (m, 1H), 4.75-4.73 (m, 8H), 4.73-4.71 (m, 6H), 4.71-4.69 (m, 4H), 4.69-4.65 (m, 12H), 4.62 (d, J=3.9 Hz, 1H), 4.52-4.43 (m, 8H), 4.40 (d, J=11.0 Hz, 1H), 4.35-4.23 (m, 7H), 4.23-4.12 (m, 8H), 4.07-4.01 (m, 4H), 3.98 (d, J=10.3 Hz, 1H), 3.88-3.79 (m, 6H), 3.79-3.73 (m, 3H), 3.72 (s, 3H), 3.69-3.66 (m, 2H), 3.65-3.58 (m, 2H), 3.58-3.55 (m, 2H), 3.54-3.46 (m, 4H), 3.41 (t, J=9.1 Hz, 2H), 3.35-3.29 (m, 4H), 3.29-3.27 (m, 2H), 3.27-3.20 (m, 5H), 2.0 (s, 12H), 1.99 (s, 3H), 1.97 (s, 3H); $^{13}$C-NMR (125 MHz, CDCl$_3$) δ 170.6, 170.5, 165.9, 165.8, 165.7, 155.3, 150.5, 137.9, 137.8, 137.6, 137.5, 137.4, 133.4, 130.0, 129.9, 129.7, 129.1, 128.6, 128.5, 128.4, 128.3, 128.2, 128.1, 127.9, 127.8, 125.4, 118.4, 114.7, 98.2, 97.9, 97.8, 97.4, 80.7, 79.4, 79.3, 77.0, 75.2, 75.1, 74.7, 74.3, 74.1, 73.9, 73.8, 73.4, 73.2, 73.0, 72.9, 72.3, 72.1, 70.5, 70.2, 69.6, 69.3, 69.2, 68.9, 68.1, 67.9, 67.8, 64.2, 64.1, 63.8, 62.8, 62.5, 61.6, 61.2, 55.7, 20.8, 20.7.

Synthesis of 51

Compound 51 is prepared from compound 45 following general procedure F: 760 mg, 92%, R$_f$=0.07 (Toluene/EtOAc 7:3). $^{13}$C-NMR (125 MHz, CDCl$_3$) δ 170.6, 170.5, 170.45, 170.4, 165.0, 155.6, 151.1, 138.3, 138.2, 138.1, 137.9, 137.6, 137.4, 137.3, 133.7, 133.6, 133.4, 129.8, 129.6, 129.1, 129.0, 128.7, 128.6, 128.5, 128.4, 128.3, 128.2, 128.1, 128.0, 128.0, 127.9, 127.8, 127.7, 127.6, 127.2, 127.1, 118.4, 114.6, 101.1, 101.0, 100.9 (2C), 100.4, 97.6, 97.3 (3C), 97.2, 83.5, 83.4, 83.35, 80.3, 78.0, 77.9, 77.8, 77.7, 77.6, 77.5, 75.6, 75.3, 75.2, 75.1, 75.0, 74.9, 74.8, 74.6, 74.5, 74.4, 73.9, 73.5, 73.45, 73.4, 72.3, 70.0, 69.6, 69.5, 63.3, 62.9, 62.8, 62.7, 62.6, 62.2, 62.0, 61.8, 61.5, 61.4, 61.3, 55.6, 20.8

General Procedure G1 (GPG1): TEMPO/BAIB Oxidation and Esterification by Diazomethane.

A solution of starting material in acetonitrile (5 mL for 32 μmol) and water (0.9 mL) is treated with TEMPO (0.2 equiv.) and BAIB (2.5 equiv. per hydroxyl group) at room temperature for 4-24 hours. After TLC (EtOAc: petroleum ether, 3:2) indicates the completion of the reaction chloroform and water are added. The solution is acidified with diluted HCl, back-extracted with chloroform, dried and concentrated. The residue is dissolved in dry ether and treated with an excess of freshly prepared diazomethane solution in ether until TLC (EtOAc: petroleum ether, 2:3) indicates the formation of methyl esters. The residues are purified by silica gel chromatography (EtOAc: petroleum ether, 2:3) to furnish the esters.

General Procedure G2 (GPG2): TEMPO/BAIB Oxidation and Esterification with TMS-Diazomethane.

A solution of starting material in acetonitrile (5 mL for 32 μmol) and water (0.9 mL) is treated with TEMPO (0.2 equiv.) and BAIB (2.5 equiv. per hydroxyl group) at room temperature for 4-24 hours. After TLC (EtOAc: petroleum ether, 3:2) indicated the completion of the reaction chloroform and water are added. The solution is acidified with diluted HCl, back-extracted with chloroform, dried and concentrated. The residue is dissolved in diethyl ether/methanol (3:2) and a 2M solution of TMS-diazomethane in hexane (1.5 eq per carboxylate) is added dropwise at 0° C. After completion (TLC: Tol/EtOAc 3:2), 0.5 mL acetic acid are added to quench the reaction. Solvents are evaporated in vacuo and the residues are purified by silica gel chromatography to furnish the esters.

General Procedure G3 (GPG3): TEMPO/BAIB Oxidation and Esterification with Iodomethane A solution of starting material in acetonitrile (5 mL for 32 μmol) and water (0.9 mL) is treated with TEMPO (0.2 equiv.) and BAIB (2.5 equiv. per hydroxyl group) at room temperature for 4-24 hours. After TLC (EtOAc: petroleum ether, 3:2) indicates the completion of the reaction chloroform and water are added. The solution is acidified with diluted HCl, back-extracted with chloroform, dried and concentrated. The residue is dissolved in anhydrous DMF (100 mL per mmol). Potassium bicarbonate (20 eq) and iodomethane (15 eq) are added and the mixture is stirred at ambient temperature for 12-24 h. The reaction mixture is concentrated and partitioned between ethyl acetate and water, washed with brine, dried over magnesium sulfate and concentrated. Purification on silica gel furnishes the esters.

Synthesis of 52

Compound 52 is prepared from compound 46 following general procedure G1: The residue is purified by silica gel chromatography (EtOAc: petroleum ether, 1:2) to furnish the disaccharide as a foam, 280 mg, 82% yield, R$_f$=0.75 (EtOAc: petroleum ether, 1:1). HRMS (ESI) calcd for C$_{122}$H$_{125}$N$_9$O$_{38}$Na(M+Na)$^+$ m/z 2346.8023. found 2346.8005. $^1$H-NMR (500 MHz, CDCl$_3$) δ 8.13-8.10 (m, 4H), 8.09 (dd, J=7.1 Hz, J=9.3 Hz, 2H), 7.55-7.47 (m, 4H), 7.47-7.40 (m, 6H), 7.37-7.32 (m, 4H), 7.31-7.28 (m, 4H), 7.28-7.26 (m, 6H), 7.25-7.22 (m, 8H), 7.18-7.15 (m, 6H), 7.15-7.12 (m, 6H), 7.03 (d, J=8.7 Hz, 2H), 6.81 (d, J=9.4 Hz, 2H), 5.72 (d, J=3.9 Hz, 1H), 5.49 (d, J=4.9 Hz, 1H), 5.45 (d, J=5.4 Hz, 1H), 5.32 (t, J=2.3 Hz, 2H), 5.19-5.14 (m, 1H), 4.99 (d, J=2.4 Hz, 1H), 4.97 (t, J=4.0 Hz, 2H), 4.91 (d, J=2.6 Hz, 1H), 4.89 (d, J=4.0 Hz, 1H), 4.81-4.78 (m, 1H), 4.78-4.75 (m, 1H), 4.74 (d, J=3.6 Hz, 1H), 4.72 (d, J=3.9 Hz, 1H), 4.66 (d, J=3.9 Hz, 1H), 4.58 (d, J=10.9 Hz, 1H), 4.48 (bs, 1H), 4.47 (d, J=3.0 Hz, 1H), 4.44-4.42 (m, 1H), 4.42 (d, J=5.4 Hz, 1H), 4.32 (d, J=2.1 Hz, 1H), 4.30-4.28 (m, 1H), 4.27 (d, J=2.2 Hz, 1H), 4.25-4.23 (m, 1H), 4.23 (d, J=3.6 Hz, 2H), 4.21-4.17 (m, 2H), 4.16 (d, J=2.2 Hz, 1H), 4.14 (t, J=6.0 Hz, 2H), 4.07-4.03 (m, 1H), 3.96-3.91 (m, 1H), 3.89 (t, J=7.8 Hz, 2H), 3.81 (d, J=3.7 Hz, 1H), 3.79-3.76 (m, 1H), 3.75 (s, 3H), 3.67 (d, J=9.6 Hz, 1H), 3.63 (s, 3H), 3.60 (d, J=8.9 Hz, 1H), 3.57 (d, J=9.1 Hz, 1H), 3.54 (s, 3H), 3.52 (d, J=9.4 Hz, 1H), 3.49 (d, J=2.8 Hz, 1H), 3.47 (d, J=2.6 Hz, 1H), 3.45 (s, 3H), 3.28 (d, J=3.6 Hz, 1H), 3.26 (d, J=3.7 Hz, 1H), 3.25 (t, J=3.5 Hz, 2H), 3.23 (t, J=3.2 Hz, 2H), 2.077 (s, 3H), 2.073 (s, 3H), 1.97 (s, 3H); $^{13}$C-NMR (CDCl$_3$) δ 170.7, 170.6, 170.5, 169.5, 169.4, 169.2, 165.6, 165.2, 155.3, 150.5, 137.9, 137.8, 137.7, 137.6, 137.55, 137.5, 137.4, 137.3, 133.6, 133.5, 129.96, 129.9, 129.5, 129.2, 129.0, 128.8, 128.7, 128.5, 128.4, 128.2, 128.1, 128.0, 127.9, 127.8, 127.5, 125.3, 117.9, 114.7, 99.1, 98.9, 98.6, 98.5, 98.4, 98.2, 98.1, 79.9, 78.4, 78.3, 77.5, 77.3, 77.0, 75.9, 75.5, 75.4, 75.0, 74.8, 74.7, 74.4, 74.3, 74.1, 72.9, 72.5, 71.5, 69.8, 69.7, 68.1, 63.5, 63.4, 63.2, 62.3, 61.7, 55.7, 52.1, 52.0, 51.7, 21.4, 20.8.

Synthesis of 53

Compound 53 is prepared from compound 47 following general procedure G3: 179 mg, 75%, $R_f$=0.55 (Toluene/ EtOAc 4:1). $^{13}$C-NMR (125 MHz, CDCl$_3$) δ 170.6, 170.5, 168.1, 167.7, 167.6, 165.0, 164.7, 155.7, 151.0, 138.2, 138.1, 137.9, 137.6, 137.5, 137.3, 137.2, 137.1, 133.7, 133.5, 129.95, 129.9, 129.8, 129.4, 129.1, 129.0, 128.9, 128.8, 128.6, 128.4, 128.3, 128.1, 128.0, 127.9, 127.8, 127.7, 127.6, 127.5, 118.7, 114.5, 101.11, 101.1, 100.7, 97.7, 97.3, 97.2, 82.9, 82.6, 82.2, 80.2, 78.0, 77.8, 77.6, 77.5, 75.6, 75.3, 75.0, 74.95, 74.9, 74.8, 74.7, 74.5, 74.4, 74.3, 74.1, 73.8, 73.6, 73.5, 69.9, 69.15, 69.1, 63.4, 62.8, 62.2, 61.55, 61.5, 55.6, 52.7, 52.1, 52.0, 20.9, 20.8

Synthesis of 54

Compound 54 is prepared from compound 48 following general procedure G1: The residue is purified by silica gel chromatography (EtOAc: petroleum ether, 2:3) to furnish the disaccharide as a foam, 72 mg, 80% yield, $R_f$=0.5 (EtOAc: petroleum ether, 2:3). HRMS (ESI) calcd for C$_{158}$H$_{162}$N$_{12}$O$_{50}$Na(M+Na)$^+$ m/z 3050.04. found 3050.0403. $^1$H-NMR (500 MHz, CDCl$_3$) δ 8.14-8.06 (m, 8H), 7.56-7.48 (m, 4H), 7.48-7.43 (m, 6H), 7.43-7.39 (m, 10H), 7.38-7.33 (m, 12H), 7.33-7.28 (m, 5H), 7.28-7.22 (m, 6H), 7.22-7.17 (m, 8H), 7.16-7.10 (m, 6H), 7.03 (d, J=8.7 Hz, 2H), 6.81 (d, J=9.3 Hz, 2H), 5.71 (d, J=3.9 Hz, 1H), 5.50 (d, J=5.1 Hz, 1H), 5.47 (d, J=6.0 Hz, 1H), 5.45 (d, J=6.0 Hz, 1H), 5.31 (t, J=2.4 Hz, 2H), 5.19-5.14 (m, 2H), 4.98 (bs, 1H), 4.97-4.94 (m, 3H), 4.92 (d, J=3.9 Hz, 1H), 4.90-4.88 (m, 3H), 4.82-4.74 (m, 4H), 4.72-4.67 (m, 2H), 4.66 (d, J=5.2 Hz, 1H), 4.58 (d, J=11.1 Hz, 1H), 4.49-4.46 (m, 2H), 4.45-4.40 (m, 2H), 4.36 (d, J=5.9 Hz, 1H), 4.32-4.30 (m, 5H), 4.29-4.21 (m, 3H), 4.21-4.15 (m, 4H), 4.15-4.10 (m, 3H), 4.09-4.02 (m, 2H), 3.96-3.92 (m, 2H), 3.91 (d, J=6.3 Hz, 1H), 3.88-3.83 (m, 2H), 3.80-3.72 (m, 2H), 3.75 (s, 3H), 3.68 (d, J=10.5 Hz, 1H), 3.63 (s, 3H), 3.61 (d, J=9.8 Hz, 1H), 3.57 (d, J=5.6 Hz, 1H), 3.53 (s, 3H), 3.52 (d, J=7.0 Hz, 1H), 3.48 (s, 3H), 3.47-3.45 (m, 2H), 3.44 (s, 3H), 3.30-3.27 (m, 1H), 3.27 (d, J=2.3 Hz, 1H), 3.26-3.24 (m, 2H), 3.24-3.22 (m, 2H), 3.21 (d, J=3.4 Hz, 1H), 2.07 (s, 3H), 2.06 (s, 6H), 1.96 (s, 3H); $^{13}$C-NMR (125 MHz, CDCl$_3$) δ 170.67, 170.6, 170.5, 169.5, 169.4, 169.2, 165.6, 165.2, 155.3, 150.5, 137.8, 137.7, 137.6, 137.3, 137.2, 133.7, 133.6, 129.96, 129.9, 129.86, 129.5, 129.2, 129.1, 128.8, 128.7, 128.5, 128.47, 128.4, 128.37, 128.3, 128.2, 128.1, 127.9, 127.8, 127.9, 127.8, 127.7, 127.6, 127.5, 117.9, 114.7, 99.1, 98.9, 98.7, 98.6, 98.3, 98.2, 98.1, 98.0, 79.9, 78.4, 77.5, 77.3, 77.1, 76.8, 76.2, 75.9, 75.8, 75.6, 75.1, 75.0, 74.9, 74.7, 74.6, 74.3, 74.1, 72.8, 72.5, 71.7, 71.1, 70.9, 70.5, 70.1, 69.8, 69.7, 68.1, 63.5, 63.4, 63.2, 63.1, 63.0, 62.3, 61.8, 61.6, 55.7, 52.1, 52.0, 20.7.

Synthesis of 55

Compound 55 is prepared from compound 49 following general procedure G2: 426 mg, 59%, $R_f$=0.5 (Toluene/EtOAc 4:1). $^{13}$C-NMR (125 MHz, CDCl$_3$) δ 170.65, 170.6, 168.1, 167.8, 167.6, 165.1, 164.75, 164.7, 155.8, 151.0, 138.2, 138.1, 137.9, 137.7, 137.6, 137.3, 137.2, 137.1, 133.8, 133.5, 129.9, 129.8, 129.5, 129.1, 129.0, 128.9, 128.8, 128.6, 128.4, 128.3, 128.1, 128.0, 127.9, 127.8, 127.7, 127.6, 118.8, 114.6, 101.2, 100.8, 97.7, 97.4, 97.3, 82.9, 82.6, 82.2, 80.3, 77.9, 75.6, 75.3, 75.1, 75.0, 74.7, 74.6, 74.5, 74.3, 74.1, 73.8, 73.6, 70.0, 69.2, 63.5, 62.8, 62.3, 61.5, 55.6, 52.8, 52.1, 52.0, 20.9

Synthesis of 56

Compound 56 is prepared from compound 50 following general procedure G1: The residue is purified by silica gel chromatography (EtOAc: petroleum ether, 2:3) to furnish the disaccharide as a foam, 92 mg, 77% yield, $R_f$=0.45 (EtOAc: petroleum ether, 2:3). HRMS (ESI) calcd for C$_{134}$H$_{199}$N$_{15}$O$_{62}$Na(M+Na)$^+$ m/z 3753.284. found 3753.281. $^1$H-NMR (500 MHz, CDCl$_3$) δ 8.13-8.07 (m, 10H), 7.57-7.52 (m, 4H), 7.52 (d, J=8.3 Hz, 1H), 7.49-7.43 (m, 10H), 7.43-7.39 (m, 8H), 7.38-7.33 (m, 14H), 7.33-7.28 (m, 10H), 7.28-7.23 (m, 12H), 7.22-7.16 (m, 6H), 7.15-7.10 (m, 4H), 7.03 (d, J=8.9 Hz, 2H), 6.81 (d, J=9.4 Hz, 2H), 5.71 (d, J=3.9 Hz, 1H), 5.50 (t, J=4.4 Hz, 2H), 5.47 (d, J=2.9 Hz, 1H), 5.45 (t, J=5.6 Hz, 2H), 5.32 (t, J=3.2 Hz, 2H), 5.20-5.13 (m, 2H), 4.99-4.94 (m, 2H), 4.93-4.88 (m, 2H), 4.82-4.79 (m, 4H), 4.79-4.75 (m, 2H), 4.75 (d, J=3.9 Hz, 1H), 4.72 (d, J=4.1 Hz, 1H), 4.69-4.67 (m, 4H), 4.67-4.64 (m, 4H), 4.58 (d, J=11.1 Hz, 1H), 4.50-4.46 (m, 3H), 4.45-4.41 (m, 2H), 4.40 (d, J=5.9 Hz, 1H), 4.36 (d, J=5.3 Hz, 1H), 4.32-4.30 (m, 3H), 4.30-4.27 (m, 5H), 4.27-4.21 (m, 4H), 4.21-4.15 (m, 2H), 4.15-4.11 (m, 3H), 4.11-4.08 (m, 3H), 4.08-4.03 (m, 2H), 3.97-3.90 (m, 2H), 3.89-3.82 (m, 2H), 3.80-3.77 (m, 2H), 3.75 (s, 3H), 3.74-3.70 (m, 2H), 3.68-3.65 (m, 2H), 3.63 (s, 3H), 3.61 (d, J=9.9 Hz, 1H), 3.57 (d, J=2.0 Hz, 1H), 3.53 (s, 3H), 3.51-3.50 (m, 1H), 3.48 (s, 3H), 3.46 (s, 3H), 3.43 (s, 3H), 3.30 (t, J=3.5 Hz, 2H), 3.28-3.26 (m, 1H), 3.26 (t, J=3.3 Hz, 2H), 3.24 (d, J=3.6 Hz, 1H), 3.22 (d, J=3.8 Hz, 1H), 2.07 (s, 6H), 2.06 (s, 6H), 1.96 (s, 3H); $^{13}$C-NMR (125 MHz, CDCl$_3$) δ 170.7, 170.64, 170.6, 170.5, 169.6, 169.55, 169.5, 169.2, 165.6, 165.22, 165.2, 165.19, 165.17, 155.3, 150.5, 137.8, 137.7, 137.66, 137.6, 137.5, 137.4, 137.3, 137.1, 133.8, 133.6, 133.5, 129.9, 129.8, 129.5, 129.2, 129.1, 128.8, 128.7, 128.5, 128.49, 128.4, 128.39, 128.37, 128.3, 128.2, 128.15, 128.1, 128.0, 127.95, 127.9, 127.8, 127.7, 127.6, 127.5, 117.97, 114.7, 99.1, 98.9, 98.8, 98.7, 98.6, 98.4, 98.2, 98.1, 98.03, 98.01, 80.0, 78.4, 78.1, 77.7, 76.2, 75.9, 75.8, 75.6, 75.5, 75.1, 75.0, 74.9, 74.7, 74.6, 74.4, 74.1, 72.9, 71.8, 71.7, 71.6, 71.3, 71.2, 70.9, 70.6, 70.1, 69.8, 69.7, 68.1, 63.2, 61.8, 61.7, 55.7, 52.1, 52.0, 51.8, 20.8.

Synthesis of 140

Compound 140 is prepared from compound 139 following general procedure G1: The residue is purified by silica gel chromatography (EtOAc: petroleum ether, 1:1) to furnish the disaccharide as a foam (325 mg, 73.3 μmol, 76% yield); TLC (EtOAc:petroleum ether, 2:3, v/v): $R_f$=0.41; HRMS (ESI) calcd for C$_{230}$H$_{236}$N$_{18}$O$_{74}$Na$_2$(M+2Na)$^{2+}$ m/z 2241.2573. found 2241.2549. $^1$H-NMR (500 MHz, CDCl$_3$) δ 8.14-8.06 (m, 10H), 7.57-7.52 (m, 4H), 7.52 (d, J=7.3 Hz, 2H), 7.49-7.43 (m, 10H), 7.43-7.40 (m, 8H), 7.37-7.33 (m, 14H), 7.32-7.27 (m, 18H), 7.26-7.21 (m, 14H), 7.21-7.15 (m, 10H), 7.15-7.11 (m, 5H), 7.03 (d, J=9.1 Hz, 2H), 6.81 (d, J=9.1 Hz, 2H), 5.72 (d, J=3.8 Hz, 1H), 5.51-5.41 (m, 4H), 5.32 (t, J=3.2 Hz, 2H), 5.20-5.14 (m, 3H), 4.99-4.95 (m, 3H), 4.94-4.87 (m, 5H), 4.84-4.73 (m, 6H), 4.72-4.68 (m, 8H), 4.67-4.64 (m, 4H), 4.58 (d, J=10.8 Hz, 1H), 4.50-4.41 (m, 5H), 4.40-4.37 (m, 6H), 4.36 (d, J=5.0 Hz, 1H), 4.33-4.28 (m, 7H), 4.27-4.16 (m, 6H), 4.16-4.12 (m, 4H), 4.11-4.09 (m, 4H), 4.08-4.03 (m, 3H), 3.97-3.90 (m, 5H), 3.89-3.82 (m, 4H), 3.81-3.75 (m, 3H), 3.74 (s, 3H), 3.68-3.65 (m, 2H), 3.64 (s, 3H), 3.62-3.54 (m, 4H), 3.53 (s, 3H), 3.51-3.50 (m, 1H), 3.49 (s, 3H), 3.47 (s, 3H), 3.46 (s, 3H), 3.43 (s, 3H), 3.31-3.27 (m, 3H), 3.26-3.24 (m, 2H), 3.24 (d, J=3.4 Hz, 1H), 3.22 (d, J=3.6 Hz, 1H), 2.07 (s, 9H), 2.06 (s, 6H), 1.96 (s, 3H); $^{13}$C-NMR (125 MHz, CDCl$_3$) δ 170.7, 170.6, 170.5, 169.6, 169.5, 169.2, 165.6, 165.2, 155.3, 150.5, 137.8, 137.7, 137.6, 137.5, 137.4, 137.3, 133.8, 133.6, 133.5, 129.9, 129.5, 129.2, 129.1, 128.8, 128.7, 128.5, 128.4, 128.3, 128.2, 128.1, 128.05, 128.01, 127.9, 127.8, 127.7, 127.6, 127.5, 117.9, 114.6, 99.1, 98.9, 98.7, 98.4, 98.2, 98.0, 80.0, 78.4, 78.1, 76.9, 76.3, 76.2, 76.1, 75.9, 75.8, 75.6, 75.5, 75.0, 74.9, 74.7, 74.4, 74.1, 72.8, 72.5, 71.8, 71.7, 71.6, 71.3, 71.2, 71.1, 70.9, 70.5, 70.1, 69.8, 69.7, 68.1, 66.6, 66.5, 63.5, 63.4, 63.2, 63.0, 62.3, 61.7, 61.6, 60.4, 55.7, 52.1, 52.0, 51.8, 20.8.

Synthesis of 57

Compound 57 is prepared from compound 51 following general procedure G2: 426 mg, 51%, $R_f$=0.46 (Toluene/ EtOAc 4:1). $^{13}$C-NMR (125 MHz, CDCl$_3$) δ 170.6, 170.5, 168.0, 167.7, 167.5, 165.0, 164.65, 164.6, 155.7, 150.9, 138.1, 138.05, 138.0, 137.6, 137.5, 137.2, 137.1, 137.0, 133.7, 133.5, 129.9, 129.8, 129.4, 129.3, 129.0, 128.9, 128.8, 128.3, 128.2, 128.1, 127.9, 127.8, 127.7, 127.6, 118.7, 114.5, 101.1, 100.7, 97.7, 97.2, 97.1, 82.9, 82.6, 82.2, 80.2, 77.8, 75.6, 75.3, 75.0, 74.9, 74.8, 74.7, 74.6, 74.5, 74.4, 74.2, 74.0, 73.7, 73.5, 69.8, 69.0, 62.7, 61.5, 61.4, 61.3, 55.6, 52.7, 52.0, 51.9, 20.8

General Procedure H (GPH): Reduction of Azide Group.

Thiolacetic acid (1 mL for 20 μmol) is added to the starting material in dry pyridine (1 mL for 20 μmol) at room temperature. The reaction mixture is stirred at room temperature for 48-72 hours. After TLC (EtOAc:Toluene, 4:1) indicates the completion of the reaction toluene is added and the solution is washed with water, diluted HCl and NaHCO$_3$ solution (sat., aq.), dried and concentrated. Chromatography (EtOAc:Toluene, 4:1) affords N-acetylated products.

Synthesis of 58

Compound 58 is prepared from compound 52 following general procedure H: The residue is purified by silica gel chromatography (Toluene: EtOAc, 1:4) to furnish the disaccharide as a foam, 215 mg, 83% yield, $R_f$=0.68 (EtOAc: petroleum ether, 4:1). HRMS (ESI) calcd for $C_{128}H_{137}N_3O_{41}Na(M+Na)^+$ m/z 2394.8625. found 2394.8635. $^1$H-NMR (500 MHz, CDCl$_3$) 7.95-7.90 (m, 6H), 7.49-7.42 (m, 6H), 7.39-7.31 (m, 12H), 7.28-7.20 (m, 10H), 7.20-7.12 (m, 10H), 7.10-7.06 (m, 6H), 6.95 (d, J=9.3 Hz, 2H), 6.73 (d, J=8.8 Hz, 2H), 5.78 (d, J=9.1 Hz, 1H), 5.70 (d, J=9.1 Hz, 1H), 5.59 (d, J=3.5 Hz, 1H), 5.28-5.25 (m, 1H), 5.24 (d, J=4.9 Hz, 1H), 5.16 (d, J=9.1 Hz, 1H), 5.12 (t, J=4.2 Hz, 2H), 5.10 (t, J=4.2 Hz, 2H), 4.89-4.85 (m, 1H), 4.84 (d, J=3.6 Hz, 1H), 4.80 (d, J=11.5 Hz, 1H), 4.74 (d, J=4.7 Hz, 1H), 4.71-4.69 (m, 1H), 4.68 (d, J=10.5 Hz, 1H), 4.63 (d, J=10.0 Hz, 1H), 4.59 (d, J=3.6 Hz, 1H), 4.55 (d, J=11.5 Hz, 1H), 4.50 (d, J=11.0 Hz, 1H), 4.38 (t, J=11.0 Hz, 2H), 4.31-4.28 (m, 1H), 4.26-4.20 (m, 1H), 4.19 (d, J=4.3 Hz, 1H), 4.17-4.15 (m, 1H), 4.14-4.11 (m, 1H), 4.11-4.08 (m, 2H), 4.07-4.04 (m, 1H), 4.03 (m, 1H), 4.02 (t, J=3.4 Hz, 2H), 4.0 (d, J=4.6 Hz, 1H), 3.97 (d, J=4.8 Hz, 1H), 3.95 (t, J=3.5 Hz, 2H), 3.93 (t, J=4.2 Hz, 2H), 3.90-3.84 (m, 1H), 3.73 (t, J=2.3 Hz, 2H), 3.71 (t, J=3.1 Hz, 2H), 3.67 (s, 3H), 3.66-3.64 (m, 1H), 3.60-3.58 (m, 1H), 3.58-3.54 (m, 1H), 3.54-3.53 (m, 1H), 3.51 (s, 6H), 3.43-3.37 (m, 1H), 3.37-3.30 (m, 1H), 3.29 (s, 3H), 2.02 (s, 6H), 2.01 (s, 3H), 1.42 (s, 3H), 1.32 (s, 3H), 1.24 (s, 3H); $^{13}$C-NMR (125 MHz, CDCl$_3$) δ 171.1, 170.9, 170.6, 170.2, 170.1, 169.9, 169.2, 169.0, 165.6, 165.4, 155.4, 150.42, 138.4, 138.3, 138.0, 137.8, 137.0, 136.8, 133.9, 133.8, 129.7, 129.0, 128.9, 128.6, 128.56, 128.5, 128.46, 128.2, 128.1, 128.0, 127.9, 127.7, 127.6, 127.4, 127.2, 118.1, 114.7, 98.4, 98.3, 98.25, 98.2, 98.1, 98.0, 97.9, 80.5, 78.2, 78.1, 77.3, 77.0, 75.1, 74.96, 74.9, 74.7, 74.2, 73.9, 73.7, 73.6, 73.2, 72.9, 72.8, 72.7, 72.5, 71.5, 71.3, 70.5, 70.4, 70.3, 70.2, 70.1, 68.7, 62.4, 61.7, 61.6, 55.6, 52.4, 52.1, 52.0, 51.9, 51.7, 22.9, 22.7, 22.6, 21.0, 20.9, 20.7.

Synthesis of 59

Compound 59 is prepared from compound 53 following general procedure H: 124 mg, 75%; $^{13}$C-NMR (125 MHz, CDCl$_3$) δ 170.7, 170.6, 170.1, 167.6, 167.4, 155.7, 150.8, 138.7, 138.1, 137.7, 136.5, 136.4, 136.3, 133.8, 133.6, 129.8, 129.2, 129.0, 128.8, 128.6, 128.55, 128.5, 128.45, 128.3, 128.2, 128.15, 128.1, 128.0, 127.9, 127.8, 127.5, 127.4, 127.3, 118.6, 114.5, 101.2, 101.1, 100.9, 99.5, 99.0, 98.7, 81.6, 81.4, 80.8, 80.5, 78.0, 77.9, 77.8, 75.4, 75.25, 75.2, 75.15, 75.0, 74.95, 74.85, 74.8, 74.4, 74.3, 73.9, 73.7, 73.6, 70.7, 70.2, 70.1, 62.2, 61.5, 61.4, 55.6, 52.8, 52.6, 52.5, 52.1, 52.0, 22.65, 22.6, 20.8, 20.77, 20.7

Synthesis of 60

Compound 60 is prepared from compound 54 following general procedure H: The residue is purified by silica gel chromatography (Toluene: EtOAc, 1:4) to furnish the disaccharide as a foam, 36 mg, 70% yield, $R_f$=0.5 (EtOAc:Toluene, 4:1). HRMS (ESI) calcd for $C_{166}H_{178}N_4O_{54}Na(M+Na)^+$ m/z 3114.1203. found 3114.1204. $^1$H-NMR (500 MHz, CDCl$_3$) 8.02 (d, J=10.1 Hz, 6H), 7.57-7.50 (m, 6H), 7.47-7.39 (m, 6H), 7.36-7.27 (m, 12H), 7.27-7.24 (m, 10H), 7.24-7.18 (m, 10H), 7.18-7.14 (m, 6H), 7.13-7.10 (m, 6H), 7.01 (d, J=9.2 Hz, 2H), 6.80 (d, J=9.2 Hz, 2H), 5.81 (d, J=9.5 Hz, 1H), 5.78 (d, J=9.3 Hz, 1H), 5.75 (d, J=9.4 Hz, 1H), 5.66 (d, J=2.0 Hz, 1H), 5.36-5.32 (m, 1H), 5.31 (t, J=5.1 Hz, 2H), 5.21-5.15 (m, 2H), 4.95-4.92 (m, 1H), 4.92 (t, J=3.5 Hz, 2H), 4.88 (d, J=11.5 Hz, 1H), 4.81 (d, J=3.8 Hz, 1H), 4.79 (t, J=4.3 Hz, 2H), 4.75 (d, J=4.5 Hz, 1H), 4.73-4.69 (m, 3H), 4.69 (d, J=2.1 Hz, 1H), 4.66 (bs, 1H), 4.64-4.61 (m, 3H), 4.61-4.58 (m, 2H), 4.58 (d, J=4.1 Hz, 1H), 4.55 (d, J=3.6 Hz, 1H), 4.46 (d, J=11.0 Hz, 1H), 4.41 (d, J=11.5 Hz, 1H), 4.36-4.34 (m, 4H), 4.33-4.25 (m, 4H), 4.23-4.21 (m, 5H), 4.21-4.19 (m, 2H), 4.19-4.17 (m, 2H), 4.17-4.13 (m, 2H), 4.13 (d, J=11.5 Hz, 1H), 4.09-4.05 (m, 1H), 4.05 (d, J=4.7 Hz, 1H), 4.02-4.0 (m, 1H), 4.0-3.95 (m, 1H), 3.81-3.79 (m, 1H), 3.79-3.76 (m, 1H), 3.75 (s, 3H), 3.74-3.70 (m, 1H), 3.67-3.61 (m, 1H), 3.59 (s, 3H), 3.57 (s, 3H), 3.50 (d, J=10.1 Hz, 1H), 3.47 (d, J=3.8 Hz, 1H), 3.44 (d, J=2.4 Hz, 1H), 3.42-3.39 (m, 1H), 3.39-3.37 (m, 1H), 3.35 (s, 3H), 3.34 (s, 3H), 2.09 (s, 3H), 2.08 (s, 3H), 2.07 (s, 3H), 1.98 (s, 3H), 1.49 (s, 3H), 1.389 (s, 3H), 1.384 (s, 3H), 1.31 (s, 3H); $^{13}$C-NMR (CDCl$_3$) δ 170.9, 170.6, 170.1, 169.9, 169.2, 165.6, 165.4, 155.4, 150.4, 138.4, 138.0, 137.8, 137.0, 136.8, 136.4, 133.8, 129.8, 129.0, 128.9, 128.6, 128.5, 128.4, 128.3, 128.2, 128.15, 128.1, 128.0, 127.7, 127.6, 127.4, 127.2, 126.9, 118.0, 114.7, 98.4, 98.37, 98.3, 98.2, 98.15, 98.1, 97.95, 97.9, 80.5, 78.1, 77.3, 77.0, 76.8, 75.4, 75.2, 75.1, 74.96, 74.9, 74.7, 73.7, 73.2, 72.9, 72.8, 72.5, 71.6, 71.4, 70.5, 70.4, 70.2, 68.7, 68.3, 62.4, 61.5, 61.6, 55.7, 52.6, 52.4, 52.37, 52.3, 52.0, 51.7, 29.7, 29.3, 20.9, 20.7.

Synthesis of 61

Compound 61 is prepared from compound 55 following general procedure H: 316 mg, 75%. $^{13}$C-NMR (125 MHz, CDCl$_3$) δ 170.7, 170.65, 170.6, 170.2, 170.1, 167.7, 167.5, 167.4, 167.3, 165.0, 164.9, 164.8, 155.7, 150.9, 138.8, 138.7, 138.1, 137.9, 137.7, 136.5, 136.4, 136.35, 136.3, 133.9, 133.6, 129.8, 129.75, 129.2, 129.1, 128.9, 128.8, 128.65, 128.6, 128.55, 128.55, 128.5, 128.4, 128.3, 128.25, 128.2, 128.1, 128.05, 128.0, 127.95, 127.85, 127.8, 127.55, 127.5, 127.45, 127.4, 127.35, 118.6, 114.5, 101.1, 100.9, 99.5, 99.0, 98.7, 98.6, 81.6, 81.4, 80.9, 80.5, 78.0, 77.9, 77.8, 76.7, 76.6, 75.4, 75.2, 75.1, 75.0, 74.95, 74.9, 74.8, 74.5, 74.45, 74.4, 73.8, 73.65, 73.6, 73.55, 70.7, 70.2, 70.1, 62.2, 61.5, 61.4, 55.6, 52.8, 52.7, 52.5, 52.1, 52.0, 22.7, 22.65, 22.65, 22.6, 21.5, 20.8, 20.75, 20.7

Synthesis of 62

Compound 62 is prepared from compound 56 following general procedure H: The residue is purified by silica gel chromatography (Toluene: EtOAc, 1:4) to furnish the disaccharide as a foam, 69 mg, 90% yield, $R_f$=0.5 (EtOAc:Toluene, 4:1). HRMS (ESI) calcd for $C_{204}H_{219}N_5O_{67}Na(M+Na)^+$ m/z 3833.398. found 3833.397. $^1$H-NMR (500 MHz, $CDCl_3$) 8.02-7.98 (m, 8H), 7.57-7.50 (m, 6H), 7.47-7.39 (m, 8H), 7.36-7.28 (m, 14H), 7.27-7.23 (m, 18H), 7.23-7.14 (m, 16H), 7.13-7.09 (m, 10H), 7.01 (d, J=8.8 Hz, 2H), 6.81 (d, J=9.1 Hz, 2H), 5.84-5.79 (m, 1H), 5.79 (d, J=10.3 Hz, 1H), 5.66 (d, J=3.4 Hz, 1H), 5.40-5.35 (m, 1H), 5.35-5.32 (m, 1H), 5.30-5.26 (m, 2H), 5.24 (d, J=8.5 Hz, 1H), 5.18-5.13 (m, 2H), 4.95-4.93 (m, 1H), 4.92-4.89 (m, 2H), 4.87 (d, J=11.4 Hz, 1H), 4.81 (d, J=4.0 Hz, 1H), 4.79-4.76 (m, 4H), 4.75-4.72 (m, 4H), 4.72-4.70 (m, 4H), 4.69-4.67 (m, 3H), 4.67-4.65 (m, 4H), 4.64-4.61 (m, 3H), 4.60-4.58 (m, 4H), 4.58-4.56 (m, 2H), 4.55 (d, J=3.6 Hz, 1H), 4.46-4.39 (m, 1H), 4.38-4.34 (m, 3H), 4.33-4.27 (m, 3H), 4.27 (d, J=4.2 Hz, 1H), 4.23-4.21 (m, 3H), 4.21-4.19 (m, 2H), 4.18-4.14 (m, 2H), 4.13-4.11 (m, 2H), 4.10-4.06 (m, 1H), 4.05 (d, J=5.1 Hz, 1H), 4.03-4.0 (m, 3H), 4.0-3.96 (m, 4H), 3.95-3.91 (m, 1H), 3.80-3.78 (m, 1H), 3.78-3.76 (m, 1H), 3.75 (s, 3H), 3.74-3.73 (m, 1H), 3.72-3.70 (m, 1H), 3.66-3.60 (m, 2H), 3.58 (s, 3H), 3.57 (s, 3H), 3.50-3.47 (m, 2H), 3.46-3.42 (m, 1H), 3.42-3.38 (m, 1H), 3.36 (s, 3H), 3.34 (s, 3H), 3.33 (s, 3H), 3.28 (d, J=6.0 Hz, 1H), 2.09 (s, 3H), 2.08 (s, 3H), 2.07 (s, 6H), 1.98 (s, 3H), 1.49 (s, 3H), 1.38 (s, 6H), 1.37 (s, 3H), 1.31 (s, 3H); $^{13}$C-NMR ($CDCl_3$) δ 171.1, 170.9, 170.6, 170.2, 169.9, 169.2, 169.0, 165.6, 165.4, 165.3, 155.4, 150.4, 138.4, 138.0, 137.8, 137.1, 136.8, 136.4, 133.9, 130.9, 129.7, 129.1, 129.0, 128.9, 128.6, 128.5, 128.2, 128.1, 128.0, 127.7, 127.4, 127.2, 127.1, 127.06, 127.0, 118.1, 114.7, 98.4, 98.33, 98.3, 98.25, 98.2, 98.1, 97.96, 97.9, 97.75, 97.7, 80.5, 78.2, 78.1, 77.3, 77.1, 75.2, 75.1, 74.98, 74.9, 74.7, 74.1, 73.7, 73.6, 72.9, 72.8, 72.6, 71.7, 71.5, 71.3, 70.5, 70.4, 70.2, 68.7, 68.3, 64.7, 62.5, 61.6, 55.7, 52.4, 52.1, 51.9, 51.7, 22.9, 22.7, 20.9, 20.8.

Synthesis of 141

Compound 141 is prepared from compound 140 following general procedure H: The residue is purified by silica gel chromatography (Toluene: EtOAc, 1:4) to furnish the disaccharide as a clear syrup, 212 mg, 46.8 μmol, 92% yield; TLC (Toluene: EtOAc, 1:4, v/v): $R_f$=0.45; HRMS (ESI) calcd for $C_{242}H_{260}N_6O_{60}Na_2(M+2Na)^{2+}$ m/z 2288.8162. found 2288.8108; $^1$H-NMR (500 MHz, $CDCl_3$) 8.03-7.97 (m, 8H), 7.58-7.50 (m, 4H), 7.48-7.39 (m, 5H), 7.36-7.28 (m, 14H), 7.28-7.22 (m, 28H), 7.22-7.14 (m, 22H), 7.14-7.1 (m, 12H), 7.02 (d, J=9.1 Hz, 2H), 6.81 (d, J=9.1 Hz, 2H), 5.88-5.79 (m, 3H), 5.67 (d, J=2.1 Hz, 1H), 5.35-5.32 (m, 2H), 5.32-5.25 (m, 3H), 5.19-5.13 (m, 3H), 4.97-4.94 (m, 1H), 4.93-4.89 (m, 2H), 4.88 (d, J=11.9 Hz, 1H), 4.82-4.76 (m, 6H), 4.75-4.70 (m, 10H), 4.70-4.68 (m, 8H), 4.68-4.62 (m, 12H), 4.61-4.58 (m, 3H), 4.58-4.54 (m, 3H), 4.47-4.43 (m, 3H), 4.43-4.35 (m, 4H), 4.34-4.25 (m, 5H), 4.25-4.23 (m, 1H), 4.22-4.19 (m, 2H), 4.19-4.15 (m, 3H), 4.15-4.12 (m, 1H), 4.11-4.06 (m, 2H), 4.06 (d, J=5.5 Hz, 1H), 4.04-4.01 (m, 2H), 4.0-3.91 (m, 5H), 3.81-3.77 (m, 2H), 3.74 (s, 3H), 3.68-3.60 (m, 4H), 3.59 (s, 3H), 3.58 (s, 3H), 3.51-3.49 (m, 1H), 3.49 (d, J=2.2 Hz, 1H), 3.47-3.45 (m, 1H), 3.45-3.43 (m, 1H), 3.43-3.38 (m, 2H), 3.37 (s, 3H), 3.35 (s, 3H), 3.34 (s, 3H), 3.33 (s, 3H), 2.1 (s, 3H), 2.09 (s, 3H), 2.08 (s, 3H), 2.07 (s, 6H), 1.98 (s, 3H), 1.49 (s, 3H), 1.39 (s, 3H), 1.38 (s, 6H), 1.37 (s, 3H), 1.31 (s, 3H); $^{13}$C-NMR (125 MHz, $CDCl_3$) δ 171.0, 170.6, 170.2, 169.9, 169.2, 169.0, 165.6, 165.4, 155.4, 150.4, 138.4, 138.0, 137.8, 137.0, 136.8, 133.9, 130.8, 129.7, 128.9, 128.6, 128.5, 128.2, 128.0, 127.7, 127.6, 127.4, 127.2, 127.1, 127.0, 125.3, 118.1, 114.7, 98.3, 98.1, 97.9, 97.8, 80.5, 78.2, 76.9, 75.1, 74.9, 74.8, 74.6, 74.1, 73.7, 73.5, 73.2, 72.9, 72.7, 72.6, 72.5, 71.6, 71.5, 70.5, 70.4, 70.2, 68.7, 68.3, 68.2, 62.4, 61.6, 60.4, 55.6, 52.4, 52.1, 52.0, 51.8, 51.7, 22.9, 22.7, 21.5, 20.9, 20.7.

Synthesis of 63

Compound 63 is prepared from compound 57 following general procedure H: 280 mg, 78%. $^{13}$C-NMR (125 MHz, $CDCl_3$) δ 170.7, 170.6, 170.2, 167.7, 167.4, 167.35, 167.3, 165.0, 164.9, 164.8, 155.7, 150.9, 138.8, 138.1, 137.9, 137.7, 136.5, 136.4, 136.3, 133.9, 133.6, 129.8, 129.2, 129.1, 128.8, 128.7, 128.6, 128.35, 128.3, 128.2, 128.1, 128.0, 127.8, 127.5, 127.4, 118.6, 114.5, 101.2, 100.9, 99.6, 99.0, 98.75, 98.7, 81.6, 81.4, 80.8, 80.6, 78.1, 77.8, 77.6, 75.4, 75.3, 75.0, 74.9, 74.8, 74.5, 74.45, 74.4, 73.9, 73.6, 70.7, 70.2, 70.1, 62.2, 61.5, 61.4, 60.4, 55.6, 53.5, 52.9, 52.7, 52.5, 52.1, 52.0, 22.7, 21.5, 20.8

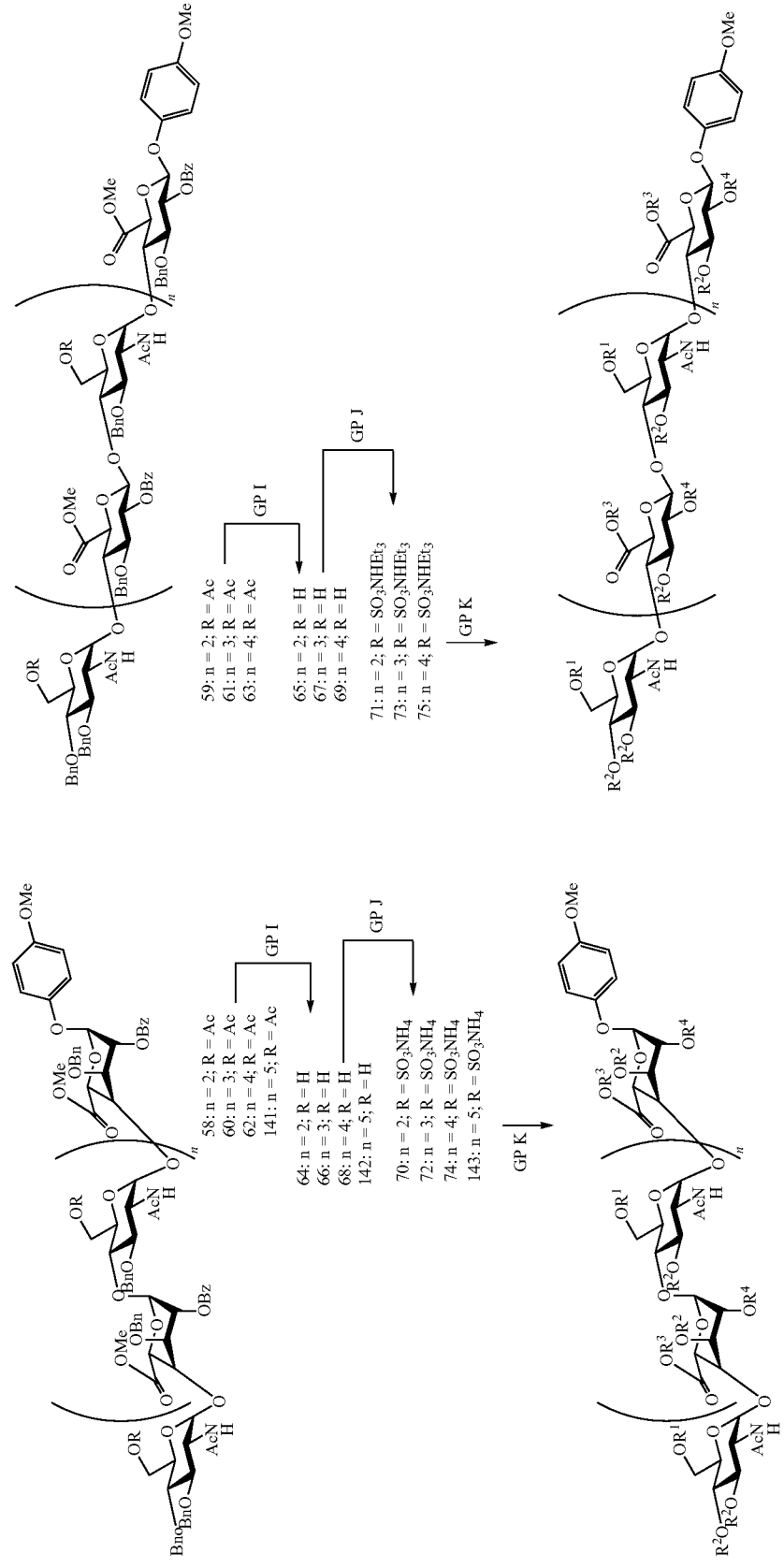

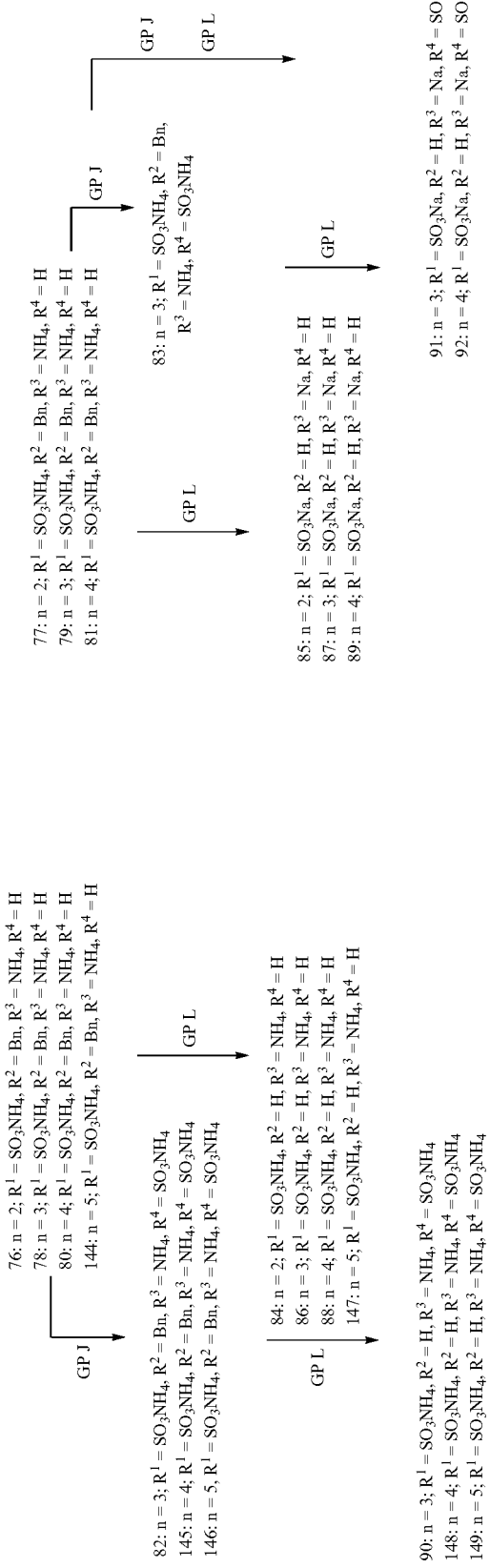

General Procedure I (GPI): Selective De-O-Acetylation.

Starting material is dissolved in dry dichloromethane (2 mL for 9 μmol) at 0° C. and treated with a solution of cold dry methanol (4 mL) containing 80 μL of acetyl chloride. Stirring of the reaction mixture is continued for 30 min at 0° and then at 23° C. for 48 h. After TLC (EtOAc) indicates the completion of the reaction dichloromethane is added and the solution is washed with water and NaHCO$_3$ solution (sat., aq.), dried and concentrated. The residues are purified by silica gel chromatography (EtOAc:MeOH, 9:1) to give de-O-acetylated products.

Synthesis of 64

Compound 64 is prepared from compound 58 following general procedure I: 152 mg, 80% yield, R$_f$=0.45 (EtOAc). HRMS (ESI) calcd for C$_{122}$H$_{131}$N$_3$O$_{38}$Na(M+Na)$^+$ m/z 2268.8308. found 2268.8289. $^1$H-NMR (500 MHz, CDCl$_3$) 7.94 (d, J=7.9 Hz, 2H), 7.89 (t, J=5.4 Hz, 4H), 7.48-7.42 (m, 4H), 7.42-7.38 (m, 6H), 7.37-7.33 (m, 6H), 7.31-7.27 (m, 6H), 7.27-7.22 (m, 8H), 7.21-7.13 (m, 4H), 7.13-7.07 (m, 4H), 7.07-7.02 (m, 4H), 6.95 (d, J=6.9 Hz, 2H), 6.92 (d, J=9.2 Hz, 2H), 6.71 (d, J=9.0 Hz, 2H), 5.72 (d, J=8.2 Hz, 1H), 5.61 (d, J=9.3 Hz, 1H), 5.57 (d, J=2.2 Hz, 1H), 5.35-5.32 (m, 1H), 5.30 (t, J=2.9 Hz, 2H), 5.17 (t, J=3.8 Hz, 2H), 5.12-5.07 (m, 2H), 4.91 (d, J=3.6 Hz, 1H), 4.87-4.85 (m, 2H), 4.84 (d, J=3.3 Hz, 1H), 4.78 (d, J=3.3 Hz, 1H), 4.75-4.74 (m, 3H), 4.73-4.71 (m, 4H), 4.70-4.67 (m, 2H), 4.67-4.65 (m, 2H), 4.65 (d, J=2.9 Hz, 1H), 4.62 (d, J=11.5 Hz, 1H), 4.58 (d, J=5.0 Hz, 1H), 4.55-4.53 (m, 1H), 4.53-4.51 (m, 1H), 4.34 (q, J=11.8 Hz, 2H), 4.22-4.17 (m, 1H), 4.15-4.10 (m, 2H), 4.09 (d, J=11.8 Hz, 1H), 4.05-4.02 (m, 1H), 4.02-3.97 (m, 2H), 3.95 (t, J=4.1 Hz, 2H), 3.91 (d, J=3.7 Hz, 1H), 3.86 (t, J=3.9 Hz, 2H), 3.72-3.67 (m, 1H), 3.65 (s, 3H), 3.63-3.58 (m, 1H), 3.57-3.54 (m, 1H), 3.54-3.51 (m, 1H), 3.50 (s, 3H), 3.47 (s, 3H), 3.44-3.40 (m, 1H), 3.40-3.38 (m, 1H), 3.38 (d, J=6.5 Hz, 1H), 3.35-3.31 (m, 1H), 3.30 (s, 3H), 1.44 (s, 3H), 1.39 (s, 3H), 1.25 (s, 3H); $^{13}$C-NMR (125 MHz, CDCl$_3$) δ 170.3, 169.9, 169.2, 169.1, 165.5, 165.4, 155.4, 150.5, 138.5, 138.4, 138.2, 138.1, 137.1, 136.9, 133.9, 133.8, 133.7, 129.8, 129.7, 129.6, 129.1, 129.0, 128.9, 128.6, 128.5, 128.4, 128.2, 128.1, 127.9, 127.89, 127.87, 127.82, 127.8, 127.7, 127.5, 127.2, 118.1, 114.7, 98.6, 98.2, 97.9, 97.8, 97.1, 96.9, 79.9, 77.7, 77.6, 77.4, 77.1, 74.9, 74.4, 74.2, 74.1, 73.3, 73.2, 73.0, 72.9, 72.8, 72.7, 72.6, 72.5, 72.4, 72.3, 72.2, 71.3, 70.9, 70.4, 69.8, 68.8, 61.5, 60.7, 60.5, 55.6, 52.6, 52.4, 52.2, 51.8, 29.6, 22.9, 22.7, 22.6.

Synthesis of 65

Compound 65 is prepared from compound 59 following general procedure I: 92 mg, 90%, R$_f$=0.35 (dichloromethane/methanol 19:1). $^{13}$C-NMR (125 MHz, CDCl$_3$) δ 170.15, 170.1, 170.0, 168.0, 167.9, 165.0, 164.95, 164.9, 155.7, 150.8, 139.0, 138.9, 138.3, 137.9, 136.5, 133.9, 133.8, 133.5, 130.9, 129.7, 129.6, 129.55, 129.3, 129.1, 128.9, 128.6, 128.5, 128.4, 128.3, 128.2, 128.15, 128.1, 128.0, 127.9, 127.8, 127.4, 127.3, 127.1, 118.6, 114.5, 100.9, 100.6, 100.5, 99.0, 98.6, 98.3, 81.4, 81.3, 81.0, 80.1, 77.8, 75.5, 75.2, 75.1, 75.0, 74.95, 74.8, 74.7, 74.2, 73.9, 73.8, 73.7, 73.3, 72.6, 72.2, 61.6, 60.1, 55.6, 52.8, 52.65, 52.6, 52.3, 52.2, 52.1, 22.7, 22.65

Synthesis of 66

Compound 66 is prepared from compound 60 following general procedure I: 21 mg, 93% yield, R$_f$=0.15 (EtOAc: petroleum ether, 4:1). HRMS (ESI) calcd for C$_{158}$H$_{170}$N$_4$O$_{50}$Na (M+Na)$^+$ m/z 2946.0781. found 2946.0757. $^1$H-NMR (500 MHz, CDCl$_3$) 8.03 (d, J=7.6 Hz, 2H), 7.98-7.93 (m, 4H), 7.57-7.49 (m, 4H), 7.47-7.41 (m, 6H), 7.40-7.37 (m, 8H), 7.36-7.30 (m, 12H), 7.30-7.20 (m, 16H), 7.19-7.15 (m, 8H), 7.14-7.11 (m, 5H), 7.02 (d, J=9.0 Hz, 2H), 6.81 (d, J=8.6 Hz, 2H), 5.72 (d, J=3.9 Hz, 2H), 5.70 (d, J=3.9 Hz, 2H), 5.65 (d, J=2.1 Hz, 1H), 5.62 (d, J=9.5 Hz, 1H), 5.41-5.38 (m, 1H), 5.38-5.34 (m, 1H), 5.23 (t, J=4.8 Hz, 2H), 5.20-5.16 (m, 2H), 5.16 (d, J=8.6 Hz, 2H), 4.98 (d, J=3.7 Hz, 1H), 4.95 (d, J=3.1 Hz, 1H), 4.93 (d, J=3.1 Hz, 1H), 4.86-4.83 (m, 2H), 4.81 (t, J=7.1 Hz, 2H), 4.77 (t, J=2.4 Hz, 2H), 4.74 (d, J=2.7 Hz, 1H), 4.72 (d, J=11.7 Hz, 1H), 4.68 (d, J=6.8 Hz, 1H), 4.65-4.62 (m, 6H), 4.62-4.60 (m, 6H), 4.60-4.59 (m, 4H), 4.58-4.56 (m, 4H), 4.40 (t, J=11.8 Hz, 2H), 4.29 (d, J=3.6 Hz, 1H), 4.27 (d, J=2.8 Hz, 1H), 4.25 (d, J=3.5 Hz, 1H), 4.22-4.21 (m, 1H), 4.21 (d, J=3.8 Hz, 2H), 4.18 (d, J=3.4 Hz, 1H), 4.16 (d, J=11.8 Hz, 1H), 4.09-4.03 (m, 2H), 4.01-3.95 (m, 1H), 3.93-3.89 (m, 1H), 3.75 (s, 3H), 3.70-3.65 (m, 1H), 3.65-3.61 (m, 1H), 3.59 (s, 3H), 3.57 (s, 3H), 3.56-3.53 (m, 1H), 3.52-3.50 (m, 2H), 3.49-3.45 (m, 1H), 3.44-3.42 (m, 1H), 3.44-3.38 (m, 1H), 3.37 (s, 3H), 3.36 (s, 3H), 3.35-3.32 (m, 1H), 1.46 (s, 3H), 1.44 (s, 3H), 1.33 (s, 3H), 1.26 (s, 3H); $^{13}$C-NMR (CDCl$_3$) δ 170.2, 169.1, 155.4, 138.5, 138.1, 137.0, 136.8, 133.8, 129.7, 129.6, 129.0, 128.6, 128.2, 127.9, 127.5, 127.2, 125.3, 118.1, 114.7, 98.15, 98.0, 97.9, 97.8, 97.7, 97.4, 97.3, 97.2, 79.8, 77.3, 77.0, 76.8, 74.9, 74.7, 74.6, 73.2, 72.9, 72.8, 72.6, 72.5, 72.45, 72.4, 70.4, 69.9, 68.6, 68.4, 61.6, 60.6, 52.4, 52.2, 51.8, 29.7, 22.9, 22.7.

Synthesis of 67

Compound 67 is prepared from compound 61 following general procedure I: 101 mg, 80%, R$_f$=0.33 (dichloromethane/methanol 19:1). $^{13}$C-NMR (125 MHz, CDCl$_3$) δ 170.2, 170.15, 170.1, 167.95, 167.9, 165.1, 165.0, 164.9, 155.7, 150.8, 139.0, 138.9, 138.3, 137.9, 137.2, 136.5, 133.9, 133.8, 133.5, 129.7, 129.6, 129.5, 129.2, 129.1, 128.8, 128.6, 128.5, 128.3, 128.25, 128.2, 128.15, 128.1, 128.0, 127.9, 127.8, 127.4, 127.35, 127.3, 118.6, 114.5, 100.8, 100.6, 100.5, 100.4, 99.0, 98.6, 98.3, 98.2, 81.4, 81.3, 81.2, 81.0, 80.1, 77.8, 76.4, 76.3, 75.5, 75.15, 75.1, 75.05, 75.0, 74.95, 74.8, 74.75, 74.7, 74.2, 74.1, 73.9, 73.8, 73.3, 72.6, 72.4, 72.3, 61.6, 60.1, 60.0, 55.6, 52.8, 52.65, 52.6, 52.3, 52.15, 52.1, 22.65, 22.6

Synthesis of 68

Compound 68 is prepared from compound 62 following general procedure I: 27 mg, 87% yield, R$_f$=0.41 (EtOAc). HRMS (ESI) calcd for C$_{194}$H$_{209}$N$_5$O$_{62}$Na(M+Na)$^+$ m/z 3623.33. found 3623.2315. $^1$H-NMR (500 MHz, CDCl$_3$) 8.03-8.0 (m, 2H), 7.97-7.92 (m, 6H), 7.58-7.52 (m, 4H), 7.52-7.48 (m, 6H), 7.47-7.41 (m, 8H), 7.40-7.35 (m, 12H), 7.35-7.30 (m, 12H), 7.30-7.21 (m, 16H), 7.21-7.18 (m, 4H), 7.17-7.14 (m, 8H), 7.14-7.10 (m, 5H), 7.01 (d, J=9.2 Hz, 2H), 6.80 (d, J=9.2 Hz, 2H), 5.75-5.69 (m, 2H), 5.68-5.60 (m, 2H), 5.42-5.37 (m, 2H), 5.37-5.34 (m, 2H), 5.23-5.13 (m, 2H), 4.98 (d, J=3.5 Hz, 1H), 4.95 (d, J=3.0 Hz, 1H), 4.93-4.90 (m, 2H), 4.87-4.82 (m, 2H), 4.81 (d, J=11.1 Hz, 1H), 4.78 (t, J=3.9 Hz, 2H), 4.74 (d, J=2.7 Hz, 1H), 4.72-4.70 (m, 6H), 4.70-4.67 (m, 6H), 4.67 (d, J=6.8 Hz, 1H), 4.64-4.62 (m, 4H), 4.62-4.60 (m, 4H), 4.60 (d, J=4.3 Hz, 1H), 4.58 (d, J=4.3 Hz, 1H), 4.41-4.33 (m, 4H), 4.29-4.21 (m, 6H), 4.21 (d, J=4.6 Hz, 1H), 4.19 (d, J=4.6 Hz, 1H), 4.16 (d, J=11.2 Hz, 2H), 4.12-4.09 (m, 2H), 4.09-4.02 (m, 4H), 4.01-3.95 (m, 2H), 3.95-3.89 (m, 1H), 3.75 (s, 3H), 3.72-3.65 (m, 1H), 3.65-3.60 (m, 1H), 3.59 (s, 3H), 3.57 (s, 3H), 3.50-3.44 (m, 1H), 3.44-3.39 (m, 1H), 3.37 (s, 3H), 3.35 (s, 3H), 3.34 (s, 3H), 1.46 (s, 3H), 1.45 (s, 3H), 1.43 (s, 3H), 1.33 (s, 3H), 1.25 (s, 3H); $^{13}$C-NMR (CDCl$_3$) δ 170.3, 169.9, 169.2, 169.1, 165.5, 165.4, 155.4, 138.5, 138.2, 138.1, 137.1, 136.8, 133.9, 129.8, 129.6, 129.0, 128.6, 128.5, 128.2, 127.9, 127.5, 127.4, 127.2, 118.1, 114.7, 98.6, 98.5, 98.3, 98.2, 98.1, 97.8, 97.7, 97.1, 97.0, 79.9, 77.6, 77.3, 77.0, 76.8, 74.9, 74.8, 74.6, 73.4, 72.9, 72.6, 72.5, 72.4, 72.3, 70.9, 70.2, 68.7, 68.4, 60.6, 55.7, 52.6, 52.1, 51.8, 29.7, 22.9, 22.7.

Synthesis of 142

Compound 142 is prepared from compound 141 following general procedure I: 142 mg, 33.2 μmol, 100% yield, TLC (EtOAc): $R_f$=0.38; HRMS (ESI) calcd for $C_{230}H_{248}N_6O_{74}Na_2(M+2Na)^{2+}$ m/z 2162.7844. found 2162.7808. $^1$H-NMR (500 MHz, CDCl$_3$) 8.02-7.99 (m, 2H), 7.97-7.91 (m, 8H), 7.58-7.50 (m, 6H), 7.47-7.40 (m, 12H), 7.39-7.31 (m, 18H), 7.30-7.17 (m, 28H), 7.17-7.09 (m, 16H), 7.03-7.0 (m, 5H), 7.0 (d, J=9.0 Hz, 2H), 6.79 (d, J=9.0 Hz, 2H), 5.96-5.81 (m, 2H), 5.66 (d, J=2.3 Hz, 1H), 5.44-5.40 (m, 2H), 5.40-5.35 (m, 2H), 5.29 (d, J=8.8 Hz, 1H), 5.24-5.20 (m, 1H), 5.20-5.13 (m, 2H), 5.0-4.89 (m, 3H), 4.88 (d, J=3.7 Hz, 1H), 4.85 (d, J=11.2 Hz, 1H), 4.81-4.75 (m, 10H), 4.75-4.72 (m, 8H), 4.72-4.66 (m, 10H), 4.66-4.64 (m, 6H), 4.64-4.56 (m, 10H), 4.42-4.34 (m, 8H), 4.32-4.23 (m, 6H), 4.23-4.14 (m, 5H), 4.11-4.05 (m, 6H), 4.03-3.97 (m, 4H), 3.96-3.90 (m, 8H), 3.74 (s, 3H), 3.70-3.62 (m, 4H), 3.59 (s, 3H), 3.54 (s, 3H), 3.50-3.44 (m, 2H), 3.44-3.38 (m, 2H), 3.36 (s, 3H), 3.35 (s, 6H), 3.33 (s, 3H), 1.45 (s, 3H), 1.43 (s, 6H), 1.42 (s, 3H), 1.32 (s, 6H); $^{13}$C-NMR (125 MHz, CDCl$_3$) δ 170.5, 170.4, 170.0, 169.3, 169.1, 169.0, 165.5, 165.4, 155.4, 150.4, 138.5, 138.2, 138.1, 137.4, 137.1, 136.9, 136.8, 133.9, 129.7, 129.6, 129.1, 129.0, 128.6, 128.4, 128.2, 128.1, 127.9, 127.8, 127.7, 127.5, 127.4, 127.2, 118.1, 114.7, 98.5, 98.2, 98.1, 97.7, 96.9, 96.8, 96.7, 80.0, 77.2, 77.0, 76.9, 76.7, 76.4, 76.2, 75.1, 74.9, 74.8, 74.7, 74.5, 74.4, 74.1, 73.9, 73.8, 73.3, 73.2, 73.0, 72.8, 72.7, 72.6, 72.5, 72.4, 72.1, 72.0, 71.2, 71.0, 70.8, 70.2, 69.9, 69.7, 68.8, 68.6, 68.3, 67.4, 67.1, 66.7, 66.5, 66.4, 66.3, 66.2, 61.4, 60.5, 55.6, 52.6, 52.4, 52.2, 51.8, 22.9, 22.7, 22.6, 20.9.

Synthesis of 69

Compound 69 is prepared from compound 63 following general procedure I: 120 mg, 91%, $R_f$=0.3 (dichloromethane/methanol 19:1). $^{13}$C-NMR (125 MHz, CDCl$_3$) δ 170.2, 170.1, 170.0, 167.9, 165.1, 165.0, 164.9, 155.7, 150.9, 139.0, 138.3, 137.9, 137.2, 136.5, 133.9, 133.8, 133.6, 129.7, 129.6, 129.3, 129.1, 128.9, 128.6, 128.5, 128.3, 128.25, 128.2, 128.1, 128.0, 127.9, 127.8, 127.4, 118.6, 114.5, 100.9, 100.6, 100.5, 100.4, 99.0, 98.6, 98.3, 98.2, 81.4, 81.3, 81.2, 81.1, 80.1, 77.8, 76.7, 76.4, 76.3, 75.5, 75.2, 75.1, 75.0, 74.8, 74.7, 74.4, 74.2, 74.1, 74.0, 73.8, 73.3, 72.6, 72.4, 72.35, 61.6, 60.1, 60.0, 55.6, 52.8, 52.65, 52.6, 52.3, 52.1, 22.7, 22.65

General Procedure J (GPJ): O-Sulfation.

Sulfur trioxide trimethylamine complex (5 equiv per hydroxyl group) is added to the starting materials in dry DMF (3 mL for 50 mg). The mixture is heated at 50-60° C. under argon for 48-72 h. MeOH (1 mL) is added and the mixture stirred for 15 min and concentrated in vacuo. Chromatography (dichloromethane:methanol:aq. ammonia, 7:2:0.5) affords O-sulfated products.

General Procedure K (GPK): Saponification.

Starting material is dissolved in methanol and water (4/1, v/v, 1.25 mL for 20 mg) containing 2M solution of sodium hydroxide (50 microL per 1.25 mL of reaction mixture) at 0° C. The reaction mixture is stirred at room temperature for 48-72 hours. After TLC (EtOAc:EtOH:water, 3:1:1) indicates the completion of the reaction, the volume of the solvents is reduced in vacuo. The solution is applied to a column of silica for flash chromatography (dichloromethane:methanol:aq. ammonia, 7:2:0.5) to furnish the de-O-benzoylated products.

General Procedure L (GPL): Global Debenzylation.

Starting material is dissolved in THF and water (1/1, v/v, 3 mL for 10 mg) containing aqueous ammonia solution (150 L per 3 mL of reaction mixture) and treated with palladium hydroxide on carbon (20% Pd, 5 times the weight of starting material). The reaction mixture is stirred for 24-48 hours under hydrogen at ambient temperature and pressure. After TLC (EtOAc:EtOH:water, 2:1:1) indicates the completion of the reaction the catalyst is filtered off and washed with 50% aqueous THF. The solution is concentrated to dryness and chromatography of the residue (dichloromethane:methanol:aq. ammonia, 5:4:1) gives the final products as ammonium salts. Some of the resulting materials are dissolved in water, passed through a Dowex 50WX8-200 (Na$^+$) resin column (8×1 cm) and eluted with water. Fractions containing the products are evaporated and dried in vacuo to furnish sodium salts of final products.

Synthesis of 70

Compound 70 is prepared from compound 64 following general procedure J: 135 mg, 81% yield, $R_f$=0.2 (dichloromethane:methanol:aq. ammonia, 7:2:0.5). HRMS (ESI) calcd for $C_{122}H_{131}N_3O_{47}S_3Na(M+Na)^+$ m/z 2508.7013. found 2508.65. $^1$H-NMR (500 MHz, MeOD) 8.13-8.08 (m, 4H), 8.02 (d, J=7.3 Hz, 2H), 7.63 (q, J=7.0 Hz, 2H), 7.56 (t, J=7.6 Hz, 2H), 7.52 (q, J=9.8 Hz, 2H), 7.44 (t, J=8.0 Hz, 2H), 7.34-7.28 (m, 8H), 7.27-7.23 (m, 8H), 7.22-7.17 (m, 8H), 7.16-7.13 (m, 6H), 7.12-7.07 (m, 6H), 6.99 (d, J=9.1 Hz, 2H), 6.84 (d, J=9.1 Hz, 2H), 5.74 (d, J=3.1 Hz, 1H), 5.61 (d, J=3.9 Hz, 1H), 5.55 (d, J=3.9 Hz, 1H), 5.31 (t, J=3.7 Hz, 2H), 5.26-5.23 (m, 2H), 5.23-5.20 (m, 2H), 5.08 (d, J=3.3 Hz, 2H), 5.04 (d, J=3.4 Hz, 1H), 4.99 (d, J=3.3 Hz, 1H), 4.97 (d, J=3.1 Hz, 1H), 4.89-4.81 (m, 2H), 4.80-4.77 (m, 2H), 4.75 (d, J=3.5 Hz, 1H), 4.73-4.69 (m, 3H), 4.68 (d, J=11.6 Hz, 1H), 4.61 (d, J=11.1 Hz, 1H), 4.49 (t, J=7.5 Hz, 2H), 4.41-4.39 (m, 1H), 4.38-4.35 (m, 1H), 4.34-4.32 (m, 2H), 4.32-4.29 (m, 1H), 4.28-4.22 (m, 2H), 4.21-4.18 (m, 1H), 4.17-4.14 (m, 2H), 4.13 (d, J=3.9 Hz, 1H), 4.10-4.07 (m, 1H), 4.04 (t, J=9.5 Hz, 2H), 4.0 (t, J=9.5 Hz, 2H), 3.86-3.80 (m, 2H), 3.72 (s, 3H), 3.66 (t, J=7.2 Hz, 2H), 3.60 (d, J=9.2 Hz, 1H), 3.55-3.49 (m, 2H), 3.49-3.46 (m, 1H), 3.45 (s, 3H), 3.31 (s, 3H), 3.30 (s, 3H), 1.65 (s, 3H), 1.48 (s, 3H), 1.44 (s, 3H); $^{13}$C-NMR (125 MHz, MeOD) δ 173.6, 173.3, 171.3, 171.1, 170.8, 167.4, 167.3, 157.0, 151.9, 140.0, 139.8, 138.99, 138.9, 138.8, 134.8, 134.7, 134.6, 131.2, 130.9, 130.8, 130.1, 130.0, 129.9, 129.6, 129.5, 129.4, 129.3, 129.2, 129.1, 129.0, 128.9, 128.8, 128.7, 128.5, 128.4, 128.1, 119.4, 115.7, 99.6, 99.4, 99.3, 98.4, 98.1, 97.3, 81.4, 79.8, 79.7, 79.2, 76.1, 75.8, 75.6, 75.3, 75.2, 74.9, 74.6, 74.2, 74.1, 74.0, 73.3, 72.9, 72.7, 72.2, 72.1, 71.9, 71.8, 71.7, 70.9, 70.6, 70.5, 67.3, 66.3, 56.1, 54.3, 53.8, 53.2, 53.0, 52.9, 22.9, 22.8, 227.

Synthesis of 71

Compound 71 is prepared from compound 65 following general procedure J: 86 mg, 99%, $R_f$=0.18 (dichloromethane/methanol/triethylamine 90:9:1). $^{13}$C-NMR (125 MHz, CDCl$_3$) δ 170.6, 170.5, 170.2, 168.5, 168.3, 167.9, 165.3, 165.2, 165.0, 155.7, 150.8, 139.1, 139.0, 138.6, 138.4, 137.1, 136.7, 133.6, 133.5, 130.0, 129.7, 129.2, 129.1, 129.0, 128.8, 128.6, 128.5, 128.4, 128.2, 128.1, 128.0, 127.8, 127.7, 127.6, 127.5, 127.4, 127.3, 118.7, 114.5, 100.7, 100.0, 99.8, 98.1, 97.8, 96.8, 81.8, 81.6, 81.4, 79.8, 77.8, 76.7, 76.6, 75.8, 75.2, 75.1, 74.85, 74.8, 74.7, 74.5, 74.3, 74.2, 74.0, 73.9, 73.7, 73.6, 70.8, 70.5, 70.0, 65.6, 64.2, 64.0, 55.6, 52.7, 52.4, 52.1, 52.0, 51.9, 46.5, 23.0, 22.8, 22.7, 8.9

Synthesis of 72

Compound 72 is prepared from compound 66 following general procedure J: 13 mg, 78% yield, $R_f$=0.2 (dichloromethane:methanol:aq. ammonia, 7:2:0.5). HRMS (ESI) calcd for $C_{158}H_{170}N_4O_{62}S_4Na(M+Na)^+$ m/z 3265.9053. found 3265.8494. $^1$H-NMR (500 MHz, MeOD) 8.13-8.08 (m, 6H), 8.01 (d, J=7.5 Hz, 2H), 7.63-7.59 (m, 2H), 7.59-7.54 (m, 2H), 7.53-7.47 (m, 2H), 7.46-7.41 (m, 6H), 7.33-7.28 (m, 10H), 7.28-7.22 (m, 15H), 7.22-7.18 (m, 10H), 7.17-7.14 (m, 6H), 7.13 (d, J=7.4 Hz, 2H), 7.09 (d, J=7.2 Hz, 2H), 6.99 (d, J=9.1 Hz, 2H), 6.84 (d, J=8.9 Hz, 2H), 5.73 (d, J=3.4 Hz, 1H), 5.59 (d, J=3.9 Hz, 1H), 5.56-5.52 (m, 2H), 5.31-5.28 (m, 2H), 5.25-5.17 (m, 3H), 5.07 (d, J=3.6 Hz, 1H), 5.03 (t, J=3.9 Hz, 2H), 4.99 (d, J=3.9 Hz, 1H), 4.97-4.96 (m, 2H), 4.88 (d, J=3.0 Hz, 1H), 4.81-4.76 (m, 3H), 4.74-4.72 (m, 2H), 4.72-4.70 (m, 2H), 4.70-4.68 (m, 3H), 4.68-4.65 (m, 2H), 4.63 (d, J=11.5 Hz, 1H), 4.50 (d, J=10.4 Hz, 2H), 4.39-4.32 (m, 6H), 4.32-4.28 (m, 4H), 4.27-4.22 (m, 4H), 4.21-4.17 (m, 2H), 4.17-4.11 (m, 3H), 4.10 (t, J=3.8 Hz, 2H), 4.08 (t, J=3.8 Hz, 2H), 4.03-3.98 (m, 3H), 3.98-3.94 (m, 2H), 3.84-3.79 (m, 2H), 3.73 (s, 3H), 3.63-3.57 (m, 2H), 3.56-3.50 (m, 2H), 3.49-3.47 (m, 2H), 3.47 (s, 3H), 3.30 (s, 3H), 3.28 (s, 3H), 3.27 (s, 3H), 1.65 (s, 3H), 1.49 (s, 3H), 1.47 (s, 3H), 1.44 (s, 3H); $^{13}$C-NMR (125 MHz, MeOD) δ 173.6, 173.3, 171.2, 170.8, 167.3, 157.0, 152.0, 140.0, 139.8, 138.9, 138.88, 138.83, 138.7, 134.8, 134.6, 131.2, 130.8, 130.1, 130.0, 129.9, 129.5, 129.3, 129.2, 129.1, 128.9, 128.8, 128.7, 128.5, 128.4, 128.2, 128.0, 119.5, 115.8, 99.66, 99.4, 99.3, 99.1, 98.3, 98.0, 97.2, 81.4, 79.8, 79.1, 76.1, 75.8, 75.6, 75.5, 74.2, 74.9, 74.6, 74.5, 74.2, 74.1, 73.3, 72.9, 72.6, 72.5, 72.1, 71.8, 70.8, 70.7, 70.5, 67.2, 66.3, 56.1, 54.3, 53.8, 53.2, 53.0, 22.9, 22.8, 22.7.

Synthesis of 73

Compound 73 is prepared from compound 67 following general procedure J: 46 mg, quant., $R_f$=0.15 (dichloromethane/methanol/triethylamine 90:9:1). $^{13}$C-NMR (125 MHz, CDCl$_3$) δ 170.5, 170.4, 170.1, 168.4, 168.35, 168.3, 167.9, 165.3, 165.2, 165.0, 155.7, 150.8, 139.1, 139.0, 138.6, 138.4, 137.1, 136.8, 133.6, 133.5, 130.1, 129.7, 129.2, 129.1, 129.0, 128.8, 128.6, 128.5, 128.4, 128.3, 128.2, 128.1, 127.8, 127.7, 127.6, 127.5, 127.4, 118.7, 114.5, 100.7, 100.1, 99.9, 98.3, 97.8, 96.8, 81.7, 81.4, 79.7, 77.8, 76.7, 76.6, 76.0, 75.2, 75.1, 74.9, 74.8, 74.7, 74.6, 74.4, 74.3, 74.1, 73.9, 73.8, 73.7, 73.6, 70.9, 70.6, 70.1, 65.5, 64.1, 64.0, 63.9, 55.6, 52.7, 52.6, 52.4, 52.2, 52.1, 52.0, 51.95, 51.9, 46.3, 23.1, 22.8, 22.7, 9.8

Synthesis of 74

Compound 74 is prepared from compound 68 following general procedure J: 25 mg, 94% yield, $R_f$=0.15 (dichloromethane:methanol:aq. ammonia, 7:2:0.5). HRMS (ESI) calcd for C$_{194}$H$_{209}$N$_5$O$_{77}$S$_5$Na$_3$ (M+3Na)$^{3+}$ m/z 4069.09. found 4070.2. $^1$H-NMR (500 MHz, MeOD) 8.13-8.08 (m, 8H), 8.01 (d, J=8.9 Hz, 2H), 7.64-7.59 (m, 6H), 7.59-7.54 (m, 6H), 7.53-7.45 (m, 4H), 7.44-7.39 (m, 6H), 7.32-7.28 (m, 12H), 7.28-7.21 (m, 14H), 7.21-7.19 (m, 10H), 7.18-7.13 (m, 8H), 7.12-7.06 (m, 4H), 6.99 (d, J=9.5 Hz, 2H), 6.84 (d, J=9.5 Hz, 2H), 5.73 (d, J=3.4 Hz, 1H), 5.59 (d, J=4.0 Hz, 1H), 5.56-5.52 (m, 2H), 5.31-5.28 (m, 2H), 5.24-5.20 (m, 3H), 5.19-5.16 (m, 3H), 5.08 (d, J=4.2 Hz, 1H), 5.03-5.0 (m, 2H), 4.99-4.96 (m, 2H), 4.87 (d, J=2.9 Hz, 1H), 4.81-4.76 (m, 3H), 4.75-4.70 (m, 4H), 4.70-4.64 (m, 5H), 4.62 (d, J=11.2 Hz, 1H), 4.49 (d, J=11.2 Hz, 2H), 4.39-4.34 (m, 6H), 4.33-4.27 (m, 8H), 4.26-4.21 (m, 6H), 4.20-4.17 (m, 8H), 4.17-4.12 (m, 8H), 4.11-4.04 (m, 2H), 4.03-3.96 (m, 3H), 3.84-3.80 (m, 2H), 3.74 (s, 3H), 3.64-3.61 (m, 2H), 3.61-3.56 (m, 2H), 3.55-3.50 (m, 1H), 3.48-3.43 (m, 2H), 3.47 (s, 3H), 3.31 (s, 3H), 3.30 (s, 3H), 3.28 (s, 3H), 3.26 (s, 3H), 1.65 (s, 3H), 1.49 (s, 3H), 1.48 (s, 3H), 1.47 (s, 3H), 1.43 (s, 3H); $^{13}$C-NMR (MeOD) δ 173.5, 170.8, 167.3, 158.1, 153.2, 139.9, 138.8, 134.7, 131.2, 130.9, 129.9, 129.5, 129.3, 129.1, 128.9, 128.8, 128.5, 128.4, 128.2, 128.0, 119.5, 115.8, 99.7, 99.5, 99.3, 99.2, 98.5, 98.3, 97.2, 97.1, 79.9, 76.1, 75.5, 75.1, 74.5, 74.1, 71.9, 66.3, 56.1, 53.8, 52.9, 49.6, 22.8.

Synthesis of 143

Compound 143 is prepared from compound 142 following general procedure J: 132 mg, 27.7 μmol, 83% yield, $R_f$=0.15 (dichloromethane:methanol:aq. ammonia, 7:2:0.5); HRMS (ESI) calcd for C$_{230}$H$_{248}$N$_6$O$_{92}$S$_6$Na$_3$ (M+3Na)$^{+3}$ m/z 1608.0852. found 1608.0801. $^1$H-NMR (500 MHz, MeOD) 8.15-8.08 (m, 8H), 8.01 (d, J=8.6 Hz, 2H), 7.65-7.57 (m, 5H), 7.55-7.44 (m, 8H), 7.44-7.40 (m, 6H), 7.35-7.28 (m, 24H), 7.27-7.21 (m, 18H), 7.20-7.14 (m, 16H), 7.14-7.05 (m, 8H), 6.99 (d, J=9.0 Hz, 2H), 6.84 (d, J=9.0 Hz, 2H), 5.74 (d, J=4.3 Hz, 1H), 5.61 (d, J=3.0 Hz, 1H), 5.58-5.53 (m, 3H), 5.32 (t, J=3.8 Hz, 2H), 5.26-5.21 (m, 2H), 5.21-5.16 (m, 2H), 5.06 (d, J=3.4 Hz, 1H), 5.03-4.99 (m, 2H), 4.99 (d, J=3.4 Hz, 1H), 4.96 (d, J=2.4 Hz, 1H), 4.88 (d, J=2.4 Hz, 1H), 4.82-4.73 (m, 3H), 4.75-4.71 (m, 4H), 4.70-4.65 (m, 5H), 4.62 (d, J=11.0 Hz, 1H), 4.52-4.44 (m, 8H), 4.39-4.35 (m, 10H), 4.35-4.27 (m, 12H), 4.26-4.18 (m, 6H), 4.18-4.11 (m, 12H), 4.11-4.04 (m, 4H), 4.04-3.95 (m, 4H), 3.87-3.81 (m, 2H), 3.73 (s, 3H), 3.71 (s, 3H), 3.69 (s, 6H), 3.64-3.57 (m, 4H), 3.56-3.51 (m, 2H), 3.31 (s, 3H), 3.30 (s, 6H), 3.29 (d, J=4.5 Hz, 1H), 1.67 (s, 3H), 1.51 (s, 3H), 1.50 (s, 6H), 1.49 (s, 3H), 1.46 (s, 3H); $^{13}$C-NMR (125 MHz, MeOD) δ 173.5, 173.3, 171.2, 170.9, 167.5, 167.4, 167.3, 164.9, 157.1, 152.0, 140.0, 139.9, 139.0, 138.9, 138.8, 138.7, 134.9, 134.7, 131.2, 130.9, 130.8, 130.0, 129.6, 129.3, 129.2, 129.17, 129.12, 129.0, 128.9, 128.7, 128.6, 128.4, 128.2, 119.5, 115.8, 99.7, 99.3, 98.5, 98.4, 98.2, 97.4, 81.4, 79.8, 79.2, 76.2, 76.1, 76.0, 75.6, 75.2, 74.6, 74.2, 74.0, 73.5, 73.1, 72.7, 72.6, 72.2, 72.1, 71.9, 70.9, 70.7, 70.6, 67.3, 66.3, 56.2, 55.2, 54.3, 53.8, 53.2, 53.1, 52.9, 48.6, 22.9, 22.8, 22.7.

Synthesis of 145

Compound 145 is prepared from compound 80 following general procedure J: 69 mg, 18.1 μmol, 98% yield, $R_f$=0.15 (dichloromethane:methanol:aq. ammonia, 7:2:0.5); HRMS (ESI) calcd for C$_{154}$H$_{178}$N$_5$O$_{87}$S$_{10}$NH$_4$ (M−4H)$^{−4}$ m/z 956.1735. found 956.1740. $^1$H-NMR (500 MHz, MeOD) 7.45-7.42 (m, 4H), 7.35-7.31 (m, 6H), 7.30-7.27 (m, 18H), 7.26-7.22 (m, 12H), 7.22-7.19 (m, 10H), 7.19-7.15 (m, 5H), 7.07 (d, J=9.0 Hz, 2H), 6.85 (d, J=9.1 Hz, 2H), 5.88 (d, J=3.0 Hz, 1H), 5.60-5.56 (m, 2H), 5.02-4.93 (m, 5H), 4.92-4.74 (m, 12H), 4.74-4.70 (m, 3H), 4.70-4.61 (m, 6H), 4.59-4.49 (m, 5H), 4.39-4.33 (m, 8H), 4.33-4.23 (m, 10H), 4.23 (d, J=9.5 Hz, 1H), 4.19-4.16 (m, 6H), 4.16-4.13 (m, 6H), 4.13 (d, J=3.5 Hz, 1H), 4.08-4.03 (m, 4H), 4.02-3.99 (m, 2H), 3.98-3.96 (m, 1H), 3.96-3.92 (m, 2H), 3.90-3.82 (m, 3H), 3.81-3.78 (m, 2H), 3.73 (s, 3H), 3.66-3.61 (m, 2H), 3.31 (s, 3H), 3.309 (s, 3H), 3.306 (s, 3H), 3.303 (s, 3H), 3.29 (s, 3H), 1.96 (s, 3H), 1.93 (s, 6H), 1.92 (s, 3H); $^{13}$C-NMR (125 MHz, MeOD) δ 175.9, 174.1, 159.2, 156.6, 152.1, 140.3, 139.7, 139.2, 138.7, 129.7, 129.6, 129.5, 129.4, 129.3, 129.1, 128.9, 128.8, 128.7, 128.6, 128.2, 119.4, 115.7, 99.7, 99.6, 99.5, 99.4, 99.2, 98.9, 81.8, 79.3, 76.3, 75.3, 74.0, 72.8, 72.7, 72.6, 71.5, 69.3, 67.9, 67.2, 56.1, 54.5, 49.5, 41.0, 23.3.

Synthesis of 146

Compound 146 is prepared from compound 144 following general procedure J: 69 mg, 18.1 μmol, 98% yield, $R_f$=0.15 (dichloromethane:methanol:aq. ammonia, 7:2:0.5); HRMS (ESI) calcd for C$_{182}$H$_{212}$N$_6$O$_{104}$S$_{12}$Na(M+Na)$^+$ m/z 4553.81. found 4553.01. $^1$H-NMR (500 MHz, MeOD) 7.46-7.41 (m, 4H), 7.35-7.31 (m, 6H), 7.30-7.27 (m, 24H), 7.26-7.23 (m, 16H), 7.22-7.18 (m, 10H), 7.18-7.13 (m, 5H), 7.07 (d, J=8.9 Hz, 2H), 6.84 (d, J=9.0 Hz, 2H), 5.88 (d, J=3.0 Hz, 1H), 5.61-5.55 (m, 2H), 5.04-4.94 (m, 5H), 4.93-4.74 (m, 12H), 4.74-4.69 (m, 3H), 4.69-4.60 (m, 6H), 4.59-4.46 (m, 5H), 4.41-4.35 (m, 10H), 4.33-4.26 (m, 10H), 4.26 (d, J=11.0 Hz, 1H), 4.2-4.11 (m, 8H), 4.08-4.03 (m, 5H), 4.03 (d, J=9.8 Hz, 1H), 3.98-3.96 (m, 5H), 3.96-3.92 (m, 5H), 3.91-3.85 (m, 3H), 3.83-3.80 (m, 2H), 3.80-3.77 (m, 2H), 3.76-3.73 (m, 1H), 3.73 (s, 3H), 3.66-3.61 (m, 2H), 3.313 (s, 3H), 3.31 (s, 3H), 3.306 (s, 6H), 3.303 (s, 3H), 3.3 (s, 3H), 1.97 (s, 6H), 1.95 (s, 3H), 1.94 (s, 6H), 1.92 (s, 3H); $^{13}$C-NMR (125 MHz, MeOD) δ 176.0, 175.5, 174.1, 159.2, 156.6, 152.1, 140.3, 139.7, 139.1, 138.7, 129.7, 129.5, 129.3, 129.2, 129.0, 128.9, 128.8, 128.7, 128.6, 128.5, 128.2, 119.4, 115.7, 99.7, 99.6, 99.5, 99.4, 98.9, 98.2, 96.7, 81.8, 79.3, 76.3, 75.3, 74.0, 72.7, 72.6, 72.5, 72.2, 71.5, 70.0, 69.3, 68.0, 67.2, 56.1, 54.5, 49.5, 41.0, 23.3.

Synthesis of 75

Compound 75 is prepared from compound 69 following general procedure J: 130 mg, quant., $R_f$=0.15 (dichloromethane/methanol/triethylamine 90:9:1); MS (ESI, negative mode) calcd for $C_{194}H_{209}N_5O_{77}S_5$ (M−5HNEt$_3$+2H)$^{2-}$ m/z (%): 1999.05 (30), 1999.55 (70), 2000.05(100), 2000.55 (90), 2001.06 (65), 2001.56 (25) found 1999.05 (30), 1999.55 (70), 2000.05(90), 2000.55 (80), 2001.05 (65), 2001.55 (35). $^{13}$C-NMR (125 MHz, CDCl$_3$) δ 170.35, 170.3, 168.5, 168.3, 168.25, 168.2, 167.9, 165.2, 165.1, 155.6, 150.9, 139.1, 138.6, 138.4, 137.0, 133.4, 130.0, 129.7, 129.3, 129.1, 129.0, 128.8, 128.5, 128.4, 128.3, 128.2, 128.0, 127.9, 127.8, 127.7, 127.6, 127.5, 127.3, 127.2, 118.6, 114.4, 100.4, 100.0, 99.9, 98.3, 97.5, 96.8, 81.9, 81.4, 79.8, 77.7, 76.4, 76.0, 75.0, 74.9, 74.8, 74.6, 74.5, 74.4, 74.1, 74.0, 73.7, 73.5, 70.9, 70.4, 70.0, 65.4, 63.9, 55.6, 54.5, 52.6, 52.1, 51.85, 51.8, 46.3, 23.1, 22.8, 8.6

Synthesis of 76

Compound 76 is prepared from compound 70 following general procedure K: 52 mg, 81% yield, $R_f$=0.2 (EtOAc: EtOH:water, 3:1:1). HRMS (ESI) calcd for $C_{98}H_{113}N_3O_{44}S_3Na_2$(M+2Na)$^{2+}$ m/z 2177.5654. found 2177.62. $^1$H-NMR (500 MHz, MeOD) 7.44-7.40 (m, 3H), 7.39-7.35 (m, 5H), 7.34-7.31 (m, 5H), 7.29-7.26 (m, 5H), 7.26-7.21 (m, 8H), 7.20-7.17 (m, 6H), 7.15-7.13 (m, 3H), 7.09 (d, J=8.9 Hz, 2H), 6.85 (d, J=8.9 Hz, 2H), 5.49 (d, J=4.0 Hz, 1H), 5.30 (d, J=4.6 Hz, 1H), 5.25 (d, J=4.3 Hz, 1H), 4.87-4.77 (m, 6H), 4.76-4.74 (m, 2H), 4.73-4.68 (m, 2H), 4.67-4.65 (m, 2H), 4.65-4.61 (m, 3H), 4.61 (d, J=4.6 Hz, 1H), 4.46 (d, J=10.7 Hz, 1H), 4.40 (d, J=11.5 Hz, 1H), 4.34-4.29 (m, 6H), 4.26-4.17 (m, 8H), 4.13-4.04 (m, 5H), 4.0-3.95 (m, 3H), 3.94-3.84 (m, 2H), 3.82-3.77 (m, 2H), 3.73 (s, 3H), 3.71-3.65 (m, 2H), 3.65-3.59 (m, 2H), 1.79 (s, 3H), 1.69 (s, 3H), 1.66 (s, 3H); $^{13}$C-NMR (125 MHz, MeOD) δ 173.2, 156.5, 152.4, 139.9, 139.8, 139.5, 139.1, 129.6, 129.5, 129.3, 129.0, 128.8, 128.75, 128.7, 128.6, 119.2, 115.7, 101.7, 100.9, 100.5, 99.2, 98.1, 82.2, 79.1, 76.2, 76.1, 74.9, 73.0, 71.6, 68.6, 67.6, 67.3, 56.1, 54.3, 49.5, 22.9.

Synthesis of 77

Compound 77 is prepared from compound 71 following general procedure K: 29 mg, 72%, $R_f$=0.15 (EtOAc/ethanol/water 3:1:1). $^{13}$C-NMR (125 MHz, methanol-D4, HSQC) S 129.6, 129.3, 129.2, 129.1, 128.5, 119.4, 115.5, 104.1, 103.8, 98.1, 86.3, 82.1, 80.9, 79.4, 78.6, 77.9, 76.4, 76.3, 75.9, 75.8, 75.6, 75.3, 75.2, 75.1, 74.9, 74.8, 71.2, 67.4, 67.0, 56.1, 54.6, 53.9, 47.4, 23.0, 9.7

Synthesis of 78

Compound 78 is prepared from compound 72 following general procedure K: 29 mg, 85% yield, $R_f$=0.22 (EtOAc: EtOH:water, 3:1:1). HRMS (ESI) calcd for $C_{126}H_{146}N_4O_{58}S_4Na$(M+Na)$^+$ m/z 2793.7379. found 2793.7398. $^1$H-NMR (500 MHz, MeOD) 7.43-7.40 (m, 4H), 7.40-7.36 (m, 5H), 7.35-7.31 (m, 8H), 7.30-7.25 (m, 10H), 7.25-7.22 (m, 8H), 7.21-7.15 (m, 6H), 7.15-7.11 (m, 4H), 7.09 (d, J=9.0 Hz, 2H), 6.85 (d, J=9.0 Hz, 2H), 5.48 (d, J=3.4 Hz, 1H), 5.27 (d, J=3.9 Hz, 1H), 5.24 (d, J=4.5 Hz, 1H), 5.21 (d, J=4.5 Hz, 1H), 4.87-4.85 (m, 3H), 4.84-4.77 (m, 4H), 4.77-4.74 (m, 2H), 4.74-4.70 (m, 2H), 4.70-4.68 (m, 2H), 4.66-4.60 (m, 3H), 4.45-4.43 (m, 1H), 4.43-4.41 (m, 1H), 4.40-4.38 (m, 1H), 4.38-4.34 (m, 5H), 4.34-4.32 (m, 3H), 4.32-4.30 (m, 4H), 4.29-4.27 (m, 2H), 4.27-4.25 (m, 3H), 4.25-4.20 (m, 4H), 4.19 (d, J=3.7 Hz, 1H), 4.17 (d, J=3.1 Hz, 1H), 4.13-4.05 (m, 4H), 4.04 (t, J=4.1 Hz, 1H), 4.01 (d, J=4.1 Hz, 1H), 3.97-3.93 (m, 3H), 3.92-3.83 (m, 4H), 3.82-3.76 (m, 2H), 3.74 (s, 3H), 3.73-3.68 (m, 2H), 3.67-3.60 (m, 2H), 1.80 (s, 3H), 1.66 (s, 3H), 1.63 (s, 3H), 1.62 (s, 3H); $^{13}$C-NMR (125 MHz, MeOD) δ 176.5, 175.7, 175.4, 156.7, 155.8, 154.1, 139.8, 139.1, 129.7, 129.6, 129.5, 129.4, 129.3, 129.2, 129.1, 128.9, 128.8, 128.7, 128.5, 119.3, 115.7, 102.4, 102.3, 101.8, 101.7, 101.6, 100.1, 97.9, 97.8, 87.3, 86.5, 81.7, 81.1, 76.6, 76.2, 76.1, 73.1, 72.9, 71.6, 69.5, 68.7, 67.4, 56.1, 54.4, 53.9, 53.5, 22.9.

Synthesis of 79

Compound 79 is prepared from compound 73 following general procedure K: 29 mg, 94%, $R_f$=0.6 (EtOAc/ethanol/water 2:2:1). $^{13}$C-NMR (125 MHz, methanol-D4) δ 176.6, 175.8, 175.3, 173.1, 173.0, 155.9, 153.2, 140.3, 139.9, 139.6, 129.9, 129.5, 129.4, 129.2, 129.1, 128.6, 128.5, 119.6, 115.5, 104.1, 104.0, 103.9, 98.6, 98.2, 98.0, 86.4, 86.1, 85.8, 81.8, 80.5, 79.3, 78.3, 78.2, 77.6, 76.6, 76.2, 75.9, 75.8, 75.7, 75.3, 75.1, 74.9, 74.8, 74.6, 71.3, 71.2, 71.1, 67.4, 67.1, 56.1, 54.4, 53.5, 53.4, 53.3, 23.0

Synthesis of 80

Compound 80 is prepared from compound 74 following general procedure K: 14 mg, 82% yield, $R_f$=0.21 (EtOAc: EtOH:water, 3:1:1). $^1$H-NMR (500 MHz, MeOD) 7.43-7.40 (m, 5H), 7.39-7.35 (m, 6H), 7.35-7.30 (m, 12H), 7.29-7.23 (m, 16H), 7.22-7.15 (m, 12H), 7.15-7.13 (m, 4H), 7.09 (d, J=9.0 Hz, 2H), 6.85 (d, J=9.2 Hz, 2H), 5.47 (d, J=4.0 Hz, 1H), 5.27 (d, J=3.9 Hz, 1H), 5.24-19 (m, 3H), 4.94-4.75 (m, 8H), 4.74-4.72 (m, 6H), 4.72-4.69 (m, 2H), 4.69-4.67 (m, 4H), 4.66-4.60 (m, 3H), 4.46-4.42 (m, 8H), 4.41-4.38 (m, 10H), 4.37-4.34 (m, 4H), 4.33-4.28 (m, 5H), 4.27-4.23 (m, 6H), 4.23-4.17 (m, 8H), 4.14-4.06 (m, 4H), 4.04-3.97 (m, 3H), 3.93-3.82 (m, 4H), 3.80-3.76 (m, 3H), 3.74 (s, 3H), 3.73-3.66 (m, 2H), 3.66-3.63 (m, 2H), 1.81 (s, 3H), 1.65 (s, 3H), 1.62 (s, 6H), 1.61 (s, 3H); $^{13}$C-NMR (125 MHz, MeOD) δ 173.2, 156.5, 152.5, 139.9, 139.5, 139.2, 129.7, 129.6, 129.4, 129.1, 129.0, 128.9, 128.9, 128.8, 128.7, 128.5, 119.2, 115.7, 101.7, 100.8, 99.9, 99.8, 79.2, 76.1, 72.9, 71.6, 70.5, 69.2, 56.1, 55.1, 54.4, 49.6, 30.9, 30.7, 22.9.

Synthesis of 144

Compound 144 is prepared from compound 143 following general procedure K: 85 mg, 20.98 μmol, 76% yield, $R_f$=0.2 (EtOAc:EtOH:water, 3:1:1); HRMS (ESI) calcd for $C_{192}H_{210}N_6O_{86}S_6Na_2$(M+2Na)$^{42}$ m/z 2046.5131. found 2046.5109. $^1$H-NMR (500 MHz, MeOD) 7.43-7.38 (m, 4H), 7.36-7.32 (m, 6H), 7.32-7.29 (m, 24H), 7.30-7.25 (m, 20H), 7.25-7.23 (m, 6H), 7.23-7.18 (m, 5H), 7.09 (d, J=8.9 Hz, 2H), 6.84 (d, J=8.9 Hz, 2H), 5.49-5.47 (m, 2H), 5.40 (d, J=5.3 Hz, 1H), 5.34-5.32 (m, 2H), 5.28-5.25 (m, 4H), 5.24-5.21 (m, 3H), 5.03-4.79 (m, 12H), 4.79-4.75 (m, 6H), 4.75-4.73 (m, 4H), 4.73-4.67 (m, 6H), 4.66-4.59 (m, 7H), 4.66-4.60 (m, 3H), 4.49-4.41 (m, 8H), 4.39-4.31 (m, 8H), 4.31-4.24 (m, 5H), 4.24-4.19 (m, 6H), 4.17-4.12 (m, 3H), 4.11-4.05 (m, 5H), 4.05-3.98 (m, 3H), 3.94-3.81 (m, 4H), 3.79-3.74 (m, 3H), 3.73 (s, 3H), 3.66-3.62 (m, 3H), 1.82 (s, 3H), 1.66 (s, 3H), 1.628 (s, 6H), 1.621 (s, 3H), 1.61 (s, 3H); $^{13}$C-NMR (125 MHz, MeOD) δ 175.8, 173.3, 156.5, 152.4, 140.2, 140.1, 139.9, 139.7, 139.5, 139.2, 139.1, 130.5, 129.9, 129.7, 129.6, 129.5, 129.3, 129.2, 129.1, 128.9, 128.8, 128.7, 128.6, 101.7, 98.1, 101.8, 101.7, 99.7, 99.6, 98.4, 98.3, 98.1, 82.2, 80.8, 79.2, 76.9, 76.5, 76.3, 75.9, 75.3, 74.9, 73.0, 72.8, 72.3, 71.5, 70.7, 70.3, 69.8, 68.4, 67.6, 56.2, 55.2, 54.3, 49.9, 39.3, 22.9.

Synthesis of 81

Compound 81 is prepared from compound 75 following general procedure K: 75 mg, 75%, $R_f$=0.05 (EtOAc/ethanol/water 3:1:1). MS (ESI, negative mode) calcd for $C_{154}H_{159}N_5O_{72}S_5$ (M−10HNEt$_3$+8H)$^{2-}$ m/z (%): 1703.95 found 1703.93. $^{13}$C-NMR (125 MHz, methanol-D4) δ 175.9, 175.2, 174.4, 173.1, 172.9, 156.9, 153.2, 140.4, 140.3, 139.9, 139.6, 129.5, 129.4, 139.35, 129.3, 129.2, 129.0, 128.6, 128.5, 119.6, 115.5, 104.1, 104.05, 104.0, 103.9, 98.7, 98.2, 86.4, 86.1, 85.8, 81.9, 80.4, 80.2, 79.3, 78.2, 77.9, 77.7, 76.6, 76.5, 76.3, 75.9, 75.8, 75.7, 75.6, 75.3, 75.2, 75.1, 74.7, 71.4, 71.1, 67.3, 67.0, 56.1, 54.3, 53.4, 22.9

Synthesis of 82

Compound 82 is prepared from compound 78 following general procedure J: 24 mg, 90% yield, $R_f$=0.15 (dichloromethane:methanol:aq. ammonia, 7:2:0.5). $^1$H-NMR (500 MHz, MeOD) 7.47-7.42 (m, 4H), 7.40-7.35 (m, 6H), 7.35-7.31 (m, 8H), 7.30-7.25 (m, 6H), 7.25-7.20 (m, 7H), 7.20-7.15 (m, 8H), 7.14-7.11 (m, 6H), 7.08 (d, J=8.3 Hz, 2H), 6.85 (d, J=9.0 Hz, 2H), 5.89-5.86 (m, 1H), 5.62-5.57 (m, 1H), 5.55 (d, J=9.8 Hz, 1H), 5.49 (d, J=6.9 Hz, 1H), 5.44-5.40 (m, 4H), 5.39-5.36 (m, 3H), 5.35-5.32 (m, 4H), 5.29-5.27 (m, 3H), 5.26 (t, J=9.8 Hz, 2H), 4.99-4.75 (m, 3H), 4.75-4.72 (m, 4H), 4.71-4.67 (m, 2H), 4.67-4.59 (5H), 4.59-4.50 (m, 8H), 4.38-4.28 (m, 6H), 4.27-4.13 (m, 4H), 4.12-4.01 (m, 6H), 4.0-3.81 (m, 2H), 3.80-3.76 (m, 2H), 3.74 (s, 3H), 3.72-3.67 (m, 2H), 3.67-3.60 (m, 2H), 1.62 (s, 3H), 1.61 (s, 3H), 1.49 (s, 3H), 1.48 (s, 3H); $^{13}$C-NMR (125 MHz, MeOD) δ 174.1, 173.3, 156.6, 140.2, 139.8, 139.1, 139.0, 138.6, 129.7, 129.5, 129.3, 129.28, 129.2, 129.1, 129.0, 128.9, 128.8, 128.3, 128.2, 119.4, 115.7, 99.5, 99.2, 99.1, 99.0, 98.7, 98.5, 76.2, 76.1, 73.7, 73.1, 71.6, 68.9, 67.4, 56.1, 54.4, 53.8, 23.3, 22.9.

Synthesis of 83

Compound 83 is prepared from compound 79 following general procedure J: 15 mg, quant. $^{13}$C-NMR (125 MHz, methanol-D4, HSQC) δ 130.0, 129.9, 129.5, 129.4, 129.2, 128.8, 120.1, 115.5, 102.4, 101.6, 101.5, 98.6, 97.5, 97.4, 83.9, 81.9, 81.5, 81.1, 81.0, 80.4, 79.8, 79.6, 79.3, 78.2, 76.6, 76.5, 76.1, 76.0, 75.9, 75.6, 75.5, 75.0, 74.9, 74.8, 74.5, 74.4, 74.3, 73.9, 71.6, 71.4, 71.3, 67.4, 67.0, 66.8, 56.2, 53.4, 52.9, 22.1

Synthesis of 84

Compound 84 is prepared from compound 76 following general procedure L: 9 mg, 85% yield, $R_f$=0.2 (EtOAc:EtOH: water, 2:1:1). HRMS (ESI) calcd for $C_{49}H_{71}N_3O_{44}S_3Na$ (M+Na)$^+$ m/z 1547.2368. found 1547.26. $^1$H-NMR (500 MHz, D$_2$O) 7.13 (d, J=9.2 Hz, 2H), 6.98 (d, J=9.1 Hz, 2H), 5.45 (d, J=3.2 Hz, 1H), 5.16 (d, J=3.8 Hz, 1H), 5.14 (d, J=3.8 Hz, 1H), 4.98 (d, J=3.2 Hz, 1H), 4.89-4.86 (m, 1H), 4.75 (d, J=3.2 Hz, 1H), 4.33 (d, J=3.0 Hz, 1H), 4.30 (d, J=3.0 Hz, 1H), 4.23 (d, J=13.0 Hz, 1H), 4.17-4.15 (m, 4H), 4.11 (t, J=3.5 Hz, 2H), 4.08-4.04 (m, 5H), 4.04-4.02 (m, 2H), 4.01-3.92 (m, 5H), 3.93 (d, J=3.5 Hz, 1H), 3.91-3.88 (m, 2H), 3.88-3.84 (m, 3H), 3.79 (s, 3H), 3.75-3.70 (m, 4H), 3.69-3.67 (m, 2H), 3.67-3.65 (m, 2H), 3.65-3.63 (m, 2H), 3.56-3.55 (m, 1H), 3.54-3.53 (m, 1H), 3.52-3.51 (m, 1H), 1.99 (s, 6H), 1.98 (s, 3H); $^{13}$C-NMR (125 MHz, D$_2$O) δ 174.5, 174.4, 1742, 154.8, 150.3, 119.3, 115.2, 101.9, 101.8, 100.7, 100.6, 94.9, 77.1, 76.8, 74.2, 74.1, 73.9, 71.1, 70.4, 69.9, 69.4, 69.2, 69.18, 69.1, 68.9, 68.8, 68.5, 68.4, 67.9, 66.5, 66.2, 55.9, 53.6, 53.4, 48.9, 22.0.

Synthesis of 85

Compound 85 is prepared from compound 77 following general procedure L: 4 mg, 92%, $R_f$=0.1 (EtOAc/ethanol/water 2:2:1). $^{13}$C-NMR (125 MHz, D$_2$O) δ 175.0, 174.9, 174.7, 174.5, 174.3, 154.8, 151.0, 118.4, 115.1, 102.1, 102.0, 101.3, 97.0, 96.7, 77.7, 77.3, 76.8, 76.5, 76.4, 76.3, 76.1, 76.0, 73.6, 73.5, 73.4, 70.7, 70.1, 69.1, 69.0, 68.8, 68.5, 67.9, 66.4, 65.8, 55.9, 53.6, 53.1, 22.0

Synthesis of 86

Compound 86 is prepared from compound 78 following general procedure L: 4 mg, 94% yield, $R_f$=0.2 (EtOAc:EtOH: water, 2:1:1). HRMS (ESI) calcd for $C_{63}H_{92}N_4O_{58}S_4Na_3$ (M+3Na)$^{3+}$ m/z 2029.2948. found 2029.2834. $^1$H-NMR (500 MHz, D$_2$O) 7.13 (d, J=9.2 Hz, 2H), 6.98 (d, J=9.2 Hz, 2H), 5.47 (d, J=3.4 Hz, 1H), 5.17 (d, J=4.2 Hz, 1H), 5.14 (d, J=3.4 Hz, 1H), 4.99-4.96 (m, 2H), 4.96 (d, J=3.41 Hz, 1H), 4.81 (d, J=2.3 Hz, 1H), 4.77 (d, J=3.0 Hz, 1H), 4.73-4.65 (m, 3H), 4.33-4.30 (m, 3H), 4.30 (d, J=3.7 Hz, 1H), 4.22-4.20 (m, 2H), 4.19-4.17 (m, 4H), 4.17-4.15 (m, 2H), 4.12 (t, J=3.0 Hz, 2H), 4.08-4.04 (m, 5H), 4.04-4.02 (m, 4H), 4.0-3.94 (m, 5H), 3.94-3.89 (m, 4H), 3.89-3.86 (m, 2H), 3.83-3.81 (m, 3H), 3.79 (s, 3H), 3.75-3.69 (m, 4H), 3.68-3.67 (m, 2H), 3.66-3.65 (m, 2H), 3.64-3.63 (m, 2H), 3.57-3.56 (m, 1H), 3.55-3.54 (m, 1H), 3.53-3.52 (m, 1H), 1.99 (s, 6H), 1.98 (s, 6H); $^{13}$C-NMR (125 MHz, D$_2$O) δ 119.1, 115.3, 101.9, 100.0, 98.8, 98.5, 76.7, 76.5, 76.3, 76.2, 76.1, 76.0, 7456, 73.3, 73.2, 69.2, 69.0, 68.9, 68.8, 65.9, 55.9, 53.5, 22.0.

Synthesis of 87

Compound 87 is prepared from compound 79 following general procedure L: 15 mg, 69%, $R_f$=0.1 (EtOAc/ethanol/water 2:2:1). $^{13}$C-NMR (125 MHz, D$_2$O, HSQC) δ 118.4, 115.1, 102.1, 101.1, 96.8, 77.5, 76.6, 76.3, 76.2, 76.1, 76.0, 75.9, 73.6, 73.4, 73.2, 70.6, 69.1, 69.0, 68.8, 68.7, 66.4, 65.8, 55.9, 53.1, 22.0

Synthesis of 88

Compound 88 is prepared from compound 80 following general procedure L: 6 mg, 93% yield, $R_f$=0.15 (EtOAc: EtOH:water, 2:1:1). HRMS (ESI) calcd for $C_{77}H_{113}N_5O_{72}S_5Na$ (M+Na)$^+$ m/z 2442.38. found 2442.0. $^1$H-NMR (500 MHz, D$_2$O) 7.16 (d, J=8.9 Hz, 2H), 7.01 (d, J=8.9 Hz, 2H), 5.47 (d, J=4.0 Hz, 1H), 5.18 (d, J=4.2 Hz, 1H), 4.99 (d, J=3.5 Hz, 1H), 4.84 (d, J=3.8 Hz, 1H), 4.73-4.69 (m, 3H), 4.36-4.30 (m, 5H), 4.24 (d, J=11.5 Hz, 1H), 4.18-4.16 (m, 5H), 4.12-4.09 (m, 6H), 4.09-4.03 (m, 10H), 4.03-3.95 (m, 12H), 3.94-3.92 (m, 8H), 3.92-3.86 (m, 6H), 3.81 (s, 3H), 3.78-3.68 (m, 10H), 3.59-3.57 (m, 2H), 3.57-3.55 (m, 2H), 3.54-3.53 (m, 2H), 2.0 (s, 15H); $^{13}$C-NMR (125 MHz, D$_2$O) δ 174.5, 174.4, 154.8, 119.3, 115.2, 101.9, 101.8, 100.7, 100.6, 94.7, 76.8, 74.3, 73.9, 71.1, 70.3, 69.9, 69.8, 69.4, 69.2, 69.1, 68.7, 68.6, 66.2, 55.9, 53.6, 22.0.

Synthesis of 147

Compound 147 is prepared from compound 144 following general procedure L: 26 mg, 9.03 μmol, 91% yield; $R_f$=0.15 (EtOAc:EtOH:water, 2:1:1); HRMS (ESI) calcd for $C_{91}H_{125}N_6O_{86}S_6Na_9$ (M−3H)$^{3-}$ m/z 1024.7598. found: 1024.7605. $^1$H-NMR (500 MHz, D$_2$O) 7.16 (d, J=8.1 Hz, 2H), 7.0 (d, J=8.1 Hz, 2H), 5.50 (d, J=3.4 Hz, 1H), 5.19 (bd, 1H), 5.16-5.12 (m, 3H), 5.04-4.99 (m, 3H), 4.9-4.86 (m, 1H), 4.76-4.74 (m, 2H), 4.74-4.68 (m, 5H), 4.68-4.65 (m, 2H), 4.35-4.28 (m, 5H), 4.26-4.18 (m, 6H), 4.16-4.13 (m, 1H), 4.11-4.06 (m, 8H), 4.03-3.97 (m, 10H), 3.97-3.90 (m, 12H), 3.81 (s, 3H), 3.78-3.70 (m, 12H), 3.68-3.64 (m, 2H), 3.64-3.63 (m, 2H), 3.63-3.62 (m, 2H), 3.59-3.58 (m, 1H), 3.57-3.55 (m, 1H), 3.55-3.54 (m, 1H), 3.53-3.50 (m, 1H), 2.01 (s, 18H); $^{13}$C-NMR (125 MHz, D$_2$O) δ 174.5, 173.5, 119.2, 115.2, 101.9, 101.8, 100.6, 95.2, 95.1, 77.2, 74.2, 73.9, 70.0, 69.9, 69.6, 69.4, 69.2, 69.1, 68.9, 68.1, 66.2, 55.9, 53.6, 22.1.

Synthesis of 89

Compound 89 is prepared from compound 81 following general procedure L: 9 mg, 41%, $R_f$=0.1 (EtOAc/ethanol/water 2:2:1); MS (ESI, neg. mode) calcd for $C_{77}H_{113}N_5O_{72}S_5Na$(M−9Na+8H)$^-$ m/z 2440.37, 2441.37, 2442.37, 2443.37, 2444.37. found 2440.38, 2441.37, 2442.40, 2443.38, calcd for $C_{77}H_{113}N_5O_{72}S_5Na$(M−10Na+9H)$^-$ m/z 2418.39, 2419.39, 2420.39, 2421.39, 2422.39. found 2418.39, 2419.42, 2420.38, 2421.43, 2422.38. $^{13}$C-NMR (125 MHz, D$_2$O) δ 175.4, 175.1, 174.6, 174.4, 154.9, 118.5, 115.2, 102.1, 102.0, 96.8, 77.7, 77.5, 76.8, 76.6, 76.5, 76.4, 76.3, 76.2, 73.6, 70.7, 70.1, 69.1, 68.8, 65.9, 61.3, 55.9, 53.6, 53.1, 22.0

Synthesis of 90

Compound 90 is prepared from compound 82 following general procedure L: 11 mg, 78% yield, $R_f$=0.15 (EtOAc: EtOH:water, 2:1:1). HRMS (ESI) calcd for $C_{63}H_{86}N_4O_{70}S_8Na_{10}(M+4H)^{4+}$ m/z 626.0008. found 626.001. $^1$H-NMR (500 MHz, D$_2$O) 7.15 (d, J=9.2 Hz, 2H), 6.99 (d, J=9.2 Hz, 2H), 5.68 (d, J=3.6 Hz, 1H), 5.18-5.15 (m, 2H), 5.14 (d, J=3.6 Hz, 1H), 5.0-4.93 (m, 2H), 4.89-4.86 (m, 2H), 4.84-4.80 (m, 4H), 4.78 (d, J=3.6 Hz, 1H), 4.73-4.63 (m, 3H), 4.47 (d, J=4.1 Hz, 1H), 4.35-4.26 (m, 6H), 4.26-4.21 (m, 8H), 4.19-4.17 (m, 4H), 4.16-4.15 (m, 2H), 4.12-4.10 (m, 2H), 4.07-4.0 (m, 10H), 4.0-3.93 (m, 8H), 3.92-3.86 (m, 5H), 3.79 (s, 3H), 3.77-3.73 (m, 4H), 3.73-3.68 (m, 2H), 3.68-3.66 (m, 2H), 3.66-3.65 (m, 2H), 3.64 (d, J=2.4 Hz, 1H), 3.62-3.61 (m, 1H), 3.56 (d, J=4.3 Hz, 1H), 3.54 (d, J=4.5 Hz, 1H), 3.52 (d, J=4.6 Hz, 1H), 2.04 (s, 3H), 2.03 (s, 3H), 1.99 (s, 3H), 1.98 (s, 3H); $^{13}$C-NMR (125 MHz, D$_2$O) δ 174.8, 174.5, 119.6, 115.2, 101.9, 101.8, 100.6, 94.2, 74.2, 73.6, 71.1, 70.1, 69.9, 69.4, 69.2, 68.8, 66.5, 55.9, 53.5, 48.9, 22.3, 22.0.

Synthesis of 148

Compound 148 is prepared from compound 145 following general procedure L: 40 mg, 14.18 μmol, 90% yield; $R_f$=0.15 (EtOAc:EtOH:water, 2:1:1); HRMS (ESI) calcd for C77H113N5O87S10 $C_{77}H_{102}N_5O_{87}S_{10}Na_{11}$ $(M-4H)^{4-}$ m/z 764.7374. found 764.7418. $^1$H-NMR (500 MHz, D$_2$O) 7.18 (d, J=8.3 Hz, 2H), 7.06 (d, J=8.3 Hz, 2H), 5.69 (d, J=3.4 Hz, 1H), 5.18 (bd, 1H), 5.15 (bd, 1H), 4.91 (bd, 1H), 4.76 (d, J=3.8 Hz, 1H), 4.73-4.69 (m, 5H), 4.68 (d, J=3.8 Hz, 1H), 4.36-4.25 (m, 8H), 4.25 (d, J=11.4 Hz, 1H), 4.12-4.09 (m, 3H), 4.07-3.99 (m, 16H), 3.99-3.94 (m, 6H), 3.83-3.80 (m, 3H), 3.81 (s, 3H), 3.80-3.71 (m, 12H), 3.71-3.66 (m, 6H), 3.58-3.52 (m, 4H), 3.57-3.55 (m, 3H), 3.54-3.53 (m, 3H), 2.05 (s, 15H); $^{13}$C-NMR (125 MHz, D$_2$O) δ 175.4, 174.8, 154.8, 119.7, 115.2, 101.9, 99.3, 99.2, 99.1, 93.7, 93.6, 73.8, 71.1, 70.1, 69.4, 67.9, 66.5, 69.2, 69.1, 68.7, 68.6, 55.9, 53.5, 22.3.

Synthesis of 149

Compound 149 is prepared from compound 146 following general procedure L: 25 mg, 7.44 μmol, 84% yield; $R_f$=0.15 (EtOAc:EtOH:water, 2:1:1); HRMS (ESI) calcd for $C_{91}H_{121}N_6O_{104}S_{12}Na_{13}$ $(M-5H)^{5-}$ m/k 728.1862. found 728.1872. $^1$H-NMR (500 MHz, D$_2$O) 7.18 (d, J=9.0 Hz, 2H), 7.07 (d, J=9.0 Hz, 2H), 5.71 (d, J=3.4 Hz, 1H), 5.22-5.17 (m, 2H), 5.17-5.12 (m, 3H), 5.07-5.03 (m, 3H), 5.01 (bd, 1H), 4.88 (bd, 1H), 4.76-4.75 (m, 2H), 4.75-4.69 (m, 5H), 4.68-4.65 (m, 2H), 4.50-4.47 (m, 1H), 4.50-4.47 (m, 1H), 4.36-4.32 (m, 3H), 4.32-4.29 (m, 4H), 4.36-4.32 (m, 3H), 4.29-4.25 (m, 5H), 4.25-4.21 (m, 2H), 4.16-4.12 (m, 1H), 4.10-4.06 (m, 8H), 4.06-4.0 (m, 10H), 4.0-3.93 (m, 8H), 3.93-3.88 (m, 4H), 3.82 (s, 3H), 3.80-3.72 (m, 10H), 3.72-3.70 (m, 2H), 3.68-3.66 (m, 2H), 3.66-3.64 (m, 2H), 3.59-3.56 (m, 1H), 3.56-3.55 (m, 1H), 3.54-3.53 (m, 1H), 3.52-3.50 (m, 1H), 2.06 (s, 18H); $^{13}$C-NMR (125 MHz, D$_2$O) δ 174.9, 174.0, 119.6, 115.2, 99.9, 99.6, 99.3, 98.8, 98.7, 94.6, 94.5, 94.0, 76.5, 73.9, 71.5, 71.2, 70.3, 69.9, 69.8, 69.6, 69.3, 67.5, 66.5, 64.5, 55.9, 53.4, 22.3.

Synthesis of 91

Compound 91 is prepared from compound 83 following general procedure L: 8 mg, 90%, $R_f$=0.05 (EtOAc/ethanol/water 2:2:1). $^{13}$C-NMR (125 MHz, D$_2$O, HSQC) δ 118.6, 115.0, 99.9, 99.8, 97.5, 97.1, 80.4, 80.0, 78.0, 77.6, 77.5, 76.8, 76.4, 76.3, 75.4, 74.8, 70.5, 70.0, 69.6, 69.1, 69.0, 68.8, 68.5, 66.3, 65.8, 61.2, 61.1, 55.7, 53.2, 22.0

Synthesis of 92

Compound 92 is prepared from compound 81 following general procedures J followed by L: 6 mg, quant. $R_f$=0.05 (EtOAc/ethanol/water 2:2:1). $^{13}$C-NMR (125 MHz, D$_2$O) δ 174.8, 174.6, 174.4, 174.3, 155.8, 142.3, 118.7, 115.1, 100.0, 99.9, 97.5, 97.2, 97.1, 96.9, 96.8, 80.0, 77.8, 77.5, 76.5, 76.1, 75.9, 75.5, 75.3, 70.7, 69.1, 68.8, 68.7, 68.6, 65.8, 55.9, 53.3, 22.0

Scheme 9

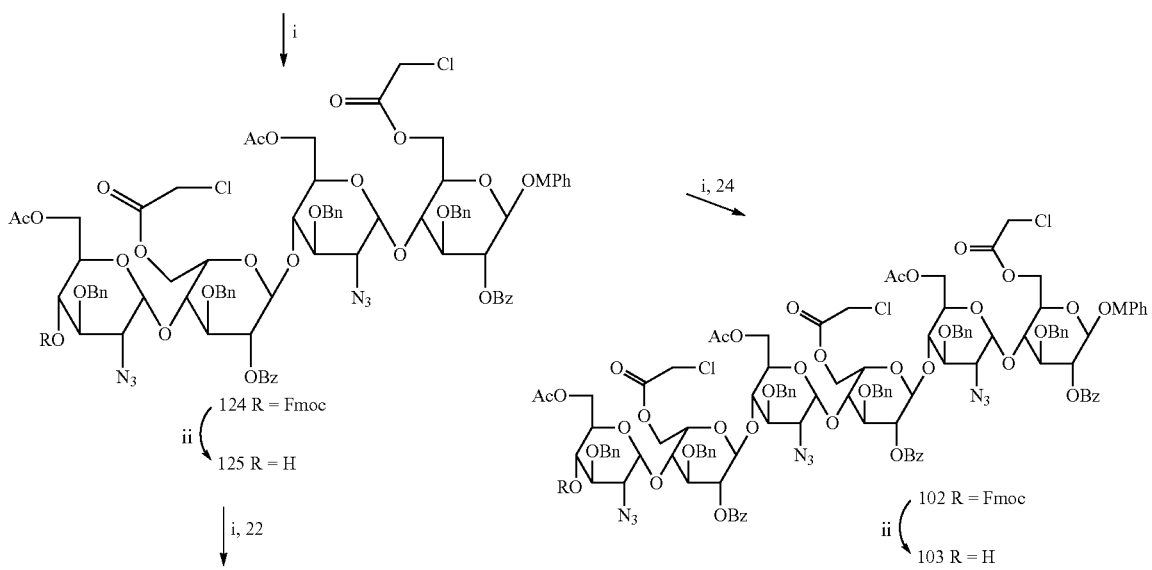

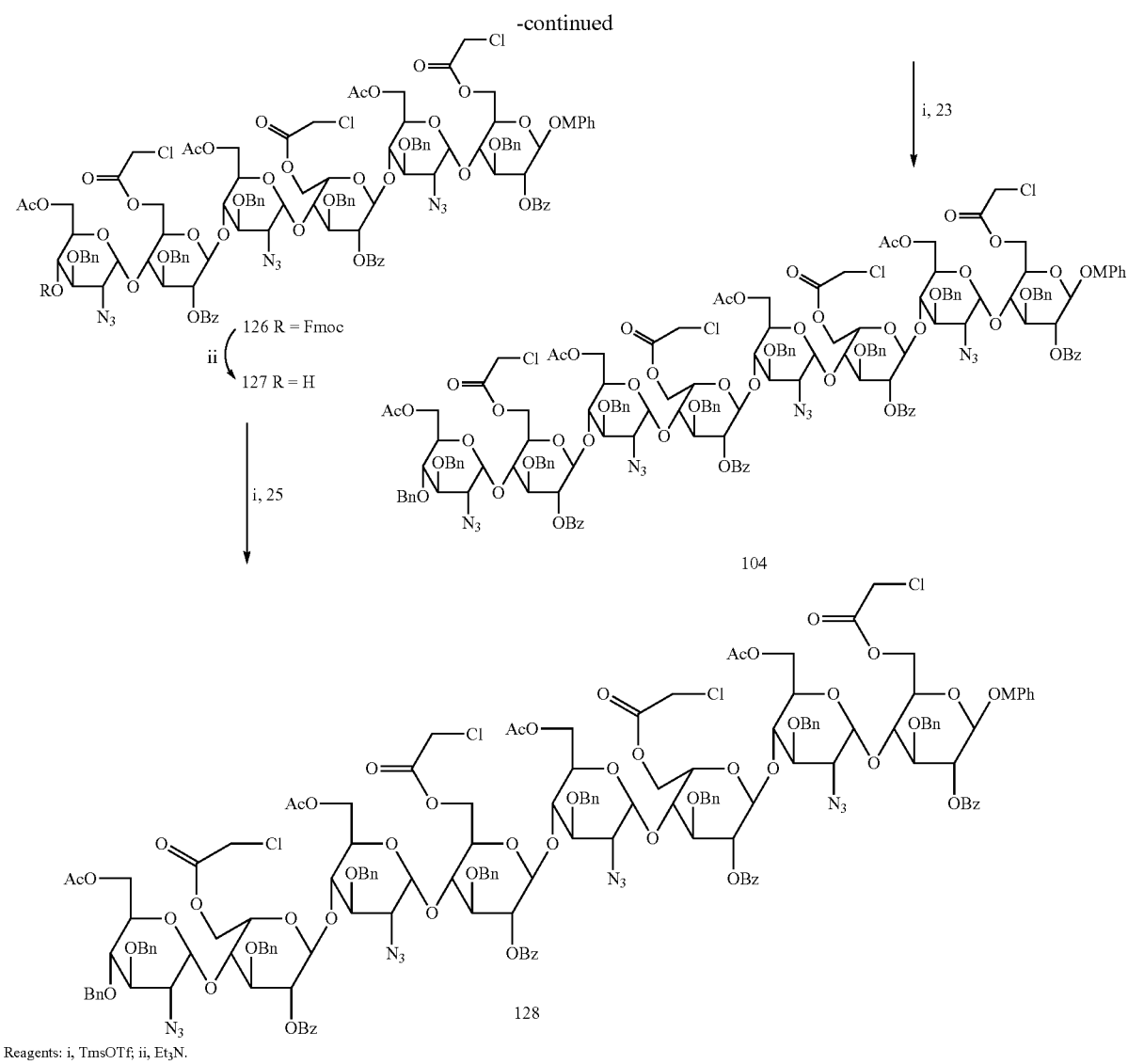
Reagents: i, TmsOTf; ii, Et₃N.
Scheme 10
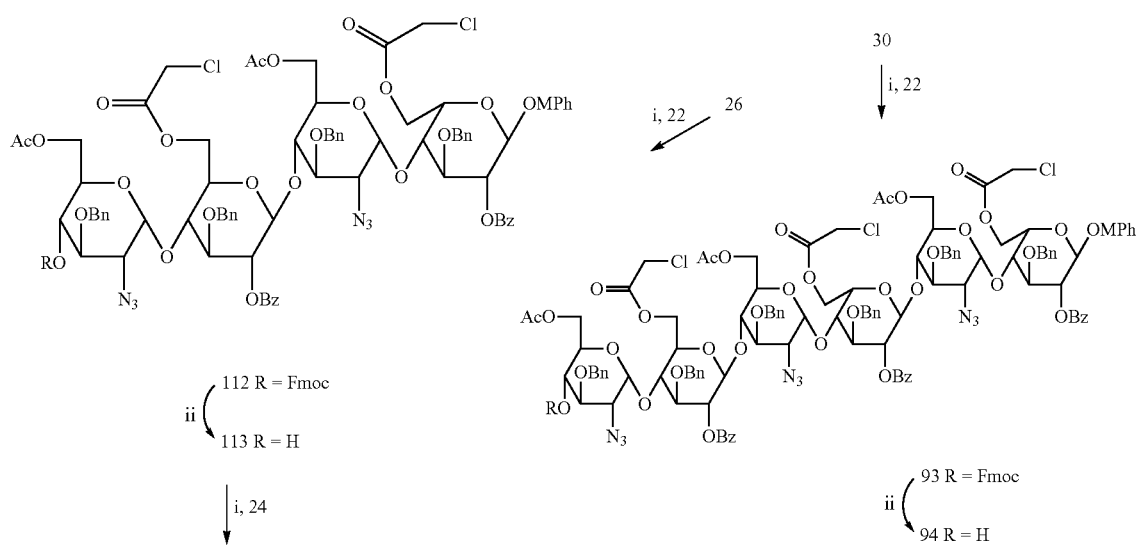

89 90
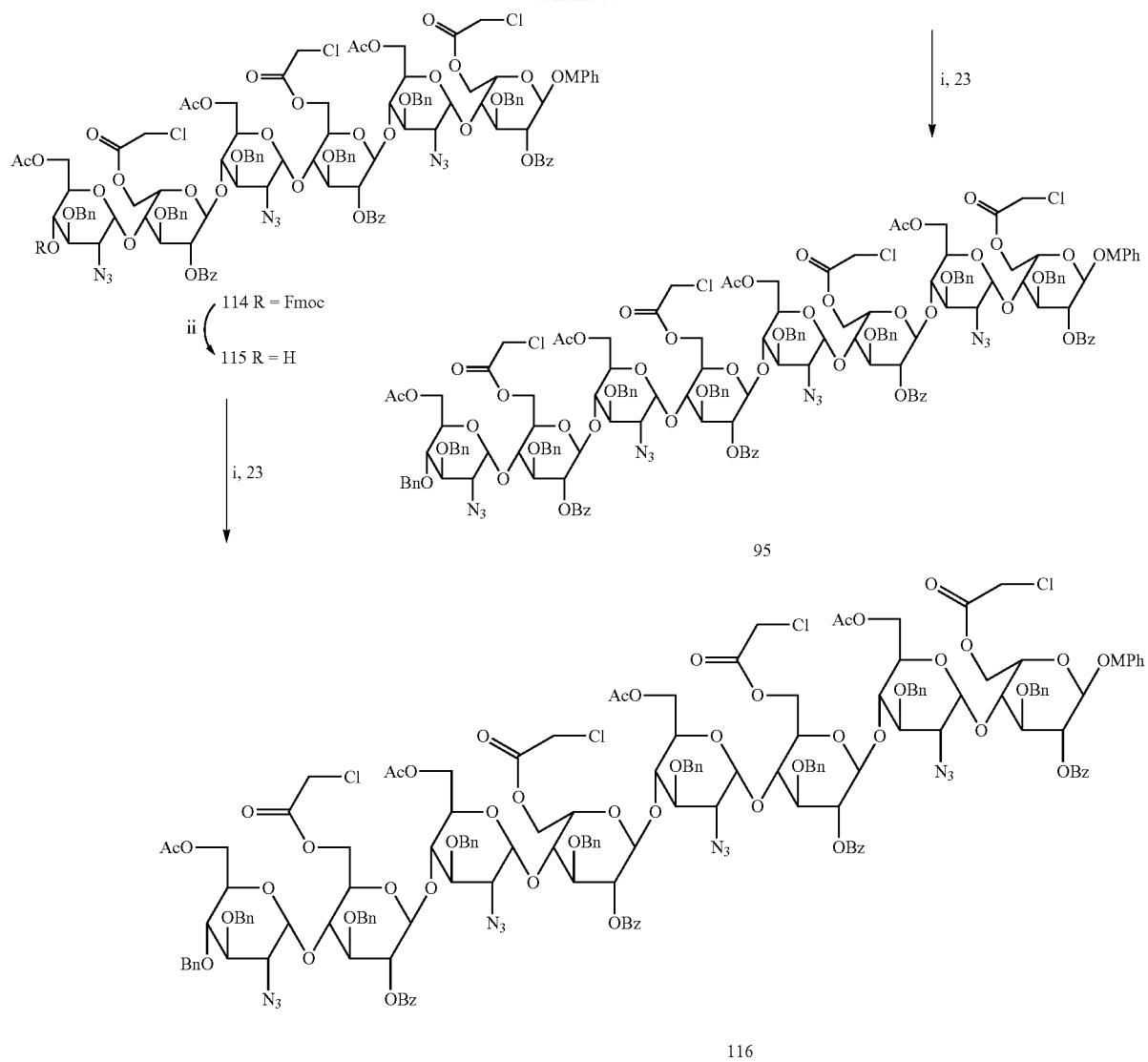
Reagents: i, TmsOTf; ii, Et₃N.
Scheme 11
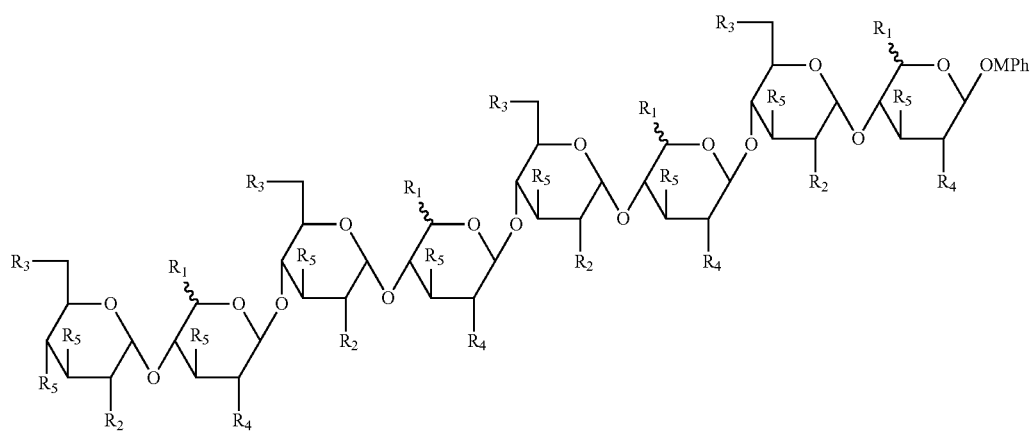

-continued

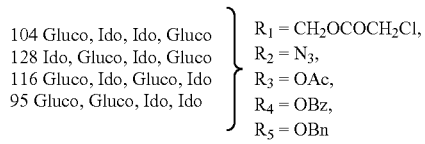
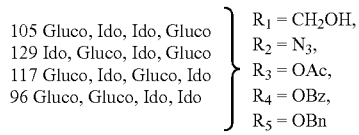

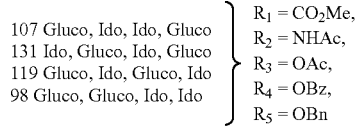
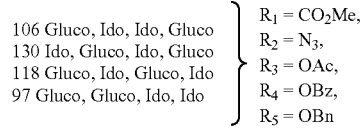

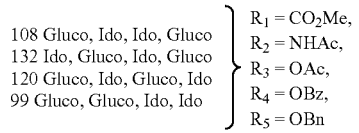
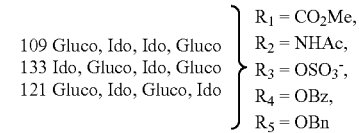

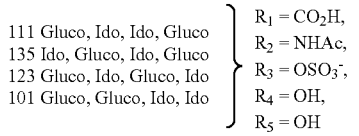
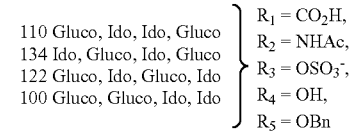

Reagents: i, DABCO, $CH_3CN$/EtOH, 70° C.; ii, TEMPO, BAIB, aq $CH_3CN$, then $CH_2N_2$; iii, py, HSAc; iv, HCl, MeOH/DCM; v, $SO_3NMe_3$, DMF, 60° C.; vi, NaOH aq MeOH, vii, $H_2$, $Pd(OH)_2$/C, aq THF.

Synthesis of 93

Compound 93 is prepared from compounds 30 and 22 following general procedure E.

$^1$H NMR; ($CDCl_3$) δ 8.15-8.03 (m, 6H), 7.75-7.05 (m, 47H), 7.03 (d, J=9.2 Hz, 2H), 6.83 (d, J=9.2 Hz, 2H), 5.61 (s, 1H), 5.46 (d, J=4.2 Hz, 1H), 5.37-5.34 (m, 2H), 5.11, (t, J=4.2 Hz, 1H), 5.02 (d, J=4.0 Hz, 1H), 4.99 (d, J=11.7 Hz, 1H), 4.92-3.50 (m, 56H), 3.34 (dd, J=10.1, 3.9 Hz, 1H), 3.27 (dd, J=10.1, 3.9 Hz, 1H), 3.22 (dd, J=9.9, 3.9 Hz, 1H), 2.01, 1.99, 1.97 (s, 3H each). $^{13}$C NMR; δ 170.6, 170.4, 166.9, 166.7, 166.6, 165.7, 165.4, 164.9, 155.2, 154.1, 150.2, 143.2, 143.0, 141.3, 138.2, 137.7, 137.6, 137.3, 137.1, 137.1, 133.7, 133.5, 133.4, 129.9, 129.7, 129.4, 129.0, 128.8, 128.7, 128.7, 128.4, 128.3, 128.2, 128.2, 128.1, 128.0, 127.9, 127.6, 127.3, 127.2, 125.3, 125.1, 124.9, 120.1, 118.3, 114.6, 100.9, 98.6, 98.2, 97.8, 97.7, 97.5, 82.7, 79.5, 78.9, 78.1, 77.7, 77.5, 75.5, 75.3, 75.2, 74.9, 74.7, 74.6, 74.1, 73.6, 72.4, 72.3, 72.1, 70.4, 70.3, 69.9, 68.8, 68.3, 67.6, 65.7, 65.0, 64.9, 63.8, 63.2, 63.2, 62.6, 62.2, 61.9, 61.8, 55.7, 46.7, 40.6, 40.5, 40.4, 20.7.

Synthesis of 94

Compound 94 is prepared from compound 93 following general procedure D.

$^1$H NMR; ($CDCl_3$) δ 8.15-8.03 (m, 6H), 7.59-7.05 (m, 39H), 7.03 (d, J=9.3 Hz, 2H), 6.84 (d, J=9.3 Hz, 2H), 5.61 (s, 1H), 5.44 (d, J=3.9 Hz, 1H), 5.36-5.32 (m, 2H), 5.10 (t, J=4.5 Hz, 1H), 5.02 (d, J=4.1 Hz, 1H), 4.98 (d, J=11.7 Hz, 1H), 4.93-4.36 (m, 16H), 4.31-3.38 (m, 37H), 3.29-3.20 (m, 3H), 2.97 (s, 1H), 2.06, 1.98, 1.96 (s, 3H each). $^{13}$C NMR; 171.9, 170.6, 170.5, 166.9, 166.7, 166.6, 165.7, 165.4, 165.0, 155.2, 150.2, 138.3, 137.8, 137.7, 137.6, 137.3, 137.2, 133.7, 133.5, 133.4, 129.9, 129.7, 129.4, 129.0, 128.8, 128.7, 128.7, 128.4, 128.4, 128.4, 128.3, 128.2, 128.2, 128.1, 128.1, 128.0, 127.9, 127.8, 127.6, 127.4, 127.2, 118.3, 114.6, 100.9, 98.6, 98.4, 98.2, 97.7, 97.5, 82.8, 79.2, 78.9, 78.0, 77.8, 75.5, 75.4, 75.0, 74.9, 74.7, 74.6, 74.1, 73.5, 72.4, 72.4, 72.1, 71.4, 70.6, 70.4, 70.3, 69.9, 68.3, 67.6, 65.7, 64.9, 64.9, 63.8, 63.3, 63.2, 62.7, 62.6, 62.2, 61.9, 55.7, 40.6, 40.5, 40.4, 20.8, 20.7.

Synthesis of 95

Compound 95 is prepared from compounds 94 and 23 following general procedure E.

$^1$H NMR; ($CDCl_3$) δ 8.15-8.04 (m, 8H), 7.58-7.05 (m, 57H), 7.03 (d, J=9.3 Hz, 2H), 6.83 (d, J=9.3 Hz, 2H), 5.61 (s, 1H), 5.45 (d, J=4.2 Hz, 1H), 5.37-5.34 (m, 3H), 5.27 (t, J=8.2 Hz, 1H), 5.11-5.05 (m, 2H), 5.00-4.95 (m, 2H), 4.91-4.53 (m, 18H), 4.48 (d, J=10.1 Hz, 1H), 4.42 (dd, J=11.5, 8.1 Hz, 1H), 4.34-3.48 (m, 51H), 3.32-3.18 (m, 4H), 2.00, 1.99, 1.98, 1.95 (s, 3H each). $^{13}$C NMR; δ 170.6, 170.5, 170.4, 166.9, 166.7, 166.6, 166.4, 165.7, 165.4, 165.0, 164.9, 155.2, 150.2, 138.2, 137.7, 137.6, 137.5, 137.3, 137.3, 133.7, 133.5, 133.4, 130.0, 129.9, 129.7, 129.4, 129.0, 128.9, 128.8, 128.7, 128.6, 128.6, 128.5, 128.4, 128.4, 128.3, 128.3, 128.2, 128.1, 128.1, 127.9, 127.8, 127.6, 127.5, 127.4, 127.4, 127.3, 118.3, 114.6, 100.9, 100.8, 98.5, 98.3, 98.1, 97.8, 97.7, 97.5, 82.8, 80.1, 78.9, 77.9, 77.9, 77.8, 77.7, 77.6, 75.6, 75.5, 75.2, 75.1, 74.9, 74.8, 74.7, 74.6, 74.2, 73.6, 72.4, 72.3, 72.1, 70.4, 69.9, 69.8, 68.3, 67.8, 65.7, 65.0, 64.9, 64.5, 63.8, 63.2, 63.2, 63.1, 62.7, 62.4, 62.2, 61.8, 55.7, 40.7, 40.6, 40.5, 40.3, 20.8, 20.7.

Synthesis of 96

Compound 96 is prepared from compound 95 following general procedure F.

$^1$H NMR; (CDCl$_3$) δ 8.14-8.04 (m, 8H), 7.58-7.09 (m, 57H), 7.06 (d, J=9.2 Hz, 2H), 6.83 (d, J=9.2 Hz, 2H), 5.63 (s, 1H), 5.52 (d, J=4.2 Hz, 1H), 5.42 (d, J=4.1 Hz, 1H), 5.35 (s, 1H), 5.32 (t, J=8.6 Hz, 1H), 5.26 (t, J=8.5 Hz, 1H), 5.09 (t, J=2.9 Hz, 1H), 5.04-4.98 (m, 3H), 4.86-3.46 (m, 60H), 3.32-3.24 (m, 9H), 3.07 (br s, 1H), 2.95 (br s, 1H), 2.00, 1.99, 1.98, 1.97 (s, 3H each). $^{13}$C NMR; δ 170.6, 170.45, 170.40, 165.78, 165.66, 165.05, 164.94, 155.25, 150.38, 138.14, 137.72, 137.60, 137.49, 137.37, 133.60, 133.48, 133.28, 129.91, 129.83, 129.55, 129.11, 129.08, 128.74, 128.67, 128.57, 128.45, 128.41, 128.35, 128.24, 128.15, 128.07, 128.04, 127.95, 127.82, 127.74, 127.62, 127.10, 126.95, 118.34, 114.70, 101.06, 98.09, 98.03, 97.90, 97.63, 97.32, 83.54, 80.28, 79.30, 78.32, 77.99, 77.79, 77.73, 77.64, 75.56, 75.21, 75.14, 74.97, 74.85, 74.54, 74.44, 74.35, 74.17, 73.58, 73.46, 73.39, 72.90, 72.29, 72.11, 70.42, 69.99, 69.60, 69.52, 69.15, 68.89, 67.93, 67.85, 64.08, 63.35, 63.25, 62.86, 62.68, 62.01, 61.81, 61.61, 61.41, 60.92, 55.66, 20.81, 20.76, 20.70.

Synthesis of 97

Compound 97 is prepared from compound 96 following general procedure G2.

$^1$H NMR; (CDCl$_3$) δ 8.12-8.02, (m, 8H), 7.61-7.04 (m, 57H), 7.01 (d, J=9.1 Hz, 2H), 6.80 (d, J=9.1 Hz, 2H), 5.69 (s, 1H), 5.46 (d, J=6.3 Hz, 1H), 5.43-5.38 (m, 5H), 5.34 (dd, J=8.7, 8.1 Hz, 1H), 5.30 (t, J=2.1 Hz, 1H), 5.17-5.14 (m, 2H), 4.98-4.54 (m, 19H), 4.43 (d, J=10.5 Hz, 1H), 4.37 (d, J=10.9 Hz, 1H), 4.31-4.08 (m, 11H), 4.05 (t, J=2.8 Hz, 1H), 4.01 (t, J=7.2 Hz, 1H), 3.94-3.65 (m, 16H), 3.59-3.42 (m, 12H), 3.34-3.30 (m, 2H), 3.24-3.17 (m, 3H), 2.97 (s, 3H), 2.09, 2.07, 2.01, 2.00 (s, 3H each). $^{13}$C NMR; δ 170.75, 170.61, 170.38, 169.67, 169.16, 167.70, 167.50, 165.62, 165.10, 164.66, 155.25, 150.49, 138.12, 137.86, 137.57, 137.52, 137.40, 137.17, 137.07, 133.92, 133.73, 133.64, 133.53, 129.97, 129.90, 129.71, 129.47, 129.13, 129.05, 128.94, 128.86, 128.80, 128.76, 128.55, 128.41, 128.33, 128.24, 128.16, 128.06, 128.03, 127.93, 127.77, 127.63, 127.51, 127.46, 125.32, 117.97, 114.66, 101.15, 101.08, 98.89, 98.58, 98.17, 97.83, 97.67, 97.22, 82.81, 82.56, 80.22, 78.31, 77.80, 77.64, 77.51, 77.48, 76.05, 75.58, 75.45, 75.37, 75.28, 75.01, 74.96, 74.86, 74.81, 74.60, 74.35, 73.68, 73.51, 72.86, 72.47, 72.09, 71.45, 69.85, 69.78, 69.38, 69.08, 68.10, 63.41, 63.32, 62.82, 62.73, 62.20, 61.57, 61.42, 55.66, 52.72, 52.08, 51.96, 51.75, 20.87, 20.81.

Synthesis of 98

Compound 98 is prepared from compound 97 following general procedure H.

$^1$H NMR; (CDCl$_3$) δ 8.07-7.99 (m, 8H), 7.60-7.41 (m, 12H), 7.35-6.98 (m, 47H), 6.79 (d, J=9.1 Hz, 2H), 5.79 (d, J=9.6 Hz, 1H), 5.72 (d, J=9.6 Hz, 1H), 5.65 (d, J=1.6 Hz, 1H), 5.54 (d, J=9.5 Hz, 1H), 5.42 (t, J=8.4 Hz, 1H), 5.39-5.29 (m, 3H), 5.15 (t, J=5.4 Hz, 1H), 4.99-4.96 (m, 2H), 4.94-4.91 (m, 3H), 4.88-3.90 (m, 44H), 3.86-3.59 (m, 9H), 3.74 (s, 3H), 3.57-3.47 (m, 2H), 3.55, 3.54 (s, 3H each), 3.38-3.32 (m, 1H), 3.36, 3.24, 2.10, 2.01, 1.97, 1.91, 1.40, 1.39, 1.38, 1.31 (s, 3H each). $^{13}$C NMR; δ 171.11, 170.70, 170.64, 170.58, 170.32, 170.12, 170.02, 169.28, 169.01, 167.41, 167.20, 165.59, 165.31, 164.87, 164.67, 155.39, 150.41, 138.72, 138.45, 138.12, 137.85, 137.70, 137.03, 136.81, 136.38, 136.32, 133.97, 133.87, 133.81, 129.73, 129.04, 128.98, 128.85, 128.72, 128.62, 128.55, 128.49, 128.32, 128.24, 128.12, 128.09, 128.02, 127.95, 127.78, 127.72, 127.60, 127.50, 127.41, 127.36, 127.30, 127.23, 127.02, 125.31, 118.07, 117.81, 114.68, 101.32, 101.12, 99.50, 98.72, 98.08, 97.81, 97.57, 81.57, 81.40, 80.50, 78.10, 77.89, 77.82, 76.75, 75.42, 75.27, 75.18, 75.02, 74.95, 74.87, 74.73, 74.34, 73.76, 73.55, 72.91, 72.70, 72.56, 71.86, 70.86, 70.70, 70.20, 70.10, 69.77, 68.77, 68.33, 62.19, 61.67, 61.53, 61.38, 55.64, 52.82, 52.52, 52.48, 52.09, 51.97, 51.91, 51.78, 22.76, 22.64, 21.45, 20.98, 20.79, 20.76, 20.71.

Synthesis of 99

Compound 99 is prepared from compound 98 following general procedure I.

$^1$H NMR; (CDCl$_3$) δ 8.03-7.92 (m, 8H), 7.58-7.40 (m, 12H), 7.35-6.95 (m, 47H), 6.78 (d, J=9.1 Hz, 2H), 5.75 (d, J=9.0 Hz, 1H), 5.69 (d, J=9.5 Hz, 1H), 5.63 (d, J=2.0 Hz, 1H), 5.52 (d, J=9.1 Hz, 1H), 5.43 (t, J=8.3 Hz, 1H), 5.37-5.32 (m, 3H), 5.28 (d, J=8.5 Hz, 1H), 5.19 (t, J=4.5 Hz, 1H), 5.07 (d, J=3.5 Hz, 1H), 5.00-4.77 (m, 10H), 4.71-4.45 (m, 1H), 4.32 (d, J=12.2 Hz, 1H), 4.22 (dt, J=10.0, 3.6 Hz, 1H), 4.17-3.19 (m, 36H), 3.74, 3.56, 3.54, 3.24, 3.23, 1.47, 1.45, 1.43, 1.33 (s, 3H each). $^{13}$C NMR; δ 170.58, 170.19, 170.09, 170.04, 169.09, 169.05, 167.93, 165.55, 165.38, 165.05, 164.74, 155.39, 150.46, 138.97, 138.92, 138.50, 138.29, 137.93, 137.06, 136.95, 136.54, 133.98, 133.86, 129.75, 129.60, 129.06, 128.97, 128.88, 128.61, 128.57, 128.52, 128.48, 128.31, 128.23, 128.11, 127.98, 127.88, 127.82, 127.7, 127.41, 127.24, 118.07, 114.68, 100.64, 100.56, 98.96, 98.36, 98.27, 98.15, 97.74, 97.04, 81.41, 81.28, 80.06, 77.77, 77.54, 77.27, 76.34, 75.50, 75.16, 75.09, 74.98, 74.78, 74.68, 74.44, 74.07, 73.93, 73.72, 73.34, 73.06, 72.91, 72.79, 72.63, 72.49, 72.39, 71.94, 71.44, 70.55, 68.79, 68.48, 61.60, 60.46, 60.40, 60.10, 59.96, 55.66, 52.81, 52.64, 52.32, 52.07, 51.77, 22.66.

Synthesis of 100

Compound 100 is prepared from compound 99 following general procedures J and then K.

$^1$H NMR; (MeOD) δ 7.44-7.17 (m, 45H), 7.09 (d, J=9.1 Hz, 2H), 6.84 (d, J=9.1 Hz, 2H), 5.49 (s, 1H), 5.43 (m, 2H), 5.27 (s, 1H), 5.12-4.53 (m, 32H), 4.44-3.51 (m, 34H), 3.73 (s, 3H), 1.86, 1.84, 1.78, 1.66 (s, 3H each). $^{13}$C NMR; δ 175.40, 175.31, 174.45, 173.33, 173.25, 173.18, 173.11, 168.34, 156.54, 152.41, 140.30, 140.21, 140.04, 139.85, 139.80, 139.45, 139.21, 133.67, 130.69, 129.75, 129.60, 129.49, 129.41, 129.35, 129.29, 129.01, 128.89, 128.69, 128.60, 128.51, 128.47, 128.21, 119.28, 115.72, 103.97, 103.91, 101.99, 101.73, 98.75, 98.22, 97.35, 86.11, 85.74, 81.96, 80.94, 80.50, 80.22, 79.28, 77.93, 77.82, 77.68, 77.56, 76.67, 76.47, 76.30, 76.20, 75.97, 75.83, 75.28, 75.16, 75.09, 74.06, 73.63, 73.15, 72.90, 71.64, 71.40, 71.09, 70.11, 69.31, 68.42, 67.47, 67.30, 67.06, 56.19, 54.38, 53.56, 53.47, 23.00.

Synthesis of 101

Compound 101 is prepared from compound 100 following general procedure L.

$^1$H NMR; (D$_2$O) δ 7.13 (d, J=8.8 Hz, 2H), 6.98 (d, J=8.8 Hz, 2H), 5.46 (s, 1H), 5.41 (m, 2H), 5.16 (m, 2H), 4.98 (s, 1H), 4.79-4.68 (m, 4H), 4.57 (m, 2H), 4.44 (m, 2H), 4.36-4.33 (m, 2H), 4.23-4.15 (m, 4H), 4.11 (s, 1H), 4.07-3.69 (m, 24H), 3.80 (s, 3H), 3.56 (t, J=9.6 Hz, 1H), 3.36-3.32 (m, 2H), 2.04, 2.03 (s, 3H each), 2.01 (s, 6H). $^{13}$C NMR δ 174.97, 174.89, 174.67, 174.52, 174.43, 154.81, 150.34, 119.34, 115.18, 102.00, 101.96, 100.69, 97.08, 96.84, 94.76, 94.39, 77.37, 77.26, 76.90, 76.51, 76.28, 76.20, 74.34, 73.92, 73.57, 70.66, 70.12, 69.95, 69.59, 69.38, 69.21, 69.17, 69.08, 69.01, 68.85, 68.11, 66.41, 66.26, 65.85, 55.91, 53.67, 53.60, 53.14, 53.04, 22.04, 22.01.

Synthesis of 102

Compound 102 is prepared from compounds 125 and 24 following general procedure E. $^1$H NMR; (CDCl$_3$) δ 8.11-8.05 (m, 6H), 7.76 (m, 2H), 7.60-7.17 (m, 43H), 7.08-7.06 (m, 2H), 6.88 (d, J=9.1 Hz, 2H), 6.76 (d, J=9.1 Hz, 2H), 5.54-5.51 (m, 2H), 5.18-5.12 (m, 4H), 5.07 (d, J=7.1 Hz, 1H), 4.96 (d, J=10.4 Hz, 1H), 4.86-4.67 (m, 10H), 4.59 (dd, J=11.8, 2.6 Hz, 1H), 4.51-4.45 (m, 3H), 4.39-3.61 (m, 55H), 3.74 (s, 3H), 3.33-3.27 (m, 3H), 2.04, 2.03, 2.00 (s, 3H each). $^{13}$C NMR; δ 170.57, 170.52, 170.46, 166.82, 166.76, 165.51, 165.45, 165.08, 155.70, 154.17, 150.99, 143.20, 143.05, 141.34, 137.85, 137.72, 137.35, 137.24, 137.13, 137.06, 133.54, 133.47, 129.82, 129.52, 129.38, 128.75, 128.67, 128.59, 128.48, 128.44, 128.40, 128.30, 128.26, 128.19, 128.10, 128.02, 127.99, 127.87, 127.79, 127.67, 127.26, 125.03, 124.84, 120.14, 118.77, 114.56, 100.11, 98.81, 98.14, 97.98, 97.94, 97.79, 82.75, 78.84, 78.52, 77.92, 75.59, 75.28, 75.08, 75.01, 74.58, 74.53, 74.29, 74.21, 74.13, 73.87, 73.63, 73.54, 73.38, 72.54, 70.45, 70.32, 70.22, 69.80, 68.83, 67.73, 67.12, 64.60, 63.77, 63.68, 63.61, 63.28, 63.12, 62.19, 61.93, 55.65, 46.75, 40.64, 40.53, 20.77, 20.73, 20.63.

Synthesis of 103

Compound 103 is prepared from compound 102 following general procedure D.

$^{1}$H NMR; (CDCl$_3$) δ 8.12-8.05 (m, 6H), 7.57 (t, J=7.4 Hz, 1H), 7.53-7.48 (m, 2H), 7.46-7.40 (m, 6H), 7.34-7.19 (m, 30H), 6.88 (d, J=9.1 Hz, 2H), 6.76 (d, J=9.1 Hz, 2H), 5.54-5.51 (m, 2H), 5.18-5.14 (m, 2H), 5.12-5.10 (m, 2H), 5.07 (d, J=7.1 Hz, 1H), 4.95 (d, J=10.5 Hz, 1H), 4.86-4.67 (m, 10H), 4.61-4.55 (m, 2H), 4.51-4.44 (m, 3H), 4.41 (d, J=7.8 Hz, 1H), 4.37-4.19 (m, 8H), 4.15-3.98 (m, 8H), 3.94 (s, 2H), 3.91 (s, 2H), 3.89 (s, 2H), 3.91-3.69 (m, 8H), 3.74 (s, 3H), 3.63-3.55 (m, 2H), 3.40-3.27 (m, 3H), 3.22 (dd, J=10.1, 3.6 Hz, 1H), 2.04 (s, 6H), 2.03, 2.02 (s, 3H each). $^{13}$C NMR; δ 171.70, 170.70, 170.58, 167.02, 166.79, 166.75, 165.51, 165.08, 155.68, 150.98, 137.84, 137.74, 137.69, 137.34, 137.24, 137.20, 133.52, 133.47, 129.87, 129.81, 129.50, 129.37, 128.69, 128.58, 128.42, 128.40, 128.31, 128.24, 128.16, 128.10, 127.97, 127.78, 127.66, 118.76, 114.55, 100.11, 98.95, 98.23, 97.91, 97.79, 82.74, 79.72, 78.71, 78.50, 75.57, 75.38, 75.27, 75.19, 75.12, 74.65, 74.57, 74.28, 74.23, 73.62, 73.52, 73.43, 72.53, 71.29, 70.56, 70.48, 70.38, 70.31, 70.23, 67.76, 67.68, 64.59, 63.59, 63.27, 63.08, 62.80, 62.17, 60.39, 55.64, 40.66, 40.53, 20.74.

Synthesis of 104

Compound 104 is prepared from compounds 103 and 23 following general procedure E.

$^{1}$H NMR; (CDCl$_3$) δ 8.08-8.00 (m, 8H), 7.58-7.12 (m, 57H), 6.88 (d, J=9.1 Hz, 2H), 6.76 (d, J=9.1 Hz, 2H), 5.54-5.51 (m, 2H), 5.43 (d, J=3.8 Hz, 1H), 5.35 (t, J=8.2 Hz, 1H), 5.16 (t, J=4.3 Hz, 1H), 5.12-5.09 (m, 2H), 5.07 (d, J=7.1 Hz, 1H), 5.03 (d, J=3.8 Hz, 1H), 4.94 (d, J=10.4 Hz, 1H), 4.91-4.54 (m, 14H), 4.44 (dd, J=10.4, 7.6 Hz, 1H), 4.34-3.55 (m, 41H), 3.93, 3.89, 3.81, 3.80 (s, 2H each), 3.73 (s, 3H), 3.49 (t, J=9.4 Hz, 1H), 3.32-3.20 (m, 4H), 2.03, 2.00, 1.99, 1.96 (s, 3H each). $^{13}$C NMR; δ 170.58, 170.52, 170.43, 166.82, 166.79, 166.75, 166.60, 165.48, 165.43, 165.09, 164.94, 155.70, 150.99, 138.19, 137.84, 137.72, 137.51, 137.35, 137.25, 137.18, 133.70, 133.47, 129.83, 129.51, 129.36, 129.06, 128.80, 128.75, 128.68, 128.62, 128.57, 128.40, 128.29, 128.25, 128.19, 128.12, 128.04, 127.98, 127.79, 127.68, 127.56, 127.21, 125.33, 118.77, 114.56, 100.95, 100.11, 98.57, 98.20, 98.00, 97.91, 97.81, 82.74, 80.13, 78.66, 78.49, 78.06, 77.90, 77.75, 75.64, 75.57, 75.45, 75.23, 75.09, 74.87, 74.77, 74.60, 74.43, 74.22, 74.11, 73.62, 73.56, 72.54, 72.32, 70.49, 70.31, 69.89, 67.81, 67.62, 65.02, 64.58, 63.57, 63.50, 63.21, 62.39, 62.16, 61.88, 55.65, 40.65, 40.60, 40.53, 40.45, 21.46, 20.78, 20.70.

Synthesis of 105

Compound 105 is prepared from compound 104 following general procedure F.

$^{1}$H NMR; (CDCl$_3$) δ 8.10-8.00 (m, 8H), 7.58-7.49 (m, 3H), 7.46-7.12 (m, 54H), 6.89 (d, J=9.0 Hz, 2H), 6.76 (d, J=9.0 Hz, 2H), 5.65 (s, 1H), 5.54 (t, J=8.0 Hz, 1H), 5.50 (s, 1H), 5.31 (t, J=8.1 Hz, 1H), 5.17 (s, 1H), 5.12-5.08 (m, 3H), 4.99 (s, 1H), 4.89-4.63 (m, 12H), 4.58-4.53 (m, 3H), 4.47-4.43 (m, 2H), 4.35-3.42 (m, 40H), 3.72 (s, 3H), 3.35-3.24 (m, 6H), 3.16-3.11 (m, 1H), 3.06-3.01 (m, 1H), 2.03 (s, 3H), 1.99 (s, 6H), 1.97 (s, 3H). $^{13}$C NMR; δ 170.58, 170.42, 165.82, 165.72, 165.10, 164.96, 155.65, 151.13, 138.14, 137.88, 137.61, 137.53, 137.46, 137.34, 133.61, 133.40, 129.81, 129.63, 129.06, 128.75, 128.68, 128.55, 128.45, 128.37, 128.26, 128.14, 128.08, 128.03, 127.86, 127.77, 127.65, 126.86, 125.33, 118.51, 114.66, 101.22, 100.53, 98.12, 97.94, 97.86, 97.62, 97.42, 83.65, 83.35, 80.27, 79.21, 78.82, 78.33, 78.00, 77.78, 77.34, 77.08, 76.83, 75.55, 75.14, 75.07, 74.88, 74.81, 74.46, 74.36, 74.30, 74.17, 73.97, 73.42, 73.35, 73.06, 72.99, 72.79, 72.49, 70.22, 70.09, 69.96, 69.62, 68.82, 68.19, 67.53, 63.98, 63.46, 63.24, 62.63, 62.43, 62.10, 61.95, 61.77, 61.22, 61.02, 55.65, 21.47, 20.81.

Synthesis of 106

Compound 106 is prepared from compound 105 following general procedure G2.

$^{1}$H NMR; (CDCl$_3$) δ 8.12-8.01 (m, 8H), 7.58-7.52 (m, 4H), 7.48-7.41 (m, 8H), 7.37-7.10 (m, 45H), 6.85 (d, J=9.1 Hz, 2H), 6.73 (d, J=9.1 Hz, 2H), 5.52-5.39 (m, 6H), 5.18-5.14 (m, 2H), 5.07 (d, J=6.8 Hz, 1H), 5.03 (d, J=10.8 Hz, 1H), 4.94 (d, J=3.6 Hz, 1H), 4.91-4.86 (m, 4H), 4.82 (s, 1H), 4.80 (s, 1H), 4.78-4.63 (m, 9H), 4.55 (d, J=11.0 Hz, 1H), 4.44 (d, J=10.8 Hz, 1H), 4.37-4.18 (m, 9H), 4.14-4.01 (m, 8H), 3.97-3.69 (m, 11H), 3.72 (s, 3H), 3.59-3.42 (m, 5H), 3.51, 3.50, 3.43 (s, 3H each), 3.34-3.21 (m, 4H), 3.26 (s, 3H), 2.09, 2.08, 2.02, 2.01 (s, 3H each). $^{13}$C NMR; δ 170.76, 170.68, 170.60, 170.42, 169.73, 169.57, 168.14, 167.70, 165.22, 165.09, 165.00, 164.69, 155.70, 150.95, 137.96, 137.89, 137.76, 137.57, 137.52, 137.44, 137.39, 137.29, 137.19, 133.92, 133.81, 133.63, 133.44, 129.95, 129.86, 129.80, 129.74, 129.46, 129.11, 129.05, 128.86, 128.77, 128.55, 128.33, 128.25, 128.16, 128.06, 127.94, 127.85, 127.80, 127.59, 125.32, 118.74, 114.50, 101.19, 100.73, 98.72, 98.66, 97.91, 97.85, 97.69, 97.40, 82.49, 82.17, 80.23, 77.99, 77.74, 77.63, 77.48, 76.28, 75.95, 75.58, 75.33, 75.10, 75.02, 74.93, 74.84, 74.65, 74.57, 74.51, 74, 37, 74.26, 73.80, 73.67, 72.28, 71.62, 71.15, 69.87, 69.65, 69.45, 63.42, 62.95, 62.84, 62.19, 61.55, 55.62, 52.70, 52.22, 51.85, 51.75, 20.80, 20.75.

Synthesis of 107

Compound 107 is prepared from compound 106 following general procedure H.

$^{1}$H NMR; (CDCl$_3$) δ 8.07-8.00 (m, 8H), 7.59-7.54 (m, 4H), 7.47-7.42 (m, 6H), 7.35-7.07 (m, 47H), 6.84 (d, J=9.1 Hz, 2H), 6.73 (d, J=9.1 Hz, 2H), 5.72-5.68 (m, 2H), 5.64-5.61 (m, 2H), 5.53 (dd, J=8.5, 6.6 Hz, 1H), 5.42 (dd, J=9.0, 8.0 Hz, 1H), 5.33-5.30 (m, 2H), 5.20-5.15 (m, 2H), 5.06 (d, J=6.6 Hz, 1H), 5.05 (d, J=3.4, Hz, 1H), 4.96-4.88 (m, 5H), 4.84-4.47 (m, 18H), 4.41-4.35 (m, 4H), 4.32-3.91 (m, 19H), 3.84-3.46 (m, 10H), 3.72, 3.55, 3.49 (s, 3H each), 3.41-3.35 (m, 2H), 3.37, 3.32 (s, 3H each), 2.09, 2.08, 2.01, 1.94, 1.39 (s, 3H each), 1.38 (s, 6H), 1.35 (s, 3H). $^{13}$C NMR; δ 171.04, 170.67, 170.62, 170.21, 170.06, 169.99, 169.28, 169.16, 167.69, 167.22, 165.49, 165.21, 164.99, 164.72, 155.74, 150.86, 138.70, 138.47, 138.13, 137.70, 136.88, 136.77, 136.51, 136.37, 133.85, 133.58, 129.76, 129.70, 129.26, 129.03, 128.95, 128.62, 128.53, 128.49, 128.31, 128.23, 128.16, 128.10, 128.02, 127.90, 127.78, 127.71, 127.56, 127.37, 127.29, 127.06, 125.30, 118.61, 114.51, 101.36, 100.90, 99.62, 99.27, 98.02, 97.83, 81.40, 80.93, 80.52, 78.02, 77.90, 77.49, 75.75, 75.45, 75.31, 74.96, 74.86, 74.67, 73.93, 73.86, 73.58, 73.21, 72.08, 71.64, 71.06, 70.72, 70.65, 70.15, 69.82, 62.18, 61.52, 55.61, 52.79, 52.71, 52.53, 51.76, 51.69, 22.75, 22.71, 22.61, 22.53, 20.97, 20.95, 20.79, 20.73.

Synthesis of 108

Compound 108 is prepared from compound 107 following general procedure I.

¹H NMR; (CDCl₃) δ 8.04-8.00 (m, 4H), 7.96-7.92 (m, 4H), 7.60-7.54 (m, 4H), 7.48-7.41 (m, 8H), 7.35-7.09 (m, 45H), 6.84 (d, J=9.1 Hz, 2H), 6.73 (d, J=9.1 Hz, 2H), 5.99 (d, J=9.2 Hz, 1H), 5.91 (d, J=9.1 Hz, 1H), 5.75 (d, J=9.5 Hz, 1H), 5.63 (d, J=9.3 Hz, 1H), 5.53 (dd, J=8.5, 6.8 Hz, 1H), 5.45-5.39 (m, 2H), 5.34 (d, J=4.8 Hz, 1H), 5.21 (t, J=6.0 Hz, 1H), 5.14 (br s, 1H), 5.12 (d, J=3.5 Hz, 1H), 5.07 (d, J=6.7 Hz, 1H), 4.99 (d, J=3.5 Hz, 1H), 4.96-4.90 (m, 3H), 4.83-4.73 (m, 5H), 4.68-4.49 (m, 12H), 4.37-4.34 (m, 2H), 4.28-4.20 (m, 4H), 4.14-3.85 (m, 16H), 3.73-3.16 (m, 15H), 3.71, 3.58, 3.49, 3.35, 3.20, 1.46, 1.44, 1.44, 1.41 (s, 3H each). ¹³C NMR δ 170.72, 170.53, 170.27, 170.12, 169.15, 169.09, 167.97, 167.91, 165.55, 165.41, 165.02, 164.78, 155.73, 150.85, 138.96, 138.50, 138.45, 138.29, 137.94, 137.00, 136.87, 136.54, 133.85, 133.59, 129.74, 129.65, 129.55, 129.23, 128.98, 128.85, 128.59, 128.53, 128.34, 128.25, 128.14, 127.97, 127.92, 127.83, 127.78, 127.59, 127.37, 127.22, 127.16, 118.61, 114.52, 100.88, 100.75, 98.92, 97.63, 96.87, 96.66, 81.34, 81.07, 80.09, 77.71, 77.57, 76.75, 76.39, 76.30, 76.26, 75.43, 75.36, 75.19, 75.00, 74.76, 74.66, 74.31, 73.93, 73.77, 73.63, 73.33, 73.10, 72.94, 72.39, 71.98, 71.27, 71.10, 70.23, 67.19, 67.14, 66.53, 66.27, 66.19, 61.57, 60.51, 60.33, 59.91, 55.60, 52.73, 52.64, 52.12, 51.83, 51.76, 22.67, 22.62.

Synthesis of 109

Compound 109 is prepared from compound 108 following general procedure J.

¹H NMR; (CD₃OD) δ 8.22 (d, J=7.3 Hz, 2H), 8.12-8.09 (m, 4H), 8.04 (d, J=7.3 Hz, 2H), 7.65-7.43 (m, 12H), 7.35-7.01 (m, 43H), 6.97-6.95 (m, 2H), 6.85 (d, J=9.1 Hz, 2H), 6.75 (d, J=9.1 Hz, 2H), 5.58 (d, J=3.7 Hz, 1H), 5.53 (d, J=4.6 Hz, 1H), 5.43-5.35 (m, 4H), 5.28-5.26 (m, 2H), 5.23 (t, J=4.7 Hz, 1H), 5.17 (t, J=5.5 Hz, 1H), 5.04 (d, J=3.2 Hz, 1H), 5.01 (d, J=11.0 Hz, 1H), 4.97 (d, J=3.4 Hz, 1H), 4.86-4.14 (m, 35H), 4.09-3.90 (m, 8H), 3.74-3.48 (m, 7H), 3.63, 3.56, 3.50 (s, 3H each), 3.44-3.39 (m, 3H), 3.19, 2.98, 1.85, 1.77, 1.55, 1.47 (s, 3H each). ¹³C NMR; (CD₃OD) δ 173.53, 173.33, 173.24, 170.78, 170.49, 170.43, 170.38, 167.43, 167.26, 166.86, 166.56, 157.24, 152.36, 140.26, 140.07, 139.87, 139.82, 138.79, 138.67, 138.49, 135.11, 134.84, 131.23, 130.86, 130.61, 130.16, 130.04, 129.95, 129.86, 129.58, 129.51, 129.44, 129.36, 129.31, 129.28, 129.22, 129.11, 129.04, 128.93, 128.84, 128.59, 128.40, 128.25, 128.14, 119.51, 115.73, 101.70, 99.18, 99.08, 98.95, 97.45, 97.01, 83.95, 83.43, 81.72, 79.90, 79.60, 79.36, 78.96, 78.19, 76.87, 76.22, 75.87, 75.65, 75.41, 75.31, 75.14, 74.98, 74.79, 74.59, 74.46, 73.90, 72.82, 72.27, 71.79, 71.42, 71.13, 70.63, 66.83, 66.21, 65.74, 56.14, 54.07, 53.85, 53.66, 53.51, 53.33, 52.82, 52.58, 22.93, 22.84, 22.80.

Synthesis of 110

Compound 110 is prepared from compound 109 following general procedure K.

¹H NMR; (CD₃OD) δ 7.39-7.18 (m, 45H), 7.04 (d, J=9.1 Hz, 2H), 6.83 (d, J=9.1 Hz, 2H), 5.42-5.40 (m, 2H), 5.23 (br s, 2H), 5.11-5.07 (m, 2H), 5.01-4.54 (m, 25H), 4.47-3.51 (m, 35H), 3.74, 1.86, 1.77, 1.69, 1.62 (s, 3H each). ¹³C NMR; (CD₃OD) δ 175.75, 175.05, 173.29, 173.12, 173.00, 156.89, 153.22, 140.26, 139.98, 139.86, 139.73, 139.33, 139.19, 129.76, 129.60, 129.54, 129.49, 129.40, 129.32, 129.03, 128.86, 128.80, 128.63, 128.58, 119.55, 115.57, 103.94, 103.85, 102.28, 102.09, 98.82, 98.63, 98.03, 97.13, 86.19, 85.83, 81.96, 80.96, 80.84, 80.48, 79.34, 78.33, 78.04, 77.62, 76.62, 76.30, 75.95, 75.85, 75.65, 75.43, 75.16, 74.78, 73.99, 73.15, 71.69, 71.46, 71.35, 70.59, 70.18, 69.39, 67.41, 67.08, 56.16, 54.41, 54.30, 53.60, 23.00.

Synthesis of 111

Compound 111 is prepared from compound 110 following general procedure L.

¹H NMR; (D₂O) δ 7.10 (d, J=8.3 Hz, 2H), 6.97 (d, J=8.3 Hz, 2H), 5.42-5.39 (m, 2H), 5.15 (br s, 2H), 4.98-4.96 (m, 3H), 4.76-4.74 (m, 2H and HOD), 4.57 (d, J=7.8 Hz, 1H), 4.45 (d, J=10.8 Hz, 1H), 4.36-4.31 (m, 3H), 4.22-4.14 (m, 4H), 4.08-3.69 (m, 27H), 3.58-3.55 (m, 2H), 3.36-3.32 (m, 1H), 2.04, 2.00 (s, 6H each). ¹³C NMR δ 175.05, 174.95, 174.67, 174.52, 174.42, 154.84, 151.02, 118.38, 115.13, 102.01, 101.96, 101.91, 101.29, 97.17, 97.05, 94.48, 94.35, 77.25, 77.11, 76.92, 76.80, 76.70, 76.62, 76.44, 76.30, 76.20, 74.40, 74.22, 73.53, 73.35, 70.66, 70.10, 69.96, 69.60, 69.55, 69.41, 69.35, 69.31, 69.23, 69.13, 68.95, 68.79, 66.38, 66.23, 65.88, 55.90, 53.76, 53.65, 53.59, 53.04, 22.00.

Synthesis of 112

Compound 112 is prepared from compounds 26 and 22 following general procedure E.

¹H NMR; (CDCl₃) δ 8.13-8.08 (m, 4H), 7.76-7.73 (m, 2H), 7.60-7.53 (m, 4H), 7.49-7.33 (m, 10H), 7.30-7.13 (m, 18H), 7.01 (d, J=9.1 Hz, 2H), 6.83 (d, J=9.1 Hz, 2H), 5.57 (s, 1H), 5.48 (d, J=3.9 Hz, 1H), 5.36 (t, J=8.3 Hz, 1H), 5.33 (t, J=1.6 Hz, 1H), 4.97 (d, J=11.7 Hz, 1H), 4.86 (t, J=9.5 Hz, 1H), 4.78-4.69 (m, 4H), 4.65-4.61 (m, 2H), 4.57 (d, J=3.8 Hz, 1H), 4.49-4.45 (m, 2H), 4.33-4.13 (m, 10H), 4.05-3.58 (m, 15H), 3.77 (s, 3H), 3.51 (t, J=9.4 Hz, 1H), 3.35 (dd, J=10.2, 3.9 Hz, 1H), 3.25 (dd, J=10.1, 3.8 Hz, 1H), 2.02, 1.98 (s, 3H each). ¹³C NMR δ 170.55, 170.45, 166.87, 166.56, 165.65, 164.93, 155.23, 154.12, 150.12, 143.25, 143.01, 141.32, 138.25, 137.59, 137.19, 137.09, 133.67, 133.55, 129.89, 129.85, 129.63, 129.05, 129.02, 128.81, 128.76, 128.42, 128.25, 128.12, 128.09, 127.98, 127.93, 127.87, 127.57, 127.48, 127.25, 127.17, 125.32, 125.11, 124.91, 120.12, 118.29, 114.56, 100.88, 98.76, 97.85, 97.51, 82.67, 78.40, 77.78, 77.49, 75.43, 75.21, 74.69, 74.61, 74.57, 74.11, 72.44, 72.38, 72.28, 70.40, 69.99, 68.77, 68.09, 65.60, 65.01, 64.76, 63.34, 62.63, 62.15, 61.80, 55.70, 46.71, 40.44, 40.41, 20.69.

Synthesis of 113

Compound 113 is prepared from compound 112 following general procedure D.

¹H NMR; (CDCl₃) δ 8.13-8.08 (m, 4H), 7.57-7.52 (m, 2H), 7.49-7.13 (m, 24H), 7.01 (d, J=9.1 Hz, 2H), 6.83 (d, J=9.1 Hz, 2H), 5.57 (s, 1H), 5.45 (d, J=3.9 Hz, 1H), 5.36 (t, J=8.2 Hz, 1H), 5.32 (s, 1H), 4.97 (d, J=11.6 Hz, 1H), 4.89 (s, 2H), 4.80-4.68 (m, 4H), 4.60 (d, J=7.8 Hz, 1H), 4.57 (d, J=3.7 Hz, 1H), 4.51-4.45 (m, 2H), 4.26-4.10 (m, 5H), 4.06 (d, J=10.4 Hz, 1H), 4.00-3.96 (m, 2H), 3.90 (d, J=11.0 Hz, 1H), 3.85-3.58 (m, 12H), 3.78 (s, 3H), 3.51 (t, J=10 Hz, 1H), 3.44-3.39 (m, 1H), 3.25-3.22 (m, 2H), 2.95 (d, J=4 Hz, 1H), 2.07, 1.97 (s, 3H each). ¹³C NMR δ 171.87, 170.56, 166.90, 166.54, 165.64, 164.94, 155.21, 150.11, 138.29, 137.78, 137.58, 137.25, 133.65, 133.54, 129.88, 129.84, 129.62, 129.03, 128.79, 128.76, 128.66, 128.40, 128.20, 128.16, 128.11, 128.07, 127.97, 127.79, 127.61, 127.44, 127.10, 118.27, 114.54, 100.87, 98.77, 98.25, 97.49, 82.78, 79.16, 78.38, 77.81, 75.42, 75.14, 74.58, 74.16, 72.40, 71.35, 70.61, 69.98, 68.05, 65.58, 64.97, 64.74, 63.32, 62.71, 62.66, 62.15, 55.69, 40.43, 20.78, 20.70.

Synthesis of 114

Compound 114 is prepared from compounds 113 and 24 following general procedure E.

¹H NMR; (CDCl₃) δ 8.13-8.07 (m, 6H), 7.78-7.75 (m, 2H), 7.60-7.53 (m, 4H), 7.49-7.13 (m, 39H), 7.08-7.06 (m, 2H), 7.01 (d, J=9.1 Hz, 2H), 6.83 (d, J=9.1 Hz, 2H), 5.56 (s, 1H), 5.44 (d, J=3.9 Hz, 1H), 5.36 (d, J=8.2 Hz, 1H), 5.33 (s, 1H), 5.16-5.14 (m, 2H), 4.98 (d, J=3.8 Hz, 1H), 4.96 (d, J=5.1 Hz, 1H), 4.85 (d, J=11.4 Hz, 1H), 4.80-4.67 (m, 7H), 4.59 (d,

J=7.9 Hz, 1H), 4.57 (d, J=3.8 Hz, 1H), 4.51-4.45 (m, 3H), 4.44-4.41 (m, 1H), 4.34-4.28 (m, 2H), 4.24-4.02 (m, 15H), 3.98-3.89 (m, 6H), 3.82-3.58 (m, 13H), 3.77 (s, 3H), 3.51 (t, J=9.9 Hz, 1H), 3.33-3.29 (m, 2H), 3.24 (dd, J=10.1, 3.7 Hz, 1H), 2.05, 2.00, 1.98 (s, 3H each). $^{13}$C NMR δ 170.51, 170.48, 166.84, 166.75, 166.55, 165.65, 165.47, 164.94, 155.24, 154.19, 150.14, 143.22, 143.07, 141.38, 141.35, 138.28, 137.88, 137.82, 137.61, 137.28, 137.21, 137.09, 133.64, 133.56, 129.90, 129.86, 129.65, 129.54, 129.07, 128.92, 128.78, 128.60, 128.48, 128.43, 128.31, 128.26, 128.21, 128.14, 128.09, 128.02, 127.88, 127.81, 127.72, 127.57, 127.46, 127.27, 127.22, 125.34, 125.05, 124.85, 120.17, 120.15, 118.30, 114.56, 100.88, 98.88, 98.81, 97.99, 97.83, 97.52, 82.80, 78.71, 78.38, 77.94, 77.69, 75.45, 75.30, 75.20, 75.14, 75.02, 74.68, 74.64, 74.56, 74.44, 74.19, 73.85, 73.35, 72.46, 72.38, 70.32, 70.20, 70.02, 69.77, 68.83, 68.09, 67.08, 65.60, 64.87, 64.75, 63.90, 63.41, 63.34, 63.14, 62.11, 62.07, 61.97, 55.70, 46.77, 40.66, 40.45, 40.43, 20.80, 20.72, 20.65.

Synthesis of 115

Compound 115 is prepared from compound 114 following general procedure D.

$^{1}$H NMR; (CDCl$_3$) δ 8.13-8.07 (m, 6H), 7.58-7.41 (m, 10H), 7.34-7.12 (m, 29H), 7.01 (d, J=9.1 Hz, 2H), 6.83 (d, J=9.1 Hz, 2H), 5.56 (s, 1H), 5.43 (d, J=3.9 Hz, 1H), 5.36-5.32 (m, 2H), 5.15 (t, J=4 Hz, 1H), 5.11 (d, J=3.7 Hz, 1H), 4.98 (d, J=3.9 Hz, 1H), 4.96 (d, J=5.3 Hz, 1H), 4.84 (d, J=11.3 Hz, 1H), 4.79-4.66 (m, 7H), 4.60-4.45 (m, 6H), 4.41-4.37 (m, 2H), 4.31 (dd, J=12.2, 3.6 Hz, 1H), 4.25-4.06 (m, 10H), 3.98-3.89 (m, 5H), 3.80-3.68 (m, 11H), 3.77 (s, 3H), 3.62-3.55 (m, 4H), 3.50 (t, J=9 Hz, 1H), 3.37 (dt, J=9.4, 4.3 Hz, 1H), 3.31 (dd, J=9.8, 4.3 Hz, 1H), 3.26-3.20 (m, 2H), 2.82 (d, J=4.2 Hz, 1H), 2.04, 2.03, 1.97 (s, 3H each). $^{13}$C NMR δ 171.69, 170.67, 170.49, 166.99, 166.68, 166.53, 165.63, 165.52, 164.92, 155.21, 150.12, 138.25, 137.82, 137.68, 137.59, 137.25, 133.62, 133.55, 133.49, 129.86, 129.61, 129.51, 129.05, 128.76, 128.69, 128.59, 128.39, 128.26, 128.11, 128.06, 127.96, 127.81, 127.78, 127.55, 127.42, 127.18, 125.32, 118.28, 114.54, 100.85, 99.01, 98.79, 97.92, 97.82, 97.49, 82.76, 79.71, 78.57, 78.36, 77.64, 75.43, 75.33, 75.19, 74.75, 74.64, 74.24, 74.17, 73.41, 72.44, 72.36, 72.31, 71.27, 70.56, 70.43, 70.26, 69.99, 68.06, 67.72, 65.57, 64.82, 64.72, 63.75, 63.31, 63.09, 62.80, 62.08, 62.01, 55.69, 40.67, 40.44, 40.38, 20.79, 20.72.

Synthesis of 116

Compound 116 is prepared from compound 115 and 23 following general procedure E.

$^{1}$H NMR; (CDCl$_3$) δ 8.13-8.05 (m, 8H), 7.58-7.52 (m, 4H), 7.49-7.41 (m, 10H), 7.37-7.11 (m, 43H), 7.01 (d, J=9.1 Hz, 2H), 6.83 (d, J=9.1 Hz, 2H), 5.56 (s, 1H), 5.43-5.40 (m, 2H), 5.36-5.31 (m, 3H), 5.11 (t, J=4.1 Hz, 1H), 5.05 (d, J=3.8 Hz, 1H), 4.96 (d, J=11.7 Hz, 1H), 4.91 (d, J=10.5 Hz, 1H), 4.86 (br s, 2H), 4.83-4.74 (m, 6H), 4.70-4.62 (m, 7H), 4.59-4.55 (m, 3H), 4.48-4.45 (m, 1H), 4.30-4.12 (m, 16H), 4.06-3.56 (m, 31H), 3.77 (s, 3H), 3.53-3.46 (m, 2H), 3.31-3.19 (m, 4H), 2.01, 2.00, 1.97, 1.96 (s, 3H each). $^{13}$C NMR δ 170.49, 170.43, 166.82, 166.65, 166.58, 166.53, 165.64, 165.44, 164.93, 155.23, 150.13, 138.24, 138.19, 137.80, 137.60, 137.52, 137.24, 133.68, 133.56, 129.85, 129.62, 129.37, 129.06, 128.78, 128.62, 128.57, 128.39, 128.36, 128.20, 128.12, 128.05, 127.98, 127.79, 127.56, 127.43, 127.21, 125.32, 118.29, 114.55, 100.95, 100.84, 98.81, 98.60, 98.00, 97.82, 97.51, 82.77, 80.13, 78.52, 78.36, 78.06, 77.76, 77.61, 75.57, 75.43, 75.35, 75.29, 75.23, 75.18, 74.93, 74.77, 74.63, 74.40, 74.17, 74.11, 73.49, 72.45, 72.37, 72.32, 70.35, 70.26, 70.14, 70.01, 69.89, 68.08, 67.53, 65.59, 65.03, 64.82, 64.73, 63.38, 63.32, 63.21, 62.40, 62.08, 61.91, 55.70, 40.59, 40.45, 40.38, 20.77, 20.70.

Synthesis of 117

Compound 117 is prepared from compound 116 following general procedure F.

$^{1}$H NMR; (CDCl$_3$) δ 8.14-8.05 (m, 8H), 7.59-7.56 (m, 2H), 7.53-7.49 (m, 2H), 7.47-7.41 (m, 10H), 7.37-7.12 (m, 43H), 7.01 (d, J=9.1 Hz, 2H), 6.82 (d, J=9.1 Hz, 2H), 5.59 (s, 1H), 5.54 (d, J=4.0 Hz, 1H), 5.51 (d, J=3.9 Hz, 1H), 5.34-5.29 (m, 3H), 5.09 (t, J=2.4 Hz, 1H), 5.01 (s, 1H), 4.98 (d, J=11.7 Hz, 1H), 4.86 (br s, 3H), 4.83-4.64 (m, 11H), 4.58-4.53 (m, 4H), 4.46 (d, J=2.8 Hz, 1H), 4.45 (d, J=2.8 Hz, 1H), 4.38 (t, J=6.8 Hz, 1H), 4.29 (d, J=12.2 Hz, 1H), 4.22-3.62 (m, 29H), 3.77 (s, 3H), 3.56-3.44 (m, 9H), 3.35-3.24 (m, 6H), 3.16-3.06 (m, 3H), 2.02, 2.00, 1.96, 1.95 (s, 3H each). $^{13}$C NMR δ 170.57, 170.41, 165.71, 164.95, 155.16, 150.33, 138.12, 137.77, 137.58, 137.47, 137.36, 137.31, 137.25, 133.60, 133.44, 129.84, 129.63, 129.08, 128.74, 128.69, 128.56, 128.53, 128.45, 128.35, 128.24, 128.06, 128.02, 127.87, 127.81, 127.76, 127.64, 126.84, 126.79, 125.31, 118.22, 114.65, 101.27, 101.21, 98.58, 98.10, 97.84, 97.69, 97.60, 97.36, 83.62, 80.25, 78.95, 78.47, 78.32, 78.13, 78.01, 77.75, 75.54, 75.13, 75.04, 74.88, 74.80, 74.35, 74.27, 73.81, 73.39, 73.11, 72.99, 72.74, 72.16, 72.06, 70.08, 69.93, 69.60, 68.80, 68.33, 67.56, 63.49, 63.40, 63.22, 62.61, 62.39, 62.26, 62.10, 61.75, 61.63, 61.30, 61.02, 55.66, 20.82, 20.73, 20.64.

Synthesis of 118

Compound 118 is prepared from compound 117 following general procedure G2.

$^{1}$H NMR; (CDCl$_3$) δ 8.12-8.05 (m, 8H), 7.60-7.42 (m, 12H), 7.38-7.09 (m, 45H), 6.98 (d, J=9.1 Hz, 2H), 6.80 (d, J=9.1 Hz, 2H), 5.63 (s, 1H), 5.48 (d, J=6.4 Hz, 1H), 5.45-5.37 (m, 4H), 5.29 (t, J=2.6 Hz, 1H), 5.15 (t, J=6.9 Hz, 1H), 5.03 (d, J=10.9 Hz, 1H), 4.95-4.91 (m, 3H), 4.88 (br s, 2H), 4.83-4.55 (m, 15H), 4.44 (d, J=10.9 Hz, 1H), 4.31-3.42 (m, 31H), 3.76, 3.52, 3.51, 3.50 (s, 3H each), 3.36-3.31 (m, 2H), 3.27 (dd, J=10.3, 3.8 Hz, 1H), 3.23 (dd, J=10.3, 3.6 Hz, 1H), 3.13 (dd, J=10.3, 3.6 Hz, 1H), 2.97, 2.12, 2.03, 2.01, 2.01 (s, 3H each). $^{13}$C NMR δ 170.87, 170.60, 170.43, 169.72, 169.16, 167.69, 167.49, 165.63, 165.08, 164.69, 155.27, 150.54, 137.93, 137.56, 137.39, 137.18, 133.92, 133.63, 129.94, 129.83, 129.73, 129.35, 129.03, 128.78, 128.54, 128.31, 128.17, 128.06, 127.99, 127.91, 127.76, 127.59, 127.33, 118.10, 114.62, 101.18, 98.68, 98.27, 97.69, 97.24, 82.80, 82.47, 80.22, 78.04, 77.82, 77.72, 77.61, 75.95, 75.58, 75.31, 75.20, 75.01, 74.93, 74.82, 74.68, 74.53, 73.65, 73.45, 72.67, 72.16, 71.56, 69.86, 69.54, 69.43, 69.30, 68.50, 68.27, 63.41, 63.01, 62.88, 62.18, 61.54, 55.67, 52.69, 52.08, 51.96, 51.86, 20.81.

Synthesis of 119

Compound 119 is prepared from compound 118 following general procedure H.

$^{1}$H NMR; (CDCl$_3$) δ 8.07-7.98 (m, 8H), 7.57-7.54 (m, 4H), 7.47-7.43 (m, 8H), 7.35-7.02 (m, 45H), 6.96 (d, J=9.1 Hz, 2H), 6.78 (d, J=9.1 Hz, 2H), 5.71-5.67 (m, 2H), 5.61-5.57 (m, 2H), 5.44-5.37 (m, 3H), 5.32 (m, 2H), 5.19-5.16 (m, 2H), 5.02 (d, J=3.3 Hz, 1H), 4.96-4.77 (m, 10H), 4.69-4.47 (m, 14H), 4.40-3.91 (m, 20H), 3.84-3.27 (m, 14H), 3.75, 3.52, 3.49, 3.39, 3.29, 2.10, 2.01, 1.98, 1.94, 1.40, 1.39, 1.38, 1.30 (s, 3H each). $^{13}$C NMR δ 171.11, 170.68, 170.62, 170.27, 170.08, 169.98, 169.26, 168.92, 167.29, 167.23, 165.56, 165.37, 164.72, 155.38, 150.46, 138.70, 138.57, 138.12, 137.70, 137.04, 136.85, 136.37, 133.93, 133.86, 129.78, 129.73, 129.04, 128.98, 128.93, 128.88, 128.83, 128.71, 128.62, 128.57, 128.52, 128.30, 128.24, 128.18, 128.09, 128.06, 128.00, 127.90, 127.77, 127.67, 127.61, 127.32, 127.27, 118.11, 114.64, 101.35, 101.29, 99.60, 98.87, 98.11, 97.85, 97.77, 97.70, 81.62, 81.40, 80.51, 77.98, 77.92, 77.47, 75.45, 75.27, 75.18, 74.95, 74.85, 74.75, 74.67, 73.75, 73.59, 73.52, 73.32, 73.22, 72.66, 71.94, 70.97, 70.71, 70.46, 69.84, 69.13, 68.61, 66.97, 62.18, 61.60, 61.36, 55.65, 52.78, 52.52, 52.47, 52.17, 52.09, 51.85, 51.78, 51.68, 22.74, 22.70, 22.61, 20.96, 20.82, 20.79, 20.73.

Synthesis of 120

Compound 120 is prepared from compound 119 following general procedure I.

$^1$H NMR; (CDCl$_3$) δ 8.05-8.02 (m, 4H), 7.98 (d, J=7.3 Hz, 2H), 7.92 (d, J=7.3 Hz, 2H), 7.58-7.52 (m, 4H), 7.47-7.41 (m, 8H), 7.34-7.01 (m, 45H), 6.93 (d, J=9.1 Hz, 2H), 6.75 (d, J=9.1 Hz, 2H), 5.72 (d, J=9.4 Hz, 1H), 5.64 (d, J=8.9 Hz, 1H), 5.57-5.54 (m, 2H), 5.46-5.40 (m, 3H), 5.35-5.33 (m, 2H), 5.20 (t, J=4.2 Hz, 1H), 5.13-5.11 (m, 2H), 4.99-4.48 (m, 24H), 4.34 (d, J=12.2 Hz, 1H), 4.25-4.20 (m, 2H), 4.16-3.24 (m, 31H), 3.73, 3.52, 3.44, 3.31, 3.27, 1.46, 1.43, 1.42, 1.34 (s, 3H each). $^{13}$C NMR; δ 170.49, 170.16, 169.91, 169.06, 167.97, 167.87, 165.48, 164.79, 155.34, 150.47, 138.91, 138.59, 138.30, 137.94, 137.07, 136.99, 136.52, 133.98, 133.92, 133.84, 133.77, 129.74, 129.66, 129.54, 129.01, 128.86, 128.61, 128.51, 128.28, 128.18, 128.05, 127.99, 127.85, 127.76, 127.68, 127.50, 127.30, 118.04, 114.63, 100.81, 100.62, 99.07, 98.52, 98.42, 98.15, 97.61, 97.24, 81.45, 81.34, 80.13, 77.74, 77.56, 76.49, 75.50, 75.24, 74.98, 74.89, 74.67, 74.40, 73.76, 73.66, 73.33, 72.98, 72.85, 72.79, 72.11, 71.89, 71.47, 70.71, 68.98, 68.72, 61.62, 60.50, 60.39, 59.98, 55.64, 52.74, 52.65, 52.36, 52.25, 51.97, 51.77, 22.68, 22.65.

Synthesis of 121

Compound 121 is prepared from compound 120 following general procedure J.

$^1$H NMR; (CD$_3$OD) δ 8.24-8.22 (m, 2H), 8.18-8.16 (m, 2H), 8.11-8.09 (m, 2H), 7.98-7.96 (m, 2H), 7.68-7.45 (m, 12H), 7.36-7.08 (m, 41H), 6.98-6.96 (m, 4H), 6.92 (d, J=9.1 Hz, 2H), 6.83 (d, J=9.1 Hz, 2H), 5.57 (d, J=4.5 Hz, 1H), 5.44 (d, J=3.0 Hz, 1H), 5.39-5.21 (m, 8H), 5.02-5.00 (m, 2H), 4.96 (d, J=3.5 Hz, 1H), 4.90-4.52 (m, 24H), 4.47-4.43 (m, 2H), 4.37-4.08 (m, 15H), 4.03-3.93 (m, 6H), 3.76-3.65 (m, 3H), 3.75 (s, 3H), 3.62-3.55 (m, 4H), 3.57 (s, 3H), 3.46-3.41 (m, 2H), 3.24, 2.98, 1.86, 1.84, 1.59, 1.53 (s, 3H each).

$^{13}$C NMR; δ 173.58, 173.35, 171.09, 170.61, 170.40, 170.26, 167.34, 167.12, 166.58, 157.06, 152.01, 140.26, 140.16, 140.07, 139.92, 139.87, 139.01, 138.71, 138.47, 135.13, 134.99, 134.85, 134.66, 131.24, 131.16, 130.93, 130.86, 130.66, 130.52, 130.22, 129.97, 129.52, 129.37, 129.32, 129.25, 129.21, 129.16, 129.07, 128.99, 128.85, 128.68, 128.61, 128.42, 128.18, 119.64, 115.74, 101.96, 101.68, 99.95, 98.97, 98.71, 97.33, 84.05, 83.94, 81.71, 79.93, 79.41, 79.12, 78.98, 78.76, 78.17, 76.52, 76.23, 76.10, 75.85, 75.69, 75.41, 75.07, 75.01, 74.48, 74.07, 73.82, 72.54, 71.77, 71.59, 71.48, 70.95, 70.09, 66.85, 66.08, 65.74, 56.19, 54.09, 53.78, 53.49, 53.36, 53.10, 53.02, 52.58, 22.94, 22.85, 22.65.

Synthesis of 122

Compound 122 is prepared from compound 121 following general procedure K.

$^1$H NMR; (CD$_3$OD) δ 7.43-7.19 (m, 45H), 7.07 (d, J=9.1 Hz, 2H), 6.84 (d, J=9.1 Hz, 2H), 5.47 (d, J=1.2 Hz, 1H), 5.41 (d, J=3.8 Hz, 1H), 5.39 (d, J=3.8 Hz, 1H), 5.22 (d, J=2.5 Hz, 1H), 5.09-4.54 (m, 22H), 4.44 (d, J=11.8 Hz, 1H), 4.37-3.68 (m, 35H), 3.74 (s, 3H), 3.63-3.52 (m, 4H), 1.86, 1.78, 1.77, 1.70 (s, 3H each). $^{13}$C NMR; δ 177.80, 176.22, 176.04, 175.71, 175.63, 173.23, 173.16, 173.08, 156.51, 152.45, 140.40, 140.28, 140.15, 139.88, 139.55, 139.37, 129.48, 129.43, 129.37, 129.31, 129.25, 129.05, 128.96, 128.86, 128.79, 128.56, 128.45, 119.34, 115.66, 104.07, 103.96, 102.07, 101.71, 98.54, 98.46, 97.09, 96.08, 85.87, 81.97, 81.07, 80.82, 80.48, 79.38, 78.42, 77.64, 77.51, 76.65, 76.30, 75.94, 75.58, 75.13, 75.00, 74.70, 74.32, 73.12, 72.93, 72.32, 71.32, 71.18, 71.09, 70.55, 70.11, 68.49, 67.49, 67.07, 56.13, 54.45, 53.64, 53.59, 22.97, 22.52.

Synthesis of 123

Compound 123 is prepared from compound 122 following general procedure L.

$^1$H NMR; (D$_2$O) δ 6.99 (d, J=8.3 Hz, 2H), 6.83 (d, J=8.3 Hz, 2H), 5.30 (s, 1H), 5.26 (s, 1H), 5.22 (s, 1H), 5.02-4.99 (m, 2H), 4.82 (s, 1H), 4.61-4.54 (br s, HOD and 2H), 4.43-4.41 (m, 2H), 4.30-4.28 (m, 2H), 4.20-4.17 (m, 2H), 4.08-4.00 (m, 5H), 3.95-3.72 (m, 13H), 3.67-3.54 (m, 16H), 3.41 (t, J=9.4 Hz, 1H), 3.20-3.17 (m, 2H), 1.89, 1.85 (s, 6H each). $^{13}$C NMR δ 175.07, 174.76, 174.53, 174.49, 174.43, 174.38, 154.82, 150.34, 119.38, 115.19, 102.04, 101.96, 101.90, 100.72, 97.11, 97.06, 94.49, 94.35, 77.39, 77.16, 76.90, 76.63, 76.57, 76.28, 76.19, 74.34, 73.84, 73.56, 70.66, 70.10, 69.57, 69.40, 69.28, 69.23, 69.16, 68.96, 68.88, 68.08, 66.41, 66.23, 65.92, 55.93, 53.76, 53.60, 53.05, 22.06, 22.02.

Synthesis of 124

Compound 124 is prepared from compounds 24 and 27 following general procedure E.

$^1$H NMR; (CDCl$_3$) δ 8.11-8.05 (m, 4H), 7.76 (d, J=7.6 Hz, 2H), 7.60-7.54 (m, 3H), 7.50-7.13 (m, 27H), 7.09-7.07 (m, 2H), 6.89 (d, J=9.1 Hz, 2H), 6.76 (d, J=9.1 Hz, 2H), 5.55-5.52 (m, 2H), 5.17 (t, J=3.7 Hz, 1H), 5.14 (d, J=3.4 Hz, 1H), 5.08 (d, J=7.1 Hz, 1H), 4.97 (d, J=10.4 Hz, 1H), 4.85 (d, J=11.3 Hz, 1H), 4.81-4.74 (m, 5H), 4.70 (d, J=10.4 Hz, 1H), 4.61 (dd, J=11.5, 2.6 Hz, 1H), 4.52-4.48 (m, 2H), 4.44-4.41 (m, 1H), 4.36-4.28 (m, 3H), 4.26-4.21 (m, 4H), 4.18 (t, J=6.8 Hz, 1H), 4.12-3.94 (m, 10H), 3.90-3.80 (m, 4H), 3.74 (s, 3H), 3.72-3.68 (m, 2H), 3.34-3.31 (m, 2H), 2.06, 2.00 (s, 3H each). $^{13}$C NMR; δ 170.60, 170.50, 166.87, 166.83, 165.45, 165.11, 155.72, 154.19, 150.99, 143.20, 143.05, 141.34, 137.85, 137.34, 137.21, 137.06, 133.59, 133.49, 129.83, 129.50, 129.46, 129.06, 128.76, 128.61, 128.46, 128.42, 128.31, 128.25, 128.18, 128.01, 127.89, 127.81, 127.67, 127.27, 125.32, 125.04, 124.85, 120.14, 118.77, 114.57, 100.13, 98.86, 97.99, 97.79, 82.77, 78.64, 77.89, 75.41, 75.28, 75.18, 75.03, 74.56, 74.22, 74.13, 73.65, 73.43, 72.54, 70.32, 69.97, 68.81, 67.30, 64.65, 63.84, 63.36, 63.11, 62.25, 61.96, 55.66, 46.76, 40.66, 40.55, 20.79, 20.64.

Synthesis of 125

Compound 125 is prepared from compound 124 following general procedure D.

$^1$H NMR; (CDCl$_3$) δ 8.11-8.09 (m, 2H), 8.07-8.05 (m, 2H), 7.57 (t, J=7.4 Hz, 1H), 7.52 (t, J=7.4 Hz, 1H), 7.46-7.43 (m, 4H), 7.37-7.19 (m, 20H), 6.88 (d, J=9.1 Hz, 2H), 6.76 (d, J=9.1 Hz, 2H), 5.55-5.52 (m, 2H), 5.18 (t, J=4.2 Hz, 1H), 5.12 (d, J=3.9 Hz, 1H), 5.07 (d, J=7.1 Hz, 1H), 4.97 (d, J=10.3 Hz, 1H), 4.84 (d, J=11.3 Hz, 1H), 4.80-4.75 (m, 4H), 4.69 (d, J=10.3 Hz, 1H), 4.61-4.47 (m, 4H), 4.43 (d, J=10.8 Hz, 1H), 4.39-4.34 (m, 2H), 4.29 (dd, J=11.8, 5.8 Hz, 1H), 4.20 (d, J=11.6 Hz, 1H), 4.16-4.05 (m, 4H), 4.00 (t, J=8.7 Hz, 1H), 3.94-3.93 (m, 4H), 3.88-3.79 (m, 4H), 3.75-3.71 (m, 2H), 3.74 (s, 3H), 3.58 (dd, J=10.0, 8.8 Hz, 1H), 3.40-3.36 (m, 1H), 3.32 (dd, J=9.7, 4.0 Hz, 1H), 3.22 (dd, J=10.1, 3.7 Hz, 1H), 2.82 (d, J=4.2 Hz, 1H), 2.06, 2.04 (s, 3H each). $^{13}$C NMR; δ 171.69, 170.74, 167.01, 166.75, 165.49, 165.08, 155.69, 150.98, 137.87, 137.68, 137.34, 137.26, 133.53, 133.47, 129.83, 129.49, 129.44, 128.70, 128.55, 128.41, 128.33, 128.26, 128.10, 127.79, 127.66, 118.75, 114.55, 100.10, 99.00, 97.93, 97.78, 82.74, 79.68, 78.51, 75.61, 75.30, 75.20, 74.73, 74.56, 74.21, 73.62, 73.50, 72.52, 71.26, 70.62, 70.56, 70.29, 67.94, 64.60, 63.69, 63.27, 63.06, 62.81, 62.20, 55.65, 40.67, 40.52, 20.78, 20.72.

Synthesis of 126

Compound 126 is prepared from compounds 125 and 22 following general procedure E.

$^1$H NMR; (CDCl$_3$) δ 8.10-8.05 (m, 6H), 7.76-7.73 (m, 2H), 7.59-7.53 (m, 5H), 7.47-7.42 (m, 6H), 7.39-7.36 (m, 2H), 7.31-7.13 (m, 32H), 6.88 (d, J=9.1 Hz, 2H), 6.76 (d, J=9.1 Hz, 2H), 5.54-5.51 (m, 2H), 5.47 (d, J=3.8 Hz, 1H), 5.36 (t, J=8.1 Hz, 1H), 5.14 (t, J=4.4 Hz, 1H), 5.07-5.06 (m, 2H), 4.91 (d, J=10.5 Hz, 1H), 4.88-4.84 (m, 2H), 4.80-4.62 (m, 10H), 4.57 (dd, J=11.7, 2.5 Hz, 1H), 4.47 (dd, J=10.4, 6.7 Hz, 1H), 4.33-4.13 (m, 1H), 4.08-3.75 (m, 23H), 3.73 (s, 3H), 3.67-3.59 (m, 4H), 3.35 (dd, J=10.3, 3.9 Hz, 1H), 3.29 (dd, J=9.6, 4.0 Hz, 1H), 3.23 (dd, J=9.7, 3.8 Hz, 1H), 2.03, 2.02, 1.97 (s, 3H each). $^{13}$C NMR; δ 170.58, 170.44, 166.87, 166.74, 166.62, 165.43, 165.08, 164.93, 155.70, 154.12, 150.99, 143.25, 143.01, 141.34, 138.23, 137.86, 137.36, 137.25, 137.14, 137.09, 133.74, 133.61, 133.47, 129.83, 129.52, 129.32, 129.06, 128.82, 128.75, 128.60, 128.41, 128.32, 128.21, 127.98, 127.93, 127.80, 127.68, 127.57, 127.24, 125.33, 125.11, 124.91, 120.13, 118.77, 114.56, 100.94, 100.11, 98.62, 97.82, 82.74, 82.68, 78.46, 78.06, 77.76, 77.48, 75.67, 75.32, 75.20, 74.97, 74.77, 74.58, 74.22, 74.08, 73.58, 72.54, 72.32, 70.40, 70.31, 69.88, 68.77, 67.71, 64.96, 64.59, 63.36, 63.26, 63.17, 62.61, 62.13, 61.94, 61.81, 55.65, 46.71, 40.60, 40.53, 40.43, 20.77, 20.70.

Synthesis of 127

Compound 127 is prepared from compound 126 following general procedure D.

$^1$H NMR; (CDCl$_3$) δ 8.10-8.04 (m, 6H), 7.58-7.53 (m, 3H), 7.47-7.41 (m, 6H), 7.40-7.35 (m, 4H), 7.32-7.13 (m, 26H), 6.88 (d, J=9.1 Hz, 2H), 6.76 (d, J=9.1 Hz, 2H), 5.54-5.51 (m, 2H), 5.44 (d, J=3.9 Hz, 1H), 5.35 (t, J=8.2 Hz, 1H), 5.14 (t, J=4.4 Hz, 1H), 5.07-5.05 (m, 2H), 4.92-4.83 (m, 4H), 4.80-4.76 (m, 4H), 4.73-4.64 (m, 5H), 4.57 (dd, J=11.8, 2.6 Hz, 1H), 4.51 (dd, J=12.5, 3.6 Hz, 1H), 4.33-4.11 (m, 9H), 4.08-3.92 (m, 9H), 3.87-3.72 (m, 10H), 3.73 (s, 3H), 3.66-3.58 (m, 6H), 3.41 (dt, J=9.5, 3.9 Hz, 1H), 3.29 (dd, J=9.6, 3.9 Hz, 1H), 3.24 (t, J=4.5 Hz, 1H), 3.22 (t, J=4.1 Hz, 1H), 2.92 (d, J=4.0 Hz, 1H), 2.07, 2.03, 1.96 (s, 3H each). $^{13}$C NMR; δ 171.88, 170.57, 170.47, 166.90, 166.73, 166.61, 165.42, 165.08, 164.95, 155.70, 150.99, 138.27, 137.85, 137.78, 137.35, 137.25, 137.21, 133.71, 133.60, 133.46, 129.82, 129.52, 129.32, 129.05, 128.80, 128.74, 128.67, 128.59, 128.39, 128.31, 128.24, 128.20, 128.04, 127.96, 127.79, 127.72, 127.67, 127.60, 127.54, 127.16, 125.32, 118.77, 114.56, 100.92, 100.11, 98.61, 98.22, 97.83, 97.78, 82.81, 82.74, 79.16, 78.45, 78.05, 77.78, 75.66, 75.42, 75.25, 75.02, 74.96, 74.72, 74.57, 74.21, 74.15, 73.62, 73.57, 72.54, 72.44, 71.36, 70.62, 70.30, 69.88, 67.71, 64.92, 64.58, 63.34, 63.25, 63.15, 62.72, 62.66, 62.13, 61.95, 55.65, 40.59, 40.52, 40.43, 20.78, 20.70.

Synthesis of 128

Compound 128 is prepared from compound 127 and 25 following general procedure E.

$^1$H NMR; (CDCl$_3$) δ 8.09-8.04 (m, 8H), 7.58-7.54 (m, 3H), 7.47-7.43 (m, 7H), 7.39-7.12 (m, 47H), 6.88 (d, J=9.1 Hz, 2H), 6.76 (d, J=9.1 Hz, 2H), 5.54-5.50 (m, 2H), 5.41 (d, J=3.9 Hz, 1H), 5.33 (t, J=8.2 Hz, 1H), 5.14-5.11 (m, 3H), 5.07-5.05 (m, 2H), 4.97 (d, J=11.3 Hz, 1H), 4.91 (d, J=10.4 Hz, 1H), 4.84-4.81 (m, 2H), 4.79-4.62 (m, 10H), 4.57 (dd, J=11.7, 2.5 Hz, 1H), 4.53-4.47 (m, 3H), 4.38 (m, 1H), 4.33-3.91 (m, 22H), 3.86-3.59 (m, 15H), 3.73 (s, 3H), 3.42 (t, J=9.5 Hz, 1H), 3.31-3.21 (m, 4H), 2.03, 2.02, 1.98, 1.96 (s, 3H each). $^{13}$C NMR; δ 170.57, 170.51, 170.41, 166.86, 166.70, 166.61, 165.48, 165.40, 165.07, 164.92, 155.69, 150.98, 138.22, 137.84, 137.77, 137.45, 137.35, 137.24, 133.60, 133.45, 129.84, 129.51, 129.30, 129.05, 128.78, 128.74, 128.70, 128.62, 128.48, 128.39, 128.29, 128.24, 128.19, 128.11, 128.06, 127.97, 127.84, 127.79, 127.72, 127.67, 127.53, 127.26, 125.32, 118.77, 114.54, 100.90, 100.10, 98.80, 98.61, 97.99, 97.77, 82.78, 82.73, 80.41, 78.64, 78.44, 77.99, 77.72, 77.62, 75.69, 75.34, 75.22, 75.16, 74.92, 74.74, 74.67, 74.58, 74.21, 74.15, 73.60, 73.43, 72.53, 72.36, 70.31, 70.11, 69.88, 67.76, 67.52, 64.76, 64.57, 63.80, 63.66, 63.32, 63.23, 63.12, 62.60, 62.10, 61.98, 61.88, 55.64, 40.67, 40.59, 40.51, 40.41, 20.76, 20.72.

Synthesis of 129

Compound 129 is prepared from compound 128 following general procedure F.

$^1$H NMR; (CDCl$_3$) δ 8.11-8.04 (m, 8H), 7.59-7.50 (m, 3H), 7.47-7.12 (m, 54H), 6.89 (d, J=9.1 Hz, 2H), 6.76 (d, J=9.1 Hz, 2H), 5.63 (d, J=3.9 Hz, 1H), 5.56-5.53 (m, 2H), 5.32 (dd, J=8.8, 8.3 Hz, 1H), 5.14-5.10 (m, 3H), 5.05-5.04 (m, 2H), 4.88-4.84 (m, 2H), 4.82-4.62 (m, 14H), 4.51-4.46 (m, 3H), 4.33-4.03 (m, 16H), 3.97-3.65 (m, 18H), 3.73 (s, 3H), 3.58-3.50 (m, 6H), 3.41-3.37 (m, 2H), 3.33-3.26 (m, 6H), 3.19-3.11 (m, 2H), 2.03 (s, 6H), 1.99, 1.97 (s, 3H each). $^{13}$C NMR; δ 170.57, 170.52, 170.48, 170.42, 165.76, 165.71, 165.09, 164.95, 155.64, 151.12, 138.12, 137.88, 137.68, 137.59, 137.53, 137.48, 137.38, 137.35, 137.23, 133.63, 133.48, 133.39, 133.32, 129.83, 129.60, 129.06, 128.76, 128.68, 128.62, 128.56, 128.51, 128.41, 128.25, 128.13, 128.08, 127.96, 127.92, 127.84, 127.79, 127.75, 127.66, 126.89, 125.32, 118.52, 114.65, 101.21, 100.52, 98.21, 97.90, 97.41, 97.35, 83.64, 83.33, 80.64, 78.98, 78.74, 78.30, 77.96, 77.80, 75.25, 75.17, 75.10, 75.04, 74.89, 74.48, 74.43, 74.37, 74.32, 74.07, 73.95, 73.78, 73.44, 73.32, 73.16, 72.87, 72.51, 70.19, 70.07, 70.03, 69.65, 69.18, 67.97, 67.86, 63.83, 63.52, 63.41, 62.80, 62.62, 62.29, 62.14, 61.94, 61.71, 61.27, 61.04, 55.64, 20.83, 20.80, 20.75.

Synthesis of 130

Compound 130 is prepared from compound 129 following general procedure G2.

$^1$H NMR; (CDCl$_3$) δ 8.12-8.09 (m, 4H), 8.06-8.01 (m, 4H), 7.57-7.53 (m, 3H), 7.49-7.13 (m, 52H), 7.09-7.07 (m, 2H), 6.84 (d, J=9.1 Hz, 2H), 6.73 (d, J=9.1 Hz, 2H), 5.51-5.47 (m, 4H), 5.44 (d, J=3.8 Hz, 1H), 5.38 (t, J=8.9 Hz, 1H), 5.17-5.15 (m, 2H), 5.06 (d, J=6.8 Hz, 1H), 5.01 (d, J=10.3 Hz, 1H), 4.98-4.96 (m, 2H), 4.93-4.90 (m, 2H), 4.80-4.62 (m, 13H), 4.56 (d, J=10.9 Hz, 1H), 4.48-4.38 (m, 3H), 4.34-4.29 (m, 4H), 4.26-4.01 (m, 12H), 3.96-3.63 (m, 11H), 3.72, 3.64 (s, 3H each), 3.55-3.48 (m, 2H), 3.49 (s, 3H), 3.44-3.41 (m, 2H), 3.31-3.19 (m, 4H), 3.21, 3.13, 2.12, 2.11, 2.00, 1.96 (s, 3H each). $^{13}$C NMR; δ 170.83, 170.75, 170.47, 170.39, 169.70, 169.53, 168.10, 167.58, 165.23, 165.15, 164.99, 164.65, 155.68, 150.94, 137.97, 137.88, 137.84, 137.66, 137.54, 137.42, 137.30, 137.10, 133.93, 133.68, 133.51, 133.43, 129.97, 129.93, 129.79, 129.72, 129.45, 129.21, 129.05, 128.86, 128.80, 128.52, 128.48, 128.40, 128.33, 128.30, 128.16, 128.08, 127.96, 127.91, 127.88, 127.80, 127.58, 125.32, 118.73, 114.48, 101.18, 100.72, 99.17, 98.67, 98.24, 97.75, 97.39, 97.35, 82.71, 82.18, 80.00, 78.30, 77.93, 77.68, 77.60, 77.51, 76.05, 75.94, 75.54, 75.39, 75.19, 75.12, 75.02, 74.80, 74.75, 74.62, 74.52, 74.33, 74.21, 74.08, 73.80, 73.68, 72.06, 71.47, 70.75, 70.41, 70.11, 69.40, 63.51, 63.11, 62.90, 62.83, 62.29, 61.67, 61.53, 55.61, 52.19, 52.15, 52.08, 51.85, 20.81.

Synthesis of 131

Compound 131 is prepared from compound 130 following general procedure H.

$^1$H NMR; (CDCl$_3$) δ 8.09-8.06 (m, 2H), 8.04-8.00 (m, 6H), 7.59-7.51 (m, 4H), 7.48-7.38 (m, 8H), 7.35-7.06 (m, 45H), 6.84 (d, J=9.1 Hz, 2H), 6.73 (d, J=9.1 Hz, 2H), 5.75 (d, J=9.5 Hz, 1H), 5.68-5.60 (m, 3H), 5.52 (dd, J=8.5, 6.7 Hz, 1H), 5.42-5.37 (m, 2H), 5.33 (d, J=5.6 Hz, 1H), 5.19-5.17 (m, 2H), 5.06-5.05 (m, 2H), 5.01 (d, J=3.3 Hz, 1H), 4.94-4.75 (m, 8H), 4.69-4.47 (m, 13H), 4.42-3.92 (m, 23H), 3.86-3.46 (m, 11H), 3.71, 3.62, 3.53 (s, 3H each), 3.41-3.32 (m, 1H), 3.40, 3.34 (s, 3H each), 2.11, 2.10, 1.99, 1.93, 1.50, 1.39, 1.38, 1.36 (s, 3H each). $^{13}$C NMR; δ 171.13, 171.04, 170.66, 170.57, 170.26, 170.17, 170.0, 169.97, 169.28, 169.20, 167.69, 167.28, 165.55, 165.42, 164.99, 164.70, 155.75, 150.86, 138.74, 138.59, 138.39, 138.05, 137.81, 136.89, 136.52, 136.34, 133.94, 133.84, 133.58, 129.75, 129.27, 129.04, 128.98, 128.93, 128.75, 128.62, 128.59, 128.47, 128.27, 128.18, 128.05, 127.79, 127.61, 127.56, 127.43, 127.35, 127.32, 125.31, 118.63, 114.52, 101.36, 100.90, 99.21, 99.05, 98.00, 97.91, 97.87, 97.73, 81.58, 80.95, 80.52, 78.08, 77.91, 75.58, 75.29, 74.97, 74.92, 74.84, 74.76, 74.50, 73.86, 73.77, 73.62, 73.49, 73.34, 72.87, 72.01, 71.10, 71.03, 70.61, 70.51, 70.37, 70.12, 69.82, 62.44, 61.69, 61.52, 55.61, 52.68, 52.57, 52.41, 52.09, 51.81, 22.95, 22.76, 22.58, 20.98, 20.76.

Synthesis of 132

Compound 132 is prepared from compound 131 following general procedure I.

$^1$H NMR; (CDCl$_3$) δ 8.05-7.94 (m, 8H), 7.59-7.54 (m, 3H), 7.51-7.10 (m, 54H), 6.84 (d, J=9.1 Hz, 2H), 6.73 (d, J=9.1 Hz, 2H), 5.65 (d, J=9.3 Hz, 1H), 5.61 (d, J=9.3 Hz, 1H), 5.58-5.51 (m, 3H), 5.45 (d, J=4.3 Hz, 1H), 5.41 (t, J=8.2 Hz, 1H), 5.35 (d, J=5.2 Hz, 1H), 5.23-5.20 (m, 2H), 5.11 (d, J=3.4 Hz, 1H), 5.08-5.05 (m, 2H), 4.93-4.87 (m, 5H), 4.81-4.77 (m, 3H), 4.74-4.69 (m, 2H), 4.67-4.61 (m, 6H), 4.57-4.49 (m, 5H), 4.35-4.20 (m, 6H), 4.13-3.89 (m, 12H), 3.85 (t, J=8.2 Hz, 1H), 3.79 (d, J=10.2 Hz, 1H), 3.71 (s, 3H), 3.70-3.29 (m, 16H), 3.62, 3.56, 3.37, 3.27 (s, 3H each), 1.55, 1.45, 1.44, 1.41 (s, 3H each). $^{13}$C NMR; δ 170.45, 170.34, 169.94, 169.30, 168.98, 167.94, 165.56, 165.41, 164.99, 164.76, 155.75, 150.86, 138.98, 138.53, 138.46, 138.21, 138.09, 136.99, 136.52, 133.86, 133.58, 129.75, 129.64, 129.55, 129.26, 129.01, 128.90, 128.58, 128.51, 128.45, 128.25, 128.15, 128.03, 127.99, 127.92, 127.85, 127.76, 127.61, 127.42, 127.29, 118.61, 114.52, 100.87, 100.63, 98.87, 98.49, 97.81, 97.67, 97.47, 97.23, 81.38, 81.06, 79.84, 77.83, 76.59, 76.46, 75.37, 74.96, 74.75, 74.62, 74.49, 74.41, 74.03, 73.78, 73.34, 73.15, 73.02, 72.86, 72.77, 72.54, 71.91, 71.34, 70.91, 70.60, 70.02, 66.54, 66.36, 61.61, 60.83, 60.63, 60.39, 60.00, 55.61, 52.70, 52.58, 52.45, 52.22, 52.05, 51.78, 22.92, 22.70, 22.61.

Synthesis of 133

Compound 133 is prepared from compound 132 following general procedure J.

$^1$H NMR; (CD$_3$OD) δ 8.28 (d, J=7.5 Hz, 2H), 8.11-8.05 (m, 6H), 7.65 (t, J=7.3 Hz, 1H), 7.58-7.07 (m, 52H), 7.02-7.00 (m, 2H), 6.93-6.91 (m, 2H), 6.87 (d, J=9.1 Hz, 2H), 6.77 (d, J=9.1 Hz, 2H), 5.58-5.52 (m, 3H), 5.43-5.38 (m, 3H), 5.27-5.21 (m, 4H), 5.08 (d, J=3.0 Hz, 1H), 5.00-4.97 (m, 2H), 4.93 (d, J=2.4 Hz, 1H), 4.82-4.10 (m, 38H), 4.00-3.95 (m, 3H), 3.87-3.84 (m, 2H), 3.69-3.30 (m, 21H), 2.90 (s, 3H), 1.86, 1.82, 1.66, 1.52 (s, 3H each). $^{13}$C NMR; δ 173.60, 173.43, 173.34, 173.25, 171.20, 170.46, 170.34, 167.38, 167.28, 166.95, 166.57, 164.90, 157.13, 152.29, 140.19, 140.02, 139.97, 139.79, 138.92, 138.64, 138.54, 138.38, 135.15, 134.81, 134.64, 134.53, 131.24, 130.96, 130.87, 130.81, 130.68, 130.22, 129.99, 129.80, 129.62, 129.54, 129.43, 129.33, 129.21, 129.10, 128.93, 128.81, 128.52, 128.42, 128.05, 119.10, 115.70, 101.82, 101.19, 99.17, 99.11, 99.00, 98.57, 97.03, 84.18, 83.38, 81.40, 79.97, 79.56, 79.17, 78.60, 76.27, 76.05, 75.59, 75.39, 75.27, 75.20, 74.95, 74.62, 74.36, 74.19, 73.37, 72.39, 72.16, 71.72, 71.58, 71.50, 71.24, 70.74, 70.39, 67.24, 66.20, 66.11, 65.87, 56.22, 54.40, 53.91, 53.60, 53.48, 53.24, 53.16, 53.08, 52.44, 49.94, 22.96, 22.91, 22.79.

Synthesis of 134

Compound 134 is prepared from compound 133 following general procedure K.

$^1$H NMR; (CD$_3$OD) δ 7.43-7.11 (m, 45H), 7.04 (d, J=9.1 Hz, 2H), 6.84 (d, J=9.1 Hz, 2H), 5.41-5.39 (m, 2H), 5.25-5.23 (m, 2H), 5.09 (d, J=5.2 Hz, 1H), 5.07 (d, J=5.3 Hz, 1H), 4.98 (d, J=12.3 Hz, 1H), 4.91-4.69 (m, 11H), 4.66-4.54 (m, 8H), 4.45 (d, J=11.7 Hz, 1H), 4.39 (d, J=11.6 Hz, 1H), 4.36-4.24 (m, 5H), 4.18-3.61 (m, 32H), 3.75 (s, 3H), 3.51 (t, J=8.3 Hz, 1H), 1.82, 1.78, 1.77, 1.68 (s, 3H each). $^{13}$C NMR; δ 175.64, 175.38, 174.72, 173.31, 173.17, 172.98, 156.89, 153.22, 140.30, 140.21, 140.10, 139.89, 139.86, 139.75, 139.71, 139.34, 139.24, 129.75, 129.64, 129.59, 129.52, 129.40, 129.35, 129.26, 129.02, 128.88, 128.76, 128.69, 128.64, 128.56, 128.48, 128.35, 128.16, 127.94, 119.55, 115.55, 103.92, 103.86, 102.02, 101.68, 98.78, 98.59, 98.04, 97.25, 86.18, 85.89, 82.13, 80.94, 80.68, 80.42, 79.09, 78.25, 77.72, 76.58, 76.23, 76.09, 75.81, 75.43, 75.22, 75.08, 74.55, 74.15, 73.13, 71.62, 71.38, 70.33, 69.77, 69.45, 68.96, 67.50, 67.20, 67.03, 56.14, 54.43, 54.24, 53.62, 49.91, 49.70, 22.97.

Synthesis of 135

Compound 135 is prepared from compound 134 following general procedure L.

$^1$H NMR; (D$_2$O) δ 7.10 (d, J=7.5 Hz, 2H), 6.97 (d, J=7.5 Hz, 2H), 5.40-5.38 (m, 2H), 5.16 (s, 2H), 4.99-4.98 (m, 3H), 4.77 (br s, 2H), 4.57 (d, J=7.6 Hz, 1H), 4.44 (d, J=10.8 Hz, 1H), 4.35-4.33 (m, 3H), 4.23-4.18 (m, 4H), 4.08-4.06 (m, 3H), 4.03-4.01 (m, 2H), 3.97-3.89 (m, 8H), 3.85-3.69 (m, 14H), 3.81 (s, 3H), 3.59-3.54 (m, 2H), 3.34 (t, J=8.2 Hz, 1H), 2.05 (s, 6H), 2.02, 2.01 (s, 3H each). $^{13}$C NMR; δ 175.04, 174.71, 174.53, 174.45, 154.87, 151.03, 118.39, 115.16, 102.02, 101.96, 101.86, 101.30, 97.20, 97.14, 94.53, 94.34, 77.30, 77.11, 76.81, 76.61, 76.43, 76.21, 74.22, 73.59, 73.38, 71.14, 70.23, 69.61, 69.39, 69.25, 68.98, 68.80, 66.54, 66.24, 65.93, 55.94, 53.78, 53.49, 53.05, 22.03.

Example 3

X-Ray Crystal Structure Analysis of Compounds 13, 14, 15, 16 and 27

Compound 13 is synthesised as described in Example 2 (GPA), and crystallised from hot toluene by addition of petroleum ether. X-Ray quality crystals are obtained by vapor diffusion of petroleum ether into a solution of 13 in toluene.

Compound 14 is synthesised as described in Example 2 (GPA), and crystallised from toluene by addition of petroleum ether. X-Ray quality crystals are obtained by vapor diffusion of petroleum ether into a solution of 14 in toluene.

Compound 15 is synthesised as described in Example 2 (GPA), and crystallised from toluene by addition of petroleum ether. X-Ray quality crystals are obtained by vapor diffusion of petroleum ether into a solution of 15 in toluene.

Compound 16 is synthesised as described in Example 2 (GPA), and crystallised from ethyl acetate by addition of petroleum ether.

Compound 27 is synthesised as described in Example 2 (GPD), and crystallises directly after elution from the chromatography column. X-Ray quality crystals are obtained by vapor diffusion of petroleum ether into a solution of 27 in toluene.

Crystals of compound 13 contain two enantiomerically identical molecules which are aligned along the a axis and separated by almost exactly by half a cell (shown in FIG. 1).

Data are collected on a Bruker APEXII diffractometer. Computing details are as follows: data collection: Crystal-Clear (Rigaku, 2005); cell refinement: FSProcess (Rigaku, 1998); data reduction: FSProcess (Rigaku, 1998); program used to solve structure: SHELXS97 (Sheldrick, 2008); program used to refine structure: SHELXL97 (Sheldrick, 1997); molecular graphics: ORTEP in WinGX (Farrugia, 1999).

TABLE 1

Crystal Data for Compound 13

| | |
|---|---|
| Empirical formula | C59 H56 Cl N3 O16 |
| Formula weight | 1098.52 |
| Temperature | 123(2) K |
| Wavelength | 1.54178 A |
| Crystal system, space group | Monoclinic, P 21 |
| Unit cell dimensions | a = 10.454(2) A alpha = 90 deg. |
| | b = 35.610(7) A beta = 95.61 (3) deg. |
| | c = 14.408(3) A gamma = 90 deg. |
| Volume | 5338.0(19) $Å^3$ |
| Z, Calculated density | 4, 1.367 $Mg/m^3$ |
| Absorption coefficient | 1.271 mm −1 |
| F(000) | 2304 |
| Crystal size | 0.85 × 0.08 × 70.04 mm |
| Theta range for data collection | 6.54 to 55.00 deg. |
| Limiting indices | −10 <= h <= 8, −37 <= k <= 37, −15 <= l <= 15 |
| Reflections collected/unique | 35705/12625 [R(int) = 0.0554] |
| Completeness to theta = | 55.00 97.7% |
| Absorption correction | Semi-empirical from equivalents |
| Refinement method | Full-matrix least-squares on $F^2$ |
| Data/restraints/parameters | 12625/3/1426 |
| Goodness-of-fit on $F^2$ | 0.997 |
| Final R indices [I > 2sigma(I)] | R1 = 0.0575, wR2 = 0.1332 |
| R indices (all data) | R1 = 0.0840, wR2 = 0.1554 |
| Absolute structure parameter | 0.033(19) |
| Largest diff. peak and hole | 0.318 and −0.301 $e.Å^{-3}$ |

TABLE 2

Crystal Data for Compound 14

| | |
|---|---|
| Empirical formula | C51 H52 Cl N3 O14 |
| Formula weight | 966.41 |
| Temperature | 164(2) K |
| Wavelength | 1.54178 Å |
| Crystal system, space group | Monoclinic, P $2_1$ |
| Unit cell dimensions | a = 9.2713(7) Å, alpha = 90 deg. |
| | b = 17.4067(11) Å, beta = 97.449(7) deg. |
| | c = 15.0036(11) Å, gamma = 90 deg. |
| Volume | 2400.9(3) $Å^3$ |
| Z, Calculated density | 2, 1.337 $Mg/m^3$ |
| Absorption coefficient | 1.302 $mm^{-1}$ |
| F(000) | 1016 |
| Crystal size | 0.85 × 0.45 × 0.14 mm |
| Theta range for data collection | 7.01 to 60.01 deg. |
| Limiting indices | −10 <= h <= 10, −19 <= k <= 14, −16 <= l <= 16 |
| Reflections collected/unique | 15021/5678 [R(int) = 0.0556] |
| Completeness to theta = | 60.01 99.2% |
| Absorption correction | Semi-empirical from equivalents |
| Max. and min. transmission | 1.0, 0.521 |
| Refinement method | Full-matrix least-squares on $F^2$ |
| Data/restraints/parameters | 5678/3/558 |
| Goodness-of-fit on $F^2$ | 1.093 |
| Final R indices [I > 2sigma(I)] | R1 = 0.0596, wR2 = 0.1600 |
| R indices (all data) | R1 = 0.0695, wR2 = 0.1714 |

TABLE 2-continued

Crystal Data for Compound 14

| | |
|---|---|
| Absolute structure parameter | 0.02(3) (Flack, 1983) |
| Extinction coefficient | 0.0023(4) |
| Largest diff. peak and hole | 0.311 and −0.316 $e.Å^{-3}$ |

TABLE 3

Crystal Data for Compound 15

| | |
|---|---|
| Empirical formula | C52 H55 N3 O15 |
| Formula weight | 961.99 |
| Temperature | 118(2) K |
| Wavelength | 0.71073 Å |
| Crystal system, space group | Monoclinic, C2 |
| Unit cell dimensions | a = 38.3346(13) Å alpha = 90 deg. |
| | b = 8.0744(3) Å beta = 91.222(2) deg. |
| | c = 16.1659(6) Å gamma = 90 deg. |
| Volume | 5002.7(3) $Å^3$ |
| Z, Calculated density | 4, 1.277 $Mg/m^3$ |
| Absorption coefficient | 0.094 $mm^{-1}$ |
| F(000) | 2032 |
| Crystal size | 0.75 × 0.32 × 0.30 mm |
| Theta range for data collection | 2.58 to 26.12 deg. |
| Limiting indices | −47 <= h <= 47, −9 <= k <= 9, −19 <= l <= 19 |
| Reflections collected/unique | 51621/9796 [R(int) = 0.0350] |
| Completeness to theta = | 26.12 98.8% |
| Absorption correction | Multi-scan (Blessing, 1995) |
| Max. and min. transmission | 0.745 and 0.645 |
| Refinement method | Full-matrix least-squares on $F^2$ |
| Data/restraints/parameters | 9796/43/662 |
| Goodness-of-fit on $F^2$ | 1.079 |
| Final R indices [I > 2sigma(I)] | R1 = 0.0484, wR2 = 0.1253 |
| R indices (all data) | R1 = 0.0525, wR2 = 0.1285 |
| Absolute structure parameter | 0.0(7) (indeterminate) |
| Largest diff. peak and hole | 0.332 and −0.454 $e.Å^{-3}$ |

TABLE 4

Crystal Data for Compound 16

| | |
|---|---|
| Empirical formula | C59 H56 Cl N3 O16 |
| Formula weight | 1098.52 |
| Temperature | 123(2) K |
| Wavelength | 1.54178 A |
| Crystal system, space group | Monoclinic, P21 |
| Unit cell dimensions | a = 14.8343(11) A alpha = 90 deg. |
| | b = 8.4771(6) A beta = 91.780(7) deg. |
| | c = 21.8112(17) A gamma = 90 deg. |
| Volume | 2741.5(4) $Å^3$ |
| Z, Calculated density | 2, 1.331 $Mg/m^3$ |
| Absorption coefficient | 1.238 mm −1 |
| F(000) | 1152 |
| Crystal size | 0.6 × 0.05 × 0.02 mm |
| Theta range for data collection | 6.62 to 43.49 deg. |
| Limiting indices | −13 <= h <= 13, −7 <= k <= 7, −19 <= l <= 19 |
| Reflections collected/unique | 19701/3962 [R(int) = 0.1013] |
| Completeness to theta = | 43.49 99.3% |
| Absorption correction | Semi-empirical from equivalents |
| Refinement method | Full-matrix least-squares on $F^2$ |
| Data/restraints/parameters | 3962/55/666 |
| Goodness-of-fit on $F^2$ | 1.093 |
| Final R indices [I > 2sigma(I)] | R1 = 0.0880, wR2 = 0.2135 |
| R indices (all data) | R1 = 0.1479, wR2 = 0.2800 |
| Absolute structure parameter | 0.01(8) |
| Extinction coefficient | 0.0110(13) |
| Largest diff. peak and hole | 0.289 and −0.247 $e.Å^{-3}$ |

TABLE 5

Crystal Data for Compound 27

| | |
|---|---|
| Empirical formula | C44 H46 Cl N3 O14 |
| Formula weight | 876.29 |
| Temperature | 164(2) K |
| Wavelength | 1.54178 Å |
| Crystal system, space group | Orthorhombic, P2$_1$2$_1$2$_1$ |
| Unit cell dimensions | a = 8.1104(2) Å alpha = 90 deg. |
| | b = 19.5548(6) Å beta = 90 deg. |
| | c = 27.2321(19) Å gamma = 90 deg. |
| Volume | 4318.9(4) Å$^3$ |
| Z, Calculated density | 4, 1.348 Mg/m$^3$ |
| Absorption coefficient | 1.389 mm$^{-1}$ |
| F(000) | 1840 |
| Crystal size | 1.0 × 0.13 × 0.11 mm |
| Theta range for data collection | 6.65 to 58.93 deg. |
| Limiting indices | −6 <= h <= 8, −21 <= k <= 21, −30 <= l <= 30 |
| Reflections collected/unique | 34329/6132 [R(int) = 0.0454] |
| Completeness to theta = | 58.93 99.3% |
| Absorption correction | Semi-empirical from equivalents |
| Max. and min. transmission | 1.0, 0.717 |
| Refinement method | Full-matrix least-squares on F$^2$ |
| Data/restraints/parameters | 6132/10/527 |
| Goodness-of-fit on F$^2$ | 1.105 |
| Final R indices [I > 2sigma(I)] | R1 = 0.0638, wR2 = 0.1785 |
| R indices (all data) | R1 = 0.0827, wR2 = 0.1975 |
| Absolute structure parameter | 0.17(4) (Flack, 1983) |
| Largest diff. peak and hole | 0.415 and −0.347 e.A$^{-3}$ |

Example 4

Determination of BACE-1 Inhibition by In Vitro FRET Peptide Cleavage Assay

The ability of compounds of the invention to inhibit BACE-1 cleavage of APP is assessed using a fluorescent resonance energy transfer (FRET) peptide cleavage assay employing the FRET peptide HiLyte 488-Glu-Val-Asn-Leu-Asp-Ala-Glu-Phe-Lys(QXL520)-OH (Anaspec, Inc., CA, USA; Cat no. 60604-01). When intact, the amino terminal fluorophore is quenched, but upon enzymatic cleavage the fluorophore is released from quencher and fluoresces (520 nm). Assays are performed in triplicate in 96 well black plates (20 mM sodium acetate, 0.1% Triton-X-100, pH 4.5; 2.2 ng peptide per well and 25 ng/well of recombinant human BACE-1 (R & D Systems Cat no. 931-AS). The appropriate controls for enzyme activity (substrate plus enzyme, and substrate only) are employed and plates are incubated (1 h, 25° C., with activity stopped with 2.5 M sodium acetate). Compounds of the invention are added in the concentration range from 100-0.0001 μg/mL. Fluorescence 480ex/520em is measured on a Polarstar plate reader (BMG LabTechnologies, UK) and data are analysed by plotting log$_{10}$ concentration of compound against percent inhibition and fitting a logistic dose response sigmoidal curve using OriginPro 8 (Origin-Labs, Mass, USA).

TABLE 6

Inhibition of BACE-1 by Compounds of the Invention

| Compound No. | IC$_{50}$ μg/mL |
|---|---|
| Heparin (MW average 12 kDa) | 0.002 |
| NAcLMWH (MW average 4 kDa) | 0.007 |
| 87 | 0.56 |
| 86 | 1.9 |
| 91 | 0.012 |
| 90 | 0.010 |
| 89 | 0.66 |
| 88 | 0.53 |
| 92 | 0.011 |
| 101 | 0.26 |
| 111 | 0.22 |
| 135 | 0.38 |
| 123 | 0.37 |
| 148 | 0.007 |
| 147 | 0.1 |
| 149 | 0.005 |

Example 5

Factor Xa Anticoagulant Assay Protocol

The compound of the invention, standard or control (5 μl), is pipetted in assay buffer (0.9% sodium chloride) into a 96 well plate (Costar 3595) and 19 μl of 0.03 IU/ml human Antithrombin III (American Diagnostica Inc., product No. 433) in assay buffer is added to each well. The plate is incubated for two minutes at 37° C. 19 μl of bovine Factor Xa (14nkat/ml; Thermo Scientific; product No. 32521) in assay buffer is added to each well and incubated for one minute at 37° C. 19 μl of 2.5 mM chromogenic substrate (American Diagnostica Inc. Spectrozyme FXa Product No 222L) in assay buffer is added to each well and incubated for 2 hours at 37° C., followed by addition of 5 μl of 30% acetic acid to each well. Absorbance at 405 nm is read on a multiplate reader.

All compounds are tested in the dose range 0.004 to 50 μg/ml and none display any measurable ability to accelerate antithrombin-III mediated inactivation of Factor Xa, as measured by cleavage of a peptide substrate.

Although the invention has been described by way of example, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The invention relates to compounds that are inhibitors of BACE-1. The compounds are therefore indicated for the treatment or prevention of diseases in which the inhibition of BACE-1 is desirable, e.g. neurodegenerative disorders such as senile dementia, pre-senile dementia, multi-infarct dementia or Alzheimer's disease.

The invention claimed is:

1. An octasaccharide, decasaccharide or dodecasaccharide compound of the formula (I):

H-Q-V-W-X-Y-Z-A    (I)

where:
A is an optionally substituted alkoxy, aralkoxy, aryloxy group;
W, X, Y and Z are each independently a disaccharide of formula (i);
V is a disaccharide of formula (i) or V is absent; and
Q is a disaccharide of formula (i) or Q is absent

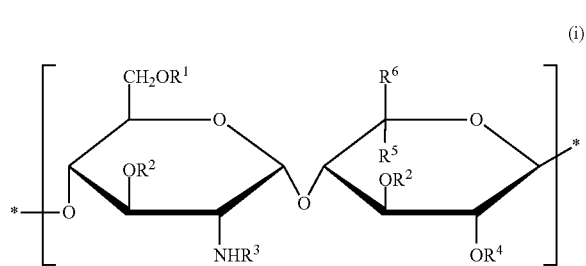

where:
R$^1$ is SO$_3$H;
R$^2$ is H;
R$^3$ is acyl;
R$^4$ is H or SO$_3$H; and
each R$^5$ and R$^6$ is independently selected from COOH and H; provided that one of R$^5$ and R$^6$ in each disaccharide is H and the other is COOH;
and provided that all R$^3$ groups in the octasaccharide, decasaccharide or dodecasaccharide are the same as each other and provided that all R$^4$ groups in the octasaccharide, decasaccharide or dodecasaccharide are the same as each other; or a pharmaceutically acceptable salt thereof.

2. A compound as claimed in claim 1 where R$^5$ is H and R$^6$ is COOH or a salt form of COOH.

3. A compound as claimed in claim 1 where R$^5$ is COOH or a salt form of COOH and R$^6$ is H.

4. A compound as claimed in claim 1 which contains at least one disaccharide of formula (i) where R$^5$ is H and R$^6$ is COOH or a salt form of COOH and at least one disaccharide of formula (i) where R$^5$ is COOH or a salt form of COOH and R$^6$ is H.

5. A compound as claimed in claim 1 where the pharmaceutically acceptable salt is an ammonium salt, a metal salt, a salt of an organic cation, or a mixture thereof.

6. A compound as claimed in claim 1 where Q and V are absent and the compound of formula (I) is an octasaccharide.

7. A compound as claimed in claim 1 where one of Q and V is a disaccharide of formula (i) and the other is absent and the compound of formula (I) is a decasaccharide.

8. A compound as claimed in claim 1 where Q and V are each independently a disaccharide of formula (i) and the compound of formula (I) is a dodecasaccharide.

9. A compound as claimed in claim 1 where R$^3$ is an acetyl group.

10. A compound as claimed in claim 1 where R$^4$ is SO$_3$H or a salt form of SO$_3$H.

11. A compound as claimed in claim 1 where R$^1$ is a salt form of SO$_3$H.

12. A compound as claimed in claim 1 where A is an optionally substituted aryloxy group.

13. A compound as claimed in claim 1, selected from the group consisting of:

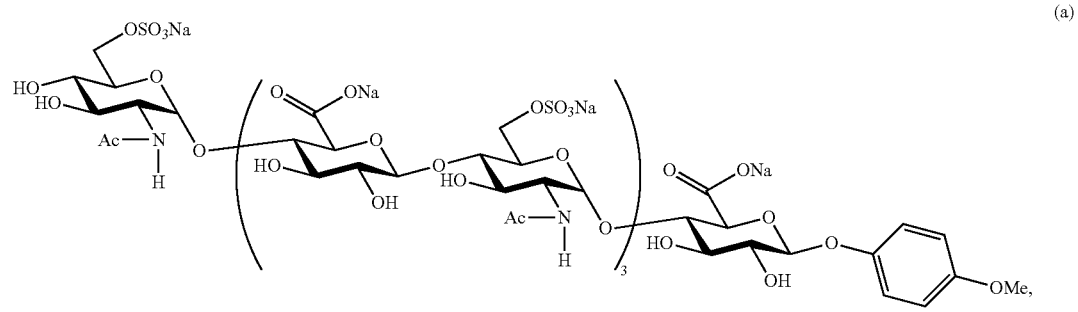

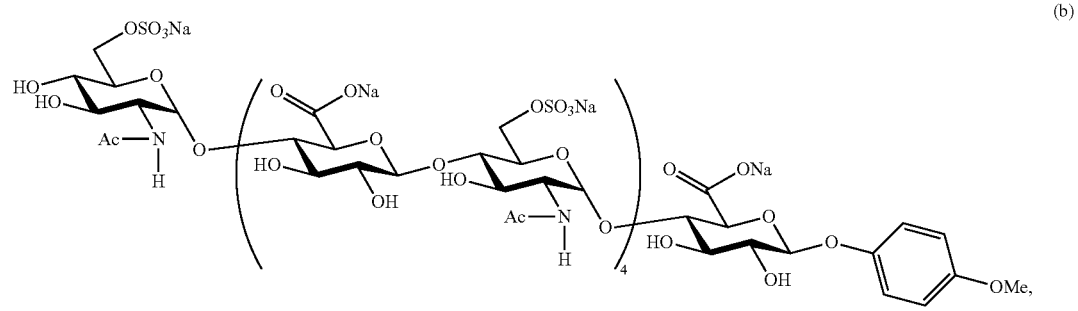

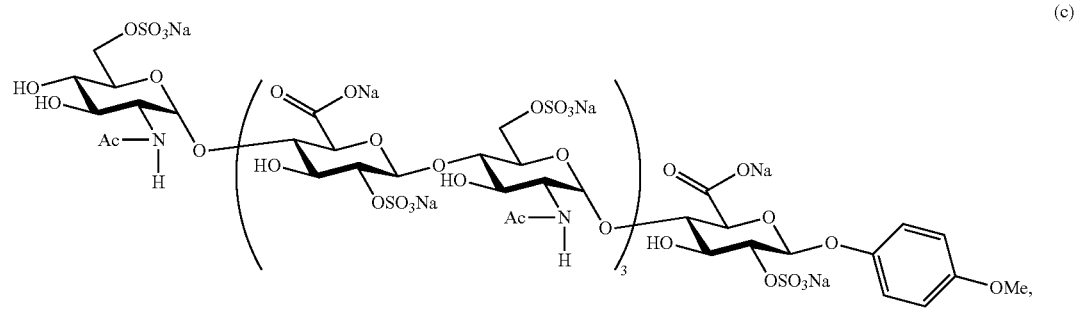

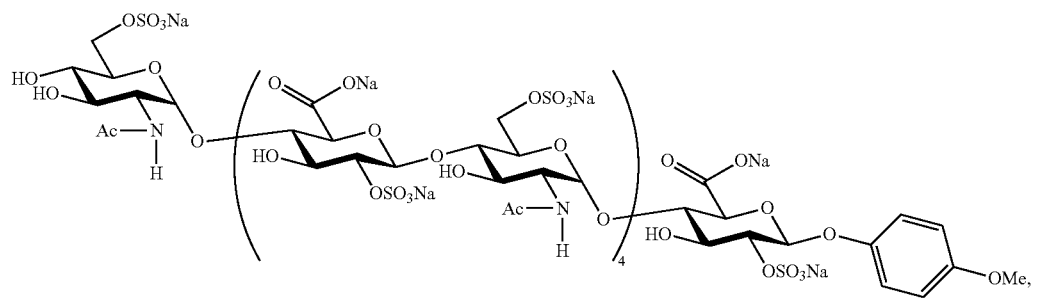
(d)
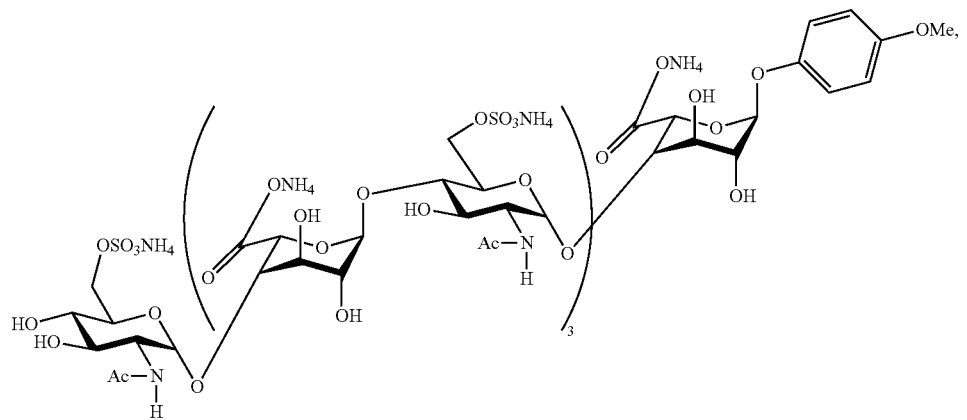
(e)
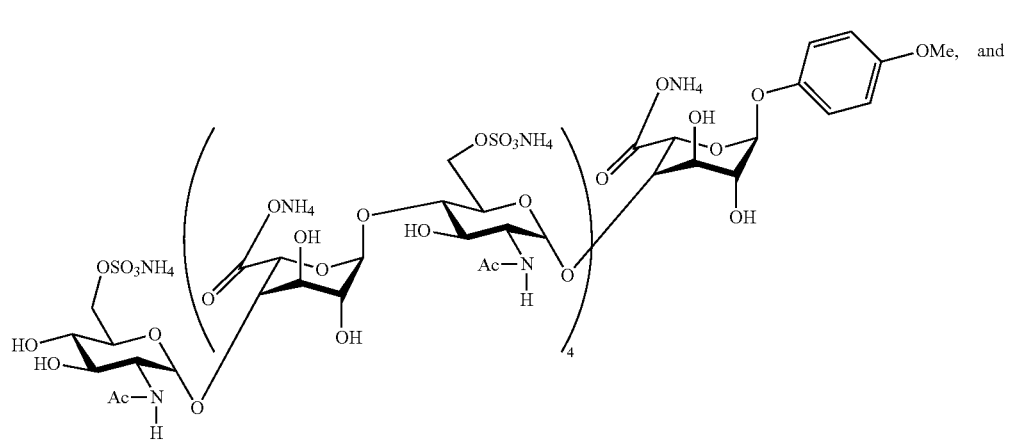
(f) and
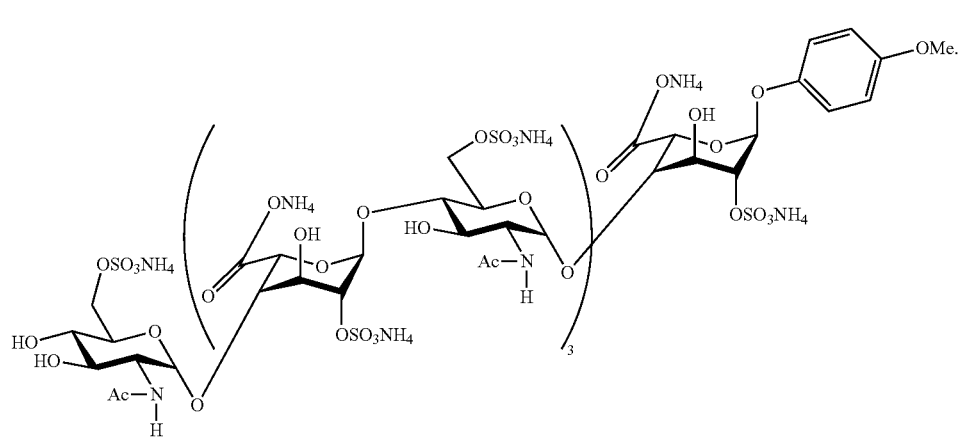
(g)

14. A compound as claimed in claim 1, selected from the group consisting of
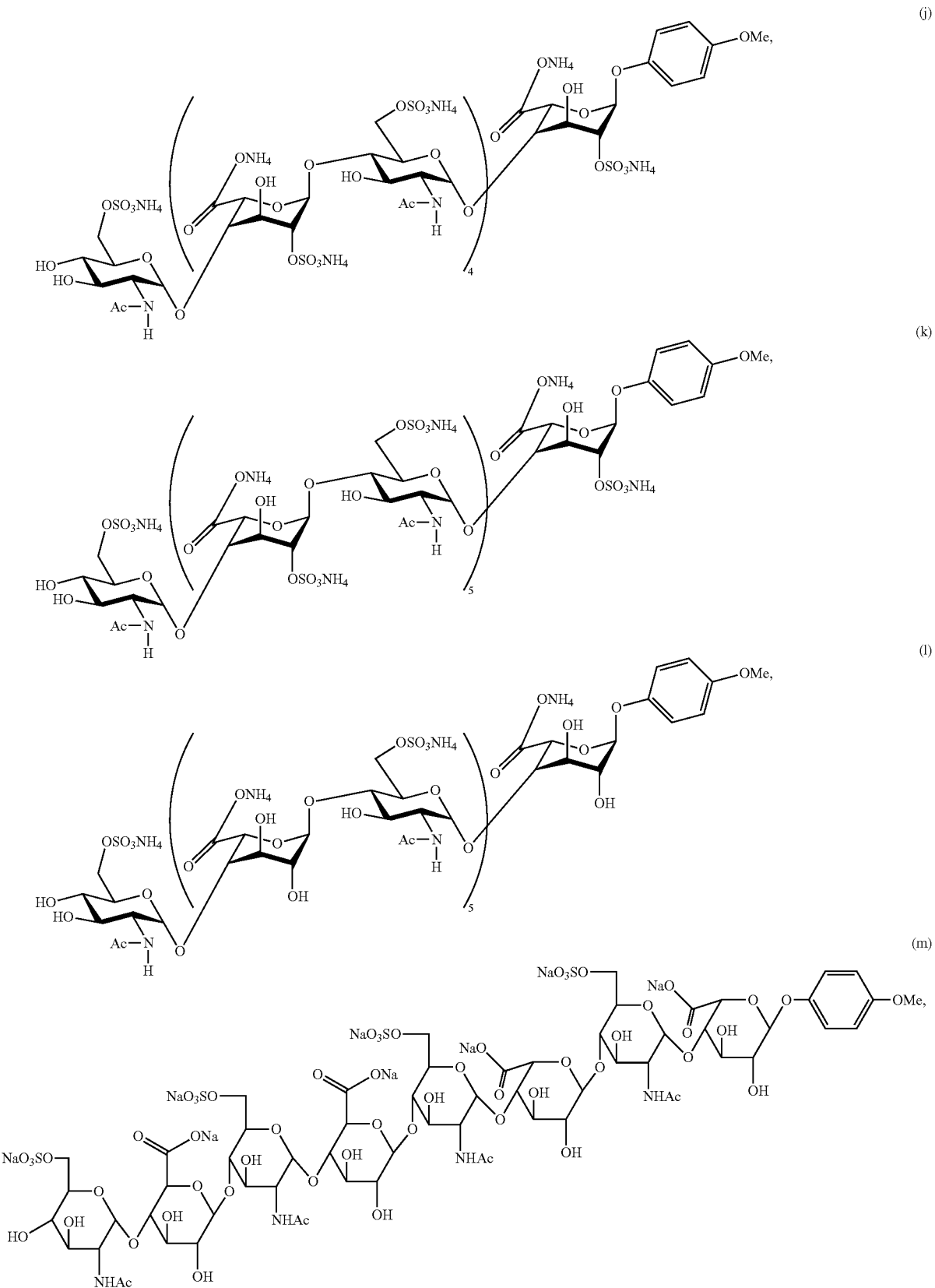

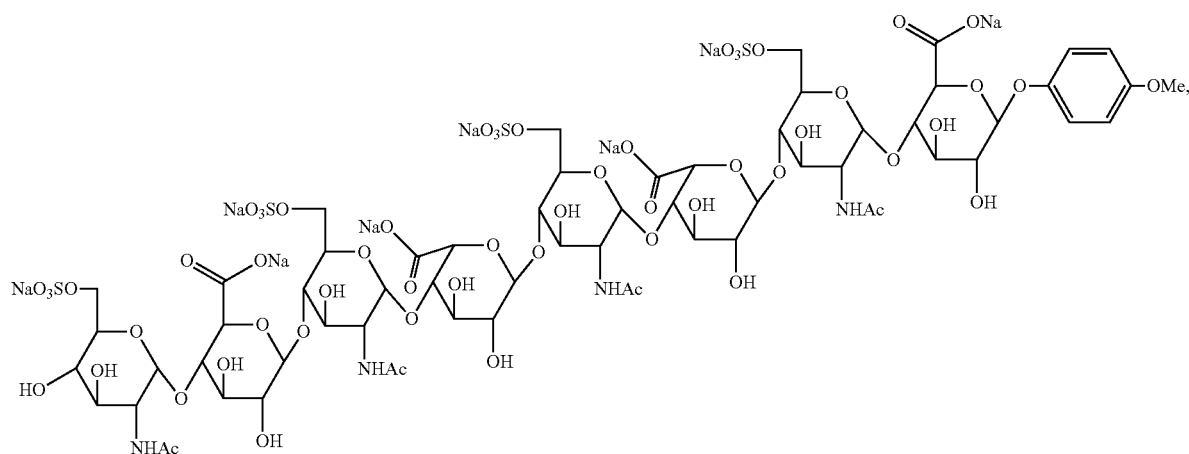

(n)

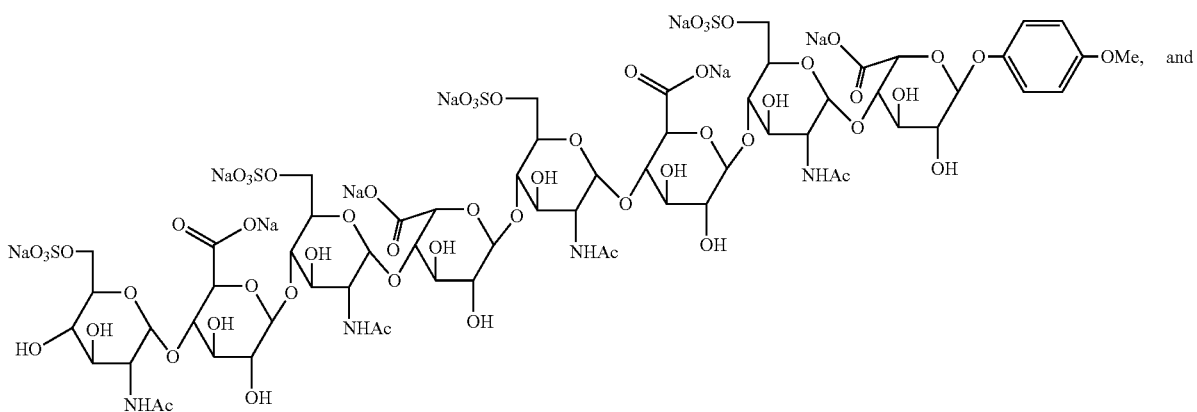

(o)

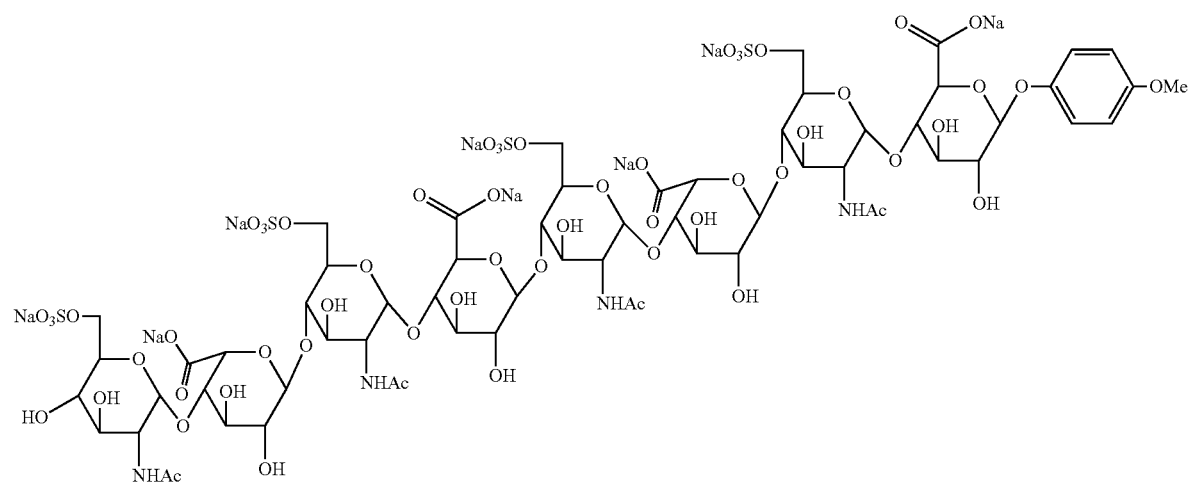

(p)

or a pharmaceutically acceptable salt thereof.

15. A pharmaceutical composition comprising a pharmaceutically effective amount of a compound as claimed in claim 1 and optionally a pharmaceutically acceptable carrier, diluent or excipient.

16. A method of treating a neurodegenerative disease or disorder in which it is desirable to inhibit BACE-1 comprising administering a pharmaceutically effective amount of a compound as claimed in claim 1 to a patient requiring treatment, wherein the disease or disorder is senile dementia, pre-senile dementia, multi-infarct dementia or Alzheimer's disease.

17. A compound as claimed in claim 2 where $R^4$ is $SO_3H$ or a salt form of $SO_3H$.

18. A compound as claimed in claim 3 where $R^4$ is $SO_3H$ or a salt form of $SO_3H$.

19. A compound as claimed in claim 4 where $R^4$ is $SO_3H$ or a salt form of $SO_3H$.

20. A compound as claimed in claim 2 where $R^1$ is a salt form of $SO_3H$.

21. A compound as claimed in claim 3 where $R^1$ is a salt form of $SO_3H$.

22. A compound as claimed in claim 4 where $R^1$ is a salt form of $SO_3H$.

* * * * *